US010815469B2

(12) United States Patent
Poma et al.

(10) Patent No.: US 10,815,469 B2
(45) Date of Patent: Oct. 27, 2020

(54) CELL-TARGETING MOLECULES COMPRISING PROTEASE-CLEAVAGE RESISTANT, SHIGA TOXIN A SUBUNIT EFFECTOR POLYPEPTIDES AND CARBOXY-TERMINAL MOIETIES

(71) Applicant: Molecular Templates, Inc., Austin, TX (US)

(72) Inventors: Eric Poma, New York, NY (US); Erin Willert, Round Rock, TX (US); Jack Higgins, Georgetown, TX (US); Jason Kim, Austin, TX (US)

(73) Assignee: Molecular Templates, Inc., Austin, TX (US)

( * ) Notice: Subject to any disclaimer, the term of this patent is extended or adjusted under 35 U.S.C. 154(b) by 0 days.

(21) Appl. No.: 15/317,892

(22) PCT Filed: Jun. 10, 2015

(86) PCT No.: PCT/US2015/035179
§ 371 (c)(1),
(2) Date: Dec. 9, 2016

(87) PCT Pub. No.: WO2015/191764
PCT Pub. Date: Dec. 17, 2015

(65) Prior Publication Data
US 2017/0101636 A1    Apr. 13, 2017

Related U.S. Application Data

(63) Continuation of application No. PCT/US2015/012970, filed on Jan. 26, 2015.
(Continued)

(51) Int. Cl.
| | | |
|---|---|---|
| C12N 9/24 | (2006.01) | |
| C07K 14/245 | (2006.01) | |
| C07K 14/25 | (2006.01) | |
| C07K 14/74 | (2006.01) | |
| C07K 14/705 | (2006.01) | |
| C07K 16/08 | (2006.01) | |
| C07K 16/10 | (2006.01) | |
| C07K 16/20 | (2006.01) | |
| C07K 16/18 | (2006.01) | |
| C07K 16/28 | (2006.01) | |
| C07K 16/30 | (2006.01) | |
| C07K 16/32 | (2006.01) | |

(Continued)

(52) U.S. Cl.
CPC .......... *C12N 9/2497* (2013.01); *C07K 14/245* (2013.01); *C07K 14/25* (2013.01); *C07K 14/70539* (2013.01); *C07K 14/70596* (2013.01); *C07K 16/085* (2013.01); *C07K 16/088* (2013.01); *C07K 16/1063* (2013.01); *C07K 16/18* (2013.01); *C07K 16/20* (2013.01); *C07K 16/286* (2013.01); *C07K 16/2866* (2013.01); *C07K 16/30* (2013.01); *C07K 16/32* (2013.01); *C12N 9/1077* (2013.01); *C12Y 204/02036* (2013.01); *C12Y 302/02022* (2013.01); *A61K 38/00* (2013.01); *A61K 2039/505* (2013.01); *C07K 2317/569* (2013.01); *C07K 2317/622* (2013.01); *C07K 2319/33* (2013.01); *C07K 2319/55* (2013.01); *C07K 2319/74* (2013.01)

(58) Field of Classification Search
None
See application file for complete search history.

(56) References Cited

U.S. PATENT DOCUMENTS

| | | |
|---|---|---|
| 5,080,898 A | 1/1992 | Murphy |
| 5,135,736 A | 8/1992 | Anderson et al. |

(Continued)

FOREIGN PATENT DOCUMENTS

| | | |
|---|---|---|
| CN | 105713087 A | 1/2016 |
| EP | 1654287 A2 | 5/2006 |

(Continued)

OTHER PUBLICATIONS

Aatsinki et al. Protein Expression and Purification 40 (2005)287-291.*

(Continued)

*Primary Examiner* — Oluwatosin A Ogunbiyi
(74) *Attorney, Agent, or Firm* — Nixon Peabody LLP; Mark J. FitzGerald; Teresa A. Ptashka

(57) ABSTRACT

The present invention provides protease-cleavage resistant molecules comprising Shiga toxin effector polypeptides capable of exhibiting potent, Shiga toxin functions (e.g. subcellular routing and cytotoxicity). The present invention also provides protease-cleavage resistant, cell-targeting molecules for targeting specific cell types, e.g., infected or malignant cells. Certain molecules of the present invention are cytotoxic, and certain cell-targeting molecules of the present invention may be used for the targeted killing of specific cell types and the treatment of a variety of diseases, disorders, and conditions, including cancers, tumors, growth abnormalities, immune disorders, and microbial infections. Certain cell-targeting molecules of the invention exhibit improved, in vivo tolerability as compared to related cell-targeted molecules comprising protease-cleavage sensitive, wild-type, Shiga toxin effector polypeptides. The cell-targeting molecules of the invention can deliver additional materials, such as, e.g., antigens, cytotoxic agents, and detection-promoting agents, into the interiors of target cells.

40 Claims, 5 Drawing Sheets

Specification includes a Sequence Listing.

Related U.S. Application Data

(60) Provisional application No. 62/010,918, filed on Jun. 11, 2014.

(51) Int. Cl.
*C12N 9/10* (2006.01)
*A61K 38/00* (2006.01)
*A61K 39/00* (2006.01)

(56) References Cited

U.S. PATENT DOCUMENTS

| | | | |
|---|---|---|---|
| 5,635,384 | A | 6/1997 | Walsh et al. |
| 5,668,255 | A | 9/1997 | Murphy |
| 6,022,950 | A | 2/2000 | Murphy |
| 6,080,400 | A | 6/2000 | Williams |
| 6,492,498 | B1 | 12/2002 | Vallera et al. |
| 6,652,857 | B2 | 11/2003 | Williams |
| 6,770,456 | B1 | 8/2004 | Coulie et al. |
| 7,267,973 | B2 | 9/2007 | Backer et al. |
| 7,527,787 | B2 | 5/2009 | Chang et al. |
| 7,700,557 | B2 | 4/2010 | Backer et al. |
| 7,713,915 | B1 | 5/2010 | Gariepy et al. |
| 7,799,900 | B2 | 9/2010 | Adams |
| 7,834,258 | B2 | 11/2010 | Choe et al. |
| 8,048,985 | B2 | 11/2011 | Harrison et al. |
| 8,147,832 | B2 | 4/2012 | Carr et al. |
| 8,337,844 | B2 | 12/2012 | Carr et al. |
| 8,470,314 | B2 | 6/2013 | Davis |
| 8,865,866 | B2 | 10/2014 | Harrison et al. |
| 8,895,006 | B2 | 11/2014 | Tumer |
| 8,969,529 | B2 | 3/2015 | O'Brien et al. |
| 9,175,059 | B2 | 11/2015 | Pieczykolan |
| 9,364,557 | B2 | 6/2016 | Neville et al. |
| 2002/0012658 | A1 | 1/2002 | Williams et al. |
| 2002/0168370 | A1 | 11/2002 | McDonald et al. |
| 2003/0166196 | A1 | 9/2003 | Better et al. |
| 2004/0141982 | A1 | 7/2004 | Lust et al. |
| 2004/0166565 | A1 | 8/2004 | Backer et al. |
| 2005/0054835 | A1 | 3/2005 | Better et al. |
| 2005/0069545 | A1 | 3/2005 | Carr et al. |
| 2009/0023649 | A1 | 1/2009 | Backer et al. |
| 2009/0156417 | A1 | 6/2009 | Gariepy et al. |
| 2009/0156502 | A1 | 6/2009 | Harrison et al. |
| 2010/0093563 | A1 | 4/2010 | Williamson et al. |
| 2011/0189209 | A1 | 8/2011 | Neville et al. |
| 2012/0039908 | A1 | 2/2012 | Combs et al. |
| 2012/0149650 | A1 | 6/2012 | Harrison et al. |
| 2012/0251542 | A1 | 10/2012 | Tumer |
| 2013/0071325 | A1 | 3/2013 | Sahin et al. |
| 2013/0189271 | A1 | 7/2013 | De Goeij et al. |
| 2013/0196928 | A1 | 8/2013 | Gariepy |
| 2015/0044210 | A1 | 2/2015 | Mechaly et al. |
| 2015/0259428 | A1 | 9/2015 | Poma et al. |
| 2016/0017047 | A1 | 1/2016 | Poma et al. |
| 2016/0068577 | A1 | 3/2016 | Poma et al. |
| 2016/0177284 | A1 | 6/2016 | Poma et al. |
| 2017/0143814 | A1 | 5/2017 | Poma et al. |
| 2017/0275382 | A1 | 9/2017 | Poma et al. |
| 2018/0057544 | A1 | 3/2018 | Poma et al. |
| 2018/0243432 | A1 | 8/2018 | Poma et al. |
| 2018/0258143 | A1 | 9/2018 | Poma et al. |
| 2018/0258144 | A1 | 9/2018 | Poma et al. |
| 2018/0291359 | A1 | 10/2018 | Poma et al. |
| 2019/0100597 | A1 | 4/2019 | Keyt et al. |
| 2019/0153044 | A1 | 5/2019 | Poma et al. |
| 2019/0153471 | A1 | 5/2019 | Paul et al. |
| 2019/0249145 | A1 | 8/2019 | Jang et al. |

FOREIGN PATENT DOCUMENTS

| | | |
|---|---|---|
| EP | 3265575 A2 | 1/2018 |
| EP | 3448874 A1 | 3/2019 |
| JP | 1993-502880 A | 5/1993 |
| JP | 2011507389 A | 6/1999 |
| JP | 2001500730 A | 1/2001 |
| JP | 2002-521019 A | 7/2002 |
| JP | 2002544173 A | 12/2002 |
| JP | 2003531588 A | 10/2003 |
| JP | 2007536905 A | 12/2007 |
| JP | 2008533977 A | 8/2008 |
| JP | 2009502936 A | 1/2009 |
| JP | 2011050388 A | 3/2011 |
| JP | 2012044997 A | 3/2012 |
| JP | 2012070737 A | 4/2012 |
| JP | 2012515551 A | 7/2012 |
| JP | 2014515921 A | 7/2014 |
| KR | 2011-0033233 A | 3/2011 |
| KR | 2011-0119725 A | 11/2011 |
| WO | 1994026910 A1 | 11/1994 |
| WO | 1996030043 A1 | 10/1996 |
| WO | 1996040200 A1 | 12/1996 |
| WO | 1998011229 A3 | 3/1998 |
| WO | 2000004926 A2 | 2/2000 |
| WO | 2000067795 A1 | 11/2000 |
| WO | 2001070945 A1 | 9/2001 |
| WO | 2001077342 A1 | 10/2001 |
| WO | 2003066854 A1 | 8/2003 |
| WO | 2004056312 A2 | 7/2004 |
| WO | 2004058158 A2 | 7/2004 |
| WO | 2005000902 A1 | 1/2005 |
| WO | 2005016969 A2 | 2/2005 |
| WO | 2005052006 A2 | 6/2005 |
| WO | 2005052129 A2 | 6/2005 |
| WO | 2006099875 A1 | 9/2006 |
| WO | 2007005874 A2 | 1/2007 |
| WO | 2007014238 A2 | 2/2007 |
| WO | 2007071061 A1 | 6/2007 |
| WO | 2008080218 A1 | 7/2008 |
| WO | WO-2008080218 A1 * | 7/2008 ....... A61K 47/48261 |
| WO | 2009017823 A2 | 2/2009 |
| WO | 2009032954 A1 | 3/2009 |
| WO | 2007098201 A2 | 4/2009 |
| WO | 2009014835 A3 | 5/2009 |
| WO | 2009064815 A1 | 5/2009 |
| WO | 2009110944 A1 | 9/2009 |
| WO | 2010011697 A1 | 1/2010 |
| WO | 2010085539 A1 | 7/2010 |
| WO | WO-2011009624 | 1/2011 |
| WO | 2012022985 A1 | 2/2012 |
| WO | 2012093158 A1 | 7/2012 |
| WO | 2012101235 A1 | 8/2012 |
| WO | WO-2012104344 | 8/2012 |
| WO | 2012154530 A1 | 11/2012 |
| WO | 2013080147 A2 | 6/2013 |
| WO | 2015063187 A1 | 10/2014 |
| WO | 2015120058 A9 | 8/2015 |
| WO | 2015191764 A1 | 12/2015 |
| WO | 2015193411 | 12/2015 |
| WO | 2016196344 A1 | 12/2016 |
| WO | 2017019623 A2 | 2/2017 |
| WO | 2018080812 A1 | 5/2018 |
| WO | 2018106895 A1 | 6/2018 |
| WO | 2018140427 A1 | 8/2018 |
| WO | 2016162749 | 9/2018 |

OTHER PUBLICATIONS

Amino Acids. https://www.promega.com/-/media/files/resources/technical-references/amino-acid-abbreviations-and-molecular-weights.pdf retrieved Feb. 26, 2018.*

Al-Jaufy, AY, et al., "Cytotoxicity of a Shiga Toxin A Subunit-CD4 Fusion Protein to Human Immunodeficiency Virus-Infected Cells", Infection and Immunity, 62(3), (1994), 956-960.

Al-Jaufy, AY, et al., "Purification and Characterization of a Shiga Toxin A Subunit-CD4 Fusion Protein Cytotoxic to Human Immunodeficiency Virus-Infected Cells", Infection and Immunity, 63(8), (1995), 3073-3078.

Cheung, MC, et al., "An evolved ribosome-inactivating protein targets and kills human melanoma cells in vitro and in vivo", Molecular Cancer, 9(28), (2010).

(56) References Cited

OTHER PUBLICATIONS

Cheung, MC, et al., "A Ribosome-inactivating Protein Toxin as a Template for Cancer Drug Discovery", thesis, University of Toronto, (2012), retrieved from http://hdl.handle.net/1807/33952.
Di, R, et al., "Identification of amino acids critical for the cytotoxicity of Shiga toxin 1 and 2 in *Saccharomyces cerevisiae*", Toxicon, 57(4), (2011), 525-539.
Garred, O, et al., "Role of processing and intracellular transport for optimal toxicity of Shiga toxin and toxin mutants", Experimental Cell Research, 218(1), (1995), 39-49.
Haddad, JE, et al., "Minimum Domain of the Shiga Toxin A Subunit Required for Enzymatic Activity", Journal of Bacteriology, 175(16), (1993), 4970-4978.

Kurmanova, A, et al., "Structural requirements for furin-induced cleavage and activation of Shiga toxin", Biochemical and Biophysical Research Communications, 357(1), (2007), 144-149.

Kyu, E, "Characterization of the A subunit mutants of Stx1 and Stx2 in *Saccharomyces cerevisiae*", thesis, Rutgers, The State University of New Jersey, New Brunswick, retrieved from http://dx.doi.org/doi:10.7282/T34F1QWJ.

Lapointe, P, et al., "A Role for the Protease-sensitive Loop Region of Shiga-like Toxin 1 in the Retrotranslocation of Its $A_1$ Domain from the Endoplasmic Reticulum Lumen", The Journal of Biological Chemistry, 280(24), (2005), 23310-23318.

Oloomi, M, et al., "In vivo Characterization of Fusion Protein Comprising of A1 Subunit of Shiga Toxin and Human GM-CSF: Assessment of Its Immunogenicity and Toxicity", Iranian Biomedical Journal, 14(4), (2010), 136-141.

Pastan, I, et al., "Immunotoxin Treatment of Cancer", Annual Review of Medicine 58, (2007), 221-237.

Poma, Eric, "De-Immunized, Shiga Toxin A Subunit Scaffolds and Cell-Targeting Molecules Comprising the Same", International Application Serial No. PCT/US2016/034778, Filed May 27, 2016.

Poma, Eric, "Cell-Targeting Molecules Comprising Shiga Toxin A Subunit Effectors and CD8+ T-Cell Epitopes", International Application Serial No. PCT/US2016/043902, Filed Jul. 25, 2016.

Protein ID ABM97743, European Molecular Biology Laboratory (EMBL), Oloomi, M, et al., "synthetic construct partial A1-GMCSF chimeric protein", Sep. 10, 2007.

Roudkenar, MH, et al., "Selective cytotoxicity of recombinant STXA1-GM-CSF protein in hematopoetic cancer cells", Cell Biology and Toxicology, 22(3), (2006), 213-219.

Sandvig, K, et al., "Entry of Shiga Toxin into Cells", Zentralblatt für Bakteriologie, 278(2-3), (1993), 296-305.

Shete, V, "Generation and Characterization of Random Site-Directed Mutants of Shiga-Like Toxin 1A by *Escherichia coli* O157:H7 in *Saccharomyces cerevisiae*", thesis, Rutgers, The State University of New Jersey, New Brunswick, (2009), retrieved from http://dx.doi.org/doi:10.7282/T300029Z.

Su, H, et al., "Clinical grade production and characterization of a fusion protein comprised of the chemokine CCL2-ligand genetically fused to a mutated and truncated form of the Shiga A1 subunit", Protein Expression and Purification, 66(2), (Jan. 1, 2009), 149-157.

Suhan, ML, and Hovde, CJ, "Disruption of an Internal Membrane-Spanning Region in Shiga Toxin 1 Reduces Cytotoxicity", Infection and Immunity, 66(11), (1998), 5252-5259.

Gannon, VP, et al., "Molecular cloning and nucleotide sequence of another variant of the *Escherichia coli* Shiga-like toxin II family", Journal of General Microbiology 136(6), (1990), 1125-1135.

Peng, KW, et al., "Oncolytic measles viruses displaying a single-chain antibody against CD38, a myeloma cell marker", Blood 101(7), (2003), 2557-2562.

Aatsinki et al. "An alternative use of basic pGEX vectors for producing both N- and C-terminal fusion proteins for production and affinity purification of antibodies", Protein Expression and Purification, 40(2), (2005), 287-291.

Ackerman et al., "SLT-VEGF Reduces Lung Metastases, Decreases Tumor Recurrence, and Improves Survival in an Orthotopic Melanoma Model", Toxins 2(9) 224-257 (2010).

Adotevi et al., "B Subunit of Shiga Toxin-Based Vaccines Synergize with α-Galactosylceramide to Break Tolerance against Self Antigen and Elicit Antiviral Immunity", The Journal of Immunology, 179(5), (2007), 3371-3379.

Antignani "Immunotoxins: The Role of the Toxin", Toxins, 5(8), (2013), 1486-1502.

Apostolpoulos et al., "MUC1 peptide epitopes associated with five different H-2 class I molecules", European Journal of Immunology, 27(10), (1997), 2579-2587.

Baker et al., "Immunogenicity of Protein Therapeutics: the Key Causes, Consequences and Challenges", Self/Nonself 1(4): 314-322 (2010).

Backer et al., "Shiga-like toxin-VEGF fusion proteins are selectively cytotoxic to endothelial cells overexpressing VEGFR-2", Journal of Controlled Release 74(1-3), 349-355 (2001).

Backer et al., "Targeting Endothelial Cells Overexpressing VEGFR-2: Selective Toxicity of Shiga-like Toxin-VEGF Fusion Proteins", Bioconjugate Chemistry 12(6) 1066-1073 (2001).

Ballard, JD, et al., "Anthrax Toxin as a Molecular Tool for Stimulation of Cytotoxic T Lymphocytes: Disulfide-Linked Epitopes, Multiple Injections, and Role of CD4+ Cells", Infection and Immunity, 66(10), (1998), 4696-4699.

Ballard, JD, et al., "Anthrax Toxin-Mediated Delivery In Vivo and In Vitro of a Cytotoxic T-Lymphocyte Epitope from Ovalbumin", Infection and Immunity, 66(2), (1998), 615-619.

Barnd et al., "Specific, Major Histocompatibility Complex-Unrestricted Recognition of Tumor-Associated Mucins by Human Cytotoxic T cells", Proceedings of the National Academy of Sciences U.S.A., 86(18): 7159-7163 (1989).

Barratt-Boyes, SM, et al., "Immunization of Chimpanzees with Tumor Antigen MUC1 Mucin Tandem Repeat Peptide Elicits Both Helper and Cytotoxic T-cell Responses", Clinical Cancer Research 5(7), (1999), 1918-1924.

Beers et al., "Antigenic modulation limits the efficacy of anti-CD20 antibodies: implications for antibody selection", Blood 1115(25): 5191-5201 (2010).

Beers et al., "CD20 as a Target for Therapeutic Type I and II Monoclonal Antibodies", Seminars in Hematology 47(2): 107-114 (2010).

Beers et al., "Type II (tositumomab) anti-CD20 monoclonal antibody outperforms type I (rituximab-like) reagents in B-cell depletion regardless of complement activation", Blood 112, 4170-4177 (2008).

Bera et al., "A Bivalent Disulfide-stabilized Fv with Improved Antigen Binding to erbB2", Journal of Molecular Biology, 281(3) 475-483 (1998).

Bera et al., "Pharmacokinetics and Antitumor Activity of a Bivalent Disulfide-stabilized Fv Immunotoxin with improved Antigen Binding to erbB2", Cancer Research 59(16): 4018-4022 (1999).

Beum et al., Loss of CD20 and Bound CD20 Antibody from Opsonized B Cells Occurs More Rapidly because of Trogocytosis Meditated by Fc Receptor-Expressing Effector Cells Than Direct Internalization by the B Cells, Journal of Immunology, 187(6) 3438-3447 (2011).

Beum et al., "The Shaving Reaction: Rituximab/CD20 Complexes Are Removed from Mantle cell Lymphoma and Chronic Lymphocytic Leukemia Cells by THP-1 Monocytes", Journal of Immunology, 176(4) 2600-2609 (2006).

Bevan et al. "Real-time 96-well antibody internalization assays using IncuCyte FabFlour Red Antibody Labeling Reagent, Application Note, Sartorious", Essen BioScience (2017).

Bibby "Orthotopic models of cancer for preclinical drug evaluation: advantages and disadvantages", European Journal of Cancer 40(6), (2004), 852-857.

Bolognesi, A, et al., "A comparison of anti-lymphocyte immunotoxins containing different ribosome-inactivating proteins and antibodies", Clinical & Experimental Immunology, 89(3), (1992), 341-346.

Bonifaz et al., "Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance", Journal of Experimental Medicine, 196(12), (2002), 1627-1638.

(56) References Cited

OTHER PUBLICATIONS

Boross et al., "Both Activating and inhibitory Fc gamma receptors mediate rituximab-induced trogocytosis of CD20 in mice", Immunology Letters 143(1) 44-52 (2012).
Boross et al., "Mechanisms of action of CD20 antibodies", American Journal of Cancer Research 2(6) 676-690 (2012).
Braslawsky et al., "Adriamycin(hydrazone)-antibody conjugates require internalization and intracellular acid hydrolysis for antitumor activity", Cancer Immunology 33: 367-374 (1991).
Bray et al., "Probing the surface of eukaryotic cells using combinatorial toxin libraries", Current Biology 11(9) 697-701 (2001).
Brieschke, B, et al., "Antigen Seeding Technology by Engineered Toxin Bodies Provides a Targeted Immuno-Oncology Approach for Treatment of Cancers", Proceedings: American Association for Cancer Research (AACR) Annual Meeting 2018, Poster 2777, Abstract #4912, (2018).
Brieschke, B, et al., "Targeted Engineered Toxin Bodies provide a novel mechanism of action against HER2 positive cancers", Cancer Research, 78 (13 Suppl), (Jul. 2008), Abstract 5769.
Brieschke, B, et al., "Targeted Engineered Toxin Bodies provide a novel mechanism of action against HER2 positive cancers", Proceedings: American Association for Cancer Research (AACR) Annual Meeting 2018, Poster #5769, (Apr. 18, 2018).
Brieschke, B, et al., "Identification and Functional Profiling of PD-L1 Targeted Engineered Toxin Bodies for Antigen Seeding Technology (AST) and Redirection of T cell Response to Tumors", 33rd Annual Meeting of the Society for Immunotherapy of Cancer (SITC), Washington, D.C., Poster # 11078, (Nov. 7-11, 2018).
Brieschke, B, et al., "Identification and functional profiling of PD-L1 targeted engineered toxin bodies for antigen seeding technology and redirection of T cell response to tumors", Journal of ImmunoTherapy of Cancer, 6(Suppl 1): 114, (Nov. 6, 2018), Abstract P9.
Brigotti, M, et al., "Damage to Nuclear DNA Induced by Shiga Toxin 1 and Ricin in Human Endothelial Cells", The FASEB Journal, 16(3), (2002), 365-372.
Brigotti et al., Change in Conformation with Reduction of a-Helix Content Causes Loss of Neutrophil Binding Activity in Fully Cytotoxic Shiga Toxin 1, The Journal of Biological Chemistry 286(40) 34514-34521 (2011).
Bujny et al., "The retromer component sorting nexin-1 is required for efficient retrograde transport of Shiga toxin from early endosome to the trans Golgi network", Journal of Cell Science, 120(Pt 12), (2007), 2010-2021.
Burgess et al., "Proteolytic cleavage at arginine residues within the hydrophillic disulphide loop of the *Escherichia coli* Shiga-like toxin I A subunit is not essential for cytotoxicity", Molecular Microbiology 10(1) 171-179 (1993).
Cao et al., "Construction of mutant genes for a non-toxic verotoxin 2 variant (VT2vp1) of *Escherichia coli* and characterization of purified mutant toxins", Microbiology and Immunology, 38(6) 441-447 (1994).
Cao et al., "Design optimization and characterization of Her2/neu-targeted immunotoxins: comparative in vitro and in vivo efficacy studies" Oncogene 33(4):1-11 (2013).
Carbonetti, NH, "Pertussis toxin and adenylate cyclase toxin: key virulence factors of Bordetella pertussis and cell biology tools", Future Microbiology 5, (2010), 455-469.
Carbonetti, NH, et al., "Intracellular Delivery of a Cytolytic T-Lymphocyte Epitope Peptide by Pertussis Toxin to Major Histocompatibility Complex Class I without Involvement of the Cytosolic Class I Antigen Processing Pathway", Infection and Immunity, 67(2), (1999), 602-607.
Rajagopalan, S, et al., "HER2-targeted engineered toxin body demonstrates selective binding and cell kill of HER2-overexpressing breast cancer", Proceedings: American Association for Cancer Research (AACR) Annual Meeting 2013, Poster, (Apr. 6-10, 2013).
Rajagopalan, S, et al., "HER2-targeted engineered toxin body demonstrates selective binding and cell kill of HER2-overexpressing breast cancer", The Journal of Cancer Research, 73(8 Suppl): Abstract #868, (Apr. 15, 2013).
Rajagopalan, S, et al., "Next-generation engineered toxin bodies: CD38, PD-L1 and HER2 targeted ETBs", The Journal of Cancer Research, 76(14 Suppl), (Jul. 15, 2016), Abstract #595 from American Association for Cancer Research (AACR) Annual Meeting 2016, (Apr. 16-20, 2016).
Ramakrishnan, S, and Houston, L, "Comparison of the Selective Cytotoxic Effects of Immunotoxins Containing Ricin A Chain or Pokeweed Antiviral Protein and Anti-Thy 1.1 Monoclonal Antibodies", Cancer Research, 44(1), (1984), 201-208.
Robinson, GL, et al., "In vivo efficacy of a CD38-specific engineered toxin body", Clinical Cancer Research, 21(17 Suppl), (Sep. 1, 2015), Abstract A15.
Robinson, GL, et al., "In vivo efficacy of a CD38-specific engineered toxin body", Proceedings: American Association for Cancer Research (AACR) Special Conference on Hematologic Malignancies: Translating Discoveries to Novel Therapies, Poster A15 (Sep. 21, 2015).
Robinson, GL, et al., "MT-3724, an engineered toxin body targeting CD20 for non-Hodgkin's lymphoma", Proceedings of the 107th Annual Meeting of the American Association for Cancer Research, Cancer Research, Jul. 15, 2016, 76(14 Suppl), Abstract 1483.
Robinson, GL, et al., "MT-4019: a de-immunized engineered toxin body targeting CD38 for multiple myeloma", Proceedings: American Association for Cancer Research (AACR) Annual Meeting 2017, Poster, Abstract 2659 (Apr. 1-5, 2017).
Romaniuk, SI, et al., "Recombinant Diphtheria toxin derivatives: Perspectives of application", Russian Journal of Bioorganic Chemistry, 38(6), (2012), 565-577.
Rossi et al., "Novel Designs of Multivalent Anti-CD20 Humanized Antibodies as Improved Lymphoma Therapeutics", Cancer Research 68(20) 8384-8392 (2008).
Rudikoff et al., "Single amino acid substitution altering antigen-binding specificity", Proceedings of the National Academy of Sciences of the USA 79:6 1979-1983 (1982).
Saijo, N, "What are the reasons for negative phase III trials of molecular-target-based drugs?", Cancer Science 95 (10), (2004), 772-776.
Sandvig, K, et al., "Protein toxins: mode of action and cell entry," Biochemical Society Transactions, 20(4), (1992), 724-727.
Saron, MF, et al., "Anti-viral protection conferred by recombinant adenylate cyclase toxins from Bordetella pertussis carrying a CD8+ T cell epitope from lymphocytic choriomeningitis virus", Proceedings of the National Academy of Sciences U.S.A., 94(7), (1997), 3314-3319.
Schindler et al., "A Phase I Study of a Combination of anti-CD19 and anti-CD22 Immunotoxins (Combotox) in Adult Patients with Refractory B-Lineage Acute Lymphoblastic Leukaemia", British Journal of Haematology, 154(4): 1-11 (2011).
Schlecht, G, et al., "Antigen Targeting to CD11b Allows Efficient Presentation of CD4+ and CD8+ T Cell Epitopes and In Vivo Th1-Polarized T Cell Priming", The Journal of Immunology, 173(10), (2004), 6089-6097.
Schuh, JC, "Trials, Tribulations, and Trends in Tumor Modeling in Mice", Toxicologic Pathology 32 (Suppl. 1), (2004), 53-66.
Schultz et al., "A Tetravalent Single-chain Antibody-Streptavidin Fusion Protein for Pretargeted Lymphoma Therapy", Cancer Research 60(23): 6663-6669 (2000).
Sebo, P, et al., "Cell-Invasive Activity of Epitope-Tagged Adenylate Cyclase of Bordetella pertussis allows In Vitro Presentation of a Foreign Epitope to CD8+ Cytotoxic T Cells", Infection and Immunity, 63(10), (1995), 3851-3857.
Sebo, P, et al., "In vivo induction of CTL responses by recombinant adenylate cyclase of Bordetella pertussis carrying multiple copies of a viral CD8+ T-cell epitope", FEMS Immunology & Medical Microbiology, 26(2), (1999), 167-173.
Shan et al., "Characterization of scFV-Ig Constructs Generated from the Anti-CD20 mAb 1F5 Using Linker Peptides of Varying Lengths", Journal of Immunology 162(11): 6589-6595 (1999).
Shaw, CA, et al., "Stimulation of CD8+ T Cells following Diphtheria Toxin-Mediated Antigen Delivery into Dendritic Cells", Infection and Immunity, 74(2), (2006), 1001-1008.

(56) References Cited

OTHER PUBLICATIONS

Shen et al., "Evaluation of four CD22 Antibodies as Ricin A Chain-Containing Immunotoxins for the In Vivo Therapy of Human B-Cell Leukemias and Lymphomas", International Journal of Cancer 42(5): 792-797 (1988).
Shiba, Y, et al., "AGAP2 regulates retrograde transport between early endosomes and the TGN", Journal of Cell Science, 123(Pt 14), (2010), 2381-2390.
Sieber et al., "Selective internalization of monoclonal antibodies by B-cell chronic lymphocytic leukemia cells", 121(3): 458-461 (2003).
Simsova, M, et al., "The adenylate cyclase toxin from Bordetella pertussis—a novel promising vehicle for antigen delivery to dendritic cells", International Journal of Medical Microbiology, 239, (2004), 571-576.
Sivam, G, et al., "Immunotoxin to a Human Melanoma-associated Antigen: Comparison of Gelonin with Ricin and Other A Chain Conjugates", Cancer Research, 47(12), (1987), 3169-3173.
Skinner et al., "Inhibition of prokaryotic translation by the Shiga toxin enzymatic subunit", Microbial Pathogenesis 24(2) 117-122 (1998).
Skinner et al., "Investigation of ribosome binding by the Shiga Toxin A1 subunit, using competition and site-directed mutagenesis", Journal of Bacteriology 179(4): 1368-1374 (1997).
Smith, DC, et al., "Exogenous Peptides Delivered by Ricin Require Processing by Signal Peptidase for Transporter Associated with Antigen Processing-Independent MHC Class I-Restricted Presentation", The Journal of Immunology, 169(1), (2002), 99-107.
Stenmark, H, et al., "Peptides fused to the amino-terminal end of Diphtheria toxin are translocated to the cytosol", The Journal of Cell Biology, 113(5), (1991), 1025-1032.
Suh, JK., et al., "Shiga Toxin Attacks Bacterial Ribosomes as Effectively as Eucaryotic Ribosomes", Biochemistry, 37(26), (1998), 9394-9398.
Tacken, PJ, et al., "Effective induction of naive and recall T-cell responses by targeting antigen to human dendritic cells via a humanized anti—DC-SIGN antibody", Blood, 106(4), (2005), 1278-85.
Tesh et al., "Comparison of the Relative Toxicities of Shiga-Like Toxins Type I and Type II for Mice", Infection and Immunity, 61(8): 3392-3402 (1993).
Thompson et al., "Improved binding of a bivalent single-chain immunotoxin results in increased efficacy for in vivo T-cell depletion", Protein Engineering 14(12): 1035-1041 (2001).
Thorpe, PE, et al., "Cytotoxicity Acquired by Conjugation of an Anti-Thy1.1 Monoclonal Antibody and the Ribosome-Inactivating Protein, Gelonin", European Journal of Biochemistry, 116(3), (1981), 447-454.
Torgersen, ML, et al., "The A-subunit of surface-bound Shiga toxin stimulates clathrin-dependent uptake of the toxin", FEBS Journal, 272(16), (2005), 4103-4013.
Tosatto et al. "Large-Scale Prediction of Protein Structure and Function from Sequence", Current Pharmaceutical Design, 12(17): 2067-2086 (2006).
Vallera et al., "Bioengineering a unique deimmunized bispecific targeted toxin that simultaneously recognizes human CD22 and CD19 Receptors in a mouse model of B-Cell metastases" Molecular Cancer Therapeutics 9(6) 1872-1883 (2010).
Varner et al., "Recent Advances in Engineering Polyvalent Biological Interactions", Biomacromolecules 16(1): 43-55 (2014).
Vervoordeldonk et al., "Preclinical studies with radiolabeled monoclonal antibodies for treatment of patients with B-cell malignancies" Cancer 73(3) 1006-1011 (1994).
Vingert, B, et al., "The Shiga toxin B-subunit targets antigen in vivo to dendritic cells and elicits anti-tumor immunity", European Journal of Immunology 36(5), (2006) 1124-1135.
Voskoglou-Nomikos, T, et al., "Clinical Predictive Value of the In Vitro Cell Line, Human Xenograft, and Mouse Allograft Preclinical Cancer Models", Clinical Cancer Research 9(11), (2003), 4227-4239.

Wales, R, et al., "Addition of an endoplasmic reticulum retrieval sequence to ricin A chain significantly increases its cytotoxicity to mammalian cells", Journal of Biological Chemistry, 268(32), (1993), 23986-23990.
Wang, E, et al., "T-cell-directed cancer vaccines: the melanoma model", Expert Opinion on Biological Therapy 1(2), (2001), 277-290.
Wargalla et al., "Rate of internalization of an immunotoxin correlates with cytotoxic activity against human tumor cells", Proceedings of the National Academy of Sciences of the USA 86:13 5146-5150 (1989).
Willert et al., "TAK-169, an exceptionally potent CD38 targeted engineered toxin body, as a novel direct cell kill approach for the treatment of multiple myeloma", Proceedings: American Association for Cancer Research (AACR) Annual Meeting 2019, Poster #2384, (Apr. 1, 2019).
Willert, EK, et al., "Engineered toxin bodies: A next-generation immunotoxin scaffold with novel immuno-oncology functionality", Proceedings: American Association for Cancer Research (AACR) Annual Meeting 2015, Poster, Abstract #2477 (Apr. 18, 2015).
Willert, EK, et al., "Engineered toxin bodies: A next-generation immunotoxin scaffold with novel immuno-oncology functionality", The Journal of Cancer Research, 75(15 Suppl): Abstract nr 2477, (Aug. 1, 2015).
Windschiegl, B, et al., "Lipid Reorganization Induced by Shiga Toxin Clustering on Planar Membranes", PLoS One, 4(7), (2009), e6238.
Lehmann, CHK, et al., "Direct Delivery of Antigens to Dendritic Cells via Antibodies Specific for Endocytic Receptors as a Promising Strategy for Future Therapies", Vaccines, 4(2):1-32 (2016).
Li et al., "Development of Novel Tetravalent Anti-CD20 Antibodies with Potent Antitumor Activity", Cancer Research 68(7) 2400-2408 (2008).
Li et al., "The CD20 Calcium Channel is Localized to Microvilli and Constitutively Associated with Membrane Rafts: Antibody binding increases the affinity of the association through an epitope-dependent cross-linking-independent mechanism", Journal of Biological Chemistry 279(19): 19893-19901 (2004).
Lim et al., "Fc gamma receptor IIb on target B cells promotes ritumixab internalization and reduces clinical efficacy", Blood 118(9): 2530-2540 (2011).
Ling et al., "Structure of the Shiga-like Toxin I B-Pentamer Complexed with an Analogue of Its Receptor Gb3", Biochemistry, 37(7): 1777-1788 (1998).
Giansanti et al., "Strategies to Improve the Clinical Utility of Saporin-Based Targeted Toxins" Toxins 10(82): 1-32 (2018).
Harwerth et al., Monoclonal Antibodies against the Extracellular Domain of the erbB-2 Receptor Function as Partial Ligand Agonists, Journal of Biol. Chem 267(21):15160-15167 (1992).
Li et al., "Clinical targeting recombinant immunotoxins for cancer therapy", Onco Targets and Therapy 10:3645-3665 (2017).
Luqman et al., "The antileukemia activity of a human antiCD40 antagonist antibody, HCD122, on human chronic lymphocytic leukemia cells", Blood 112(3) 711-720 (2008).
Lyu et al., "Cell-targeting fusion constructs containing recombinant gelonin", Methods in Enzymology vol. 502 167-214 (2012).
Maak, M, et al., "Tumor-Specific Targeting of Pancreatic Cancer with Shiga Toxin B-Subunit", Molecular Cancer Therapeutics, 10(10), (2011), 1918-1928.
Mallard, F, et al., "Direct Pathway from Early/Recycling Endosomes to the Golgi Apparatus Revealed through the Study of Shiga Toxin B-fragment Transport", The Journal of Cell Biology, 143(4), (1998), 973-990.
Mascarell, L, et al., "Induction of Neutralizing Antibodies and Th1-Polarized and CD4-Independent CD8+ T-Cell Responses following Delivery of Human Immunodeficiency Virus Type 1 Tat Protein by Recombinant Adenylate Cyclase of Bordetella pertussis", Journal of Virology, 79(15), (2005), 9872-9884.
Mazor et al., "chFRP5-ZZ-PE38, a large IgG-toxin immunoconjugate outperforms the corresponding smaller FRP5 (Fv)-ETA immunotoxin in eradicating ErbB2-expressing tumor xenografts", Cancer Letters, 257(1) 124-135: (2007).

(56) References Cited

OTHER PUBLICATIONS

Mazor, R, et al., "Identification and elimination of an immunodominant T-cell epitope in recombinant immunotoxins based on Pseudomonas exotoxin A", Proceedings of the National Academy of Sciences U.S.A., 109(51), (2012), E3597-E3603.

McCluskey et al., "Charged and hydrophobic Surfaces on the A chain of Shiga-like Toxin 1 recognize the C-terminal Domain of Ribosomal Stalk Proteins," PLoS One 7(2): (2012).

McCluskey et al., "Shiga-like Toxin 1: Molecular Mechanism of Toxicity and Discovery of Inhibitors", thesis University of Toronto (2010).

McCluskey, AJ, et al., "The Catalytic Subunit of Shiga-like Toxin 1 Interacts with Ribosomal Stalk Proteins and is Inhibited by Their Conserved C-Terminal Domain", Journal of Molecular Biology, 378(2), (2008), 375-386.

McKenzie, J, et al., "Passage through the Golgi is necessary for Shiga toxin B subunit to reach the endoplasmic reticulum",The FEBS Journal, 276(6), (2009), 1581-1595.

Michel et al., "Intracellular Accumulation of the Anti-CD20 Antibody 1F5 in B-Lymphoma Cells", Clinical Cancer Research 8(8) 2701-2713 (2002).

Miller et al., "Design, Construction, and In-Vitro analyses of Multivalent Antibodies", Journal of Immunology 170(9) 4854-4861 (2003).

Minckwitz et al., "Phase I clinical study of the recombinant antibody toxin scFv(FRPS)-ETA specific for the ErbB2/HER2 receptor in patients with advanced solid malignomas" Breast Cancer Research 7(5): 617-626 (2005).

Newland et al., "Cloning of Genes for Production of *Escherichia coli* Shiga-Like Toxin Type II", Infection and Immunity, 55(11): 2675-2680 (1987).

Ninkovic, T, et al., "Identification of O-glycosylated decapeptides within the MUC1 repeat domain as potential MHC class I (A2) binding epitopes", Molecular Immunology 47(1), (2009), 131-140.

Noakes et al., "Exploiting retrograde transport of Shiga-like Toxin 1 for the delivery of exogenous antigens into the MHC class I presentation pathway" FEBS Letters 453(1-2) 95-99 (1999).
Ohmura et al., "Characterization of non-toxic mutant toxins of Vero toxin I that were constructed by replacing amino acids in the A subunit", Microbial Pathogenesis 15(3): 169-176 (1993).
Olafsen et al., "ImmunoPET imaging of B-cell lymphoma using anti-CD20 scFv dimers (diabodies)", Protein Engineering, Design & Selection 23(4): 243-249 (2010).
Olafsen et al., "Recombinant Anti-CD20 Antibody fragments for Small-Animal PET Imaging of B-Cell Lymphomas", Journal of Nuclear Medicine 50(9): 1500-1508 (2009).
Onda, M, et al., "An immunotoxin with greatly reduced immunogenicity by identification and removal of B cell epitopes", Proceedings of the National Academy of Sciences U.S.A., 105(32), (2008), 11311-11316.
Osicka, R, et al., "Delivery of CD8+ T-cell epitopes into major histocompatibility complex class I antigen presentation", Infection and Immunity, 68(1), (2000), 247-256.
Pai-Scherf, LH, et al., "Hepatotoxicity in Cancer Patients Receiving erb-38, a Recombinant Immunotoxin That Targets the erbB2 Receptor", Clinical Cancer Research, 5(9), (1999), 2311-2315.
Paul "Fundamental Immunology" 3rd Edition Raven Press 292-295 (1993).
Perampalam, S et al., "Designing combinatorial protein libraries based on a protein toxin template", Molecular and Cellular Proteomics, 2(9), (2003), 825-915.
Perampalam, S et al., "Designing combinatorial protein libraries based on a protein toxin template", HUPO 2nd Annual & IUBMB IXI World Congress, Oct. 8-11, Montreal, Poster Session 28 Proteomics & Biotechnology, 80.16 (Oct. 2003).
Perampalam et al., "Cell-targeted Ribsosome-Inactivating Proteins derived from Protein Combinatorial Libraries", Thesis—University of Toronto (2008).
Peterson, JK, et al., "Integrating pharmacology and in vivo cancer models in preclinical and clinical drug development", European Journal of Cancer 40(6), (2004), 837-844.
Pirie et al., "Convergent Potency of Internalized Gelonin Immunotoxins across Varied Cell Lines, Antigens, and Targeting Moieties", Journal of Biological Chemistry 286(6): 4165-4172 (2011).
Pisarev, VM, et al., "T cells recognize PD(N/T)R motif common in a variable number of tandem repeat and degenerate repeat sequences of MUC1", International Immunopharmacology 5(2), (2005), 315-330.
Polito et al., "Saporin-S6: A Useful Tool in Cancer Therapy", Toxins 5: 1698-1722 (2013).
Polito et al., "The Conjugate Rituximab/saporin-S6 completely inhibits clonogenic growth of CD20-expressing cells and produces a synergistic toxic effect with Fludarabine", Leukemia 18(7): 1215-1222 (2004).
Polson et al., "Antibody-Drug Conjugates for the Treatment of Non-Hodgkin's Lymphoma: Target and Linker-Drug Selection," Cancer Research 69(6) 2358-2364 (2009).
Press et al., "Endocytosis and degradation of Monoclonal Antibodies Targeting Human B-Cell Malignancies", Cancer Research 49(17): 4906-4912 (1989).
Promega, Technical Reference, Amino Acids (2018).
Press et al., "Retention of B-Cell Specific Monoclonal Antibodies by Human Lymphoma Cells", Blood 83(5) 1390-1397 (1994).
Preville, X, et al., "Eradication of Established Tumors by Vaccination With Recombinant Bordetella pertussis Adenylate Cyclase Carrying the Human Papillomavirus 16 E7 Oncoprotein", Cancer Research, 65(2), (2005), 641-649.
Ramos et al., "The safety and efficacy profile of a PD-L1 directed Engineered Toxin Body, as a novel targeted direct-cell kill approach for the treatment of PD-L1 expressing cancers" Proceedings: American Association for Cancer Research (AACR) Annual Meeting 2019, Poster #3900, (2019).
Rajagopalan et al.,"CD-20 Specific Engineered Toxin Body Demonstrates Direct Cell Kill of Multiple B-Cell Non-Hodgkin's Lymphoma Types" Blood 122(21) 5152 (2013).
Rajagopalan, S, et al., "A novel targeted engineered toxin body for treatment of HER2 positive breast cancer", Proceedings: Thirty-Seventh Annual CTRC-AACR San Antonio Breast Cancer Symposium, Poster, #P4-15-17, (Dec. 9-13, 2014).
Rajagopalan, S, et al., "CD20-specific Engineered Toxin Body demonstrates direct cell kill of multiple B-cell Non-Hodgkin's lymphoma types", The Journal of Cancer Research, 74(19 Suppl): Abstract # 647, (Oct. 1, 2014); Proceedings: AACR Annual Meeting 2014; Apr. 5-9, 2014.
Rajagopalan, S, et al., "CD38-specific engineered toxin body: Therapeutic potential for multiple myeloma", The Journal of Cancer Research, 74(19 Suppl): Abstract #671, (Oct. 1, 2014) from American Association for Cancer Research (AACR) Annual Meeting 2014, (Apr. 5-9, 2014).
Carbonetti, NH, et al., "Stimulation of HIV gp120-specific cytolytic T lymphocyte responses in vitro and in vivo using a detoxified pertussis toxin vector", AIDS Research and Human Retroviruses, 17(9), (2001), 819-827.
Casalini et al., "Use of combination of Monoclonal Antibodies Directed Against three distinct epitopes of a Tumor-Associated Antigen: Analysis of Cell-Binding and Internalization", International Journal of Cancer, 48:2 284-290 (1991).
Cizeau, J, et al., "Fusogenics: A Recombinant Immunotoxin-Based Screening Platform to Select Internalizing Tumor-Specific Antibody Fragments", Journal of Biomolecular Screening 16(1), (2011), 90-100.
Cizeau, JPA, et al., "DeBouganin: A de-immunized toxin payload and its applications in oncology", 8th Fabisch-Symposium, 3rd Targeted Tumor Therapies, Berlin 2012, Mar. 21, 2012.
Cleton-Jansen et al., "A Single Amino Acid Substitution Changes the Substrate Specificity of Quinoprotein Glucose Dehydrogenase in Gluconobacter oxydans", Molecular and General Genetics, 229(2): 206-212 (1991).
Cragg et al., "Apparent modulation of CD20 by rituximab: an alternative explanation", Blood 103(10) 3889-3990 (2004).

(56) References Cited

OTHER PUBLICATIONS

Cuesta et al., "Mutivalent antibodies: when design surpasses evolution", Trends in Biotechnology, 28(7): 355-362 (2010).
Dadaglio, G, et al., "Induction of a Polarized Th1 Response by Insertion of Multiple Copies of a Viral T-Cell Epitope into Adenylate Cyclase of Bordetella pertussis", Infection and Immunity, 68(7), (2000), 3867-3872.
Dadaglio, G, et al., "Recombinant adenylate cyclase toxin of Bordetella pertussis induces cytotoxic T lymphocyte responses against HLA*0201-restricted melanoma epitopes", International Immunology, 15(12), (2003), 1423-1430.
Dekker et al., "Engineered Toxin Bodies delivering immunogenic MHC class I peptides to tumor cells summon polyfunctional and relevant CTL responses against cancers", Presented at: Immunology 2019™, Annual Meeting of the American Association of Immunologists, May 10, 2019, The American Association of Immunologists, Inc., San Diego, Abstract 1791.
Deresiewicz et al., "Identification of amino acids critical for the cytotoxicity of Shiga Toxin I A-chain", Biochemistry 31(12) 3272-3280 (1992).
Dermer, GB, "Another Anniversary for the War on Cancer", Bio/Technology 12, (1994), 320.
Doling, AM, et al., "Cytotoxic T-Lymphocyte Epitopes Fused to Anthrax Toxin Induce Protective Antiviral Immunity", Infection and Immunity, 67(7), (1999), 3290-3296.
Donnelly, JJ, et al., "Targeted delivery of peptide epitopes to class I major histocompatibility molecules by a modified Pseudomonas exotoxin", Proceedings of the National Academy of Sciences U.S. A., 90, (1993), 3530-3534.
Engedal, N, et al., "Shiga toxin and its use in targeted cancer therapy and imaging", Microbial Biotechnology, 4(1), (2011), 32-46.
Eriksson, K, et al., "Coupling of antigen to cholera toxin for dendritic cell vaccination promotes the induction of MHC class I-restricted cytotoxic T cells and the rejection of a cognate antigen-expressing model tumor", European Journal of Immunology, 34(5), (2004), 1272-1281.
Ewers et al., "Lipid-Mediated Endocytosis", Cold Spring Harbor Perspectives in Biology 3(8) 1-14 (2011).
Fanale, MA, et al., "Phase I/Ib study of the novel CD20-targeted immunotoxin MT-3724 in relapsed/refractory non-Hodgkin's B-cell lymphoma", Proceedings of the 107th Annual Meeting of the American Association for Cancer Research (AACR), Poster, Abstract # CT049, (Apr. 16-20, 2016).
Fanale, MA, et al., "Phase I/Ib study of the novel CD20-targeted immunotoxin MT-3724 in relapsed/refractory non Hodgkin's B-cell lymphoma", Cancer Research, 76(14 Suppl), (Jul. 2016), Abstract #CT049.
Fayolle, C, et al., "Delivery of Multiple Epitopes by Recombinant Detoxified Adenylate Cyclase of Bordetella pertussis Induces Protective Antiviral Immunity", Journal of Virology, 75(16), (2001), 7330-7338.
Fayolle, C, et al., "Therapy of Murine Tumors with Recombinant Bordetella pertussis Adenylate Cyclase Carrying a Cytotoxic T Cell Epitope", The Journal of Immunology, 162(7), (1999), 4157-4162.
Filpula, D, "Releasable PEGylation of Mesothelin Targeted Immunotoxin SSIP Achieves Single Dosage Complete Regression of a Human Carcinoma in Mice", Bioconjugate Chemistry, 18(3): 773-784 (2007).
Freshney, RI, "Culture of Animal Cells: A Manual of Basic Technique", Alan R. Liss, Inc., 1983, New York, pp. 3-4.
Garred et al., "Furin-induced cleavage and activation of Shiga toxin", Journal of Biological Chemistry, 270(18), (1995), 10817-10821.
Gavrilov et al., "Effects of Glycosylation on Antigenicity and Immunogenicity of Classical Swine Fever Virus Envelope Proteins", Virology, 420(2):135-145 (2011).
Gendler et al., "A Highly Immunogenic Region of a Human Polymorphic Epithelial Mucin Expressed by Carcinomas Is Made Up of Tandem Repeats", Journal of Biological Chemistry, 263(26): 12820-12823 (1988).
Ghetie et al., "Homodimers but not monomers of Rituxan (chimeric anti-CD20) induce apoptosis in human B-lymphoma cells and synergize with a chemotherapeutic agent and an immunotoxin", Blood 97(5) 1392-1398 (2001).
Gilliland, DG, et al., "Antibody-directed cytotoxic agents: use of monoclonal antibody to direct the action of toxin A chains to colorectal carcinoma cells", Proceedings of the National Academy of Sciences of the United States of America, 77(8), (1980), 4539-43.
Glennie et al., "Mechanisms of killing by anti-CD20 monoclonal antibodies", Molecular Immunology 44(16) 3823-3837 (2007).
Gong, J, et al., "Selection and characterization of MUC1-specific CD8+ T cells from MUC1 transgenic mice immunized with dendritic-carcinoma fusion cells", Immunology, 101(3), (2000), 316-324.
Gordon et al., "An enzymatic mutant of Shiga-like toxin II variant is a vaccine candidate for edema disease of swine", Infection and Immunity 60(2): 485-490 (1992).
Goulet et al. ,"Conjugation of Blocked Ricin to an Anti-CD19 Monoclonal Antibody Increases Antibody-Induced cell Calcium Mobilization and CD19 Internalization", Blood 90(6) 2364-2375 (1995).
Grant, K, et al., "Abstract 1380: Engineered toxin bodies with specific activity against EGFR and HER2 expressing cells" Proceedings of the 102nd Annual Meeting of the American Association for Cancer Research (AACR); Apr. 2-6, 2011; The Journal of Cancer Research, 71 (8 Suppl): Abstract #1380, (Apr. 2011).
Guermonprez, P, et al., "Les Toxines Bacteriennes Recombinantes: De Nouveaux Vecteurs Pour La Vaccination?", M/S Medecine Sciences, Societe Des Periodiques Flammarion, 16(5), (2000), 653-662.
Guermonprez, P, et al., "The Adenylate Cyclase Toxin of Bordetella pertussis Binds to Target Cells via the $\alpha M\beta 2$ Integrin (CD11b/CD18)", Journal of Experimental Medicine, 193(9), (2001), 1035-1044.
Güssow, D, Seemann, G, "Humanization of Monoclonal Antibodies", Methods in Enzymology, 203, (1991), 99-121.
Haicheur, N, et al., "The B Subunit of Shiga Toxin Fused to a Tumor Antigen Elicits CTL and Targets Dendritic Cells to Allow MHC Class I-Restricted Presentation of Peptides Derived from Exogenous Antigens", The Journal of Immunology, 165(6), (2000), 3301-3308.
Haisma et al., "Construction and Characterization of a Fusion Protein Single-Chain Anti-CD20 Antibody and Human beta-glucuronidase for Antibody-Directed Enzyme Prodrug Therapy", Blood 92:1 184-190 (1998).
Hamlin et al., "Safety and Efficacy of Anti-CD20 Immunotoxin MT-3724 in Relapsed/refractory B-cell Non-Hodgkin Lymphoma (NHL) in a Phase 1 study", American Society of Clinical Oncology Annual Meeting—Abstract 7580 (2018).
Harris "Exploiting antibody-based technologies to manage environmental pollution", Trends in Biotechnology, Diagram figure taken from 17(7): 290-296 (1999).
Head et al., Preparation of VT 1 and VT2 Hybrid Toxins from Their Purified Dissociated Subunits. Evidence for B Subunit Modulation of a Subunit Function, Journal of Biological Chemistry, 266(6): 3617-3621 (1991).
Hexham et al., "Influence of relative binding affinity on efficacy in a panel of anti-CD3 scFc immunotoxins", Molecular Immunology 38(5) 397-408 (2001).
Higgins, JP, et al., "Engineered toxin bodies with specific cell kill activity against mesenchymal cells", Cancer Research, 71(8 Suppl), (Apr. 2011), Abstract #1751.
Hiraga et al., "Down-regulation of CD20 expression in B-cell lymphoma cells after treatment with rituximab-containing combination chemotherapies: its prevalence and clinical significance", Blood 113 (20): 4885-4893 (2009).
Holubova, J, et al., "Delivery of Large Heterologous Polypeptides across the Cytoplasmic Membrane of Antigen-Presenting Cells by the Bordetella RTX Hemolysin Moiety Lacking the Adenylyl Cyclase Domain", Infection and Immunity, 80(3), (2012), 1181-1192.
Hooijberg et al., "Characterization of a series of isotype switch variants of new CD20 monoclonal antibody", Hybridoma 15(1) 23-31 (1996).

(56) References Cited

OTHER PUBLICATIONS

Hotz et al., "Specific Targeting of Tumor Endothelial Cells by a Shiga-like Toxin-Vascular Endothelial Growth Factor Fusion Protein as a Novel Treatment Strategy for Pancreatic Cancer" Neoplasia 12(10) 797-806 (2010).
Hovde et al., "Evidence that glutamic acid 167 is an active-site residue of Shiga-like toxin-I," Proceedings of the National Academy of Sciences of the United States of America, 85(8) 2568-2572 (1988).
Huang, S, et al., "The CD20-specific engineered toxin antibody MT-3724 exhibits lethal effects against mantle cell lymphoma", Blood Cancer Journal, 8(3), (2018), 33.
Huang et al. "Abstract 3651: Preclinical examination of the effects of MT-3724, an engineered toxin body targeting CD20, in mantle cell lymphoma" AACR Annual Meeting Abstract (2017).
Huang et al. "AACR 2017 | Poster 3651/24—Preclinical examination of the effects of a CD20-specific engineered toxin body, MT-3724, in Mantle Cell Lymphoma" AACR Annual Meeting, Poster 3651/24 (2017).
Iberg, A, et al., "Design and Characterization of Bispecific Engineered Toxin Bodies for Targeted Cancer Therapy", Proceedings: American Association for Cancer Research (AACR) Annual Meeting 2019, Poster #2984, (2019).
International Application Serial No. PCT/US2014/023198, International Search Report dated Sep. 18, 2014 and published Oct. 9, 2014, 5 pgs.
International Application Serial No. PCT/US2014/023198, Written Opinion dated Feb. 12, 2015, 7 pgs.
International Application Serial No. PCT/US2014/023198, Preliminary Report on Patentability dated Jan. 9, 2015 and dated Jul. 15, 2015, 8 pgs.
International Application Serial No. PCT/US2014/023231, International Search Report dated Oct. 24, 2014 and published Dec. 4, 2014, 4 pgs.
International Application Serial No. PCT/US2014/023231, Written Opinion dated Oct. 24, 2014, 6 pgs.
International Application Serial No. PCT/US2014/023231, Preliminary Report on Patentability, dated Sep. 15, 2015, 7 pgs.
International Application Serial No. PCT/US2015/012968, International Search Report dated Jul. 13, 2015 and published Jul. 30, 2015, 8 pgs.
International Application Serial No. PCT/US2015/012968, Written Opinion dated Jan. 11, 2016, 15 pgs.
International Application Serial No. PCT/US2015/012968, Preliminary Report on Patentability, dated Apr. 20, 2016 10 pgs.
International Application Serial No. PCT/US2015/012970, International Search Report dated Jun. 26, 2015 and published Jul. 30, 2015, 5 pgs.
International Application Serial No. PCT/US2015/012970, Written Opinion dated Jun. 26, 2015, 7 pgs.
International Application Serial No. PCT/US2015/012970, Preliminary Report on Patentability, dated Nov. 24, 2015 and dated Apr. 20, 2016, 10 pgs.
International Application Serial No. PCT/US2015/019684, International Search Report dated Jun. 29, 2015 and published Jul. 30, 2015, 6 pgs.
International Application Serial No. PCT/US2015/019684, Written Opinion dated Jun. 29, 2015, 8 pgs.
International Application Serial No. PCT/US2015/019708, International Search Report dated Jun. 29, 2015 and published Sep. 17, 2015, 5 pgs.
International Application Serial No. PCT/US2015/019708, Written Opinion, dated Jan. 2015, 8 pgs.
International Application Serial No. PCT/US2015/019708, Preliminary Report on Patentability, dated Sep. 13, 2016, 9 pgs.
International Application Serial No. PCT/US2015/035179, International Search Report dated Sep. 9, 2015 and published Dec. 17, 2015, 5 pgs.
International Application Serial No. PCT/US2015/035179, Written Opinion dated Sep. 9, 2015, 10 pgs.
International Application Serial No. PCT/US2015/035179, Written Opinion dated May 18, 2016, 9 pgs.
International Application Serial No. PCT/US2015/035179, Preliminary Report on Patentability dated Aug. 12, 2016, 8 pgs.
International Application Serial No. PCT/US2016/016580, International Search Report dated Apr. 22, 2016 and published Aug. 11, 2016, 4 pgs.
International Application Serial No. PCT/US2016/016580, Written Opinion, dated Apr. 22, 2016 dated Mar. 28, 2016, 5 pgs.
International Application Serial No. PCT/US2016/043902, International Search Report dated Jan. 30, 2017 and published Mar. 9, 2017, 6 pgs.
International Application Serial No. PCT/US2016/043902, Written Opinion dated Jan. 30, 2017, 9 pgs.
International Application Serial No. PCT/US2016/043902, Preliminary Report on Patentability dated Oct. 10, 2017, 7 pgs.
Ishikawa et al., "Protection against Shiga Toxin I Challenge by Immunization of Mice with Purified Mutant Shiga Toxin 1.", Infection and Immunity 71(6) 3235-3239 (2003).
Jackson et al., "Mutational analysis of the Shiga Toxin and Shiga-like toxin II enzymatic subunits", Journal of Bacteriology 172(6) 3346-3350 (1990).
Jackson, ME, et al., "The KDEL retrieval system is exploited by Pseudomonas exotoxin A, but not by Shiga-like toxin-1, during retrograde transport from the Golgi complex to the endoplasmic reticulum", Journal of Cell Science, 112(4), (1999), 467-475.
Jain, RK, "Barriers to Drug Delivery in Solid Tumors", Scientific American 271(1), (1994), 58-65.
Jilani et al., "Anti-Idiotype versus anti-mouse Ig for detecting ritumixab", Blood 103(10): 3990 (2004).
Jilani et al., "Transient down-modulation of CD20 by ritumixab in patients with chronic lymphocytic leukemia", Blood 102(10) 3514-3520 (2003).
Johannes et al., "Shiga toxins—from cell biology to biomedical applications" Nature Reviews Microbiology 8(2) 105-116 (2010).
Johannes, L, Decaudin, D, "Protein toxins: intracellular trafficking for targeted therapy" Gene Therapy, 12(18), (2005), 1360-1368.
Johannes, L, et al., "Retrograde Transport of KDEL-bearing B-fragment of Shiga Toxin", Journal of Biological Chemistry, 272(31), (1997), 19554-19561.
Johnson, N, et al., "Construction of an epitope vector utilizing the diphtheria toxin B-subunit", FEMS Microbiology Letters, 146(1), (1997), 91-96.
Jones "Critically Assessing the State-of-the-art in Protein Structure Prediction", The Pharmacogenomics Journal, 1(2): 126-134 (2001).
Jubala et al., "CD20 Expression in Normal Canine B cells and in Canine non-Hodgkin Lymphoma", Veterinary Pathology 42:4 468-476 (2005).
Karanikas et al., "Antibody and T Cell Responses of Patients with Adenocarcinoma Immunized with Mannan-MUC1 Fusion Protein", Journal of Clinical Investigation, 100(11): 2783-2792 (1997).
Kelland, LR, "'Of mice and men': values and liabilities of the athymic nude mouse model in anticancer drug development", European Journal of Cancer 40(6), (2004), 827-836.
Kim et al., "A fold-back single chain diabody format enhances the bioactivity of an anti-monkey CD3 recombinant diphtheria toxin-based immunotoxin", Protein Engineering 20(9) 425-432 (2007).
Kotera et al., "Humoral Immunity against a Tandem Repeat Epitope of Human Mucin MUC-1 in Sera from Breast, Pancreatic, and Colon Cancer Patients", Cancer Research 54(11): 2856-2860 (1994).
Lambert et al., "Purified Immunotoxins that are reactive with Human Lymphoid Cells: Monoclonal antibodies conjugated to the ribosome-inactivating proteins gelonin and the pokeweed antiviral proteins", Journal of Biological Chemistry 260(22) 12035-12041 (1985).
Laske et al., "Intraventricular Immunotoxin Therapy for Leptomeningeal Neoplasia", Neurosurgery, 41(5): 1039-1051 (1997).
Law et al., "Efficient Elimination of B-Lineage Lymphomas by Anti-CD20-Auristatin Conjugates", Clinical Cancer Research 10(23) 7842-7851 (2004).
Lazar et al., "Transforming Growth Factor alpha: Mutation of Aspartic Acid 47 and Leucine 48 Results in Different Biological Activities", Molecular and Cellular Biology, 8(3): 1247-1252 (1988).

(56) References Cited

OTHER PUBLICATIONS

Lea et al., "Proteolytic cleavage of the A subunit is essential for maximal cytotoxicity of *Escherichia coli* O157:h7 Shiga-like toxin-1", Microbiology 145(5): 999-1004 (1999).
Lee, RS, et al., "Major histocompatibility complex class I presentation of exogenous soluble tumor antigen fused to the B-fragment of Shiga toxin", European Journal of Immunology, 28, (1998), 2726-2737.
Wirth, R, et al., "Engineered Toxin Body demonstrating CD20-specific binding and cell kill in B-Cell Non-Hodgkin lymphoma cells", [abstract]. In: Proceedings of the 104th Annual Meeting of the American Association for Cancer Research, Cancer Research, Apr. 15, 2013, 73(8 Suppl), Abstract #5477.
Wirth, R, et al., "Engineered Toxin Body demonstrating CD20-specific binding and cell kill in B-Cell Non-Hodgkin lymphoma cells", Proceedings: American Association for Cancer Research (AACR) 104th Annual Meeting 2013, Poster, Abstract #5477, (Apr. 6-10, 2013).
Wu et al., "Humanization of a murine monoclonal antibody by simultaneous optimization of framework and CDR residues", J. Mol. Biol. 294: 151-162 (1999).
Wu et al., "Multimerization of a chimeric anti-CD20 single chain Fv-Fc fusion protein is mediated through variable domain exchange", Protein Engineering 14(12):1025-1033 (2001).
Yamasaki et al., "Importance of arginine at position 170 of the A subunit of Vero toxin 1 produced by enterohemorrahagic *Escherichia coli* for toxin activity" Microbial Pathogenesis 11(1) (1991).
Yu et al., "Interaction between Bevacizumab and Murine VEGF-A: A Reassessment", Investigative Ophthamology & Visual Science 49(2) 522-527 (2008).
Zacny et al., "Novel toxin library for the discovery of oncology therapeutics", Cancer Research, (Apr. 2010), 70(8 Suppl), Abstract #5506.
Zapata, G, et al., "Engineering linear F(ab')2 fragments for efficient production in *Escherichia coli* and enhanced antiproliferative activity", Protein Engineering, 8(10), (1995), 1057-1062.
Stepanov et al., "Design of Targeted B Cell Killing Agents", PloS One 6(6) e20991 (2011).
U.S. Appl. No. 14/643,619, Office Action dated Jun. 27, 2018, 48 pgs.
U.S. Appl. No. 14/774,130, Office Action dated Feb. 27, 2017, 19 pgs.
U.S. Appl. No. 14/774,130, Office Action dated Aug. 24, 2017, 20 pgs.
U.S. Appl. No. 14/774,130, Office Action dated Oct. 25, 2016, 5 pgs.
U.S. Appl. No. 14/965,882, Office Action dated Mar. 22, 2018, 12 pgs.
U.S. Appl. No. 14/965,882, Office Action dated Jun. 6, 2017, 19 pgs.
U.S. Appl. No. 15/114,474, Office Action dated Jun. 18, 2018, 20 pgs.
U.S. Appl. No. 15/114,474, Office Action dated Aug. 24, 2017, 11 pgs.
U.S. Appl. No. 15/114,474, Office Action dated Oct. 26, 2017, 24 pgs.
U.S. Appl. No. 15/125,126 Office Action dated Dec. 5, 2018, 20 pgs.
U.S. Appl. No. 15/290,266, Office Action dated Jun. 27, 2018, 32 pgs.
U.S. Appl. No. 15/317,892, Office Action dated Mar. 5, 2018, 22 pgs.
U.S. Appl. No. 15/421,758, Office Action dated Apr. 17, 2017, 22 pgs.
Lee et al., "Molecular mechanism of PD-1/PD-L1 blockade via anti-PD-L1 antibodies atezolizumab and durvalumab", Scientific Reports 7(1):5532 (2017).
Rudikoff et al. "Single amino acid substitution altering antigen-binding specificity." Proceedings of the National Academy of Sciences 79(6): 1979-1983 (1982).
Pascalis et al., "Grafting of "abbreviated" complementarity-determining regions containing specificity-determining residues essential for ligand contact to engineer a less immunogenic humanized monoclonal antibody." The Journal of Immunology 169(6): 3076-3084 (2002).
Casset et al., "A peptide mimetic of an anti-CD4 monoclonal antibody by rational design." Biochemical and Biophysical Research Communications 307(1): 198-205 (2003).
Lee et al., "Phylogenetic analysis of Shiga toxin 1 and Shiga toxin 2 genes associated with disease outbreaks." BMC Microbiology 7(1): 109 (2007).
Cao et al. "Construction and characterization of novel, recombinant immunotoxins targeting the Her2/neu oncogene product: in vitro and in vivo studies." Cancer Research 69(23): 8987-8995 (2009).
UniProtKB/Swiss-Prot P09385 (STXA_BP933), Shiga-like toxin 2 subunit A, retrieved from https://www.ncbi.nlm.nih.gov/protein/P09385.2 on Jan. 10, 2018.
Weinstein et al., "In Vivo Formation of Hybrid Toxins Comprising Shiga Toxin and the Shiga-Like Toxins and Role of the B Subunit in Localization and Cytotoxic Activity", Infection and Immunity, 57(12): 3743-3750 (1989).
Weldon et al. "A guide to Taming a Toxin: Recombinant Immunotoxins Constructed from Pseudomonas Exotoxin A for the Treatment of Cancer", FEBS Journal, 278(23): 4683-4700 (2011).
EP Application No. 182078113.1 Extended European Search Report dated Jun. 17, 2019, 10 pgs.
IL Application No. 240433 Office Action Translation dated May 30, 2019, 2 pgs.
IL Application No. 246701 Office Action Translation dated May 16, 2019, 5 pgs.
IL Application No. 247298 Office Action Translation dated May 21, 2019, 4 pgs.
IL Application No. 246632 Office Action Translation dated May 16, 2019, 5 pgs.
Boes et al., "Affinity Purification of a Framework 1 Engineered Mouse/Human Chimeric IgA2 Antibody From Tobacco", Biotechnology Bioengineering, 108(12): 2804-2814 (2011).
Lakhrif et al., "A method to confer protein L binding ability to any antibody fragment" MAbs, 8(2): 379-388 (2016).
Zahid et al., "Design and reshaping of an scFv directed against human platelet glycoprotein VI with diagnostic potential", Analytical Biochemistry, 417(2): 274-282 (2011).
U.S. Appl. No. 15/114,474, filed Jul. 27, 2016, pending, Molecular Templates, Inc.
U.S. Appl. No. 15/114,487, filed Jul. 27, 2016, pending, Molecular Templates, Inc.
U.S. Appl. No. 15/114,174, filed Aug. 5, 2016, pending, Molecular Templates, Inc.
U.S. Appl. No. 15/125,126, filed Sep. 9, 2016, pending, Molecular Templates, Inc.
U.S. Appl. No. 15/125,142, filed Sep. 9, 2016, pending, Molecular Templates, Inc.

\* cited by examiner

Figure 1. Schematic Drawing of the General Architecture of Exemplary, Shiga Toxin A Subunit Effector Polypeptides and Cell-Targeting Molecules of the Present Invention Figure 2. The Exemplary Cell-Targeted Molecule SLT-1A-FR::scFv-1 Exhibited
Resistance to Furin Proteolysis as Compared to SLT-1A-WT::scFv-1

L = molecular weight ladder
1. SLT-1A-WT::scFv1: 4°C, 25 hrs, no furin
2. SLT-1A-WT::scFv1: 30°C, 25 hrs, no furin
3. SLT-1A-WT::scFv1: 30°C, 25 hrs, 0.5 U/μg furin
4. SLT-1A-FR::scFv1: 4°C, 25 hrs, no furin
5. SLT-1A-FR::scFv1: 30°C, 25 hrs, no furin
6. SLT-1A-FR::scFv1: 30°C, 25 hrs, 0.5 U/μg furin Figure 3. The Exemplary Cell-Targeted Molecule SLT-1A-FR::scFv-2 Exhibited Resistance to Furin Proteolysis at Various Temperatures L = molecular weight ladder
1. SLT-1A-FR::scFv2: 4°C, 30 hrs, no furin
2. SLT-1A-FR::scFv2: 4°C, 30 hrs, 0.5 U/µg furin
3. SLT-1A-FR::scFv2: 30°C, 30 hrs, no furin
4. SLT-1A-FR::scFv2: 30°C, 30 hrs, 0.5 U/µg furin
5. SLT-1A-FR::scFv2: 37°C, 30 hrs, no furin
6. SLT-1A-FR::scFv2: 37°C, 30 hrs, 0.5 U/µg furin Figure 4. Specific Cytotoxicity of SLT-1A-FR::scFv-1 and SLT-1A-WT::scFv-1 to Target Positive Cells Figure 5. Lack of Specific Cytotoxicity of SLT-1A-FR::scFv-1 and SLT-1A-WT::scFv-1 to Target Negative Cells Figure 6. Improvement in *In Vivo* Tolerability of SLT-A1-FR::scFv-1 as Compared to SLT-A1-WT::scFv-1: The protease-cleavage resistant SLT-1A-FR::scFv-1 was better tolerated than the protease-cleavage sensitive SLT-1A-WT::scFv-1 at dosages of 2.5 mg per kg per injection for three injections Figure 7. SLT-1A-FR::scFv-2 Inhibited the Growth of Human Tumor Cells *In Vivo* in a Murine Xenograft Model for Human Cancer

CELL-TARGETING MOLECULES COMPRISING PROTEASE-CLEAVAGE RESISTANT, SHIGA TOXIN A SUBUNIT EFFECTOR POLYPEPTIDES AND CARBOXY-TERMINAL MOIETIES

SEQUENCE LISTING

The instant application contains a Sequence Listing which has been submitted electronically in ASCII format and is hereby incorporated by reference in its entirety. Said ASCII copy, created on Jul. 16, 2015, is named 14-07PCT_SL.txt and is 188,629 bytes in size.

FIELD OF THE INVENTION

The present invention relates to Shiga toxin effector polypeptides derived from A Subunits of naturally occurring Shiga toxins and cell-targeted molecules comprising the same, wherein there is a disrupted furin-cleavage site near the carboxy terminus of a Shiga toxin A1 fragment derived region, and, optionally, a molecular moiety associated carboxy-terminal to the Shiga toxin A1 fragment derived region. The Shiga toxin effector polypeptides described herein are beneficial as components of cell-targeted molecules, e.g. therapeutics and/or diagnostics. For example, the Shiga toxin effector polypeptides described herein may be used as components of cytotoxic, cell-targeted molecules, e.g. immunotoxins and ligand-toxin fusions, for use in the targeted killing of specific cell types. Molecules of the present invention may have reduced non-specific toxicity after administration to an organism but without any apparent effect on specifically targeted cytotoxicity. In addition, molecules of the present invention may have improved stability during production, storage, and administration. Certain molecules of the present invention comprise binding regions for mediating cell targeting and catalytically active, Shiga toxin effector polypeptides for effectuating cytotoxicity. Molecules of the present invention have uses, e.g., as components of therapeutics and diagnostics for the diagnosis, prognosis, and treatment of a variety of diseases, disorders and conditions, including cancers, tumors, immune disorders, and microbial infections.

BACKGROUND

Shiga toxins have been engineered for use in therapeutic applications by rational alterations to the toxin's structure, characteristics, and biological activities (see, e.g. patents U.S. Pat. No. 7,713,915, EP1051482, EP1727827, EP1945660; and patent applications: US2009/0156417 A1, EP2228383 B1, EP2402367 A1, US2013/0196928 A1, WO 2014/164680, WO 2014/164693, WO 2015/113005, WO 2015/113007, WO 2015/120058, WO 2015/138435, and WO 2015/138452, the disclosures of each of which is incorporated by reference herein in its entirety). Shiga toxins and components thereof may be used to engineer therapeutic molecules, such as, e.g. immunotoxins and ligand-toxin fusions which exploit the combination of the high cytotoxicity of Shiga toxins with high-affinity target binding for precise targeting in vivo. In particular, the catalytic A Subunits of Shiga toxins are stable, enzymatically active, and cytotoxic even if truncated or fused to other protein domains (Haddad J et al., *J Bacteriol* 175: 4970-8 (1993); Backer M et al., *J Control Release* 74: 349-55 (2001); Backer M, Backer J, *Bioconjug Chem* 12: 1066-73 (2001); LaPointe P et al., *J Biol Chem* 280: 23310-18 (2005); Di R et al., *Toxicon* 57: 525-39 (2011)). When designing synthetic molecules comprising Shiga toxin A Subunit polypeptides, the natural mechanism of Shiga toxin intoxication may be an important consideration.

Numerous bacterial toxins depend on site-specific processing by host-cell, intracellular proteases for optimal cytotoxicity, such as, e.g., for toxin activation and/or subcellular routing (see e.g. Thomas G, *Nat Rev Mol Cell Biol* 3: 753-66 (2002)). Shiga toxins employ site-specific cleavage for both toxin activation and subcellular routing. Shiga toxin activity is increased by proteolytic cleavage (Brown J et al., *FEBS Lett* 117: 84-8 (1980); Reisbig R et al., *J Biol Chem* 256: 8739-44 (1981)). Shiga toxins require the intracellular cleavage of their A Subunits by the endoprotease furin in intoxicated cells for the most efficient killing of intoxicated cells (Garred Ø et al., *Exp Cell Res* 218: 39-49 (1995); Garred Ø et al., *J Biol Chem* 270: 10817-21 (1995); Lea N et al., *Microbiology* 145: 999-1004 (1999); Kurmanova A et al., *Biochem Biophys Res Commun* 357: 144-9 (2007)). This proteolytic processing must be accounted for in the design of molecules comprising Shiga toxin A Subunit derived components to supply the most efficient toxin activation and/or subcellular routing required for maximal, Shiga toxin cytotoxicity (see Garred Ø et al., *Exp Cell Res* 218: 39-49 (1995); Lea N et al., *Microbiology* 145: 999-1004 (1999); Kurmanova A et al., *Biochem Biophys Res Commun* 357: 144-9 (2007)).

The Shiga toxin family of related protein toxins, notably toxins isolated from *S. dysenteriae* and *E. coli*, is composed of various naturally occurring toxins which are structurally and functionally related (Johannes L, Römer W, *Nat Rev Microbiol* 8: 105-16 (2010)). Members of the Shiga toxin family share the same overall structure and mechanism of action (Engedal, N et al., *Microbial Biotech* 4: 32-46 (2011)). Members of the Shiga toxin family are employed by bacteria as virulence factors during infection of a host (Johannes L, Römer W, *Nat Rev Microbiol* 8: 105-16 (2010)). In infected hosts, Shiga toxins are cytotoxic because of the toxins' potent abilities to inhibit protein synthesis and to trigger apoptotic cell death (Johannes L, Römer W, *Nat Rev Microbiol* 8: 105-16 (2010)). The potent cytotoxic effects of Shiga toxins on host cells can result in hemorrhagic colitis and hemolytic uremic syndrome in humans (Johannes L, Römer W, *Nat Rev Microbiol* 8: 105-16 (2010)).

Members of the Shiga toxin family share a common, multimeric, protein structure characterized by an $A(B)_5$ arrangement of Shiga protein subunits (Johannes L, Römer W, *Nat Rev Microbiol* 8: 105-16 (2010)). Each Shiga toxin is composed of two protein subunits, A and B, that associate in an $A(B)_5$ arrangement to form a holotoxin protein complex. The Shiga toxin A Subunit is an approximately 32-33 kiloDaltons (kDa) monomer that contains an enzymatic domain, and the Shiga toxin B Subunit is an approximately 7.6-7.7 kDa subunit that associates with four other Shiga toxin B Subunits to form an approximately 38.1-38.5 kDa pentamer of Shiga toxin B Subunits. The pentamer of B subunits associates with one A subunit to form the Shiga holotoxin, which is about 70-72 kDa (O'Brien A, Holmes, R, *Microbiol Rev* 51: 206-20 (1987)). Overall, the Shiga toxin A Subunit forms a single globular protein with a helix that extends into the B subunit pentamer within the holotoxin (Fraser M et al., *Acta Crystallogr Sect F Struct Biol Cryst Commun* 62: 627-30 (2006)).

Efficient cell killing by Shiga toxins requires the intracellular cleavage of the Shiga toxin A Subunit in a conserved, surface-exposed, extended loop, structure by the endoprotease furin (Garred Ø et al., *Exp Cell Res* 218: 39-49 (1995); Garred Ø et al., *J Biol Chem* 270: 10817-21 (1995); Lea N et al., *Microbiology* 145: 999-1004 (1999); Kurmanova A et al., *Biochem Biophys Res Commun* 357: 144-9 (2007)). The amino-terminal fragment of the furin-cleaved, Shiga-toxin A Subunit is called the Shiga toxin "A1 fragment" (or Stxn-A1, SLTn-A1, SLT-nA1), and the carboxy-terminal fragment of the A Subunit is called the Shiga toxin "A2 fragment." The Shiga toxin A1 fragment is an approximately 27.5 kDa polypeptide which contains the catalytic domain of the Shiga toxin (Fraser M et al., *Nat Struct Biol* 1: 59-64 (1994)).

Only the Shiga toxin A1 fragment localizes to the cytosol in intoxicated cells as the Shiga toxin A2 fragment and B Subunits remain in the endoplasmic reticulum (Tam P, Lingwood C, *Microbiology* 153: 2700-10 (2007)). The proteolytic cleavage of Shiga toxin A Subunits at this conserved, extended loop structure contributes to the liberation of the catalytic A1 fragment and the subcellular routing of the A1 fragment to the cytosol (Johannes L, Römer W, *Nat Rev Microbiol* 8: 105-16 (2010)). The Shiga toxin A2 fragment is an approximately 4.5-4.7 kDa polypeptide that is superfluous for catalytic activity (Haddad J et al., *J Bacteriol* 175: 4970-8 (1993); Backer M et al., *J Control Release* 74: 349-55 (2001); Backer M, Backer J, *Bioconjug Chem* 12: 1066-73 (2001); LaPointe P et al., *J Biol Chem* 280: 23310-18 (2005); Di R et al., *Toxicon* 57: 525-39 (2011)).

Furin is a specialized serine endoprotease which is expressed by a wide variety of cell types, in all human tissues examined, and by most animal cells (see Shiryaev S et al., *J Biol Chem* 282: 20847-53 (2007)). Furin cleaves polypeptides comprising accessible motifs often centered on the minimal, dibasic, consensus motif R-x-(R/K/x)-R (Thomas G, *Nat Rev Mol Cell Biol* 3: 735-66 (2002); Tian S, *Biochem Insights* 2: 9-20 (2009)). The A Subunits of members of the Shiga toxin family comprise a conserved, surface-exposed, extended loop structure (e.g. 242-261 in StxA and SLT-1A, and 241-260 in SLT-2) with a conserved S-R/Y-x-x-R motif which is cleaved by furin (Garred Ø et al., *Exp Cell Res* 218: 39-49 (1995); Garred Ø et al., *J Biol Chem* 270: 10817-21 (1995); Kurmanova A et al., *Biochem Biophys Res Commun* 357: 144-9 (2007); Faqerquist C, Sultan O, *J Biomed Biotechnol* 2010: 123460 (2010)). The surface exposed, extended loop structure positioned at amino acid residues 242-261 in StxA is required for furin-induced cleavage of StxA, including features flanking the minimal, furin-cleavage motif R-x-x-R (Kurmanova A et al., *Biochem Biophys Res Commun* 357: 144-9 (2007)).

During Shiga toxin intoxication, the A Subunit is proteolytically cleaved by furin at the carboxy bond of a conserved arginine residue (e.g. the arginine residue at position 251 in StxA and SLT-1A and the arginine residue at position 250 in Stx2A and SLT-2A) (Garred Ø et al., *Exp Cell Res* 218: 39-49 (1995); Garred Ø et al., *J Biol Chem* 270: 10817-21 (1995); Faqerquist C, Sultan O, *J Biomed Biotechnol* 2010: 123460 (2010)). Furin cleavage of Shiga toxin A Subunits occurs in endosomal and/or Golgi compartments (Garred Ø et al., *J Biol Chem* 270: 10817-21 (1995); Kurmanova A et al., *Biochem Biophys Res Commun* 357: 144-9 (2007)).

The dissociation of the Shiga toxin A1 fragment from the A2 fragment is required for activation of the catalytic domain of the A1 fragment (Garred Ø et al., *Exp Cell Res* 218: 39-49 (1995); Garred Ø et al., *J Blot Chem* 270: 10817-21 (1995); Kurmanova A et al., *Biochem Biophys Res Commun* 357: 144-9 (2007)). The catalytic domains of Shiga toxins are inactiv before furin cleavage possibly because the A2 portion of the A Subunit occludes the active site cleft of the A1 portion, with methionine-260 of the A2 portion protruding into and blocking the active site of the A1 portion (Lea N et al., *Microbiology* 145: 999-1004 (1999); see also Fraser M et al., *Nat Struct Biol* 1: 59-64 (1994)).

The dissociation of the Shiga toxin A1 fragment from the A2 fragment and the rest of the Shiga holotoxin is required for the translocation of the A1 fragment from the lumen of the endoplasmic reticulum to the cytosol (LaPointe P et al., *J Biol Chem* 280: 23310-18 (2005); Li S et al., *PLoS One* 7: e41119 (2012)). The liberation of the A1 fragment exposes a hydrophobic domain which triggers a series of complex steps: 1) recognition of the A1 fragment by the endoplasmic-reticulum-associated degradation (ERAD) system, 2) unfolding, 3) retrotranslocation across the endoplasmic reticulum membrane, and 4) refolding to a catalytic formation in the cytosol (Li S et al., *PLoS One* 7: e41119 (2012)).

First, the carboxy terminus of the Shiga toxin A1 fragment, which is exposed after furin cleavage and liberation from the rest of the Shiga holotoxin, is recognized by the ERAD system. The ERAD system identifies terminally misfolded proteins in the ER, tags them with polyubiquitin, and exports them to the cytosol for proteasomal destruction (Smith M et al., *Science* 334: 1086-90 (2011)). The A1 fragments of Shiga toxins exploit the ERAD pathway to gain access to the cytosol perhaps by mimicking an unfolded ERAD substrate via a locally misfolded, polypeptide region, comprising a patch of relatively hydrophobic amino acid residues, located on the carboxy terminals of A1 fragments created by furin cleavage (LaPointe P et al., *J Biol Chem* 280: 23310-18 (2005); Yu M, Haslam D, *Infect Immun* 73: 2524-32 (2005); Li S et al., *PLoS One* 7: e41119 (2012)). The partially unfolded, hydrophobic patch of amino acid residues near the carboxy terminus of Shiga toxin A1 fragments exposed by furing cleavage can be recognized by endoplasmic reticulum chaperone proteins of the ERAD system LaPointe P et al., *J Biol Chem* 280: 23310-18 (2005); Yu M, Haslam D, *Infect Immun* 73: 2524-32 (2005); Li S et al., *PLoS One* 7: e41119 (2012)).

When a Shiga toxin A1 fragment first enters the cytosol of an intoxicated eukaryotic cell, it is believed to be polyubiqutinated and in a substantially disordered conformation as a result of being unfolded, thus A1 fragments must both avoid proteasomal degradation and refold into a catalytically active conformation in order to exert their cytotoxic catalytic activity (Tam P, Lingwood C, *Microbiology* 153: 2700-10 (2007); Li S et al., *PLoS One* 7: e41119 (2012)). Once in the cytosol, an active Shiga toxin A1 fragment can irreversibly cripple one eukaryotic ribosome after another via the A1 fragment's potent enzymatic activity at a rate of approximately 700 ribosomes per minute (Brigotti M et al., *Toxicon* 35:1431-1437 (1997); Tam P, Lingwood C, *Microbiology* 153: 2700-10 (2007)). After a threshold number of ribosomes is inactivated, an intoxicated host cell is predicted to experience sufficient reduction in protein synthesis to induce cell death via apoptosis (Iordanov M et al., *Mol Cell Biol* 17: 3373-81 (1997); Smith W et al., *Infect Immun* 71: 1497-504 (2003); Lee S et al., *Cell Microbiol* 10: 770-80 (2008); Tesh V, *Future Microbiol* 5: 431-53 (2010)).

Intracellular, furin cleavage of the Shiga toxin A Subunit between the A1 and A2 fragments is important for maximal Shiga toxin cytotoxicity. Experiments have shown maximal Shiga holotoxin cytotoxicity requires 1) the minimal furin-cleavage site R/Y-x-x-R located between the A1 and A2 fragments in the Shiga toxin A Subunit; 2) certain amino acid residues in the surface-exposed, extended loop structure in the Shiga toxin A Subunit comprising the minimal furin-cleavage site; and 3) the cellular expression of furin by intoxicated vertebrate cells.

Human cells lacking furin are protected against Shiga toxin cytotoxicity, and these same furin-deficient cells can be made Shiga toxin sensitive by the forced expression of furin (Garred Ø et al., *J Biol Chem* 270: 10817-21 (1995); Kurmanova A et al., *Biochem Biophys Res Commun* 357: 144-9 (2007)).

Furin was shown to be necessary for maximal Shiga toxin cytotoxicity in certain human cancer cells (Garred Ø et al., *J Biol Chem* 270: 10817-21 (1995); Kurmanova A et al., *Biochem Biophys Res Commun* 357: 144-9 (2007)). Shiga toxins with disrupted furin-cleavage sites and/or mutations in conserved, surface-exposed, extended loop structures show reduced cytotoxicity. Disrupting the S-R/Y-x-x-R furin-cleavage motif in the surface-exposed, extended loop of Shiga toxin A Subunits with amino acid residue substitutions or deletions resulted in less efficient cleavage of the A Subunits and less efficient ribosome inhibition in vertebrate cells (Burgess B, Roberts L, *Mol Microbiol* 10: 171-9 (1993); Garred Ø et al., *Exp Cell Res* 218: 39-49 (1995); Lea N et al., *Microbiology* 145: 999-1004 (1999); Kurmanova A et al., *Biochem Biophys Res Commun* 357: 144-9 (2007)). The disruption of the furin-cleavage motif in the A Subunit of SLT-1 reduced its ribosome inhibition activity by 60-fold (Lea N et al., *Microbiology* 145: 999-1004 (1999)). In addition, disruption of the flanking regions of the furin-cleavage motif without disrupting the minimal furin-cleavage motif R-x-x-R also reduced the ribosome inhibition activity of Stx (Kurmanova A et al., *Biochem Biophys Res Commun* 357: 144-9 (2007)).

The Shiga toxin cytotoxicity can be increased for both furin-cleavage resistant, Shiga toxin mutants and for furin-deficient cells by pretreatment of Shiga holotoxins with furin in vitro before intoxicating cells. Shiga toxin A Subunits can be efficiently cleaved in vitro by furin (Garred Ø et al., *Exp Cell Res* 218: 39-49 (1995)). Pretreatment of Stx with furin in vitro before administration to furin-deficient human cells resulted in an increase in ribosome inhibition activity by 30-50 fold (Garred Ø et al., *Exp Cell Res* 218: 39-49 (1995); Kurmanova A et al., *Biochem Biophys Res Commun* 357: 144-9 (2007)). Similarly, pretreatment of a furin-cleavage resistant, mutant, Shiga toxin with trypsin in vitro resulted in increased ribosome inhibition in intoxicated vertebrate cells as compared to cells intoxicated with untreated, furin-cleavage resistant, Shiga toxins (Kurmanova A et al., *Biochem Biophys Res Commun* 357: 144-9 (2007)).

The dissociation of the A1 fragment from the A2 fragment might be required for activation of the catalytic domain of the A1 fragment (Garred Ø et al., *Exp Cell Res* 218: 39-49 (1995); Garred Ø et al., *J Blot Chem* 270: 10817-21 (1995); Kurmanova A et al., *Biochem Biophys Res Commun* 357: 144-9 (2007)). The catalytic domains of Shiga toxins might be inactiv before furin cleavage because the catalytic domain is sterically blocked (Lea N et al., *Microbiology* 145: 999-1004 (1999); see also Fraser M et al., *Nat Struct Biol* 1: 59-64 (1994)).

The model of Shiga toxin cytotoxicity is that intracellular proteolytic processing of Shiga toxin A Subunits by furin in intoxicated cells is essential for 1) liberation of the A1 fragment from the rest of the Shiga holotoxin, 2) escape of the A1 fragment from the endoplasmic reticulum by exposing a hydrophobic domain in the carboxy terminus of the A1 fragment, and 3) enzymatic activation of the A1 fragment (see Johannes L, Römer W, *Nat Rev Microbiol* 8: 105-16 (2010)). The efficient liberation of the Shiga toxin A1 fragment from the A2 fragment and the rest of the components of the Shiga holotoxin in the endoplasmic reticulum of intoxicated cells is essential for efficient intracellular routing to the cytosol, maximal enzymatic activity, efficient ribosome inactivation, and achieving optimal cytotoxicity, i.e. comparable to a wild-type Shiga toxin.

The liberation of the Shiga toxin A1 fragment from all other moieties may be required both for 1) exposing the carboxy terminus of the A1 fragment for recognition by cellular factors within the endoplasmic reticulum of intoxicated cells and 2) maximizing catalytic activity.

The liberation of the Shiga toxin A1 fragment is required to expose the carboxy terminus of the A1 fragment. The hydrophobic region around 224 to 241 in the carboxy-terminal region of the A1 fragment of StxA is believed to play a role in the retrotranslocation of the A1 fragment from the lumen of the endoplasmic reticulum to the cytosol (Suhan M, Hovde C, *Infect Immun* 66: 5252-9 (1998); LaPointe P et al., *J Biol Chem* 280: 23310-18 (2005)). Several amino residues in this hydrophobic region become more surface accessible after cleavage of Shiga toxin A Subunits in both Stx1A and Stx2A (Di R et al., *Toxicon* 57: 525-39 (2011)). Thus, the liberation of the Shiga toxin A1 fragment and the exposure of its carboxy-terminal hydrophobic region might trigger the transport of the A1 fragment from the endoplasmic reticulum to the cytosol (Suhan M, Hovde C, *Infect Immun* 66: 5252-9 (1998); LaPointe P et al., *J Biol Chem* 280: 23310-18 (2005); Di R et al., *Toxicon* 57: 525-39 (2011)). In addition, the carboxy terminus of the A1 fragment may function as a ligand recognized and bound by an endoplasmic reticular receptor, other than a chaperone protein, which contributes to the efficient retrotranslocation of the A1 fragment (LaPointe P et al., *J Biol Chem* 280: 23310-18 (2005)).

Structural changes which enhance cytotoxicity of the Shiga toxin A1 fragment could occur after liberation of the A1 fragment from all other moieties. The free Shiga toxin A1 fragment might exhibit optimal catalytic activity, such as, e.g., by exposing certain catalytic regions buried in the Shiga holotoxin structure (see Tesh V et al., *Infect Immun* 61: 3392-402 (1993); Di R et al., *Toxicon* 57: 525-39 (2011)). Shiga toxin catalytic activation after proteolytic cleavage and exposure to reducing conditions or enhancement of Shiga toxin toxicity after proteolytic processing and exposure to reducing conditions are most likely the result of separation of the A1 fragment from the A2 fragment (Tesh V et al., *Infect Immun* 61: 3392-402 (1993)). Structural changes to the Shiga toxin A1 fragment after dissociation from the rest of the Shiga holotoxin may relate to functional changes, such as, e.g. the ability to form a newly folded structure which is more catalytically active after being unfolded by the ERAD machinery and translocated to the cytosol, the ability of the cytosolic A1 fragment to evade degradation by the proteasome, and the ability to form structures with more open catalytic active sites and/or binding clefts which enhances enzymatic activity (Di R et al., *Toxicon* 57: 525-39 (2011)).

For example, the catalytic residues N75 and Y77 in Stx1A may become more solvent exposed after liberation of the Shiga toxin A1 fragment and many of the residues in the carboxy terminus of the A1 fragment of both Stx1 and Stx2 from around amino acid residue positions 205 to 250 may undergo significant changes in surface accessibility after liberation of the A1 fragment (Di R et al., *Toxicon* 57: 525-39 (2011)). In particular, the amino acid residues in regions 240-251 of Stx1A and 239-250 of Stx2A exhibited a dramatic increase in surface exposure after liberation of Shiga toxin A1 fragments (Di R et al., *Toxicon* 57: 525-39 (2011)). Another example is that the amino acid residues in regions 42-49 and 246-250 of Stx2A may become more solvent exposed after liberation of Shiga toxin A1 fragments (Smith M et al., *Infect Immun* 77: 2730-40 (2009); Di R et al., *Toxicon* 57: 525-39 (2011)). Thus, the liberation of the Shiga toxin A1 fragment from all other moieties may be required for maximal Shiga toxin cytotoxicity due to structural and functional changes which enhance the sub-cellular routing of the A1 fragment to the cytosol of intoxicated cells, enzymatic activity of the A1 fragment in the cytosol of intoxicated cells, and persistence of the A1 fragment in the cytosol of intoxicated cells.

In summary, maximal, Shiga toxin cytotoxicity is believed to require the cleavage of Shiga toxin A Subunit, exposure in the endoplasmic reticulum of a hydrophobic region proximal to the carboxy terminus of the A1 fragment, and the liberation of the A1 fragment from the rest of the holotoxin, all of which might result in multiple structural and functional changes to the A1 fragment. In addition, it is believed that optimal intracellular transport of Shiga toxin A1 fragments to the cytosol requires the same events: A Subunit cleavage, exposure of the A1 fragment carboxy terminus, and the liberation of the A1 fragment from all other molecular moieties. In the absence of furin-cleavage of the Shiga toxin A Subunit, sub-cellular routing of Shiga toxin catalytic domains can occur but is suboptimal, less efficient, and results in reductions in the efficacy of ribosome inhibition (Garred Ø et al., *Exp Cell Res* 218: 39-49 (1995); Lea N et al., *Microbiology* 145: 999-1004 (1999); Kurmanova A et al., *Biochem Biophys Res Commun* 357: 144-9 (2007)).

Because furin proteolytic processing of Shiga toxin A Subunits in intoxicated vertebrate cells is critical for maximal cytotoxicity, it is important when designing cytotoxic molecules derived from Shiga toxin A Subunits to maintain or compensate for this naturally occurring proteolytic processing in order to preserve maximal, Shiga toxin cytotoxicity. There was no known solution which fully compensated for the lack of furin-cleavage of structures comprising a furin-cleavage resistant, Shiga toxin A Subunit linked to a carboxy-terminal moiety which perturbs the native subcellular routing and/or cytotoxicity of the Shiga toxin A1 fragment derived component.

It would be desirable to have cytotoxic molecules comprising Shiga toxin A Subunit derived components which are as cytotoxic as possible. It would also be desirable to have improved, cell-targeted molecules comprising Shiga toxin effector polypeptide components that maintain high potency for killing specific cell types in various medical applications. However, there remains a need in the art for ways of engineering cytotoxic molecules comprising Shiga toxin A Subunit derived regions with reduced nonspecific toxicities, improved stabilities, increased in vivo half-lives, and/or improved toxicity profiles after administration to organisms when the cytotoxic molecules comprise carboxy terminal molecular moieties, such as, e.g., cell-targeting, immunoglobulin-type binding regions.

SUMMARY OF THE INVENTION

The present invention provides various protease-cleavage resistant, Shiga A Subunit toxin effector polypeptides and cytotoxic molecules comprising the same which may be used as components of various compositions of matter, such as cell-targeted molecules and diagnostic compositions. The present invention also provides various cell-targeting molecules comprising protease-cleavage resistant, Shiga toxin effector polypeptides functionally associated with binding regions to effectuate cell targeting. The association of cell-targeting binding regions with protease-cleavage resistant, Shiga toxin effector polypeptides enables the engineering of cell-type specific targeting of the potent Shiga toxin cytotoxicity and/or cytostasis while simultaneously improving in vivo tolerability. Certain cell-targeting molecules of the present invention have improved usefulness for administration to vertebrates as either a therapeutic and/or diagnostic agent because of the reduced likelihood of producing non-specific toxicities at a given dosage.

In certain embodiments, the cell-targeted molecule of the present invention comprises 1) a binding region comprising an immunoglobulin-type binding region comprising one or more polypeptides and capable of specifically binding at least one extracellular target biomolecule, and 2) a Shiga toxin effector polypeptide comprising a Shiga toxin A1 fragment region having a carboxy terminus and a disrupted furin-cleavage motif at the carboxy terminus of the A1 fragment region. In certain embodiments of the cell-targeted molecule of the invention, the binding region is associated with the carboxy terminus of the Shiga toxin effector polypeptide. In certain embodiments of the cell-targeted molecule of the invention, the binding region is fused to the Shiga toxin effector polypeptide. In certain embodiments of the cell-targeted molecule of the invention, the binding region is fused to the Shiga toxin effector polypeptide to form a single, continuous polypeptide. In certain further embodiments of the cell-targeted molecule of the invention, the binding region is fused to the carboxy terminus of the Shiga toxin effector polypeptide, whether directly or indirectly. In certain embodiments, the molecular moiety sterically covers the carboxy terminus of the A1 fragment region. In certain embodiments of the cell-targeted molecule of the invention, the Shiga toxin effector polypeptide is linked to the binding region by at least one covalent bond which is not a disulfide bond. In certain further embodiments of the cell-targeted molecule of the invention, the immunoglobulin-type binding region is selected from the group consisting of: single-domain antibody (sdAb) fragment, nanobody, heavy-chain antibody domain derived from a camelid ($V_HH$ fragment), heavy-chain antibody domain derived from a cartilaginous fish, immunoglobulin new antigen receptor (IgNAR), $V_{NAR}$ fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronectin-derived 10th fibronectin type III domain (10Fn3), tenascin type III domain, ankyrin repeat motif domain, low-density-lipoprotein-receptor-derived A-domain (LDLR-A), lipocalin (anticalin), Kunitz domain, Protein-A-derived Z domain, gamma-B crystalline-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain further embodiments of the cell-targeted molecule of the invention, the binding region is capable of binding to the extracellular target biomolecule selected from the group consisting of: CD20, CD22, CD40, CD79, CD25, CD30, HER2/neu/ErbB2, EGFR, EpCAMs (e.g. EGP-2, EGP-40), EphB2, prostate-specific membrane antigen, Cripto, endoglin, fibroblast activated protein, Lewis-Y, CD19, CD21, CS1/SLAMF7, CD33, CD52, CD133, CEA, gpA33, mucin, TAG-72, carbonic anhydrase IX, folate binding protein, ganglioside GD2, ganglioside GD3, ganglioside GM2, ganglioside Lewis-Y2, VEGFR, Alpha Vbeta3, Alpha5beta1, ErbB1/EGFR, Erb3, c-MET, IGF1R, EphA3, TRAIL-R1, TRAIL-R2, RANKL, FAP, tenascin, CD64, mesothelin, BRCA1, MART-1/MelanA, gp100, tyrosinase, human tyrosinase-related protein 1 (TYRP1), human tyrosinase-related protein 2, TRP-1, TRP-2, MAGE-1, MAGE-3, GAGE-1/2, BAGE, RAGE, NY-ESO-1, CDK-4, beta-catenin, MUM-1, caspase-8, KIAA0205, HPVE6, SART-1, PRAME, carcinoembryonic antigen, prostate specific antigen, prostate stem cell antigen, human aspartyl (asparaginyl) beta-hydroxylase, EphA2, HER3/ErbB-3, MUC1, MART-1/MelanA, gp100, tyrosinase associated antigen, HPV-E7, Epstein-Barr virus antigen, Bcr-Abl, alpha-fetoprotein antigen, 17-A1, bladder tumor antigen, CD38, CD15, CD23, CD52, CD133, CD53, CD88, CD129, CD183, CD191, CD193, CD244, CD294, CD305, C3AR, FceRIa, galectin-9, mrp-14, Siglec-8, Siglec-10, CD49d, CD13, CD44, CD54, CD63, CD69, CD123, TLR4, FceRIa, IgE, CD107a, CD203c, CD14, CD68, CD80, CD86, CD105, CD115, F4/80, ILT-3, galectin-3, CD11a-c, GITRL, MHC Class II, CD284-TLR4, CD107-Mac3, CD195-CCR5, HLA-DR, CD16/32, CD282-TLR2, CD11c, and any immunogenic fragment of any of the foregoing. For certain embodiments, administration of the cell-targeted molecule of the invention to a cell physically coupled with an extracellular target biomolecule of the binding region, the cell-targeted molecule is capable of causing death of the cell. For certain further embodiments, administration of the cell-targeted molecule of the invention to two different populations of cell types which differ with respect to the presence or level of an extracellular target biomolecule, the cell-targeted molecule is capable of causing cell death of the cell-types physically coupled with an extracellular target biomolecule of the cell-targeted molecule's binding region at a $CD_{50}$ that is at least three times less than the $CD_{50}$ observed for cell types which are not physically coupled with an extracellular target biomolecule of the cell-targeted molecule's binding region. For certain embodiments, administration of the cell-targeted molecule of the invention to a first population of cells whose members are physically coupled to extracellular target biomolecules of the cell-targeted molecule's binding region, and a second population of cells whose members are not physically coupled to any extracellular target biomolecule of the binding region, the cytotoxic effect of the cell-targeted molecule to members of said first population of cells relative to members of said second population of cells is at least 3-fold greater. For certain embodiments, administration of the cell-targeted molecule of the invention to a first population of cells whose members are physically coupled to a significant amount of the extracellular target biomolecule of the cell-targeted molecule's binding region, and a second population of cells whose members are not physically coupled to a significant amount of any extracellular target biomolecule of the binding region, the cytotoxic effect of the cell-targeted molecule to members of said first population of cells relative to members of said second population of cells is at least 3-fold greater. For certain embodiments, administration of the cell-targeted molecule of the invention to a first population of target biomolecule positive cells, and a second population of cells whose members do not express a significant amount of a target biomolecule of the cell-targeted molecule's binding region at a cellular surface, the cytotoxic effect of the cell-targeted molecule to members of the first population of cells relative to members of the second population of cells is at least 3-fold greater. In certain further embodiments of the cell-targeted molecule of the invention, the Shiga toxin effector polypeptide comprises or consists essentially of the polypeptide shown in any one of SEQ ID NOs: 4-49. In certain further embodiments, the cell-targeted molecule of the invention comprises or consists essentially of the polypeptide shown in any one of SEQ ID NOs: 50-61. In certain further embodiments, the cell-targeted molecule of the invention further comprises a carboxy-terminal endoplasmic reticulum retention/retrieval signal motif of a member of the KDEL family ('KDEL' disclosed as SEQ ID NO:62). In certain further embodiments, the cell-targeted molecule of the invention comprises the carboxy-terminal endoplasmic reticulum retention/retrieval signal motif selected from the group consisting of: KDEL (SEQ ID NO: 62), HDEF (SEQ ID NO: 63), HDEL (SEQ ID NO: 64), RDEF (SEQ ID NO: 65), RDEL (SEQ ID NO: 66), WDEL (SEQ ID NO: 67), YDEL (SEQ ID NO:-68), HEEF (SEQ ID NO: 69, HEEL (SEQ ID NO: 70), KEEL (SEQ ID NO: 71), REEL (SEQ ID NO: 72), KAEL (SEQ ID NO: 73), KCEL (SEQ ID NO: 74), KFEL (SEQ ID NO: 75), KGEL (SEQ ID NO: 76), KHEL (SEQ ID NO: 77), KLEL (SEQ ID NO: 78), KNEL (SEQ ID NO:-79), KQEL (SEQ ID NO: 80), KREL (SEQ ID NO: 81), KSEL (SEQ ID NO: 82), KVEL (SEQ ID NO: 83), KWEL (SEQ ID NO: 84), KYEL (SEQ ID NO: 85), KEDL (SEQ ID NO: 86), KIEL (SEQ ID NO: 87), DKEL (SEQ ID NO: 88), FDEL (SEQ ID NO: 89), KDEF (SEQ ID NO:-90), KKEL (SEQ ID NO: 91), HADL (SEQ ID NO: 92), HAEL (SEQ ID NO: 93), HIEL (SEQ ID NO: 94), HNEL (SEQ ID NO: 95), HTEL (SEQ ID NO: 96), KTEL (SEQ ID NO: 97), HVEL (SEQ ID NO: 98), NDEL (SEQ ID NO: 99), QDEL (SEQ ID NO: 100), REDL (SEQ ID NO:-101), RNEL (SEQ ID NO: 102), RTDL (SEQ ID NO: 103), RTEL (SEQ ID NO: 104), SDEL (SEQ ID NO: 105), TDEL (SEQ ID NO: 106), and SKEL (SEQ ID NO: 107). In certain further embodiments of the cell-targeted molecule of the invention, the Shiga toxin effector polypeptide comprises a mutation relative to a naturally occurring A Subunit of a member of the Shiga toxin family which reduces or eliminates the enzymatic activity of the Shiga toxin effector polypeptide but does not reduce the subcellular routing to the cytosol, of at least a part of the Shiga toxin effector polypeptide, below the subcellular routing level of a wild-type, Shiga toxin effector polypeptide.

In certain embodiments, the cell-targeted molecule of the present invention comprises 1) a Shiga toxin effector polypeptide comprising a Shiga toxin A1 fragment region having a carboxy terminus and a disrupted furin-cleavage motif, at the carboxy terminus of the A1 fragment region, comprising one or more mutations in the minimal, furin-cleavage motif relative to a wild-type, Shiga toxin A Subunit; and 2) a binding region capable of specifically binding at least one extracellular target biomolecule and associated with the carboxy terminus of the Shiga toxin effector polypeptide. In these embodiments of the cell-targeted molecules of the invention, a mutation in the minimal, furin-cleavage motif is an amino acid deletion, insertion, and/or substitution of at least one amino acid residue in the R/Y-x-x-R furin cleavage motif. In certain embodiments of the cell-targeted molecule of the invention, the Shiga toxin effector polypeptide is linked to the binding region by at least one covalent bond which is not a disulfide bond. In certain embodiments of the cell-targeted molecule of the invention, the binding region is fused to the carboxy terminus of the Shiga toxin effector polypeptide, whether directly or indirectly. In certain embodiments of the cell-targeted molecule of the invention, the binding region is fused to the carboxy terminus of the Shiga toxin effector polypeptide to form a single, continuous polypeptide. In certain embodiments, the binding region sterically covers the carboxy terminus of the A1 fragment region. In certain further embodiments of the cell-targeted molecule of the invention, the immunoglobulin-type binding region is selected from the group consisting of: single-domain antibody (sdAb) fragment, nanobody, heavy-chain antibody domain derived from a camelid ($V_HH$ fragment), heavy-chain antibody domain derived from a cartilaginous fish, immunoglobulin new antigen receptor (IgNAR), $V_{NAR}$ fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronectin-derived $10^{th}$ fibronectin type III domain (10Fn3), tenascin type III domain, ankyrin repeat motif domain, low-density-lipoprotein-receptor-derived A-domain (LDLR-A), lipocalin (anticalin), Kunitz domain, Protein-A-derived Z domain, gamma-B crystalline-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain further embodiments of the cell-targeted molecule of the invention, the binding region is capable of binding to the extracellular target biomolecule selected from the group consisting of: CD20, CD22, CD40, CD79, CD25, CD30, HER2/neu/ErbB2, EGFR, EpCAMs (e.g. EGP-2, EGP-40), EphB2, prostate-specific membrane antigen, Cripto, endoglin, fibroblast activated protein, Lewis-Y, CD19, CD21, CS1/SLAMF7, CD33, CD52, CD133, CEA, gpA33, mucin, TAG-72, carbonic anhydrase IX, folate binding protein, ganglioside GD2, ganglioside GD3, ganglioside GM2, ganglioside Lewis-Y2, VEGFR, Alpha Vbeta3, Alpha5beta1, ErbB1/EGFR, Erb3, c-MET, IGF1R, EphA3, TRAIL-R1, TRAIL-R2, RANKL, FAP, tenascin, CD64, mesothelin, BRCA1, MART-1/MelanA, gp100, tyrosinase, human tyrosinase-related protein 1 (TYRP1), human tyrosinase-related protein 2, TRP-1, TRP-2, MAGE-1, MAGE-3, GAGE-1/2, BAGE, RAGE, NY-ESO-1, CDK-4, beta-catenin, MUM-1, caspase-8, KIAA0205, HPVE6, SART-1, PRAME, carcinoembryonic antigen, prostate specific antigen, prostate stem cell antigen, human aspartyl (asparaginyl) beta-hydroxylase, EphA2, HER3/ErbB-3, MUC1, MART-1/MelanA, gp100, tyrosinase associated antigen, HPV-E7, Epstein-Barr virus antigen, Bcr-Abl, alpha-fetoprotein antigen, 17-A1, bladder tumor antigen, CD38, CD15, CD23, CD52, CD133, CD53, CD88, CD129, CD183, CD191, CD193, CD244, CD294, CD305, C3AR, FceRIa, galectin-9, mrp-14, Siglec-8, Siglec-10, CD49d, CD13, CD44, CD54, CD63, CD69, CD123, TLR4, FceRIa, IgE, CD107a, CD203c, CD14, CD68, CD80, CD86, CD105, CD115, F4/80, ILT-3, galectin-3, CD11a-c, GITRL, MHC Class II, CD284-TLR4, CD107-Mac3, CD195-CCR5, HLA-DR, CD16/32, CD282-TLR2, CD11c, and any immunogenic fragment of any of the foregoing. For certain further embodiments of the cell-targeted molecule of the invention, administration of the cell-targeted molecule to a cell physically coupled with an extracellular target biomolecule of the binding region, the cell-targeted molecule is capable of causing death of the cell. For certain further embodiments, administration of the cell-targeted molecule of the invention to two different populations of cell types which differ with respect to the presence or level of an extracellular target biomolecule, the cell-targeted molecule is capable of causing cell death of cell-types physically coupled with an extracellular target biomolecule of the cell-targeted molecule's binding region at a $CD_{50}$ that is at least three times less than the $CD_{50}$ observed for cell types which are not physically coupled with an extracellular target biomolecule of the cell-targeted molecule's binding region. For certain embodiments, administration of the cell-targeted molecule of the invention to a first population of cells whose members are physically coupled to extracellular target biomolecules of the cell-targeted molecule's binding region, and a second population of cells whose members are not physically coupled to any extracellular target biomolecule of the binding region, the cytotoxic effect of the cell-targeted molecule to members of said first population of cells relative to members of said second population of cells is at least 3-fold greater. For certain embodiments, administration of the cell-targeted molecule of the invention to a first population of cells whose members are physically coupled to a significant amount of the extracellular target biomolecule of the cell-targeted molecule's binding region, and a second population of cells whose members are not physically coupled to a significant amount of any extracellular target biomolecule of the binding region, the cytotoxic effect of the cell-targeted molecule to members of said first population of cells relative to members of said second population of cells is at least 3-fold greater. For certain embodiments, administration of the cell-targeted molecule of the invention to a first population of target biomolecule positive cells, and a second population of cells whose members do not express a significant amount of a target biomolecule of the cell-targeted molecule's binding region at a cellular surface, the cytotoxic effect of the cell-targeted molecule to members of the first population of cells relative to members of the second population of cells is at least 3-fold greater. In certain further embodiments of the cell-targeted molecule of the invention, the Shiga toxin effector polypeptide comprises or consists essentially of the polypeptide shown in any one of SEQ ID NOs: 4-36. In certain further embodiments, the cell-targeted molecule of the invention comprises or consists essentially of the polypeptide shown in any one of SEQ ID NOs: 50-61. In certain further embodiments, the cell-targeted molecule of the invention further comprises a carboxy-terminal endoplasmic reticulum retention/retrieval signal motif of a member of the KDEL family ('KDEL' disclosed as SEQ ID NO: 62). In certain further embodiments, the cell-targeted molecule of the invention comprises the carboxy-terminal endoplasmic reticulum retention/retrieval signal motif selected from the group consisting of: KDEL (SEQ ID NO: 62), HDEF (SEQ ID NO: 63), HDEL (SEQ ID NO: 64), RDEF (SEQ ID NO: 65), RDEL (SEQ ID NO: 66), WDEL (SEQ ID NO: 67, YDEL (SEQ ID NO:-68), HEEF (SEQ ID NO: 69, HEEL (SEQ ID NO: 70), KEEL (SEQ ID NO: 71), REEL (SEQ ID NO: 72), KAEL (SEQ ID NO: 73), KCEL (SEQ ID NO: 74), KFEL (SEQ ID NO: 75), KGEL (SEQ ID NO: 76), KHEL (SEQ ID NO: 77), KLEL (SEQ ID NO: 78), KNEL (SEQ ID NO:-79), KQEL (SEQ ID NO: 80), KREL (SEQ ID NO: 81), KSEL (SEQ ID NO: 82), KVEL (SEQ ID NO: 83), KWEL (SEQ ID NO: 84), KYEL (SEQ ID NO: 85), KEDL (SEQ ID NO: 86), KIEL (SEQ ID NO: 87), DKEL (SEQ ID NO: 88), FDEL (SEQ ID NO: 89), KDEF (SEQ ID NO:-90), KKEL (SEQ ID NO: 91), HADL (SEQ ID NO: 92), HAEL (SEQ ID NO: 93), HIEL (SEQ ID NO: 94), HNEL (SEQ ID NO: 95), HTEL (SEQ ID NO: 96), KTEL (SEQ ID NO: 97), HVEL (SEQ ID NO: 98), NDEL (SEQ ID NO: 99), QDEL (SEQ ID NO: 100), REDL (SEQ ID NO:-101), RNEL (SEQ ID NO: 102), RTDL (SEQ ID NO: 103), RTEL (SEQ ID NO: 104), SDEL (SEQ ID NO: 105), TDEL (SEQ ID NO: 106), and SKEL (SEQ ID NO: 107). In certain further embodiments of the cell-targeted molecule of the invention, the Shiga toxin effector polypeptide comprises a mutation relative to a naturally occurring A Subunit of a member of the Shiga toxin family which reduces or eliminates the enzymatic activity of the Shiga toxin effector polypeptide but does not reduce the subcellular routing to the cytosol, of at least a part of the Shiga toxin effector polypeptide, below the subcellular routing level of a wild-type, Shiga toxin effector polypeptide.

In certain embodiments, the cytotoxic molecule of the present invention comprises a Shiga toxin effector polypeptide comprising 1) a Shiga toxin A1 fragment region having a carboxy terminus and 2) a disrupted furin-cleavage motif at the carboxy terminus of the A1 fragment region; wherein the cytotoxic molecule is capable, when a component of a first cell-targeted molecule comprising a binding region capable of specifically binding at least one extracellular target biomolecule and a molecular moiety associated with the carboxy terminus of the Shiga toxin effector polypeptide, of exhibiting cytotoxicity equivalent to cytotoxicity of a second cell-targeted molecule consisting of the cell-targeted molecule except for the Shiga toxin effector polypeptide consists of a wild-type, Shiga toxin A1 polypeptide. This means the second cell-targeted molecule comprises the same binding region and the same molecular moiety as the first cell-targeted molecule of the invention but instead of comprising the same Shiga toxin effector polypeptide, the second cell-targeted molecule comprises a wild-type, Shiga toxin effector polypeptide comprising a Shiga toxin A1 fragment region (e.g. amino acids 1-251 of SEQ ID NO:1 or SEQ ID NO:2, or amino acids 1-250 of SEQ ID NO:3) having a carboxy terminus and a wild-type furin-cleavage site at the carboxy terminus of the A1 fragment region of the wild-type, Shiga toxin effector polypeptide; wherein the molecular moiety associated with the carboxy terminus of the wild-type, Shiga toxin A1 polypeptide with the same association as in the first cell-targeted molecule. In certain further embodiments, the molecular moiety comprises at least one amino acid residue fused to the carboxy terminus of the Shiga toxin effector polypeptide, either directly or indirectly. In certain embodiments, the molecular moiety sterically covers the carboxy terminus of the A1 fragment region. In certain embodiments, the molecular moiety comprises a peptide and/or polypeptide derived from the Shiga toxin A2 fragment of a naturally occurring Shiga toxin. In certain embodiments, the Shiga toxin effector polypeptide is linked to the molecular moiety by at least one covalent bond which is not a disulfide bond. In certain further embodiments, the molecular moiety comprises a polypeptide fused to the carboxy terminus of the Shiga toxin effector polypeptide to form a single, continuous polypeptide. In certain further embodiments of the cytotoxic molecule of the invention, the disrupted furin-cleavage motif comprises at least one mutation relative to a wild-type, Shiga toxin A Subunit, the mutation altering at least one amino acid residue in the region natively positioned 1) at 248-251 of the A Subunit of Shiga-like toxin 1 (SEQ ID NO:1) or Shiga toxin (SEQ ID NO:2), or 2) at 247-250 of the A Subunit of Shiga-like toxin 2 (SEQ ID NO:3). In certain further embodiments of the cytotoxic molecule of the invention, the mutation is an amino acid residue substitution of an arginine residue with a non-positively charged, amino acid residue. In certain further embodiments of the cytotoxic molecule of the invention, the Shiga toxin effector polypeptide comprises or consists essentially of the polypeptide shown in any one of SEQ ID NOs: 4-49. In certain further embodiments of the cytotoxic molecule of the invention, the first cell-targeted molecule is capable of exhibiting improved, in vivo tolerability compared to the second cell-targeted molecule. In certain further embodiments of the cytotoxic molecule of the invention, the Shiga toxin effector polypeptide comprises a mutation relative to a naturally occurring A Subunit of a member of the Shiga toxin family which reduces or eliminates the enzymatic activity of the Shiga toxin effector polypeptide but does not reduce the subcellular routing to the cytosol, of at least a part of the Shiga toxin effector polypeptide, below the subcellular routing level of a wild-type, Shiga toxin effector polypeptide.

In certain embodiments of the cytotoxic molecule of the present invention, the Shiga toxin effector polypeptide does not consist of the polypeptide shown in SEQ ID NO:2 further comprising both of the following amino acid residue substitutions: R248H and R251H. In certain embodiments of the cytotoxic molecule, the Shiga toxin effector polypeptide does not comprise both of the following amino acid residue substitutions: R248H and R251H. In certain embodiments of the cytotoxic molecule, the Shiga toxin effector polypeptide does not consist of the polypeptide shown in SEQ ID NO:1 further comprising both of the following amino acid residue substitutions: R248G and R251G. In certain embodiments of the cytotoxic molecule, the Shiga toxin effector polypeptide does not comprise both of the following amino acid residue substitutions: R248G and R251G. In certain embodiments of the cytotoxic molecule, the Shiga toxin effector polypeptide does not consist of the polypeptide shown in SEQ ID NO:1 further comprising all of the following amino acid residue substitutions: A246G, S247A, A253G, and S254A. In certain embodiments of the cytotoxic molecule, the Shiga toxin effector polypeptide does not comprise all of the following amino acid residue substitutions: A246G, S247A, A253G, and S254A. In certain embodiments of the cytotoxic molecule, the Shiga toxin effector polypeptide does not consist of the polypeptide shown in SEQ ID NO:1 further comprising all of the following amino acid residue substitutions: A246G, S247A, R248G, R251G, A253G, and S254A. In certain embodiments of the cytotoxic molecule, the Shiga toxin effector polypeptide does not comprise all of the following amino acid residue substitutions: A246G, S247A, R248G, R251G, A253G, and S254A. In certain embodiments of the cytotoxic molecule, the Shiga toxin effector polypeptide does not consist of the polypeptide shown in SEQ ID NO:2 further comprising the deletion of the region natively positioned at 247-252. In certain embodiments of the cytotoxic molecule, the Shiga toxin effector polypeptide does not comprise a Shiga toxin effector polypeptide comprising the deletion of the region natively positioned at 247-252. In certain embodiments of the cytotoxic molecule, the Shiga toxin effector polypeptide does not consist of the polypeptide shown in SEQ ID NO:2 further comprising both of the following deletions: 245-247 and 253-255. In certain embodiments of the cytotoxic molecule, the Shiga toxin effector polypeptide does not comprise both of the following deletions: 245-247 and 253-255.

In certain embodiments, the cytotoxic, cell-targeted molecule of the present invention comprises 1) a binding region capable of specifically binding at least one extracellular target biomolecule, 2) a Shiga toxin effector polypeptide comprising a Shiga toxin A1 fragment region having a carboxy terminus and a disrupted furin-cleavage motif at the carboxy terminus of the A1 fragment region, and 3) a molecular moiety associated with the carboxy terminus of the Shiga toxin effector polypeptide; and wherein the cytotoxic, cell-targeted molecule is capable of exhibiting cytotoxicity equivalent to cytotoxicity of a second cell-targeted molecule consisting of the cell-targeted molecule except for the Shiga toxin effector polypeptide consists of a wild-type, Shiga toxin A1 polypeptide. This means the second cell-targeted molecule comprises the same binding region and the same molecular moiety as the cytotoxic, cell-targeted molecule of the invention but instead of comprising the same Shiga toxin effector polypeptide, the second cell-targeted molecule comprises a wild-type, Shiga toxin effector polypeptide comprising a Shiga toxin A1 fragment region having a carboxy terminus and a wild-type furin-cleavage site at the carboxy terminus of the A1 fragment region of the wild-type, Shiga toxin effector polypeptide; wherein the molecular moiety associated with the carboxy terminus of the wild-type, Shiga toxin A1 polypeptide with the same association as in the first cell-targeted molecule. In certain embodiments of the cytotoxic, cell-targeted molecule of the invention, the molecular moiety sterically covers the carboxy terminus of the A1 fragment region. In certain embodiments of the cytotoxic, cell-targeted molecule of the invention, the binding region sterically covers the carboxy terminus of the A1 fragment region. In certain further embodiments of the cytotoxic, cell-targeted molecule of the invention, the molecular moiety comprises the binding region. In certain embodiments of the cytotoxic, cell-targeted molecule of the invention, the molecular moiety comprises a peptide and/or polypeptide derived from the Shiga toxin A2 fragment of a naturally occurring Shiga toxin. In certain further embodiments of the cytotoxic, cell-targeted molecule of the invention, the binding region comprises a polypeptide comprising an immunoglobulin-type binding region. In certain further embodiments of the cytotoxic, cell-targeted molecule of the invention, the immunoglobulin-type binding region is selected from the group consisting of: single-domain antibody (sdAb) fragment, nanobody, heavy-chain antibody domain derived from a camelid ($V_HH$ fragment), heavy-chain antibody domain derived from a cartilaginous fish, immunoglobulin new antigen receptor (IgNAR), $V_{NAR}$ fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronectin-derived $10^{th}$ fibronectin type III domain (10Fn3), tenascin type III domain, ankyrin repeat motif domain, low-density-lipoprotein-receptor-derived A-domain (LDLR-A), lipocalin (anticalins), Kunitz domain, Protein-A-derived Z domain, gamma-B crystalline-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain embodiments of the cytotoxic, cell-targeted molecule of the invention, the Shiga toxin effector polypeptide is linked to the molecular moiety by at least one covalent bond which is not a disulfide bond. In certain further embodiments, the molecular moiety comprises at least one amino acid residue fused to the carboxy terminus of the Shiga toxin effector polypeptide. In certain further embodiments of the cytotoxic, cell-targeted molecule of the invention, the molecular moiety comprises a polypeptide fused to the carboxy terminus of the Shiga toxin effector polypeptide to form a single, continuous polypeptide. For certain embodiments, administration of the cytotoxic, cell-targeted molecule of the invention to two different populations of cell types which differ with respect to the presence or level of an extracellular target biomolecule, the cell-targeted molecule is capable of causing cell death of the cell-types physically coupled with an extracellular target biomolecule of the cell-targeted molecule's binding region at a $CD_{50}$ that is at least three times less than the $CD_{50}$ observed for cell types which are not physically coupled with an extracellular target biomolecule of the cell-targeted molecule's binding region. For certain embodiments, administration of the cytotoxic, cell-targeted molecule of the invention to a first population of cells whose members are physically coupled to extracellular target biomolecules of the cell-targeted molecule's binding region, and a second population of cells whose members are not physically coupled to any extracellular target biomolecule of the binding region, the cytotoxic effect of the cell-targeted molecule to members of said first population of cells relative to members of said second population of cells is at least 3-fold greater. For certain embodiments, administration of the cytotoxic, cell-targeted molecule of the invention to a first population of cells whose members are physically coupled to a significant amount of the extracellular target biomolecule of the cell-targeted molecule's binding region, and a second population of cells whose members are not physically coupled to a significant amount of any extracellular target biomolecule of the binding region, the cytotoxic effect of the cell-targeted molecule to members of said first population of cells relative to members of said second population of cells is at least 3-fold greater. For certain embodiments, administration of the cytotoxic, cell-targeted molecule of the invention to a first population of target biomolecule positive cells, and a second population of cells whose members do not express a significant amount of a target biomolecule of the cell-targeted molecule's binding region at a cellular surface, the cytotoxic effect of the cell-targeted molecule to members of the first population of cells relative to members of the second population of cells is at least 3-fold greater. In certain further embodiments of the cytotoxic, cell-targeted molecule of the invention, the binding region is capable of binding to the extracellular target biomolecule selected from the group consisting of: CD20, CD22, CD40, CD79, CD25, CD30, HER2/neu/ErbB2, EGFR, EpCAMs (e.g. EGP-2, EGP-40), EphB2, prostate-specific membrane antigen, Cripto, endoglin, fibroblast activated protein, Lewis-Y, CD19, CD21, CS1/SLAMF7, CD33, CD52, CD133, CEA, gpA33, mucins, TAG-72, carbonic anhydrase IX, folate binding protein, ganglioside GD2, ganglioside GD3, ganglioside GM2, ganglioside Lewis-Y2, VEGFR, Alpha Vbeta3, Alpha5beta1, ErbB1/EGFR, Erb3, c-MET, IGF1R, EphA3, TRAIL-R1, TRAIL-R2, RANKL, FAP, tenascin, CD64, mesothelin, BRCA1, MART-1/MelanA, gp100, tyrosinase, human tyrosinase-related protein 1 (TYRP1), human tyrosinase-related protein 2, TRP-1, TRP-2, MAGE-1, MAGE-3, GAGE-1/2, BAGE, RAGE, NY-ESO-1, CDK-4, beta-catenin, MUM-1, caspase-8, KIAA0205, HPVE6, SART-1, PRAME, carcinoembryonic antigen, prostate specific antigen, prostate stem cell antigen, human aspartyl (asparaginyl) beta-hydroxylase, EphA2, HER3/ErbB-3, MUC1, MART-1/MelanA, gp100, tyrosinase associated antigen, HPV-E7, Epstein-Barr virus antigen, Bcr-Abl, alpha-fetoprotein antigen, 17-A1, bladder tumor antigen, CD38, CD15, CD23, CD52, CD133, CD53, CD88, CD129, CD183, CD191, CD193, CD244, CD294, CD305, C3AR, FceRIa, galectin-9, mrp-14, Siglec-8, Siglec-10, CD49d, CD13, CD44, CD54, CD63, CD69, CD123, TLR4, FceRIa, IgE, CD107a, CD203c, CD14, CD68, CD80, CD86, CD105, CD115, F4/80, ILT-3, galectin-3, CD11a-c, GITRL, MHC Class II, CD284-TLR4, CD107-Mac3, CD195-CCR5, HLA-DR, CD16/32, CD282-TLR2, CD11c, and any immunogenic fragment of any of the foregoing. In certain further embodiments of the cytotoxic, cell-targeted molecule of the invention, the Shiga toxin effector polypeptide comprises or consists essentially of the polypeptide shown in any one of SEQ ID NOs: 4-49. In certain further embodiments, the cytotoxic, cell-targeted molecule of the invention comprises or consists essentially of the polypeptide shown in any one of SEQ ID NOs: 50-61. In certain further embodiments, the cell-targeted molecule of the invention further comprises a carboxy-terminal endoplasmic reticulum retention/retrieval signal motif of a member of the KDEL family ('KDEL' disclosed as SEQ ID NO: 62). In certain further embodiments, the cell-targeted molecule of the invention comprises the carboxy-terminal endoplasmic reticulum retention/retrieval signal motif selected from the group consisting of: KDEL (SEQ ID NO: 62), HDEF (SEQ ID NO: 63), HDEL (SEQ ID NO: 64), RDEF (SEQ ID NO: 65), RDEL (SEQ ID NO:-66), WDEL (SEQ ID NO: 67, YDEL (SEQ ID NO: 68), HEEF (SEQ ID NO: 69, HEEL (SEQ ID NO: 70), KEEL (SEQ ID NO: 71), REEL (SEQ ID NO: 72), KAEL (SEQ ID NO: 73), KCEL (SEQ ID NO: 74), KFEL (SEQ ID NO: 75), KGEL (SEQ ID NO: 76), KHEL (SEQ ID NO:-77), KLEL (SEQ ID NO: 78), KNEL (SEQ ID NO: 79), KQEL (SEQ ID NO: 80), KREL (SEQ ID NO: 81), KSEL (SEQ ID NO: 82), KVEL (SEQ ID NO: 83), KWEL (SEQ ID NO: 84), KYEL (SEQ ID NO: 85), KEDL (SEQ ID NO: 86), KIEL (SEQ ID NO: 87), DKEL (SEQ ID NO: 88), FDEL (SEQ ID NO: 89), KDEF (SEQ ID NO: 90), KKEL (SEQ ID NO: 91), HADL (SEQ ID NO: 92), HAEL (SEQ ID NO: 93), HIEL (SEQ ID NO: 94), HNEL (SEQ ID NO: 95), HTEL (SEQ ID NO: 96), KTEL (SEQ ID NO: 97), HVEL (SEQ ID NO: 98), NDEL (SEQ ID NO:-99), QDEL (SEQ ID NO: 100), REDL (SEQ ID NO: 101), RNEL (SEQ ID NO: 102), RTDL (SEQ ID NO: 103), RTEL (SEQ ID NO: 104), SDEL (SEQ ID NO: 105), TDEL (SEQ ID NO:-106), and SKEL (SEQ ID NO: 107). In certain further embodiments of the cytotoxic, cell-targeted molecule of the invention, the cell-targeted molecule is capable of exhibiting improved, in vivo tolerability compared to the second cell-targeted molecule. In certain further embodiments of the cell-targeted molecule of the invention, the Shiga toxin effector polypeptide comprises a mutation relative to a naturally occurring A Subunit of a member of the Shiga toxin family which reduces or eliminates the enzymatic activity of the Shiga toxin effector polypeptide but does not reduce the subcellular routing to the cytosol of at least a part of the Shiga toxin effector polypeptide below the subcellular routing level of a wild-type, Shiga toxin effector polypeptide. In certain embodiments, the cell-targeted molecule of the present invention does not comprise a carboxy-terminal, binding region comprising a fragment of an immune cell surface receptor. In certain embodiments of the cell-targeted molecule of the present invention, the binding region does not comprise a fragment of a human, immune cell surface co-receptor. In certain further embodiments of the cell-targeted molecule of the present invention, the binding region does not comprise a fragment of human CD4, a type-I transmembrane glycoprotein. In certain embodiments, the cell-targeted molecules of the present invention does not comprise a Shiga toxin effector polypeptide comprising amino acids 1-247 of SEQ ID NO:2, 45-247 of SEQ ID NO:2, and/or 75-247 of SEQ ID NO:2 fused to a carboxy-terminal, binding region comprising a fragment of human CD4 corresponding to amino acid residues 19-183.

In certain embodiments, the cytotoxic, cell targeted molecule of the present invention comprises 1) a binding region capable of specifically binding at least one extracellular target biomolecule; 2) a Shiga toxin effector polypeptide comprising a Shiga toxin A1 fragment region having a carboxy terminus and a disrupted furin-cleavage motif at the carboxy terminus of the A1 fragment region; and 3) a molecular moiety associated with the carboxy terminus of the Shiga toxin effector polypeptide; and wherein the cytotoxic, cell-targeted molecule is capable of exhibiting improved, in vivo tolerability compared to in vivo tolerability of a second cell-targeted molecule consisting of the cell-targeted molecule except for the Shiga toxin effector polypeptide consists of a wild-type, Shiga toxin A1 polypeptide. This means the second cell-targeted molecule comprises the same binding region and the same molecular moiety as the cytotoxic, cell-targeted molecule of the invention but instead of comprising the same Shiga toxin effector polypeptide, the second cell-targeted molecule comprises a wild-type, Shiga toxin effector polypeptide comprising a Shiga toxin A1 fragment region having a carboxy terminus and a wild-type furin-cleavage site at the carboxy terminus of the A1 fragment region of the wild-type, Shiga toxin effector polypeptide; wherein the molecular moiety associated with the carboxy terminus of the wild-type, Shiga toxin A1 polypeptide with the same association as in the first cell-targeted molecule. In certain embodiments of the cytotoxic, cell targeted molecule of the invention, the Shiga toxin effector polypeptide is not cytotoxic and the molecular moiety is toxic. In certain embodiments of the cytotoxic, cell-targeted molecule of the invention, the molecular moiety sterically covers the carboxy terminus of the A1 fragment region. In certain embodiments of the cytotoxic, cell-targeted molecule of the invention, the binding region sterically covers the carboxy terminus of the A1 fragment region. In certain embodiments of the cytotoxic, cell targeted molecule of the invention, the molecular moiety comprises the binding region. In certain embodiments of the cytotoxic, cell-targeted molecule of the invention, the Shiga toxin effector polypeptide is linked to the molecular moiety by at least one covalent bond which is not a disulfide bond. In certain further embodiments, the molecular moiety comprises at least one amino acid residue fused to the carboxy terminus of the Shiga toxin effector polypeptide. In certain further embodiments of the cytotoxic, cell-targeted molecule of the invention, the molecular moiety comprises a polypeptide fused to the carboxy terminus of the Shiga toxin effector polypeptide to form a single, continuous polypeptide. In certain embodiments of the cytotoxic, cell-targeted molecule of the invention, the molecular moiety comprises a peptide and/or polypeptide derived from the Shiga toxin A2 fragment of a naturally occurring Shiga toxin. For certain further embodiments, administration of the cytotoxic, cell-targeted molecule of the invention to two different populations of cell types which differ with respect to the presence or level of an extracellular target biomolecule, the cell-targeted molecule is capable of causing cell death of the cell-types physically coupled with an extracellular target biomolecule of the cell-targeted molecule's binding region at a $CD_{50}$ that is at least three times less than the $CD_{50}$ observed for cell types which are not physically coupled with an extracellular target biomolecule of the cell-targeted molecule's binding region. For certain embodiments, administration of the cytotoxic, cell-targeted molecule of the invention to a first population of cells whose members are physically coupled to extracellular target biomolecules of the cell-targeted molecule's binding region, and a second population of cells whose members are not physically coupled to any extracellular target biomolecule of the binding region, the cytotoxic effect of the cell-targeted molecule to members of said first population of cells relative to members of said second population of cells is at least 3-fold greater. For certain embodiments, administration of the cytotoxic, cell-targeted molecule of the invention to a first population of cells whose members are physically coupled to a significant amount of the extracellular target biomolecule of the cell-targeted molecule's binding region, and a second population of cells whose members are not physically coupled to a significant amount of any extracellular target biomolecule of the binding region, the cytotoxic effect of the cell-targeted molecule to members of said first population of cells relative to members of said second population of cells is at least 3-fold greater. For certain embodiments, administration of the cytotoxic, cell-targeted molecule of the invention to a first population of target biomolecule positive cells, and a second population of cells whose members do not express a significant amount of a target biomolecule of the cell-targeted molecule's binding region at a cellular surface, the cytotoxic effect of the cell-targeted molecule to members of the first population of cells relative to members of the second population of cells is at least 3-fold greater. In certain embodiments of the cytotoxic, cell targeted molecule of the invention, the binding region comprises a polypeptide comprising an immunoglobulin-type binding region. In certain further embodiments of the cytotoxic, cell-targeted molecule of the invention, the immunoglobulin-type binding region is selected from the group consisting of: single-domain antibody (sdAb) fragment, nanobody, heavy-chain antibody domain derived from a camelid ($V_HH$ fragment), heavy-chain antibody domain derived from a cartilaginous fish, immunoglobulin new antigen receptor (IgNAR), $V_{NAR}$ fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronectin-derived $10^{th}$ fibronectin type III domain (10Fn3), tenascin type III domain, ankyrin repeat motif domain, low-density-lipoprotein-receptor-derived A-domain (LDLR-A), lipocalin (anticalin), Kunitz domain, Protein-A-derived Z domain, gamma-B crystalline-derived domain, ubiquitin-derived domain, Sac7d-derived polypeptide (affitin), Fyn-derived SH2 domain, miniprotein, C-type lectin-like domain scaffold, engineered antibody mimic, and any genetically manipulated counterparts of any of the foregoing which retain binding functionality. In certain further embodiments of the cytotoxic, cell-targeted molecule of the invention, the Shiga toxin effector polypeptide comprises or consists essentially of the polypeptide shown in any one of SEQ ID NOs: 4-49. In certain further embodiments of the cytotoxic, cell-targeted molecule of the invention, the molecular moiety comprises at least one amino acid residue fused to the carboxy terminus of the Shiga toxin effector polypeptide, either directly or indirectly. In certain further embodiments, the cytotoxic, cell-targeted molecule of the invention comprises or consists essentially of the polypeptide shown in any one of SEQ ID NOs: 50-61. In certain further embodiments, the cytotoxic, cell-targeted molecule of the invention further comprises a carboxy-terminal endoplasmic reticulum retention/retrieval signal motif of a member of the KDEL family ('KDEL' disclosed as SEQ ID NO: 62). In certain further embodiments, the cytotoxic, cell-targeted molecule of the invention comprises the carboxy-terminal endoplasmic reticulum retention/retrieval signal motif selected from the group consisting of: KDEL (SEQ ID NO: 62), HDEF (SEQ ID NO: 63), HDEL (SEQ ID NO: 64), RDEF (SEQ ID NO: 65), RDEL (SEQ ID NO:-66), WDEL (SEQ ID NO: 67), YDEL (SEQ ID NO: 68), HEEF (SEQ ID NO: 69, HEEL (SEQ ID NO: 70), KEEL (SEQ ID NO: 71), REEL (SEQ ID NO: 72), KAEL (SEQ ID NO: 73), KCEL (SEQ ID NO: 74), KFEL (SEQ ID NO: 75), KGEL (SEQ ID NO: 76), KHEL (SEQ ID NO:-77), KLEL (SEQ ID NO: 78), KNEL (SEQ ID NO: 79), KQEL (SEQ ID NO: 80), KREL (SEQ ID NO: 81), KSEL (SEQ ID NO: 82), KVEL (SEQ ID NO: 83), KWEL (SEQ ID NO: 84), KYEL (SEQ ID NO: 85), KEDL (SEQ ID NO: 86), KIEL (SEQ ID NO: 87), DKEL (SEQ ID NO:-88), FDEL (SEQ ID NO: 89), KDEF (SEQ ID NO: 90), KKEL (SEQ ID NO: 91), HADL (SEQ ID NO: 92), HAEL (SEQ ID NO: 93), HIEL (SEQ ID NO: 94), HNEL (SEQ ID NO: 95), HTEL (SEQ ID NO: 96), KTEL (SEQ ID NO: 97), HVEL (SEQ ID NO: 98), NDEL (SEQ ID NO:-99), QDEL (SEQ ID NO: 100), REDL (SEQ ID NO: 101), RNEL (SEQ ID NO: 102), RTDL (SEQ ID NO: 103), RTEL (SEQ ID NO: 104), SDEL (SEQ ID NO: 105), TDEL (SEQ ID NO:-106), and SKEL (SEQ ID NO: 107). In certain further embodiments of the cytotoxic, cell-targeted molecule of the invention, the Shiga toxin effector polypeptide comprises a mutation relative to a naturally occurring A Subunit of a member of the Shiga toxin family which reduces or eliminates the enzymatic activity of the Shiga toxin effector polypeptide but does not reduce the subcellular routing to the cytosol of at least a part of the Shiga toxin effector polypeptide below the subcellular routing level of a wild-type, Shiga toxin effector polypeptide.

In certain embodiments, the cell-targeted molecule of the present invention, whether cytotoxic or non-cytotoxic, does not comprise a naturally occurring Shiga toxin B Subunit. In certain embodiments, the cell-targeted molecule of the invention does not comprise any polypeptide comprising or consisting essentially of a functional binding domain of a native, Shiga toxin B subunit. Rather, in certain embodiments of the cell-targeted molecules of the invention, the Shiga toxin A Subunit derived regions are functionally associated with heterologous binding regions to effectuate cell targeting.

In certain embodiments, the cell-targeted molecule of the present invention, whether cytotoxic or non-cytotoxic, does not comprise any Shiga toxin A2 fragment of a member of the Shiga toxin family or functional fragment thereof. In certain embodiments, the cell-targeted molecule of the invention does not comprise, carboxy-terminal of the disrupted furin-cleavage motif, any amino acid sequence from a native, wild-type, Shiga toxin A2 fragment.

In certain embodiments, the cytotoxic molecule of the present invention does not comprise any Shiga toxin A2 fragment of a member of the Shiga toxin family or functional fragment thereof. In certain embodiments, the cytotoxic molecule of the present invention does not comprise, carboxy-terminal of the disrupted furin-cleavage motif, any amino acid sequence from a native, wild-type, Shiga toxin A2 fragment.

In certain embodiments of the cytotoxic, cell-targeted molecule of the present invention, the Shiga toxin effector polypeptide does not consist of the polypeptide shown in SEQ ID NO:2 further comprising both of the following amino acid residue substitutions: R248H and R251H. In certain embodiments of the cytotoxic, cell-targeted molecule, the Shiga toxin effector polypeptide does not comprise both of the following amino acid residue substitutions: R248H and R251H. In certain embodiments of the cytotoxic, cell-targeted molecule, the Shiga toxin effector polypeptide does not consist of the polypeptide shown in SEQ ID NO:1 further comprising both of the following amino acid residue substitutions: R248G and R251G. In certain embodiments of the cytotoxic, cell-targeted molecule, the Shiga toxin effector polypeptide does not comprise both of the following amino acid residue substitutions: R248G and R251G. In certain embodiments of the cytotoxic, cell-targeted molecule, the Shiga toxin effector polypeptide does not consist of the polypeptide shown in SEQ ID NO:1 further comprising all of the following amino acid residue substitutions: A246G, S247A, A253G, and S254A. In certain embodiments of the cytotoxic, cell-targeted molecule, the Shiga toxin effector polypeptide does not comprise all of the following amino acid residue substitutions: A246G, S247A, A253G, and S254A. In certain embodiments of the cytotoxic, cell-targeted molecule, the Shiga toxin effector polypeptide does not consist of the polypeptide shown in SEQ ID NO:1 further comprising all of the following amino acid residue substitutions: A246G, S247A, R248G, R251G, A253G, and S254A. In certain embodiments of the cytotoxic, cell-targeted molecule, the Shiga toxin effector polypeptide does not comprise all of the following amino acid residue substitutions: A246G, S247A, R248G, R251G, A253G, and S254A. In certain embodiments of the cytotoxic, cell-targeted molecule, the Shiga toxin effector polypeptide does not consist of the polypeptide shown in SEQ ID NO:2 further comprising the deletion of the region natively positioned at 247-252. In certain embodiments of the cytotoxic, cell-targeted molecule, the Shiga toxin effector polypeptide does not comprise a Shiga toxin effector polypeptide comprising the deletion of the region natively positioned at 247-252. In certain embodiments of the cytotoxic, cell-targeted molecule, the Shiga toxin effector polypeptide does not consist of the polypeptide shown in SEQ ID NO:2 further comprising both of the following deletions: 245-247 and 253-255. In certain embodiments of the cytotoxic, cell-targeted molecule, the Shiga toxin effector polypeptide does not comprise both of the following deletions: 245-247 and 253-255.

The present invention also provides pharmaceutical compositions comprising a molecule of the invention and at least one pharmaceutically acceptable excipient or carrier; and the use of such a molecule or a composition comprising it in making such pharmaceutical compositions and in methods of the invention as further described herein. In certain embodiments of the present invention are pharmaceutical compositions comprising any cytotoxic molecule of the present invention and at least one pharmaceutically acceptable excipient or carrier.

Beyond the molecules of the present invention, polynucleotides capable of encoding any of the foregoing, e.g., a polypeptide comprising a protease-cleavage resistant, Shiga toxin effector polypeptide or protein of a molecule of the present invention, are within the scope of the present invention, as well as expression vectors which comprise a polynucleotide of the invention and host cells comprising an expression vector of the invention. Host cells comprising an expression vector may be used, e.g., in methods for producing a molecule of the invention (e.g. polypeptide or protein), or a polypeptide component or fragment thereof, by recombinant expression.

The present invention also encompasses any composition of matter of the present invention which is immobilized on a solid substrate. Such arrangements of the compositions of matter of the present invention may be utilized, e.g., in methods of screening molecules as described herein.

Beyond the compositions of matter of the present invention, the present invention is directed to a variety of methods, such as, e.g., methods which use a composition of matter of the invention and/or methods which create a composition of matter of the invention.

In certain embodiments of the present invention is a method for improving the in vivo tolerability and/or in vitro stability of a molecule comprising 1) a Shiga toxin effector polypeptide comprising a Shiga toxin A1 fragment region having a carboxy terminus and a furin-cleavage site proximal to the carboxy terminus of the A1 fragment region, and 2) a heterologous, molecular moiety associated with the carboxy terminus of the Shiga toxin effector polypeptide and comprising a binding region capable of specifically binding at least one extracellular target biomolecule; the method comprising the step of disrupting a furin-cleavage motif comprising the furin-cleavage site. In certain embodiments of this method, the disrupting step involves creating a mutation, truncation, and/or amino acid functional group modification which reduces the protease-cleavage sensitivity of the carboxy terminus of the Shiga toxin effector polypeptide. In certain embodiments of this method, the heterologous, molecular moiety sterically covers the carboxy terminus of the A1 fragment region. The present invention also encompasses any molecule created using this method which is capable of exhibiting improved in vivo tolerability as compared to a parental molecule comprising an undisrupted furin-cleavage motif proximal to the carboxy terminus of the A1 fragment region.

In certain embodiments of the present invention is a method for improving the in vivo tolerability and/or in vitro stability of a molecule comprising 1) a Shiga toxin effector polypeptide comprising a Shiga toxin A1 fragment region having a carboxy terminus and a furin-cleavage site proximal to the carboxy terminus of the A1 fragment region, and 2) a heterologous, molecular moiety associated with the carboxy terminus of the Shiga toxin effector polypeptide and which is toxic; the method comprising the step of disrupting a furin-cleavage motif comprising the furin-cleavage site. In certain embodiments of this method, the disrupting step involves creating a mutation, truncation, and/or amino acid functional group modification which reduces the protease-cleavage sensitivity of the carboxy terminus of the Shiga toxin effector polypeptide. In certain embodiments of this method, the heterologous, molecular moiety sterically covers the carboxy terminus of the A1 fragment region. The present invention also encompasses any molecule created using this method which is capable of exhibiting improved in vivo tolerability as compared to a parental molecule comprising an undisrupted furin-cleavage motif proximal to the carboxy terminus of the A1 fragment region.

Among certain embodiments of the present invention is a method of killing a cell comprising the step of contacting the cell with any of the above cell-targeted molecules of the present invention or the above pharmaceutical composition of the present invention. In certain embodiments, the step of contacting the cell(s) occurs in vitro. In certain other embodiments, the step of contacting the cell(s) occurs or in vivo. In further embodiments of the cell killing methods, the method is capable of selectively killing cell(s) and/or cell types preferentially over other cell(s) and/or cell types when contacting a mixture of cells which differ with respect to the extracellular presence and/or expression level of an extracellular target biomolecule of the binding region of the protein.

The present invention further provides methods of treating diseases, disorders, and/or conditions in patients comprising the step of administering to a patient in need thereof a therapeutically effective amount of a molecule or a pharmaceutical composition of the invention. In certain embodiments, the disease, disorder, or condition to be treated using this method of the invention is selected from: a cancer, tumor, growth abnormality, immune disorder, or microbial infection. In certain embodiments of this method, the cancer to be treated is selected from the group consisting of: bone cancer, breast cancer, central/peripheral nervous system cancer, gastrointestinal cancer, germ cell cancer, glandular cancer, head-neck cancer, hematological cancer, kidney-urinary tract cancer, liver cancer, lung/pleura cancer, prostate cancer, sarcoma, skin cancer, and uterine cancer. In certain embodiments of this method, the immune disorder to be treated is an immune disorder associated with a disease selected from the group consisting of: amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjorgren's syndrome, ulcerative colitis, and vasculitis.

Among certain embodiments of the present invention is a composition comprising a molecule of the invention (e.g. polypeptide or protein), compound comprising a molecule of the invention, or a composition of the invention (e.g. pharmaceutical composition) for the treatment or prevention of a cancer, immune disorder, or microbial infection. Among certain embodiments of the present invention is the use of a compound (e.g. protein) or composition of the invention in the manufacture of a medicament for the treatment or prevention of a cancer, tumor, immune disorder, or microbial infection.

Certain embodiments of the molecules of the present invention may be used to deliver one or more additional exogenous materials into a cell physically coupled with an extracellular target biomolecule of the molecule of the present invention. Additionally, the present invention provides a method for delivering exogenous material to the inside of a cell(s) comprising contacting the cell(s), either in vitro or in vivo, with a molecule, pharmaceutical composition, and/or diagnostic composition of the present invention. The present invention further provides a method for delivering exogenous material to the inside of a cell(s) in a patient in need thereof, the method comprising the step of administering to the patient a molecule of the present invention, wherein the target cell(s) is physically coupled with an extracellular target biomolecule of the molecule of the present invention.

The use of any composition of the present invention (e.g. a cell-targeted molecule, a pharmaceutical composition, or diagnostic composition) for the diagnosis, prognosis, and/or characterization of a disease, disorder, and/or condition is within the scope of the present invention. Among certain embodiments of the present invention is the use of one or more compositions of matter of the invention (e.g. a pharmaceutical composition) in the treatment or prevention of a cancer, tumor, or immune disorder. Among certain embodiments of the present invention is the use of one or more compositions of matter of the invention (e.g. a pharmaceutical composition) in the manufacture of a medicament for the treatment or prevention of a cancer, tumor, or immune disorder.

Among certain embodiments of the present invention is a diagnostic composition comprising a molecule of the invention (e.g. molecule, cell-targeted molecule, polypeptide or protein) and a detection promoting agent for the collection of information, such as diagnostically useful information about a cell type, tissue, organ, disease, disorder, condition, and/or patient.

Among certain embodiments of the present invention is the method of detecting a cell using a molecule and/or diagnostic composition of the invention comprising the steps of contacting a cell with said molecule and/or diagnostic composition and detecting the presence of said molecule and/or diagnostic composition. In certain embodiments, the step of contacting the cell(s) occurs in vitro. In certain embodiments, the step of contacting the cell(s) occurs or in vivo. In certain embodiments, the step of detecting the cell(s) occurs in vitro. In certain embodiments, the step of detecting the cell(s) occurs or in vivo.

For example, a diagnostic composition of the invention may be used to detect a cell in vivo by administering to a mammalian subject a composition comprising molecule of the present invention which comprises a detection promoting agent and detecting the presence of the molecule of the present invention either in vitro or in vivo. The information collected may regard the presence of a cell physically coupled with an extracellular target of the binding region of the molecule of the present invention and may be useful in the diagnosis, prognosis, characterization, and/or treatment of a disease, disorder, or condition. Certain compounds (e.g. polypeptides and proteins), compositions (e.g. pharmaceutical compositions), and methods of the invention may be used to determine if a patient belongs to a group that responds to a pharmaceutical composition of the invention.

Among certain embodiments of the present invention are kits comprising a composition of matter of the present invention, and optionally, instructions for use, additional reagent(s), and/or pharmaceutical delivery device(s).

These and other features, aspects and advantages of the present invention will become better understood with regard to the following description, appended claims, and accompanying figures. The aforementioned elements of the invention may be individually combined or removed freely in order to make other embodiments of the invention, without any statement to object to such combination or removal hereinafter.

BRIEF DESCRIPTION OF THE FIGURES

FIG. 1 shows the general arrangement of certain exemplary molecules of the invention, each comprising a protease-cleavage resistant, Shiga toxin A Subunit effector polypeptide. Certain exemplary molecules of the invention comprise a protease-cleavage resistant, Shiga toxin A Subunit effector polypeptide associated, proximal to its carboxy terminus, with a molecular moiety. The "N" and "C" denote an amino-terminus and carboxy-terminus, respectively, of a polypeptide component of the molecule.

FIG. 2 shows the furin-cleavage resistance of the exemplary, cytotoxic, cell-targeted molecule (SLT-1A-FR::scFv-1), which comprises a Shiga toxin effector polypeptide comprising a disrupted furin-cleavage motif, as compared to a nearly identical, cytotoxic, cell-targeted molecule comprising a Shiga toxin effector polypeptide comprising a wild-type, furin-cleavage site. FIG. 2 shows a Coomassie-stained, polyacrylamide gel after electrophoresis of protein samples treated with either purified, recombinant, human furin or various negative control conditions. The lanes of the gel are numbered, and the figure legend indicates pre-treatment conditions of each cell-targeted molecule sample prior to loading sample to the gel: the temperature in degrees Celsius (° C.), the pre-treatment duration in hours (denoted by "hrs"), and whether any furin was added by denoting the amount of furin activity units (U) per microgram (μg) of sample cytotoxic protein (labeled "U/μg furin") or "no furin" for zero U/μg furin. The lane marked "L" shows the migration pattern of a protein molecular weight ladder, and the approximate size of each ladder protein band is labeled in kiloDaltons (kDa). The figure legend indicates which Shiga toxin effector polypeptide was present in each cell-targeted molecule sample per lane, either 1) a wild-type furin-cleavage site (WT) or 2) a disrupted furin-cleavage motif (FR). The treated samples were subjected to 0.5 furin activity units per microgram of cell-targeted molecule (U/µg furin) at 30° C. for 25 hours (hrs). FIG. 2 shows SLT-1A-FR::scFv-1 was resistant to 0.5 furin activity units per microgram of SLT-1A-FR::scFv-1 at 30° C.

FIG. 3 shows the furin resistance at multiple temperatures of the exemplary, cytotoxic, cell-targeted molecule (SLT-1A-FR::scFv-2), which comprises a Shiga toxin effector polypeptide comprising a disrupted furin-cleavage motif. FIG. 3 shows a Coomassie-stained, polyacrylamide gel after electrophoresis of protein samples treated with either purified, recombinant, human furin or no furin. The lanes of the gel are numbered, and the figure legend indicates pre-treatment conditions of each cell-targeted molecule sample prior to loading sample to the gel: the temperature in degrees Celsius (° C.), the pre-treatment duration in hours (denoted by "hrs"), and whether any furin was added by denoting the amount of furin activity units per microgram of sample cytotoxic protein (labeled "U/µg furin") or "no furin" for zero U/µg furin. The lane marked "L" shows the migration pattern of a protein molecular weight ladder, and the approximate size of each ladder protein band is labeled in kiloDaltons (kDa). FIG. 3 shows SLT-1A-FR::scFv-2 was resistant to 0.5 furin activity units per microgram of SLT-1A-FR::scFv-2 at temperatures ranging from 4° to 37° C.

FIG. 4 graphically shows that the exemplary, protease-cleavage resistant, cytotoxic, cell-targeted molecule SLT-1A-FR::scFv-1 exhibited cell-targeted cytotoxicity comparable to a nearly identical, cytotoxic, cell-targeted molecule comprising a Shiga toxin effector polypeptide with a wild-type, furin-cleavage site. The percent viability of target positive cells was plotted over the logarithm to base 10 of the cell-targeted molecule concentration administered to the cells.

FIG. 5 graphically shows that the exemplary, protease-cleavage resistant, cytotoxic, cell-targeted molecule SLT-1A-FR::scFv-1 exhibited non-targeted cytotoxicity comparable a nearly identical, cytotoxic, cell-targeted molecule comprising a Shiga toxin effector polypeptide with a wild-type, furin-cleavage site. SLT-1A-FR::scFv-1 also showed non-targeted cytotoxicity comparable to an untargeted, wild-type, Shiga toxin A Subunit construct. The percent viability of target negative cells was plotted over the logarithm to base 10 of the cell-targeted molecule concentration administered to the cells.

FIG. 6 shows the improved survival of mice administered repeat doses of SLT-A1-FR::scFv-1 as compared to SLT-A1-WT::scFv-1. FIG. 6 shows Kaplan-Meier survival plots of mice administered 2.5 milligram per kilogram of body mass per injection of protease-cleavage sensitive SLT-1A-WT::scFv-1 or the exemplary, cytotoxic, cell-targeted molecule SLT-1A-FR::scFv-1 for a total of three injections. The y-axis is in percent survival of mice within a dosage group, and the x-axis is in days. Mice exhibited superior tolerability to the protease-cleavage resistant, cell-targeted molecule SLT-1A-FR::scFv-1 over time as compared to their tolerability of the protease-cleavage sensitive SLT-1A-WT::scFv-1.

FIG. 7 shows the exemplary, cytotoxic, cell-targeted molecule SLT-1A-FR::scFv-2 inhibited the growth of target positive, human tumor cells in vivo in a murine xenograft model of human cancer. FIG. 7 shows the tumor burden as assayed by bioluminescence per individual mouse over time based on the expression of a luciferase reporter by human tumor cells. An individual mouse is represented by each symbol plotted on the graph, i.e. open triangle, filled triangle, open circle, or filled square. The Y-axis is the total bioluminescence signal of an individual mouse, which represents the tumor burden, in millions of photons per second (photons/sec), and the X-axis is the injection dose which ranged from 0 to 2 milligrams of SLT-1A-FR::scFv-2 per kilogram of body mass per injection. The four, x-axis, dose groups correspond to four groups of mice. The experiment included four groups of ten mice divided by the injection dosage of exemplary, cytotoxic, cell-targeted molecule received: Group #1—mice received zero milligrams of SLT-1A-FR::scFv-2, Group #2—mice received 0.05 milligrams of SLT-1A-FR::scFv-2 per kilogram of body mass, Group #3—mice received 0.5 milligrams of SLT-1A-FR::scFv-2 per kilogram of body mass, and Group #4—mice received 2 milligrams of SLT-1A-FR::scFv-2 per kilogram of body mass. The experiment was run for at least 4 weeks. FIG. 7 shows both the dosage- and time-dependence of the inhibition of human tumor cell growth exhibited by the exemplary, cytotoxic, protease-cleavage resistant, cell-targeted molecule SLT-1A-FR::scFv-2.

DETAILED DESCRIPTION

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope of the invention to those skilled in the art.

In order that the present invention may be more readily understood, certain terms are defined below. Additional definitions may be found within the detailed description of the invention.

As used in the specification and the appended claims, the terms "a," "an" and "the" include both singular and the plural referents unless the context clearly dictates otherwise.

As used in the specification and the appended claims, the term "and/or" when referring to two species, A and B, means at least one of A and B. As used in the specification and the appended claims, the term "and/or" when referring to greater than two species, such as A, B, and C, means at least one of A, B, or C, or at least one of any combination of A, B, or C (with each species in singular or multiple possibility).

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout this specification, the term "including" is used to mean "including but not limited to." "Including" and "including but not limited to" are used interchangeably.

The term "amino acid residue" or "amino acid" includes reference to an amino acid that is incorporated into a protein, polypeptide, or peptide. The term "polypeptide" includes any polymer of amino acids or amino acid residues. The term "polypeptide sequence" refers to a series of amino acids or amino acid residues which physically compose a polypeptide. A "protein" is a macromolecule comprising one or more polypeptides or polypeptide "chains." A "peptide" is a small polypeptide of sizes less than a total of 15-20 amino acid residues. The term "amino acid sequence" refers to a series of amino acids or amino acid residues which physically comprise a peptide or polypeptide depending on the length. Unless otherwise indicated, polypeptide and protein sequences disclosed herein are written from left to right representing their order from an amino terminus to a carboxy terminus.

The terms "amino acid," "amino acid residue," "amino acid sequence," or polypeptide sequence include naturally occurring amino acids (including L and D isosteriomers) and, unless otherwise limited, also include known analogs of natural amino acids that can function in a similar manner as naturally occurring amino acids, such as selenocysteine, pyrrolysine, N-formylmethionine, gamma-carboxyglutamate, hydroxyprolinehypusine, pyroglutamic acid, and selenomethionine. The amino acids referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid or Aspartate | Asp | D |
| Cysteine | Cys | C |
| Glutamic Acid or Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The phrase "conservative substitution" with regard to a polypeptide, refers to a change in the amino acid composition of the polypeptide that does not substantially alter the function and structure of the overall polypeptide (see Creighton, *Proteins: Structures and Molecular Properties* (W. H. Freeman and Company, New York (2nd ed., 1992)).

As used herein, the terms "expressed," "expressing," or "expresses," and grammatical variants thereof, refer to translation of a polynucleotide or nucleic acid into a polypeptide or protein. The expressed polypeptides or proteins may remain intracellular, become a component of the cell surface membrane or be secreted into an extracellular space.

As used herein, cells which express a significant amount of an extracellular target biomolecule at least one cellular surface are "target positive cells" or "target+ cells" and are cells physically coupled to the specified extracellular target biomolecule.

As used herein, the symbol "α" is shorthand for an immunoglobulin-type binding region capable of binding to the biomolecule following the symbol. The symbol "α" is used to refer to the functional characteristic of an immunoglobulin-type binding region based on its capability of binding to the biomolecule following the symbol.

For purposes of the claimed invention, the term "associated" or "association" with regard to two molecular components refers to the state of the two components being joined, attached, connected, linked, or otherwise coupled to form a single molecule and includes covalent and/or non-covalent associations.

For purposes of the present invention, the term "linked" refer to two or more molecular components associated by one or more atomic interactions such that a single molecule is formed and wherein the atomic interactions includes at least one covalent bond.

For purposes of the present invention, the term "fused" refers to two or more proteinaceous components associated by at least one covalent bond which is a peptide bond. Non-limiting examples of two proteinaceous components fused together include, e.g., an amino acid, peptide, or polypeptide fused to a polypeptide via a peptide bond such that the resulting molecule is a single, continuous polypeptide.

The symbol "::" means the polypeptide regions before and after it are fused together to form a continuous polypeptide.

For purposes of the present invention, the term "effector" means providing a biological activity, such as cytotoxicity, biological signaling, enzymatic catalysis, subcellular routing, and/or intermolecular binding resulting in the recruitment of a factor(s) and/or allosteric effect(s).

For purposes of the present invention, the phrase "Shiga toxin effector polypeptide," "Shiga toxin A Subunit effector polypeptide," "Shiga toxin effector region," or "Shiga toxin effector polypeptide region" refers to a polypeptide derived from a Shiga toxin A Subunit of a member of the Shiga toxin family that is capable of exhibiting at least one Shiga toxin function. Shiga toxin functions include, e.g., promoting cell entry, deforming lipid membranes, stimulating clathrin-mediated endocytosis, directing its own subcellular routing, directing its own retrograde transport, avoiding intracellular degradation, catalytically inactivating ribosomes, effectuating cytotoxicity, and effectuating cytostatic effects.

For purposes of the present invention, the phrase "derived from" means that the polypeptide comprises amino acid sequences originally found in a protein and which may now comprise additions, deletions, truncations, or other alterations from the original sequence such that overall function and structure are substantially conserved. The skilled worker will be able to identify the parental molecule from which a derived polypeptide region was derived using techniques known in the art, e.g., polypeptide sequence alignment software.

For purposes of the present invention, the term "Shiga toxin A1 fragment region" refers to a polypeptide region consisting essentially of a Shiga toxin A1 fragment and/or derived from a Shiga toxin A1 fragment of a Shiga toxin.

For purposes of the present invention, the term "heterologous" means of a different source than a Shiga holotoxin, e.g. a heterologous molecular moiety or polypeptide is one that is not natively found as part of or linked to a naturally occurring, A Subunit of a native, Shiga toxin expressed by a naturally occurring bacterial species.

For purposes of the present invention and with regard to the associations between components of a molecule of the present invention, the term "disulfide bond" includes symmetric disulfide bonds and unsymmetric disulfide bonds.

For purposes of the present invention, the phrase "carboxy terminus region of a Shiga toxin A1 fragment" refers to a polypeptide region derived from a naturally occurring Shiga toxin A1 fragment, the region beginning with a hydrophobic residue (e.g. V236 of StxA-A1 and SLT-1A1, and V235 of SLT-2A1) that is followed by a hydrophobic residue and the region ending with the furin-cleavage site conserved among Shiga toxin A1 fragment polypeptides and ending at the junction between the A1 fragment and the A2 fragment in native, Shiga toxin A Subunits. For purposes of the present invention, the carboxy-terminal region of a Shiga toxin A1 fragment includes a peptidic region derived from the carboxy terminus of a Shiga toxin A1 fragment polypeptide, such as, e.g., a peptidic region comprising or consisting essentially of the carboxy terminus of a Shiga toxin A1 fragment. Non-limiting examples of peptidic regions derived from the carboxy terminus of a Shiga toxin A1 fragment include the amino acid residue sequences natively positioned from position 236 to position 239, 240, 241, 242, 243, 244, 245, 246, 247, 248, 249, 250, or 251 in Stx1A (SEQ ID NO:2) or SLT-1A (SEQ ID NO:1); and from position 235 to position 239, 240, 241, 242, 243, 244, 245, 246, 247, 248, 249, or 250 in SLT-2A (SEQ ID NO:3).

For purposes of the present invention, the term "proximal" to the carboxy terminus of an A1 fragment polypeptide with regard to an associated molecular moiety refers to molecular distance of twelve, amino acid residues or less of the amino acid residue defining the last residue in the A1 fragment polypeptide region.

For purposes of the present invention, the phrase "sterically covers the carboxy terminus of the A1 fragment-derived region" includes any molecular moiety of a size of 4.5 kDa or greater covalently linked to an amino acid residue in the carboxy terminus of the A1 fragment-derived region, such as, e.g., the amino acid residue derived from the amino acid residue natively positioned at any one of positions 236 to 251 in Stx1A (SEQ ID NO:2) or SLT-1A (SEQ ID NO:1) or from 235 to 250 in SLT-2A (SEQ ID NO:3). For purposes of the present invention, the phrase "sterically covers the carboxy terminus of the A1 fragment-derived region" also includes any molecular moiety of a size of 4.5 kDa or greater covalently linked to an amino acid residue in the carboxy terminus of the A1 fragment-derived region, such as, e.g., the amino acid residue carboxy terminal to the last amino acid A1 fragment-derived region or the Shiga toxin effector polypeptide. For purposes of the present invention, the phrase "sterically covers the carboxy terminus of the A1 fragment-derived region" also includes any molecular moiety of a size of 4.5 kDa or greater physically preventing cellular recognition of the carboxy terminus of the A1 fragment-derived region, such as, e.g. recognition by the ERAD machinery.

For purposes of the claimed invention, the phrase "furin-cleavage motif at the carboxy terminus of the A1 fragment region" refers to a specific, furin-cleavage motif conserved among Shiga toxin A Subunits and bridging the junction between the A1 fragment and the A2 fragment in native, Shiga toxin A Subunits.

For purposes of the present invention, the phrase "furin-cleavage site proximal to the carboxy terminus of the A1 fragment region" refers to any identifiable, furin-cleavage site having an amino acid residue within seven, amino acid residues or less of the amino acid residue defining the last residue in the A1 fragment region.

For purposes of the present invention, a Shiga toxin effector function is a biological activity conferred by a polypeptide derived from a Shiga toxin A Subunit. Non-limiting examples of Shiga toxin effector functions include cellular internalization, subcellular routing, catalytic activity, and cytotoxicity. Shiga toxin catalytic activities include, for example, ribosome inactivation, protein synthesis inhibition, N-glycosidase activity, polynucleotide:adenosine glycosidase activity, RNAase activity, and DNAase activity. Shiga toxins are ribosome inactivating proteins (RIPs). RIPs can depurinate nucleic acids, polynucleosides, polynucleotides, rRNA, ssDNA, dsDNA, mRNA (and polyA), and viral nucleic acids (Barbieri L et al., *Biochem J* 286: 1-4 (1992); Barbieri L et al., *Nature* 372: 624 (1994); Ling J et al., *FEBS Lett* 345: 143-6 (1994); Barbieri L et al., *Biochem J* 319: 507-13 (1996); Roncuzzi L, Gasperi-Campani A, *FEBS Lett* 392: 16-20 (1996); Stirpe F et al., *FEBS Lett* 382: 309-12 (1996); Barbieri L et al., *Nucleic Acids Res* 25: 518-22 (1997); Wang P, Tumer N, *Nucleic Acids Res* 27: 1900-5 (1999); Barbieri L et al., *Biochim Biophys Acta* 1480: 258-66 (2000); Barbieri L et al., *J Biochem* 128: 883-9 (2000); Brigotti M et al., *Toxicon* 39: 341-8 (2001); Brigotti M et al., *FASEB J* 16: 365-72 (2002); Bagga S et al., *J Biol Chem* 278: 4813-20 (2003); Picard D et al., *J Biol Chem* 280: 20069-75 (2005)). Some RIPs show antiviral activity and superoxide dismutase activity (Erice A et al., *Antimicrob Agents Chemother* 37: 835-8 (1993); Au T et al., *FEBS Lett* 471: 169-72 (2000); Parikh B, Tumer N, *Mini Rev Med Chem* 4: 523-43 (2004); Sharma N et al., *Plant Physiol* 134: 171-81 (2004)). Shiga toxin catalytic activities have been observed both in vitro and in vivo. Assays for Shiga toxin effector activity can measure various activities, such as, e.g., protein synthesis inhibitory activity, depurination activity, inhibition of cell growth, cytotoxicity, supercoiled DNA relaxation activity, and/or nuclease activity.

As used herein, the retention of Shiga toxin effector function refers to a level of Shiga toxin functional activity, as measured by an appropriate quantitative assay with reproducibility comparable to a wild-type, Shiga toxin effector polypeptide control. For ribosome inhibition, Shiga toxin effector function is exhibiting an $IC_{50}$ of 10,000 picomolar (pM) or less. For cytotoxicity in a target positive cell kill assay, Shiga toxin effector function is exhibiting a $CD_{50}$ of 1,000 nanomolar (nM) or less, depending on the cell type and its expression of the appropriate extracellular target biomolecule.

For purposes of the present invention and with regard to the Shiga toxin effector function of a molecule of the present invention, the term "reasonable activity" refers to an activity level of a Shiga toxin effector biological activity equal or greater to a minimum activity level defined with reference to the Shiga toxin effector activity level of a polypeptide comprising only wild-type, Shiga toxin polypeptide sequences. For the Shiga toxin effector function of cytotoxicity, a reasonable level of activity includes being within 500-fold of a molecule comprising a wild-type, Shiga toxin construct and, if noted, any other molecular structure(s).

As used herein, the exhibition of "significant" Shiga toxin effector function refers to a level of Shiga toxin functional activity, as measured by an appropriate quantitative assay with reproducibility comparable to a wild-type, Shiga toxin effector polypeptide comprising a full-length Shiga toxin A1 fragment. For in vitro ribosome inhibition, significant Shiga toxin effector function is exhibiting an $IC_{50}$ of 300 pM or less depending on the source of the ribosomes (e.g. bacteria, archaea, or eukaryote (algae, fungi, plants, or animals)). This is significantly greater inhibition as compared to the approximate $IC_{50}$ of 100,000 pM for the catalytically inactive SLT-1A 1-251 double mutant (Y77S/E167D). For cytotoxicity in a target positive cell kill assay in laboratory cell culture, significant Shiga toxin effector function is exhibiting a $CD_{50}$ of 100, 50, or 30 nM or less, depending on the cell line and its expression of the appropriate extracellular target biomolecule. This is significantly greater cytotoxicity to the appropriate target cell line as compared to the SLT-1A component alone, without a cell targeting binding region, which has a $CD_{50}$ of 100-10,000 nM, depending on the cell line.

It should be noted that even if the cytotoxicity of a Shiga toxin effector polypeptide is reduced relative to a wild-type Shiga toxin effector, in practice, applications using attenuated, Shiga toxin effector polypeptides may be equally or more effective than those using wild-type, Shiga toxin effector polypeptides because the highest potency variants might exhibit undesirable effects which are minimized or reduced in reduced-potency variants. Wild-type, Shiga toxin effector polypeptides are very potent, being able to kill with only one molecule reaching the cytosol or perhaps 40 molecules being internalized (Tam P, Lingwood C, *Microbiology* 153: 2700-10 (2007)). Shiga toxin effector polypeptides with even considerably reduced Shiga toxin effector functions, such as, e.g., subcellular routing or cytotoxicity, as compared to wild-type, Shiga toxin effector polypeptides may still be potent enough for practical applications involving targeted cell killing and/or detection of certain subcellular compartments of specific cell types.

For some samples, accurate values for either $IC_{50}$ or $CD_{50}$ might be unobtainable due to the inability to collect the required data points for an accurate curve fit. Inaccurate $IC_{50}$ and/or $CD_{50}$ values should not be considered when determining significant Shiga toxin effector function activity. Data insufficient to accurately fit a curve as described in the analysis of the data from exemplary Shiga toxin effector function assays, such as, e.g., assays described in the Examples, should not be considered as representative of actual Shiga toxin effector function. For example, theoretically, neither an $IC_{50}$ nor $CD_{50}$ can be determined if greater than 50% ribosome inhibition or cell death, respectively, does not occur in a concentration series for a given sample.

The failure to detect activity in Shiga toxin effector function may be due to improper expression, polypeptide folding, and/or polypeptide stability rather than a lack of cell entry, subcellular routing, and/or enzymatic activity. Assays for Shiga toxin effector functions may not require much of the molecule of the invention to measure significant amounts of Shiga toxin effector function activity. To the extent that an underlying cause of low or no effector function is determined empirically to relate to protein expression or stability, one of skill in the art may be able to compensate for such factors using protein chemistry and molecular engineering techniques known in the art, such that a Shiga toxin functional effector activity may be restored and measured. As examples, improper cell-based expression may be compensated for by using different expression control sequences; improper polypeptide folding and/or stability may benefit from stabilizing terminal sequences, or compensatory mutations in non-effector regions which stabilize the three-dimensional structure of the protein, etc. When new assays for individual Shiga toxin functions become available, Shiga toxin effector polypeptides may be analyzed for any level of those Shiga toxin effector functions, such as for being within a certain-fold activity of a wild-type, Shiga toxin effector polypeptide. Examples of meaningful activity differences are, e.g., Shiga toxin effector polypeptides that have 1000-fold or 100-fold or less the activity of a wild-type, Shiga toxin effector polypeptide; or that have 3-fold to 30-fold or more activity compared to a functional knock-down or knockout Shiga toxin effector polypeptide.

Certain Shiga toxin effector functions are not easily measurable, e.g. subcellular routing activity. Currently there is no routine, quantitative assay to distinguish whether the failure of a Shiga toxin effector polypeptide to be cytotoxic is due to improper subcellular routing, but at a time when tests are available, Shiga toxin effector polypeptides may be analyzed for any significant level of subcellular routing as compared to the appropriate wild-type, Shiga toxin effector polypeptide. However, if a Shiga toxin effector polypeptide of the invention exhibits cytotoxicity equivalent to a wild-type, Shiga toxin A Subunit construct, then the subcellular routing activity level is inferred to be equivalent to the subcellular routing activity level of a wild-type, Shiga toxin A Subunit construct.

The term "selective cytotoxicity" with regard to the cytotoxic activity of a cytotoxic molecule refers to the relative levels of cytotoxicity between a targeted cell population and a non-targeted bystander cell population, which can be expressed as a ratio of the half-maximal cytotoxic concentration ($CD_{50}$) for a targeted cell type over the $CD_{50}$ for an untargeted cell type to show preferentiality of cell killing of the targeted cell type.

The effectiveness and potency of immunotoxins and ligand-toxin fusions as cytotoxic molecules is influenced by the densities of their target antigen(s) on a target cell surface (see e.g. Decket T et al., *Blood* 103: 2718-26 (2004); Du X et al., *Blood* 111: 338-43 (2008); Baskar S et al., *mAbs* 4: 349-61 (2012)), epitope location (Press 0 et al., *J Immunol* 141: 4410-7 (1988); Godal A et al., *In J Cancer* 52: 631-5 (1992); Yazdi P et al., *Cancer Res* 55: 3763-71 (1995)), rate of internalization of the surface bound cytotoxic molecule (see e.g. Du X et al., *Cancer Res* 68: 6300-5 (2008)), and the intracellular itinerary (Tortorella L et al., *PLoS One* 7: e47320 (2012)).

The cell surface representation and/or density of a given extracellular target biomolecule may influence the applications for which certain cell-targeted molecules of the present invention may be most suitably used. Differences in cell surface representation and/or density of a given target biomolecule between cells may alter the internalization and/or cytotoxicity of a given cell-targeted molecule of the invention both quantitatively and qualitatively. The cell surface representation and/or density of a given target biomolecule can vary greatly among target biomolecule positive cells or even on the same cell at different points in the cell cycle or cell differentiation. The total cell surface representation of a given target biomolecule on a particular cell or population of cells may be determined using methods known to the skilled worker, such as the fluorescence-activated cell sorting (FACS) flow cytometry method.

Introduction

The present invention provides protease-cleavage resistant molecules comprising Shiga toxin A Subunit effectors with disrupted furin-cleavage motifs which are capable of exhibiting wild-type, Shiga toxin cytotoxicity. Previously, Shiga toxin A Subunit fusion constructs were shown to be cytotoxic and capable of self-directing their own intracellular routing to deliver an enzymatically active toxin fragment to the cytosol (Backer M et al., *J Control Release* 74: 349-55 (2001); Backer M, Backer J, *Bioconjug Chem* 12: 1066-73 (2001)); however, the maintenance of the furin-cleavage site was believed to be important for maintaining maximal cytotoxicity.

When designing synthetic Shiga toxin A Subunit constructs, the natural mechanism of Shiga toxin intoxication should be considered, such as, e.g., liberation of the A1 fragment via intracellular proteolysis by furin and retrotranslocation of the A1 fragment to the cytosol. The jettisoning of all molecular moieties carboxy-terminal to the Shiga toxin A1 fragment could be required both for 1) exposing the carboxy terminus of the A1 fragment for recognition by cellular factors within the endoplasmic reticulum of intoxicated cells to promote efficient routing to the cytosol and 2) maximizing catalytic activity as the A1 fragment is refolded into a structure in the cytosol in the absence of any carboxy-terminal moieties. These mechanisms might all contribute to the maximal, Shiga toxin cytotoxicity observed for wild-type, Shiga toxins.

Because furin proteolytic processing of Shiga toxin A Subunits of Shiga holotoxins in intoxicated vertebrate cells is critical for efficient cytotoxicity, it was thought that furin-cleavage must be maintained or compensated for this naturally occurring proteolytic processing in order to preserve the efficient, native, subcellular routing and catalytic activation of the highly evolved and potent, Shiga toxin cytotoxicity mechanism. The separation of the Shiga toxin A1 fragment from the A2 fragment must be maintained, mimicked, or otherwise compensated for in order to both 1) make a carboxy terminus of the A1 fragment or a carboxy terminus resembling a natural A1 fragment accessible in the endoplasmic reticulum for efficient transport to the cytosol and 2) deliver a stable and optimal catalytic A1 fragment structure to the cytosol.

Previously, there has not been any demonstration of a Shiga toxin A Subunit derived structure comprising a heterologous, carboxy-terminal moiety and which lacks a furin cleavage event but that still exhibits maximal, wild-type, Shiga toxin cytotoxicity in terms of efficiency and potency. In particular, there was no known Shiga toxin A Subunit derived structure which obviates proteolytic processing for maximal Shiga toxin cytotoxicity when the carboxy terminus of the Shiga toxin A1 fragment derived region was covalently linked to and sterically covered by a relatively large, molecular moiety, such as, e.g., a cell-targeting, immunoglobulin-type binding region.

Surprisingly, exemplary molecules of the present invention comprising Shiga toxin effector polypeptides with disrupted furin-cleavage motifs exhibited sufficient, Shiga toxin effector functions to provide maximal, wild-type, Shiga toxin cytotoxicity while simultaneously allowing the linkage of relatively large (greater than 28 kDa), molecular moieties to their carboxy terminals (see Examples, infra). As described in detail in the Examples below, exemplary molecules of the present invention, each comprising a Shiga toxin A Subunit derived polypeptide comprising a catalytic domain, exhibit Shiga toxin cytotoxic potency and efficiency comparable to cell-targeted molecules comprising furin-cleavable, Shiga toxin A Subunit effector polypeptides, such as wild-type, Shiga toxin A Subunit polypeptides. There was no need for any additional engineering of a compensatory feature, e.g., such as adding an ectopic protease-cleavage site. These observations lead to the design of improved cell-targeted molecules comprising protease-cleavage resistant, Shiga toxin A Subunit derived polypeptides wherein the molecules exhibited cytotoxicity equivalent to cell-targeted molecules comprising a wild-type, Shiga toxin A1 fragment.

The present invention provides protease-cleavage resistant molecules comprising Shiga toxin A Subunit effector polypeptides comprising disrupted furin-cleavage motifs. Cytotoxic molecules of the present invention comprising either 1) a catalytically active, protease-cleavage resistant, Shiga toxin effector polypeptide and/or 2) a cytotoxic molecular moiety may be used in applications for killing cells. Molecules of the present invention comprising catalytically active, protease-cleavage resistant, Shiga toxin effector polypeptides may be used as components of immunotoxins and ligand-toxin fusions for the targeted killing of specific cell types and the treatment of a variety of diseases, including cancers, immune disorders, and microbial infections. Cell-targeted molecules of the present invention have various uses, e.g., for targeted cell killing, delivering exogenous materials into specific cell types, obtaining diagnostic information, and as therapeutics for the treatment of a variety of diseases, disorders, and conditions, including cancers, immune disorders, and microbial infections. The cytotoxic cell-targeted molecules of the present invention are also useful for applications involving the targeted killing of specific cell types and the treatment of a variety of diseases, including cancers, immune disorders, and microbial infections. The present invention also provides a specific way of engineering Shiga toxin A Subunit derived molecules, e.g. immunotoxins or ligand-toxin fusions, comprising a molecular moiety carboxy-terminal to a Shiga toxin A1 fragment region which involves disrupting the furin-cleavage motif at the carboxy terminus of the Shiga toxin A1 fragment derived region.

The General Structure of Cytotoxic Molecules and Cell-Targeting Molecules of the Invention The present invention provides various cytotoxic and cell-targeted molecules, the molecules each comprising a Shiga toxin effector polypeptide comprising a Shiga toxin A1 fragment derived region and a disrupted furin-cleavage motif at the carboxy terminus of the Shiga toxin A1 fragment derived region. The cytotoxic and cell-targeted molecules of the present invention are furin-cleavage resistant as compared to related molecules comprising wild-type, Shiga toxin A1 fragments. In addition to being furin-cleavage resistant, the molecules of the invention are generally more protease-cleavage resistant and, thus, may exhibit desirable properties such as, e.g., decreased in vivo toxicities, increased stability, increased storage half-lives, and/or increased in vivo half-lives.

The cytotoxic molecules of the present invention also comprise a molecular moiety associated with the carboxy terminus of the Shiga toxin effector polypeptide. An example of a molecular moiety is a cell-targeting, immunoglobulin-type, binding region comprising one or more polypeptides that binds with high affinity to a cell-surface biomolecule.

The cell-targeted molecules of the present invention also comprise a binding region capable of specifically binding at least one extracellular target biomolecule in physical association with a cell, such as a target biomolecule expressed on the surface of a cell. The linking of cell-targeting binding regions with Shiga toxin effector polypeptides described herein enables the engineering of cell-type specific targeting of the potent Shiga toxin cytotoxicity despite the lack of furin proteolytic processing of the Shiga toxin A Subunit derived polypeptide region. This general structure of the cell-targeting molecules of the present invention is modular in that any number of diverse cell-targeting binding regions may be associated to various, furin-cleavage resistant, Shiga toxin effector polypeptides to produce variations of the same general structure.

The present invention is based on the unexpected discovery that the disruption of a furin protease site which natively links the Shiga toxin A1 fragment to the A2 fragment did not diminish its cytotoxicity when linked to a relatively large (greater than 28 kDa), carboxy-terminal molecular moiety. Surprisingly, maximal, wild-type, Shiga toxin cytotoxicity is possible in the absence of a furin cleavage event despite the presence of a large carboxy-terminal moiety that might interfere with a Shiga toxin A Subunit's natural mechanism of jettisoning all other large molecular moieties to expose a carboxy-terminal hydrophobic domain leading to 1) recognition of the carboxy terminus of the A1 fragment by the ERAD system, 2) unfolding of the A1 fragment, 3) ubiquitination of the A1 fragment, 4) retrotranslocation of the catalytic domain from the endoplasmic reticulum to the cytosol, 5) avoiding degradation of the catalytic domain by the proteasome, and 6) refolding of a catalytic domain comprising polypeptide to form a fully active enzymatic structure (see Suhan M, Hovde C, *Infect Immun* 66: 5252-9 (1998); LaPointe P et al., *J Biol Chem* 280: 23310-18 (2005); Yu M, Haslam D, *Infect Immun* 73: 2524-32 (2005); Falguieres T, Johannes L, *Biol Cell* 98: 125-34 (2006); Di R et al., *Toxicon* 57: 525-39 (2011); Li S, *PLoS One* 7: e41119 (2012)).

Prior to the discovery described herein, it was though that in the design of Shiga toxin A Subunit derived fusion proteins intended to have optimal cytotoxicity, the furin-cleavage event must either be maintained or compensated for. By maintaining a furin-cleavage event within the Shiga toxin A Subunit derived region, a Shiga toxin A Subunit A1 fragment-like polypeptide can be liberated from the any moiety associated with its carboxy terminus and which is sterically covering the carboxy terminus of the A1 fragment in order to improve the ribosome inhibition activity of the entire molecule by 60-fold or more (see Lea N et al., *Microbiology* 145: 999-1004 (1999)). Then the liberated carboxy terminus of the A1 fragment-like polypeptide can signal with its hydrophobic domain to the intoxicated cell's ERAD machinery for translocation from the lumen of the endoplasmic reticulum to the cytosol, the A1 fragment-like polypeptide can be unfolded, a Shiga catalytic domain comprising polypeptide can be efficiently translocated to the cytosol, and the catalytic domain can refold into an active confirmation in the cytosol similar to as what occurs for the wild-type, Shiga toxin. In addition, if an A2 fragment-like region was present in the fusion protein, then the A1 fragment might become more catalytically activated after dissociation from any A2 fragment-like region. Alternatively, compensation for a lack of a furin-cleavage event might be accomplished by presenting the Shiga toxin A Subunit derived polypeptide in a "pre-processed" form proximal to a carboxy terminus of the fusion protein such that the carboxy terminus of the molecule mimics a furin cleaved Shiga toxin A1 fragment.

A. Protease-Cleavage Resistant, Shiga Toxin A Subunit Effector Polypeptides

All the cytotoxic molecules and cell-targeting molecules of the present invention each comprise a furin-cleavage resistant, Shiga toxin effector polypeptide. These furin-cleavage resistant, Shiga toxin effector polypeptides are each derived from an A Subunit of member of the Shiga toxin family and comprise 1) a Shiga toxin A1 fragment derived polypeptide having a carboxy terminus and 2) a disrupted furin-cleavage motif at the carboxy terminus of the Shiga toxin A1 fragment polypeptide region.

For purposes of the present invention, the phrase "furin-cleavage resistant" means the polypeptide region exhibits less furin cleavage than a carboxy terminus of a Shiga toxin A1 fragment in a wild-type, Shiga toxin A Subunit or a carboxy terminus of the Shiga toxin A1 fragment derived region of construct where the naturally occurring furin-cleavage motif is undisrupted, i.e. comprises only wild-type, naturally occurring sequences as exhibited by naturally occurring Shiga toxin A Subunits in the analogous polypeptide region.

A Shiga toxin effector polypeptide is a polypeptide derived from a Shiga toxin A Subunit of a member of the Shiga toxin family. The Shiga toxin family of protein toxins is composed of various naturally occurring toxins which are structurally and functionally related, e.g., Shiga toxin, Shiga-like toxin 1, and Shiga-like toxin 2 (Johannes L, Römer W, *Nat Rev Microbiol* 8: 105-16 (2010)). Members of the Shiga toxin family share the same overall structure and mechanism of action (Engedal, N et al., *Microbial Biotech* 4: 32-46 (2011)). For example, Stx, SLT-1 and SLT-2 display indistinguishable enzymatic activity in cell free systems (Head S et al., *J Biol Chem* 266: 3617-21 (1991); Tesh V et al., *Infect Immun* 61: 3392-402 (1993); Brigotti M et al., *Toxicon* 35:1431-1437 (1997)).

The Shiga toxin family encompasses true Shiga toxin (Stx) isolated from *S. dysenteriae* serotype 1, Shiga-like toxin 1 variants (SLT1 or Stx1 or SLT-1 or Slt-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one residue from Stx, and both have been referred to as Verocytotoxins or Verotoxins (VTs) (O'Brien, *Curr Top Microbiol Immunol* 180: 65-94 (1992)). Although SLT1 and SLT2 variants are only about 53-60% similar to each other at the amino acid sequence level, they share mechanisms of enzymatic activity and cytotoxicity common to the members of the Shiga toxin family (Johannes L, Römer W, *Nat Rev Microbiol* 8: 105-16 (2010)). Over 39 different Shiga toxins have been described, such as the defined subtypes Stx1a, Stx1c, Stx1d, and Stx2a-g (Scheutz F et al., *J Clin Microbiol* 50: 2951-63 (2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Bielaszewska M et al., *Appl Environ Micrbiol* 73: 3144-50 (2007); Zhaxybayeva O, Doolittle W, *Curr Biol* 21: R242-6 (2011)). As an example of interspecies transfer, a Shiga toxin was discovered in a strain of *A. haemolyticus* isolated from a patient (Grotiuz G et al., *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz, *J Clin Microbiol* 50: 2951-63 (2012)).

Shiga toxin A Subunits of members of the Shiga toxin family comprise conserved, furin-cleavage site at the carboxy terminals of their A1 fragment regions important for Shiga toxin function. Furin-cleavage site motifs and furin-cleavage sites can be identified by the skilled worker and/or by using the information herein.

Consensus motifs in substrates cleaved by furin have been identified with some degree of specificity. A furin-cleavage site motif has been described which comprises a region of 20 amino acid residues which can be labeled P14 through P6' (Tian S, *Biochem Insights* 2: 9-20 (2009); Tian S, Jianhua W, *Int J Biol Sci* 6: 89-95 (2010); Tian S et al., *Int J Mol Sci* 12: 1060-5 (2011); Tian S et al., *Sci Rep* 2: 261 (2012)) using the nomenclature described in Schechter I, Berger, A, *Biochem Biophys Res Commun* 32: 898-902 (1968). According to this nomenclature, the cleavage site is at the carboxy bond of the amino acid reside designated P1 and the residues are numbered P2, P3, P4, etc, in the direction going toward the amino terminus from this reference P1 residue. The residues going toward the carboxy terminus from the P1 reference residue are numbered with the prime notation P2', P3', P4', etc.

A general, furin-cleavage site is often described by the consensus motif R-x-x-R which corresponds to P4-P3-P2-P1; where "R" represents an arginine residue (see Table A, supra), a dash "-" represents a peptide bond, and a lowercase "x" represents any amino acid residue (Schalken J et al., *J Clin Invest* 80: 1545-9 (1987); Bresnahan P et al., *J Cell Biol* 111: 2851-9 (1990); Hatsuzawa K et al., *J Biol Chem* 265: 22075-8 (1990); Wise R et al., *Proc Natl Acad Sci USA* 87: 9378-82 (1990); Molloy S et al., *J Biol Chem* 267: 16396-402 (1992)). However, other residues and positions may help to further define furin-cleavage motifs (Hosaka M et al., *J Biol Chem* 266: 12127-30 (1991); Oda K et al., *Biochem Biophys Res Commun* 179: 1181-6 (1991); Leduc R et al., *J Biol Chem* 267: 14304-8 (1992); Watanabe T et al., *J Biol Chem* 267: 8270-4 (1992)). A slightly more refined furin-cleavage site motif is often reported as the consensus motif R-x-[K/R]-R (where a forward slash "/" means "or" and divides alternative amino acid residues at the same position), which corresponds to P4-P3-P2-P1, because it was observed that furin has a strong preference for cleaving substrates containing this motif (see Rockwell N et al., *Chem Rev* 102: 4525-48 (2002); Remade A et al., *J Biol Chem* 283: 20897-906 (2008); Tian S, *Biochem Insights* 2: 9-20 (2009); Tian S, Jianhua W, *Int J Blot Sci* 6: 89-95 (2010); Tian S et al., *Int J Mol Sci* 12: 1060-5 (2011); Tian S et al., *Sci Rep* 2: 261 (2012)).

Consistent with this, many furin inhibitors comprise peptides comprising the motif R-x-x-R (see e.g. Misumi Y et al., *Biochem Biophys Res Commun* 171: 236-42 (1990); Hallenberger S et al., Nature 360: 358-61 (1992); Garten W et al., *Biochimie* 76: 217-25 (1994); Angliker H, *J Med Chem* 38: 4014-8 (1995); Van Rompaey L et al., *Biochem J* 326: 507-514 (1997); Cameron A et al., *J Biol Chem* 275: 36741-9 (2000); Jean F et al., *Proc Natl Acad Sci USA* 97: 2864-9 (2000); Basak A, Lazure C, *Biochem J* 373: 231-9 (2003); Kacprzak M et al., *J Biol Chem* 279: 36788-94 (2004)). An example of a synthetic inhibitor of furin is R—V-K-R (see e.g. Henrich S et al., *Nat Struct Biol* 10: 520-6 (2003)). In general, a polypeptide comprising a surface accessible, dibasic amino acid motif with two positively charged, amino acids separated by two amino acid residues may be predicted to be a furin-cleavage sensitive with cleavage occurring at the carboxy bond of the last basic amino acid in the motif (Rockwell N et al., *Chem Rev* 102: 4525-48 (2002); Remade A et al., *J Biol Chem* 283: 20897-906 (2008)).

In addition to the minimal, furin-cleavage site of R-x-x-R, a larger, furin-cleavage site motif has been described with certain amino acid residue preferences at certain positions. By comparing various known furin substrates, certain physicochemical properties have been characterized for the amino acids residues in a 20 amino acid residue long, furin-cleavage site motif. The P6 to P2' region of the furin-cleavage motif delineates the core furin-cleavage site which physically interacts with the enzymatic domain of furin. The two flanking regions P14 to P7 and P3' to P6' are often hydrophilic being rich in polar, amino acid residues to increase the surface accessibility of the core furin-cleavage site located between them.

In general, the furin-cleavage motif region from position P5 to P1 tends to comprise amino acid residues with a positive charge and/or high isoelectric points. In particular, the P1 position, which marks the position of furin proteolysis, is generally occupied by an arginine but other positively charged, amino acid residues may occur in this position. Positions P2 and P3 tend to be occupied by flexible, amino acid residues, and in particular P2 tends to be occupied by arginine, lysine, or sometimes by very small and flexible amino acid residues like glycine. The P4 position tends to be occupied by positively charged, amino acid residues in furin substrates. However, if the P4 position is occupied by an aliphatic, amino acid residue, then the lack of a positively charged, functional group can be compensated for by a positively charged residue located at position(s) P5 and/or P6 (Tian S, Jianhua W, *Int. J Biol Sci* 6: 89-95 (2010)). Positions P1' and P2' are commonly occupied by aliphatic and/or hydrophobic amino acid residues, with the P1' position most commonly being occupied by a serine (Tian S, *Biochem Insights* 2: 9-20 (2009); Tian S et al., *Sci Rep* 2: 261 (2012)).

The two, hydrophilic, flanking regions tend to be occupied by amino acid residues which are polar, hydrophilic, and/or have smaller amino acid functional groups; however, in certain verified furin substrates, the flanking regions of the core furin-cleavage motif do not contain any consensus, hydrophilic, amino acid residues (see Tain S, *Biochem Insights* 2: 9-20 (2009)). In the furin-cleavage motifs of some viral proteins, positions P3' to P6' are occupied by amino acid residues with small, hydrophobic, functional groups, such as, e.g., alanines, glycines, and prolines (Tian S, *Biochem Insights* 2: 9-20 (2009); Tian S et al., *Sci Rep* 2: 261 (2012)). Although not required for furin proteolysis, the presence of positively charged, amino acid residue(s) at position P5 and/or P6 might increase furin-cleavage efficiency. In Shiga toxin A Subunits, the conserved furin-cleavage motif located at the junction of the Shiga toxin A1 fragment and A2 fragment might have optimized competing functions, such as, e.g., balancing efficient furin-cleavage with exposing an unstructured, hydrophobic patch at the carboxy terminus of the A1 fragment after cleavage.

The cytotoxic molecules and cell-targeting molecules of the present invention each comprise a Shiga toxin effector polypeptide comprising a disrupted furin-cleavage motif at the carboxy terminus of the A1 fragment region.

For purposes of the claimed invention, the term "furin-cleavage site" refers to a minimal, furin-cleavage consensus site R/Y-x-x-R in the protease sensitive loop of Shiga toxin A Subunits.

For purposes of the present invention, the term "furin-cleavage motif" refers to a polypeptide consisting essentially of a twenty, amino acid residue, consensus polypeptide sequence (P14 to P6') as described herein, which comprises 1) a minimal, furin-cleavage motif P4 to P1, 2) a core, furin-cleavage motif P6 to P2', and 3) two, flanking, polypeptide regions P14 to P7 and P3' to P6'.

For purposes of the present invention, a "disrupted furin-cleavage motif" is an alteration to one or more amino acid residues derived from the 20 amino acid residue region which is a furin-cleavage motif found in native, Shiga toxin A Subunits at the junction between the Shiga toxin A1 fragment and A2 fragment regions and positioned such that furin cleavage of a Shiga toxin A Subunit results in the production of the A1 and A2 fragments; wherein the disrupted furin-cleavage motif exhibits reduced furin cleavage compared to a reference molecule comprising a wild-type, Shiga toxin A1 fragment region fused to a carboxy terminal polypeptide of a size large enough to monitor furin cleavage using the appropriate assay. A reduction in furin cleavage may be determined by the skilled worker using assays known in the art and/or described herein. For example, a reduction in furin cleavage of one molecule compared to a reference molecule may be determined using an in vitro, furin cleavage assay described in the Examples below, conducted using the same conditions, and then performing a quantitation of the band density of any fragments resulting from cleavage. In certain embodiments of the molecules of the present invention, the disrupted furin-cleavage motif exhibits a reduction in in vitro furin cleavage of 30%, 40%, 50%, 60%, 70%, 80%, 90%, 95%, 97%, 98% or greater compared to a reference molecule comprising a wild-type, Shiga toxin A1 fragment fused at its carboxy terminus to a polypeptide, such as, e.g., the reference molecule SLT-1A-WT::scFv-1 described in the Examples.

The 20 amino acid residue furin-cleavage motif found in native, Shiga toxin A Subunits at the junction between the Shiga toxin A1 fragment and A2 fragment furin-cleavage motif is well characterized in certain Shiga toxins. For example in StxA (SEQ ID No:2) and SLT-1A (SEQ ID NO:1), this furin-cleavage motif is natively positioned from L238 to F257, and in SLT-2A (SEQ ID NO:3), this furin-cleavage motif is natively positioned from V237 to Q256. Based on amino acid homology, experiment, and/or furin-cleavage assays described herein, the skilled worker can identify furin-cleavage motifs in other native, Shiga toxin A Subunits, where the motifs are predicted to result in the production of A1 and A2 fragments after furin cleavage of those Shiga toxin A Subunits by an intoxicated eukaryotic cell.

Alterations to an amino acid residue in the furin-cleavage motif include various mutations as well as post-translation modifications, such as, e.g., glycosylation and the like which involve linking a bulky molecule to the functional group of an amino acid residue. A mutation to an amino acid residue in the furin-cleavage motif includes a deletion, insertion, inversion, substitution, and/or carboxy-terminal truncation of the furin-cleavage motif. Because it has been disrupted, certain disrupted furin-cleavage motifs may not be easily recognizable as being related to any furin-cleavage motif; however, the carboxy terminus of the Shiga toxin A1 fragment region will be recognizable and will define where the furin-cleavage motif would be located were it not disrupted. For example, a disrupted furin-cleavage motif may comprise less than the twenty, amino acid residues of the furin-cleavage motif and representing a carboxy-terminal truncation as compared to a Shiga toxin A Subunit and/or Shiga toxin A1 fragment.

For purposes of the present invention with regard to a furin-cleavage site or furin-cleavage motif, the term "disruption", "disrupting", or "disrupted" refers to an alteration from the naturally occurring furin-cleavage site, such as, e.g., a mutation, which results in a reduction in furin-cleavage at the site as compared to a wild-type Shiga toxin A Subunit. Because the furin-cleavage motif is comprised of about 20 amino acid residues, in theory, mutations, deletions, or insertions involving one or more of any one of these 20 positions can result in a reduction of furin-cleavage sensitivity (Tian S et al., *Sci Rep* 2: 261 (2012)). The disruption may or may not increase resistance to other proteases.

Examples of types of mutations which can disrupt a furin-cleavage site and furin-cleavage motif are amino acid residue deletions, insertions, inversions, and/or substitutions, including substitutions with non-standard amino acids and/or non-natural amino acids. In addition, furin-cleavage sites and furin-cleavage motifs can be disrupted by mutations comprising the modification of an amino acid by the addition of a covalently-linked chemical structure which masks at least one amino acid in the site or motif, see, e.g. PEGylation (see Zhang C et al., *BioDrugs* 26: 209-15 (2012) and small molecule adjuvants (Flower D, *Expert Opin Drug Discov* 7: 807-17 (2012)).

Mutating one or both of the two arginine residues in the minimal, furin consensus site R-x-x-R to alanine will disrupt a furin-cleavage motif and prevent furin-cleavage at that site (see e.g. Duda A et al., *J Virol* 78: 13865-70 (2004)).

Similarly, amino acid residue substitutions of one or both of the arginine residues in the minimal furin-cleavage motif R-x-x-R to any non-conservative amino acid residue known to the skilled worker will reduced the furin-cleavage sensitivity of the motif. In particular, amino acid residue substitutions of arginine to any non-basic amino acid residue which lacks a positive charge, such as, e.g., A, G, P, S, T, D, E, Q, N, C, I, L, M, V, F, W, and Y, will result in a disrupted furin-cleavage motif. Furthermore, deletions within the furin-cleavage motif of the minimal furin-cleavage site or the core, furin-cleavage motif will reduce the furin-cleavage sensitivity of the furin-cleavage motif.

In certain embodiments of the molecules of the present invention, the disrupted furin-cleavage motif comprises a disruption in terms of existence, position, or functional group of one or both of the consensus amino acid residues P1 and P4, such as, e.g., the amino acid residues in positions 1 and 4 of the minimal furin-cleavage motif R/Y-x-x-R.

In certain embodiments, the disrupted furin-cleavage motif comprises a disruption in the spacing between the consensus amino acid residues P4 and P1 in terms of the number of intervening amino acid residues being other than two, and, thus, changing either P4 and/or P1 into a different position and eliminating the P4 and/or P1 designations.

Certain furin-cleavage motif disruptions are indicated herein by reference to specific amino acid positions of native Shiga toxin A Subunits provided in the Sequence Listing, noting that naturally occurring Shiga toxin A Subunits may comprise precursor forms containing signal sequences of about 22 amino acids at their amino-terminals which are removed to produce mature Shiga toxin A Subunits and are recognizable to the skilled worker. Further, certain furin-cleavage motif disruptions comprising mutations are indicated herein by reference to specific amino acids (e.g. R for an arginine residue) natively present at specific positions within native Shiga toxin A Subunits (e.g. R251 for the arginine residue at position 251 from the amino terminus) followed by the amino acid with which that residue has been substituted in the particular mutation under discussion (e.g. R251A represents the amino acid substitution of alanine for arginine at amino acid residue 251 from the amino terminus).

In certain embodiments, the disrupted furin-cleavage motif comprises one or more amino acid residue substitutions, as compared to a wild-type, Shiga toxin A Subunit. In certain further embodiments, the disrupted furin-cleavage motif comprises one or more amino acid residue substitutions within the minimal furin-cleavage site R/Y-x-x-R, such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue. In further certain embodiments, the disrupted furin-cleavage motif comprises an un-disrupted, minimal furin-cleavage site R/Y-x-x-R but instead comprises a disrupted flanking region, such as, e.g., amino acid residue substitutions in one or more amino acid residues in the furin-cleavage motif flanking regions natively position at, e.g., 241-247 and/or 252-259.

In certain embodiments, the disruption comprises a deletion, insertion, inversion, and/or mutation of at least one amino acid residue within the protease motif region. In certain embodiments, a protease-cleavage resistant, Shiga toxin effector polypeptide may comprise a disruption of the amino acid sequence natively positioned at 249-251 of the A Subunit of Shiga-like toxin 1 (SEQ ID NO:1) or Shiga toxin (SEQ ID NO:2), or at 247-250 of the A Subunit of Shiga-like toxin 2 (SEQ ID NO:3) or the equivalent position in a conserved Shiga toxin effector polypeptide and/or non-native Shiga toxin effector polypeptide sequence. In certain further embodiments, protease-cleavage resistant, Shiga toxin effector polypeptides comprise a disruption which comprises a deletion of at least one amino acid within the protease motif region. In certain further embodiments, protease-cleavage resistant, Shiga toxin effector polypeptides comprise a disruption which comprises an insertion of at least one amino acid within the protease motif region. In certain further embodiments, the protease-cleavage resistant, Shiga toxin effector polypeptides comprise a disruption which comprises an inversion of amino acids, wherein at least one inverted amino acid is within the protease motif region. In certain further embodiments, the protease-cleavage resistant, Shiga toxin effector polypeptides comprise a disruption which comprises a mutation, such as an amino acid substitution to a non-standard amino acid or an amino acid with a chemically modified side chain. Examples of single amino acid substitutions are provided in the Examples.

In certain embodiments, the protease-cleavage resistant, Shiga toxin effector polypeptides comprise a disruption which comprises an amino acid substitution within a protease motif region, where in the substitution occurs at the natively positioned amino acid selected from the group consisting of: 247 of SEQ ID NO:3, 248 of SEQ ID NO:1 or SEQ ID NO:2, 250 of SEQ ID NO:3, 251 of SEQ ID NO:1 or SEQ ID NO:2, or the equivalent position in a conserved Shiga toxin effector polypeptide and/or non-native Shiga toxin effector polypeptide sequence. In certain further embodiments, the substitution is to any non-conservative amino acid and the substitution occurs at the natively positioned amino acid residue selected from the group consisting of: 247 of SEQ ID NO:3, 248 of SEQ ID NO:1 or SEQ ID NO:2, 250 of SEQ ID NO:3, 251 of SEQ ID NO:1 or SEQ ID NO:2, or the equivalent position in a conserved Shiga toxin effector polypeptide and/or non-native Shiga toxin effector polypeptide sequence. In certain further embodiments, the mutation comprises an amino acid substitution selected from the group consisting of: R247A, R248A, R250A R251A, or the equivalent position in a conserved Shiga toxin effector polypeptide and/or non-native Shiga toxin effector polypeptide sequence.

In certain embodiments of the molecules of the present invention, the disrupted furin-cleavage motif comprises the deletion of nine, ten, eleven, or more of the carboxy-terminal amino acid residues within the furin-cleavage motif. In these embodiments, the disrupted furin-cleavage motif will not comprise a furin-cleavage site or a minimal furin-cleavage motif. In other words, certain embodiments lack a furin-cleavage site at the carboxy terminus of the A1 fragment region.

In certain embodiments, a molecule of the present invention comprises a Shiga toxin effector polypeptide comprising a disrupted furin-cleavage motif comprising a mutation in the surface-exposed, protease sensitive loop conserved among Shiga toxin A Subunits. For example, in StxA and SLT-1A, this protease-sensitive loop is natively positioned from position 242 to position 261, and in SLT-2A, this loop is natively positioned from position 241 to position 260. Based on polypeptide sequence homology, the skilled worker can identify this conserved, protease-sensitive loop in other Shiga toxin A Subunits. In certain further embodiments, a molecule of the present invention comprises a Shiga toxin effector polypeptide comprising a disrupted furin-cleavage motif comprising a mutation in this protease-sensitive loop of Shiga toxin A Subunits, the mutation which reduce the surface accessibility of certain amino acid residues within the loop such that furin-cleavage sensitivity is reduced.

In certain embodiments, a molecule of the present invention comprises the disrupted furin-cleavage motif comprising the amino acid residue substitution of one or both of the arginine residues in the minimal, cleavage site consensus motif with A, G, or H. In certain further embodiments, the disrupted furin-cleavage motif comprises a deletion of the region natively positioned at 247-252 in StxA (SEQ ID NO:2) and SLT-1A (SEQ ID NO:3), or the region natively positioned at 246-251 in SLT-2A (SEQ ID NO:3); a deletion of the region natively positioned at 244-246 in StxA (SEQ ID NO:2) and SLT-1A (SEQ ID NO:3), or the region natively positioned at 243-245 in SLT-2A (SEQ ID NO:3); or a deletion of the region natively positioned at 253-259 in StxA (SEQ ID NO:2) and SLT-1A (SEQ ID NO:3), or the region natively positioned at 252-258 in SLT-2A (SEQ ID NO:3). Certain further embodiments comprise the disrupted furin-cleavage motif comprising a combination of any of the aforementioned mutations, where possible.

In certain embodiments, the disrupted furin-cleavage motif comprises a carboxy-terminal truncation as compared to a wild-type, Shiga toxin A Subunit, the truncation which results in the deletion of one or more amino acid residues within the furin-cleavage motif. In certain further embodiments, the disrupted furin-cleavage motif comprises the carboxy-terminal truncation which deletes one or more amino acid residues within the minimal cleavage site Y/R-x-x-R, such as, e.g., for StxA and SLT-1A derived Shiga toxin effector polypeptides, truncations ending at the natively amino acid residue position 250, 249, 248, 247, 246, 245, 244, 243, 242, 241, 240, or less; and for SLT-2A derived Shiga toxin effector polypeptides, truncations ending at the natively amino acid residue position 249, 248, 247, 246, 245, 244, 243, 242, 241, or less.

In certain embodiments, the disrupted furin-cleavage motif comprises the mutation that is a partial, carboxy-terminal truncation of the furin-cleavage motif however, certain molecules of the present invention do not comprise the disrupted furin-cleavage motif which is a complete, carboxy-terminal truncation of the entire 20 amino acid residue, furin-cleavage motif. For example, certain, cytotoxic, cell-targeted molecules of the present invention comprise a Shiga toxin effector polypeptide comprising the disrupted furin-cleavage motif comprising a partial, carboxy-terminal truncation of the A1 fragment region up to native position 240 in StxA (SEQ ID NO:2) or SLT-1A (SEQ ID NO:1) but not a carboxy-terminal truncation at position 239 or less. Similarly, certain, cytotoxic, cell-targeted molecules of the present invention comprise a Shiga toxin effector polypeptide comprising the disrupted furin-cleavage motif comprising a partial, carboxy-terminal truncation of the A1 fragment region up to native position 239 in SLT-2A (SEQ ID NO:3) but not a carboxy-terminal truncation at position 238 or less. In the largest carboxy-terminal truncation mutations comprising the disrupted furin-cleavage motif, positions P14 and P13 of the furin-cleavage motif are still present.

In certain embodiments, the disrupted furin-cleavage motif comprises both an amino acid residue substitution within the furin-cleavage motif and a carboxy-terminal truncation as compared to a wild-type, Shiga toxin A Subunit. In certain further embodiments, the disrupted furin-cleavage motif comprises both an amino acid residue substitution within the minimal furin-cleavage site R/Y-x-x-R and a carboxy-terminal truncation as compared to a wild-type, Shiga toxin A Subunit, such as, e.g., for StxA and SLT-1A derived Shiga toxin effector polypeptides, truncations ending at the natively amino acid residue position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A derived Shiga toxin effector polypeptides, truncations ending at the natively amino acid residue position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue Y247 and/or R250 substituted with any non-positively charged, amino acid residue where appropriate. In certain embodiments, the truncated Shiga toxin effector polypeptide comprising a disrupted furin-cleavage motif also comprises the furin-cleavage motif, amino acid residues at positions P9, P8, and/or P7 in order to maintain optimal cytotoxicity.

In certain embodiments, the disrupted furin-cleavage motif comprises one or more internal amino acid residue deletions, as compared to a wild-type, Shiga toxin A Subunit. In certain further embodiments, the disrupted furin-cleavage motif comprises one or more amino acid residue deletions within the minimal furin-cleavage site R/Y-x-x-R. For example, StxA and SLT-1A derived Shiga toxin effector polypeptides comprising internal deletions of the natively positioned amino acid residues R248 and/or R251, which may be combined with deletions of surrounding residues such as, e.g., 249, 250, 247, 252, etc; and SLT-2A derived Shiga toxin effector polypeptides comprising internal deletions of the natively positioned amino acid residues Y247 and/or R250, which may be combined with deletions of surrounding residues such as, e.g., 248, 249, 246, 251, etc. In certain further embodiments, the disrupted furin-cleavage motif comprises a deletion of four, consecutive, amino acid residues which deletes the minimal furin-cleavage site R/Y-x-x-R, such as, e.g., StxA and SLT-1A derived Shiga toxin effector polypeptides lacking R248-R251 and SLT-2A derived Shiga toxin effector polypeptides lacking Y247-R250. In certain further embodiments, the disrupted furin-cleavage motif comprises one or more amino acid residue deletions in the amino acid residues flanking the core furin-cleavage motif, such as, e.g., a deletion of 244-247 and/or 252-255 in SLT-1A or StxA. In certain further embodiments, the disrupted furin-cleavage motif comprises an internal deletion of the entire surface-exposed, protease-cleavage sensitive loop as compared to a wild-type, Shiga toxin A Subunit, such as, e.g., for StxA and SLT-1A derived Shiga toxin effector polypeptides, a deletion of natively positioned amino acid residues 241-262; and for SLT-2A derived Shiga toxin effector polypeptides, a deletion of natively positioned amino acid residues 240-261.

In certain embodiments, the disrupted furin-cleavage motif comprises both an internal amino acid residue deletion within the furin-cleavage motif and a carboxy-terminal truncation as compared to a wild-type, Shiga toxin A Subunit. In certain further embodiments, the disrupted furin-cleavage motif comprises both an amino acid residue deletion within the minimal furin-cleavage site R/Y-x-x-R and a carboxy-terminal truncation as compared to a wild-type, Shiga toxin A Subunit. For example, Shiga toxin effector polypeptides with a disrupted furin-cleavage motif may comprise deletions of the natively positioned amino acid residues 248-249 and/or 250-251 in a truncated StxA or SLT-1A polypeptide or the amino acid residues 247-248 and/or 249-250 in a truncated SLT-2A. In certain further embodiments, the disrupted furin-cleavage motif comprises a deletion of four, consecutive, amino acid residues which deletes the minimal furin-cleavage site R/Y-x-x-R and a carboxy-terminal truncation as compared to a wild-type, Shiga toxin A Subunit, such as, e.g., for StxA and SLT-1A derived Shiga toxin effector polypeptides, truncations ending at the natively amino acid residue position 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking R248-R251; and for SLT-2A derived Shiga toxin effector polypeptides, truncations ending at the natively amino acid residue position 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and lacking Y247-R250.

In certain embodiments, the disrupted furin-cleavage motif comprises both an amino acid residue deletion and an amino acid residue substitution as compared to a wild-type, Shiga toxin A Subunit. In certain further embodiments, the disrupted furin-cleavage motif comprises one or more amino acid residue deletions and substitutions within the minimal furin-cleavage site R/Y-x-x-R, such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In certain embodiments, the disrupted furin-cleavage motif comprises an amino acid residue deletion and an amino acid residue substitution as well as a carboxy-terminal truncation as compared to a wild-type, Shiga toxin A Subunit. In certain further embodiments, the disrupted furin-cleavage motif comprises one or more amino acid residue deletions and substitutions within the minimal furin-cleavage site R/Y-x-x-R, such as, e.g., for StxA and SLT-1A derived Shiga toxin effector polypeptides, the natively positioned amino acid residue R248 substituted with any non-positively charged, amino acid residue and/or R251 substituted with any non-positively charged, amino acid residue; and for SLT-2A derived Shiga toxin effector polypeptides, the natively positioned amino acid residue Y247 substituted with any non-positively charged, amino acid residue and/or R250 substituted with any non-positively charged, amino acid residue.

In certain further embodiments, the disrupted furin-cleavage motif comprises both an amino acid substitution within the minimal furin-cleavage site R/Y-x-x-R and a carboxy-terminal truncation as compared to a wild-type, Shiga toxin A Subunit, such as, e.g., for StxA and SLT-1A derived Shiga toxin effector polypeptides, truncations ending at the natively amino acid position 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue R248 and/or R251 substituted with any non-positively charged, amino acid residue where appropriate; and for SLT-2A derived Shiga toxin effector polypeptides, truncations ending at the natively amino acid position 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, or greater and comprising the natively positioned amino acid residue Y247 and/or R250 substituted with any non-positively charged, amino acid residue where appropriate.

In certain embodiments, the disrupted furin-cleavage motif comprises an insertion of one or more amino acid residues as compared to a wild-type, Shiga toxin A Subunit as long as the inserted amino residue(s) does not create a de novo furin-cleavage site. In certain embodiments, the insertion of one or more amino acid residues disrupts the natural spacing between the arginine residues in the minimal, furin-cleavage site R/Y-x-x-R, such as, e.g., StxA and SLT-1A derived polypeptides comprising an insertion of one or more amino acid residues at 249 or 250 and thus between R248 and R251; or SLT-2A derived polypeptides comprising an insertion of one or more amino acid residues at 248 or 249 and thus between Y247 and R250.

In certain embodiments, the disrupted furin-cleavage motif comprises both an amino acid residue insertion and a carboxy-terminal truncation as compared to a wild-type, Shiga toxin A Subunit. In certain embodiments, the disrupted furin-cleavage motif comprises both an amino acid residue insertion and an amino acid residue substitution as compared to a wild-type, Shiga toxin A Subunit. In certain embodiments, the disrupted furin-cleavage motif comprises both an amino acid residue insertion and an amino acid residue deletion as compared to a wild-type, Shiga toxin A Subunit.

In certain embodiments, the disrupted furin-cleavage motif comprises an amino acid residue deletion, an amino acid residue insertion, and an amino acid residue substitution as compared to a wild-type, Shiga toxin A Subunit.

In certain embodiments, the disrupted furin-cleavage motif comprises an amino acid residue deletion, insertion, substitution, and carboxy-terminal truncation as compared to a wild-type, Shiga toxin A Subunit.

In certain embodiments, the Shiga toxin effector polypeptide comprising a disrupted furin-cleavage motif is directly fused by a peptide bond to a molecular moiety comprising an amino acid, peptide, and/or polypeptide wherein the fused structure involves a single, continuous polypeptide. In these fusion embodiments, the amino acid sequence following the disrupted furin-cleavage motif should not create a de novo, furin-cleavage site at the fusion junction.

Shiga toxin A Subunits might have other furin-cleavage motifs besides the furin-cleavage motif in the highly conserved, surface-exposed loop structure and natively positioned in the region from L238 to F257 in StxA and SLT-1A and from V237 to Q256 in SLT-2A. For example, StxA and SLT-1A comprise a furin-cleavage motif around the natively positioned amino acid residue region 220 to 223. However, there is no evidence this second furin site in Shiga toxin A Subunits is cleaved in vivo. On the contrary, in vitro treatment of Stx2 holotoxin with human furin did not produce cleavage at any other R-x-x-R motif in the A Subunit (e.g. the motif natively positioned from amino acid residue 179 to 222) beside at Arg250, which suggests that other potential dibasic sites within Shiga toxin A Subunits are not accessible to furin (Faqerquist C, Sultan O, *J Biomed Biotechnol* 2010: 123460 (2010)). Although disrupting other cleavage sites besides might be engineered, e.g., the furin-cleavage motif at L238 to F257 in StxA1 and SLT-1A, disrupting the furin-cleavage motif natively positioned in the region from 220 to 223 in SLT-1A may reduce its cytotoxic activity below a reasonable activity (see e.g. Lea N et al., *Microbiology* 145: 999-1004 (1999)) and would provide little benefit related to protease-resistance if the protease site in the 220 to 223 region is not protease accessible.

B. Molecular Moieties Positioned Carboxy-Terminal to the Shiga Toxin Effector Polypeptide Certain molecules of the present invention comprise a molecular moiety associated with the carboxy terminus of the Shiga toxin effector polypeptide. The present invention enables the attachment of relatively large, molecular moieties carboxy terminal to furin-cleavage resistant, Shiga toxin effector polypeptides without any loss in Shiga toxin effector cytotoxicity as compared to furin-cleavable, Shiga toxin effector polypeptides. The term "molecular moiety" encompasses polypeptides, proteins, cytotoxic agents, polynucleotides, detection promoting agents, small molecule chemotherapeutic agents, polysaccharides, lipids, and other biomolecules whether naturally occurring or synthetic.

Furin proteolysis of the Shiga toxin A Subunit within an intoxicated cell provides for at least three events: exposure of the carboxy terminus of the Shiga toxin A1 fragment, liberation of the A1 fragment from all other molecular moieties, and translocation of the A1 fragment from the endoplasmic reticulum to the cytosol. The dissociation of the A1 fragment from the A2 fragment and the rest of the Shiga holotoxin is required for the translocation of the A1 fragment from the lumen of the endoplasmic reticulum to the cytosol and the only component of the Shiga holotoxin that reaches the cytosolic compartment is the A1 fragment (LaPointe P et al., *J Biol Chem* 280: 23310-18 (2005); Tam P, Lingwood C, *Microbiology* 153: 2700-10 (2007); Li S et al., *PLoS One* 7: e41119 (2012)).

One critical function of furin cleavage during Shiga toxin intoxication appears to be the exposure of the carboxy terminus of the Shiga toxin A1 fragment. Exposure of the carboxy terminus of the A1 fragment in the endoplasmic reticulum of an intoxicated cell is thought to be required for optimal subcellular routing and cytotoxicity. When a Shiga toxin A Subunit derived structure cannot expose the carboxy terminus of an A1 fragment in the endoplasmic reticulum of an intoxicated cell, then the cytotoxic effect of that structure is reduced (Burgess B, Roberts L, *Mol Microbiol* 10: 171-9 (1993); Garred Ø et al., *Exp Cell Res* 218: 39-49 (1995); Lea N et al., *Microbiology* 145: 999-1004 (1999); Kurmanova A et al., *Biochem Biophys Res Commun* 357: 144-9 (2007)). This can be explained by the persistence of one or more molecular moieties sterically covering the carboxy terminus of the Shiga toxin A1 fragment resulting in the perturbation of the normally efficient intracellular routing of the A1 fragment to the cytosol. Shiga toxin A Subunit derived structures which lack furin proteolytic processing fail to efficiently reach the cytosol of intoxicated cells (Garred Ø et al., *J Biol Chem* 270: 10817-21 (1995); Garred Ø et al., *Exp Cell Res* 218: 39-49 (1995); Lea N et al., *Microbiology* 145: 999-1004 (1999)).

Another critical function of furin cleavage during Shiga toxin intoxication is liberation of the Shiga toxin A1 fragment from the rest of the Shiga holotoxin. Liberation of the A1 fragment in the endoplasmic reticulum of an intoxicated cell is thought to be required for optimal subcellular routing and cytotoxicity. When a Shiga toxin A1 fragment cannot be furin-cleaved and liberated in the endoplasmic reticulum of an intoxicated cell, then the cytotoxic effect is reduced (Burgess B, Roberts L, *Mol Microbiol* 10: 171-9 (1993); Garred Ø et al., *Exp Cell Res* 218: 39-49 (1995); Lea N et al., *Microbiology* 145: 999-1004 (1999); Kurmanova A et al., *Biochem Biophys Res Commun* 357: 144-9 (2007)). Again, this can be explained by the persistence of one or more molecular moieties associated with the carboxy terminus of the Shiga toxin A1 fragment resulting in the perturbation of the normally efficient intracellular routing of the A1 fragment to the cytosol.

For maximal Shiga toxin cytotoxicity, models suggest that it is essential that the Shiga toxin A1 fragment is liberated from all molecular moieties associated with and/or sterically covering its carboxy-terminus for efficient cytosolic routing, optimal proteasome evasion, optimal catalytic structure formation, and maximal enzymatic activation (Garred Π et al., *Exp Cell Res* 218: 39-49 (1995); Garred Ø et al., *J Biol Chem* 270: 10817-21 (1995); Lea N et al., *Microbiology* 145: 999-1004 (1999); LaPointe P et al., *J Biol Chem* 280: 23310-18 (2005); Yu M, Haslam D, *Infect Immun* 73: 2524-32 (2005); Kurmanova A et al., *Biochem Biophys Res Commun* 357: 144-9 (2007); Smith M et al., *Infect Immun* 77: 2730-40 (2009); Di R et al., *Toxicon* 57: 525-39 (2011); Li S et al., *PLoS One* 7: e41119 (2012)). For example, the Shiga toxin A2 fragment is fused to the A1 fragment in wild-type, Shiga holotoxins and the pentamer of Shiga toxin B-Subunits is bound to the carboxy terminus of the A2 fragment (Fraser M et al., *Nat Struct Biol* 1: 59-64 (1994)). Similarly, maximal Shiga toxin cytotoxicity might require the liberation of the A1 fragment from all molecular moieties associated with its carboxy terminus, such as, e.g., moieties at least as large as the A2 fragment (4.5-4.7 kDa) and of the mass of the remainder of the Shiga holotoxin (42.7-43.2 kDa).

Relatedly, maximal, Shiga toxin cytotoxicity might require the liberation of the A1 fragment from all carboxy-terminal moieties which sterically cover the carboxy terminus of the A1 fragment as this region must be exposed for efficient translocation to the cytosol (see Suhan M, Hovde C, *Infect Immun* 66: 5252-9 (1998); LaPointe P et al., *J Biol Chem* 280: 23310-18 (2005); Yu M, Haslam D, *Infect Immun* 73: 2524-32 (2005); Li S et al., *PLoS One* 7: e41119 (2012)).

In addition, for maximal Shiga toxin cytotoxicity it might be important to liberate the A1 fragment from molecular moieties comprising cell-targeting binding domains which bind cellular membrane components, like Shiga toxin B Subunits which bind gangliosides in lipid bilayer membranes. It is possible that when the A1 fragment is covalently attached to a cell-targeting moiety bound with high affinity to an endoplasmic membrane target, then the Shiga toxin A1 fragment remains tethered to the lipid membrane of the endoplasmic reticulum in a way that perturbs mechanisms and events required for efficient A1 fragment liberation and/or translocation to the cytosol.

The present invention provides exemplary structures demonstrating that the functions of furin-cleavage of Shiga toxin A Subunits in the models described above are not required for wild-type levels of Shiga cytotoxicity exhibited by synthetic cell-targeted molecules (see Examples, infra). Apparently, the carboxy terminus of the Shiga toxin A1 fragment does not need to be exposed for efficient intracellular routing to the cytosol, and, apparently, the liberation of the A1 fragment from all other molecular moieties is not required for maximal, Shiga toxin cytotoxicity. Thus, the furin-cleavage motif of Shiga toxin A Subunits may be disrupted in cell-targeted molecules without sacrificing any cytotoxicity despite the presence of a molecular moiety located with the cell-targeted molecule carboxy terminal to the Shiga toxin effector polypeptide region.

Certain molecules of the present invention comprise a molecular moiety associated with the carboxy terminus of the Shiga toxin effector polypeptide. In certain further embodiments, the association comprises a covalent bond linking the carboxy terminus of the Shiga toxin effector polypeptide, either directly or indirectly, with the molecular moiety. In certain further embodiments, the association comprises the peptide bond which fuses the carboxy terminus of the Shiga toxin effector polypeptide with one or more amino acid residues of the molecular moiety. In certain further embodiments, the Shiga toxin effector polypeptide and the molecular moiety are fused to form a single, continuous polypeptide such that the Shiga toxin effector polypeptide is physically located within the continuous polypeptide amino-terminal to the molecular moiety.

The size of the molecular moiety may vary. Molecular moieties of the molecules of the present invention include: moieties large enough to sterically cover the carboxy terminus of a Shiga toxin A1 fragment, moieties of any size comprising binding regions capable of binding lipid membrane bound targets, moieties of any size which provide a well-structured, tertiary polypeptide structure proximal to the carboxy-terminal region of the Shiga toxin A1 fragment of the invention, moieties of any size which are more polar and hydrophilic than the carboxy terminus of Shiga toxin A1 fragments, and any moiety equal or greater than the size of a native, Shiga toxin A Subunit (approximately 28 kDa). A molecular moiety of a size equal to or greater than 28 kDa is referred to herein as "relatively large."

In certain embodiments, a molecule of the invention may comprise the molecular moiety comprising a peptide. In certain embodiments, a molecule of the invention may comprise the molecular moiety having a mass of 1.5 kDa or greater. In certain embodiments, a molecule of the invention may comprises the molecular moiety that has a mass of at least 4.5 kDa, 6, kDa, 9 kDa, 12 kDa, 15 kDa, 20 kDa, 25 kDa, 28 kDa, 30 kDa, 41 kDa, 50 kDa, 100 kDa, or greater, as long as the molecule retains the appropriate Shiga toxin biological activity noted herein.

In certain embodiments, the molecular moiety has a mass of about 4.5 kDa or another equivalent mass of a Shiga toxin A2 fragment. It was unexpected that a moiety of this size can remain attached to the carboxy terminus of the Shiga toxin A1 fragment without disrupting the efficiency of sub-cellular routing and ribosome inactivation within intoxicated cells.

In certain embodiments, the molecular moiety has a mass of about 7.6 kDa or another equivalent mass of a Shiga toxin B Subunit. It was unexpected that a moiety of this size can remain attached to the carboxy terminus of the Shiga toxin A1 fragment without disrupting the efficiency of sub-cellular routing and ribosome inactivation within intoxicated cells.

In certain embodiments, the molecular moiety has a mass of about 6-10 kDa or greater and comprises a binding region comprising an antibody mimetic or alternative antibody format, such as, e.g., engineered Armadillo repeat polypeptides (ArmRPs), engineered, fibronectin-derived, $10^{th}$ fibronectin type III (10Fn3) domain (monobodies, AdNectins™, or AdNexins™); engineered, ankyrin repeat motif containing polypeptide (DARPins™); engineered, low-density-lipoprotein-receptor-derived, A domain (LDLR-A) (Avimers™); engineered, Protein-A-derived, Z domain (Affibodies™); engineered, gamma-B crystalline-derived scaffold or engineered, ubiquitin-derived scaffold (Affilins); and Sac7d-derived polypeptides (Nanofitins® or affitins).

In certain embodiments, the molecular moiety has a mass of about 11 kDa or more and comprises a binding region comprising an immunoglobulin domain(s) and which specifically binds an extracellular target biomolecule with high affinity, such as, e.g., a $V_HH$ or nanobody. In certain further embodiments, the molecular moiety has a mass of about 24 kDa or more and comprises a binding region comprising an immunoglobulin domain and which specifically binds an extracellular target biomolecule with high affinity, such as, e.g., a scFv.

In certain embodiments, the molecular moiety has a mass of about 12 kDa or another equivalent mass of a Shiga toxin A2 fragment and B Subunit complex. It was unexpected that a moiety of this size can remain attached to the carboxy terminus of the Shiga toxin A1 fragment without disrupting the efficiency of sub-cellular routing and ribosome inactivation within intoxicated cells.

In certain embodiments, the molecular moiety has a mass of about 28 kDa. It was unexpected that a moiety of this size can remain attached to the carboxy terminus of the Shiga toxin A1 fragment without disrupting the efficiency of sub-cellular routing and ribosome inactivation within intoxicated cells; however, the Examples herein demonstrate that a furin-cleavage resistant molecule comprising a Shiga toxin A1 fragment fused to a 28 kDa molecular moiety did not exhibit any apparent disruption in sub-cellular routing, ribosome inhibition, or cytotoxicity.

In certain embodiments, the relatively large, molecular moiety has a mass of about 39 kDa or another equivalent mass of a Shiga toxin B Subunit pentamer. It was unexpected that a moiety of this size can remain attached to the carboxy terminus of the Shiga toxin A1 fragment without disrupting the efficiency of sub-cellular routing and ribosome inactivation within intoxicated cells.

In certain embodiments, the relatively large, molecular moiety has a mass of about 43.2 kDa or another equivalent mass of a Shiga toxin A2 fragment and B Subunit pentamer complex. It was unexpected that a moiety of this size can remain attached to the carboxy terminus of the Shiga toxin A1 fragment without disrupting the efficiency of sub-cellular routing and ribosome inactivation within intoxicated cells.

In certain embodiments, the molecular moiety is branched. In certain embodiments, the molecule moiety is non-proteinaceous. In certain embodiments, the molecular moiety is a cytotoxic agent or detection promoting agent, such as agents described herein.

In certain embodiments, the molecular moiety sterically covers the carboxy-terminus of the Shiga toxin A1 fragment polypeptide of the Shiga toxin effector polypeptide of the invention. For purposes of the present invention, "sterically cover" or "sterically covering" refers to a moiety covalently attached directly to the carboxy terminal region of the Shiga toxin A1 fragment polypeptide of the Shiga toxin effector polypeptide of the invention. In certain embodiments, the molecular moiety sterically covers the carboxy terminal region of the Shiga toxin A1 fragment polypeptide of the Shiga toxin effector polypeptide of the invention such that the hydrophobic region within the carboxy-terminal region of the Shiga toxin A1 fragment polypeptide of the Shiga toxin effector polypeptide of the invention remain buried and is not surface exposed in the endoplasmic reticulum, thereby keeping the carboxy terminus of the A1 fragment region covered and preventing cellular recognition of the carboxy terminus of the A1 fragment-derived region, such as, e.g. recognition by the ERAD machinery.

In certain embodiments, the molecular moiety comprises a polypeptide which is more polar and hydrophilic than the carboxy-terminal region of a Shiga toxin A1 fragment such that the hydrophobic region within the carboxy-terminal region of the Shiga toxin A1 fragment polypeptide of the Shiga toxin effector polypeptide of the invention remain buried and is not surface exposed in the endoplasmic reticulum, thereby keeping the carboxy terminus of the A1 fragment region covered and preventing cellular recognition of the carboxy terminus of the A1 fragment-derived region, such as, e.g. recognition by the ERAD machinery.

In certain embodiments, the molecular moiety comprises a binding region capable of specifically binding at least one target biomolecule which is membrane bound in the endoplasmic reticulum membrane.

In certain embodiments, the molecular moiety comprises a binding region capable of specifically binding at least one extracellular target biomolecule.

C. Cell-Targeting Molecules Comprising Protease-Cleavage Resistant, Shiga Toxin a Subunit Effector Polypeptides of the Invention The molecules of the present invention all comprise a Shiga toxin effector polypeptide comprising a disrupted furin-cleavage motif and/or furin-cleavage site. The cell-targeting molecules of the present invention comprise a protease-cleavage resistant, Shiga toxin effector polypeptide associated with a cell-targeting binding region. This means the cell-targeting molecule is more protease-cleavage resistant when compared to the same cell-targeting molecule having its furin-cleavage resistant, Shiga toxin effector polypeptide replaced with a wild-type, Shiga toxin effector polypeptide comprising a Shiga toxin A1 fragment.

Protease-cleavage resistant molecules may exhibit increased, in vivo, half-lives after administration to a vertebrate as compared to more protease-cleavage sensitive variants. Furthermore, protease-cleavage resistant, cell-targeting molecules which comprise a toxic component (e.g. a toxin effector region) may exhibit reduced non-specific toxicity as compared to more protease-cleavage sensitive variants with a greater propensity to break, thereby releasing the toxic component.

The cell-targeting molecules of the present invention may comprise a single polypeptide, multiple polypeptides in association with each other, a branched polypeptide component, and/or one or more non-polypeptide moieties.

The binding region of a cell-targeting molecule of the invention comprises a peptide or polypeptide region capable of binding specifically to a target biomolecule. In certain embodiments, the binding region of a cell-targeted molecule of the invention comprises one or more polypeptides capable of selectively and specifically binding an extracellular target biomolecule. Binding region may comprise one or more various peptidic or polypeptide moieties, such as randomly generated peptide sequences, naturally occurring ligands or derivatives thereof, immunoglobulin derived domains, synthetically engineered scaffolds as alternatives to immunoglobulin domains, and the like.

There are numerous binding regions known in the art that are useful for targeting polypeptides to specific cell-types via their binding characteristics, such as ligands, monoclonal antibodies, engineered antibody derivatives, and engineered alternatives to antibodies.

According to one specific, but non-limiting aspect, the binding region of the molecule of the invention comprises a naturally occurring ligand or derivative thereof that retains binding functionality to an extracellular target biomolecule, commonly a cell surface receptor. For example, various cytokines, growth factors, and hormones known in the art may be used to target the cell-targeted molecule to the cell-surface of specific cell types expressing a cognate cytokine receptor, growth factor receptor, or hormone receptor. Certain non-limiting examples of ligands include epidermal growth factors, fibroblast growth factors, vascular endothelial growth factors, interleukins (such as IL-2, IL-6, and IL-23), and B-cell activating factor (BAFF).

According to certain other embodiments, the binding region comprises a synthetic ligand capable of binding an extracellular target biomolecule (see e.g. Liang S et al., *J Mol Med* 84: 764-73 (2006); Ahmed S et al., *Anal Chem* 82: 7533-41 (2010); Kaur K et al., *Methods Mol Biol* 1248: 239-47 (2015)).

According to one specific, but non-limiting aspect, the binding region may comprise an immunoglobulin-type binding region. The term "immunoglobulin-type binding region" as used herein refers to a polypeptide region capable of binding one or more target biomolecules, such as an antigen or epitope. Binding regions may be functionally defined by their ability to bind to target molecules. Immunoglobulin-type binding regions are commonly derived from antibody or antibody-like structures; however, alternative scaffolds from other sources are contemplated within the scope of the term.

Immunoglobulin (Ig) proteins have a structural domain known as an Ig domain. Ig domains range in length from about 70-110 amino acid residues and possess a characteristic Ig-fold, in which typically 7 to 9 antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a complementarity determining region or complementary determining region (CDR) which is important for the specificity of antibodies binding to their epitopes. Ig-like domains are also found in non-immunoglobulin proteins and are classified on that basis as members of the Ig superfamily of proteins. The HUGO Gene Nomenclature Committee (HGNC) provides a list of members of the Ig-like domain containing family.

As used herein, the term "heavy chain variable ($V_H$) domain" or "light chain variable ($V_L$) domain" respectively refer to any antibody $V_H$ or $V_L$ domain (e.g. a human $V_H$ or $V_L$ domain) as well as any derivative thereof retaining at least qualitative antigen binding ability of the corresponding native antibody (e.g. a humanized $V_H$ or $V_L$ domain derived from a native murine $V_H$ or $V_L$ domain). A $V_H$ or $V_L$ domain consists of a "framework" region interrupted by the three CDRs or ABRs. The framework regions serve to align the CDRs for specific binding to an epitope of an antigen. From amino-terminus to carboxyl-terminus, both $V_H$ and $V_L$ domains comprise the following framework (FR) and CDR regions: FR1, CDR1, FR2, CDR2, FR3, CDR3, and FR4. For camelid $V_H$H fragments, IgNARs of cartilaginous fish, $V_{NAR}$ fragments, and derivatives thereof, there is a single heavy chain variable domain comprising the same basic arrangement: FR1, CDR1, FR2, CDR2, FR3, CDR3, and FR4.

An immunoglobulin-type binding region may be a polypeptide sequence of an antibody or antigen-binding fragment thereof wherein the amino acid sequence has been varied from that of a native antibody or an Ig-like domain of a non-immunoglobulin protein, for example by molecular engineering or selection by library screening. Because of the relevance of recombinant DNA techniques and in vitro library screening in the generation of immunoglobulin-type binding regions, antibodies can be redesigned to obtain desired characteristics, such as smaller size, cell entry, or other therapeutic improvements. The possible variations are many and may range from the changing of just one amino acid to the complete redesign of, for example, a variable region. Typically, changes in the variable region will be made in order to improve the antigen-binding characteristics, improve variable region stability, or reduce the potential for immunogenic responses.

There are numerous immunoglobulin-type binding regions contemplated as components of the molecules of the present invention, such as, e.g., the cell-targeted molecules of the present invention. An immunoglobulin binding region generally comprises one or more CDRs. In certain embodiments, the immunoglobulin-type binding region is derived from an immunoglobulin binding region, such as an antibody paratope capable of binding an extracellular target biomolecule. In certain other embodiments, the immunoglobulin-type binding region comprises an engineered polypeptide not derived from any immunoglobulin domain but which functions like an immunoglobulin binding region by providing high-affinity binding to an extracellular target biomolecule. This engineered polypeptide may optionally include polypeptide scaffolds comprising or consisting essentially of complementary determining regions from immunoglobulins as described herein.

There are also numerous binding regions in the prior art that are useful for targeting polypeptides to specific cell-types via their high-affinity binding characteristics. In certain embodiments, the binding region of the present proteins is selected from the group which includes single-domain antibody domains (sdAbs), nanobodies, heavy-chain antibody domains derived from camelids ($V_H$H fragments), bivalent nanobodies, heavy-chain antibody domains derived from cartilaginous fishes, immunoglobulin new antigen receptors (IgNARs), $V_{NAR}$ fragments, single-chain variable (scFv) fragments, multimerizing scFv fragments (diabodies, triabodies, tetrabodies), bispecific tandem scFv fragments, disulfide stabilized antibody variable (Fv) fragments, disulfide stabilized antigen-binding (Fab) fragments consisting of the $V_L$, $V_H$, $C_L$ and $C_H$1 domains, divalent F(ab')2 fragments, Fd fragments consisting of the heavy chain and $C_H$1 domains, single chain Fv-$C_H$3 minibodies, bispecific minibodies, dimeric $C_H$2 domain fragments ($C_H$2D), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, and any genetically manipulated counterparts of the foregoing that retain its paratope and binding function (see, Weiner L, *Cell* 148: 1081-4 (2012); Ahmad Z et al., *Clin Dev Immunol* 2012: 980250 (2012), for reviews).

In accordance with certain other embodiments, the binding region includes engineered, alternative scaffolds to immunoglobulin domains that exhibit similar functional characteristics, such as high-affinity and specific binding of target biomolecules, and enables the engineering of improved characteristics, such as greater stability or reduced immunogenicity. For certain embodiments of the proteins of the invention, the binding region is selected from the group which includes engineered Armadillo repeat polypeptides (ArmRPs), engineered, fibronectin-derived, $10^{th}$ fibronectin type III (10Fn3) domain (monobodies, AdNectins™, or AdNexins™); engineered, tenascin-derived, tenascin type III domain (Centryns™); engineered, ankyrin repeat motif containing polypeptide (DARPins™); engineered, low-density-lipoprotein-receptor-derived, A domain (LDLR-A) (Avimers™); lipocalin (anticalins); engineered, protease inhibitor-derived, Kunitz domain; engineered, Protein-A-derived, Z domain (Affibodies™); engineered, gamma-B crystalline-derived scaffold or engineered, ubiquitin-derived scaffold (Affilins); Sac7d-derived polypeptides (Nanoffitins® or affitins); engineered, Fyn-derived, SH2 domain (Fynomers®); and engineered antibody mimic and any genetically manipulated counterparts of the foregoing that retains its binding functionality (Worn A, Phückthun A, *J Mol Biol* 305: 989-1010 (2001); Xu L et al., *Chem Biol* 9: 933-42 (2002); Wikman M et al., *Protein Eng Des Sel* 17: 455-62 (2004); Binz H et al., *Nat Biotechnol* 23: 1257-68 (2005); Holliger P, Hudson P, *Nat Biotechnol* 23: 1126-36 (2005); Gill D, Damle N, *Curr Opin Biotech* 17: 653-8 (2006); Koide A, Koide S, *Methods Mol Biol* 352: 95-109 (2007); Byla P et al., *J Biol Chem* 285: 12096-100 (2010); Zoller F et al., *Molecules* 16: 2467-85 (2011); Alfarano P et al., *Protein Sci* 21: 1298-314 (2012); Madhurantakam C et al., *Protein Sci* 21: 1015-28 (2012); Varadamsetty G et al., *J Mol Biol* 424: 68-87 (2012)).

Among certain embodiments of the present invention, the immunoglobulin-type binding region is derived from a nanobody or single domain immunoglobulin-derived region $V_HH$. Generally, nanobodies are constructed from fragments of naturally occurring single, monomeric variable domain antibodies (sdAbs) of the sort found in camelids and cartilaginous fishes (Chondrichthyes). Nanobodies are engineered from these naturally occurring antibodies by truncating the single, monomeric variable domain to create smaller and more stable molecules, such as, e.g., IgNAR, $V_HH$, and $V_{NAR}$ constructs. Due to their small size, nanobodies are able to bind to antigens that are not accessible to whole antibodies.

Any of the above binding regions may be used as a component of the cell-targeting molecules of the present invention as long as the binding region component has a dissociation constant of $10^{-5}$ to $10^{-12}$ moles per liter, preferably less than 200 nanomolar (nM), towards an extracellular target biomolecule.

Cell-specific targeting can be accomplished by attaching molecules of the present invention to cell targeting carriers, such as, e.g., liposomes, polymers, nanocarriers, microspheres, nanospheres, dendrimers, polymeric micelles, silicon or carbon materials, such as e.g., nanotubes, nanorods and nanohorns, magnetic nanoparticles, microemulsions, and other nanostructures (Sinha R et al., *Molecular Cancer Therapeutics* 5: 1909-17 (2006); L Brinton et al., *Journal of the National Cancer Institute* 100: 1643-8 (2008); Tanaka T et al., *Biomed Micro Devices* 11: 49-63 (2009)). Attachment may be accomplished using covalent bonds and/or encapsulation.

Extracellular Target Biomolecules

The binding region of the molecule of the invention comprises a polypeptide region capable of binding specifically to an extracellular target biomolecule, preferably which is physically-coupled to the surface of a cell type of interest, such as a cancer cell, tumor cell, plasma cell, infected cell, or host cell harboring an intracellular pathogen.

The term "target biomolecule" refers to a biological molecule, commonly a protein or a protein modified by post-translational modifications, such as glycosylation, which is capable of being bound by a binding region to target a protein to a specific cell-type or location within an organism. Extracellular target biomolecules may include various epitopes, including unmodified polypeptides, polypeptides modified by the addition of biochemical functional groups, and glycolipids (see e.g. U.S. Pat. No. 5,091,178; EP 2431743). It is desirable that an extracellular target biomolecule be endogenously internalized or be readily forced to internalize upon interaction with a molecule of the invention.

For purposes of the present invention, the term "extracellular" with regard to modifying a target biomolecule refers to a biomolecule that has at least a portion of its structure exposed to the extracellular environment. Extracellular target biomolecules include cell membrane components, transmembrane spanning proteins, cell membrane-anchored biomolecules, cell-surface-bound biomolecules, and secreted biomolecules.

With regard to the present invention, the phrase "physically coupled" when used to describe a target biomolecule means both covalent and/or non-covalent intermolecular interactions that couple the target biomolecule, or a portion thereof, to the outside of a cell, such as a plurality of non-covalent interactions between the target biomolecule and the cell where the energy of each single interaction is on the order of about 1-5 kiloCalories (e.g. electrostatic bonds, hydrogen bonds, Van der Walls interactions, hydrophobic forces, etc.). All integral membrane proteins can be found physically coupled to a cell membrane, as well as peripheral membrane proteins. For example, an extracellular target biomolecule might comprise a transmembrane spanning region, a lipid anchor, a glycolipid anchor, and/or be non-covalently associated (e.g. via non-specific hydrophobic interactions and/or lipid binding interactions) with a factor comprising any one of the foregoing.

The binding regions of the proteins of the invention may be designed or selected based on numerous criteria, such as the cell-type specific expression of their target biomolecules and/or the physical localization of their target biomolecules with regard to specific cell types. For example, certain cell-targeted molecules of the present invention comprise binding domains capable of binding cell-surface targets which are expressed exclusively by only one cell-type to the cell surface. This permits the targeted cell-killing of specific cell types with a high preferentiality (at least a 3-fold cytotoxic effect) over "bystander" cell types that do not express the extracellular target biomolecule. Alternatively, the expression of the target biomolecule of the binding region may be non-exclusive to one cell type if the extracellular target biomolecule is expressed in low enough amounts and/or physically coupled in low amounts with cell types that are not to be targeted. This also permits the targeted cell-killing of specific cell types with a high preferentiality (at least a 3-fold cytotoxic effect) over "bystander" cell types that do not express significant amounts of the extracellular target biomolecule or are not physically coupled to significant amounts of the extracellular target biomolecule. A targeted cell may be killed using the cytotoxic, cell-targeted molecules of the invention under varied conditions of the cell, such as ex vivo, in vitro cultured, or in vivo—including cells in situ in their native locations within a multicellular organism.

Extracellular target biomolecules of the binding region of the proteins of the invention may include biomarkers over-proportionately or exclusively present on cancer cells, immune cells, and cells infected with intracellular pathogens, such as viruses, bacteria, fungi, prions, or protozoans.

The general structure of the cell-targeting molecules of the present invention is modular, in that various, diverse binding regions may be used with the same protease-cleavage resistant, Shiga toxin effector polypeptide to provide for diverse targeting of various extracellular target biomolecules and thus targeting of cytotoxicity, cytostasis, and/or exogenous material delivery to various diverse cell types. Protease-cleavage resistant, Shiga toxin effector polypeptides which are not cytotoxic may still be useful for delivering exogenous materials into cells, certain subcellular compartments, and/or providing efficient subcellular routing to the cytosol. Optionally, a cell-targeted molecule of the invention may further comprise a carboxy-terminal endoplasmic retention/retrieval signal motif, such as KDEL (SEQ ID NO:62).

D. Endoplasmic Reticulum Retention/Retrieval Signal Motif of a Member of the KDEL Family For purposes of the present invention, the phrase "endoplasmic reticulum retention/retrieval signal motif," KDEL-type signal motif, or signal motif refers to any member of the KDEL family capable of functioning within a eukaryotic cell to promote subcellular localization of a protein to the endoplasmic reticulum via KDEL receptors.

The carboxy-terminal lysine-asparagine-glutamate-leucine (KDEL (SEQ ID NO: 62)) sequence is a canonical, endoplasmic reticulum retention and retrieval signal motif for soluble proteins in eukaryotic cells and is recognized by KDEL receptors (see, Capitani M, Sallese M, *FEBS Lett* 583: 3863-71 (2009), for review). The KDEL family of signal motifs includes many KDEL-like motifs, such as HDEL (SEQ ID NO: 64), RDEL (SEQ ID NO: 66), WDEL (SEQ ID NO: 67), YDEL (SEQ ID NO: 68), HEEL (SEQ ID NO:-70), KEEL (SEQ ID NO: 71), REEL (SEQ ID NO: 72), KFEL (SEQ ID NO: 75), KIEL (SEQ ID NO: 87), DKEL (SEQ ID NO: 88), KKEL (SEQ ID NO: 91), HNEL (SEQ ID NO: 95), HTEL (SEQ ID NO: 96), KTEL (SEQ ID NO: 97), and HVEL (SEQ ID NO: 98), all of which are found at the carboxy-terminals of proteins which are known to be residents of the lumen of the endoplasmic reticulum of organisms throughout multiple phylogenetic kingdoms (Munro S, Pelham H, *Cell* 48: 899-907 (1987); Raykhel I et al., *J Cell Bloi* 179: 1193-204 (2007)). The KDEL signal motif family includes at least 46 polypeptide variants shown using synthetic constructs (Raykhel, *J Cell Biol* 179: 1193-204 (2007)). Additional KDEL signal motifs include ALEDEL (SEQ ID NO: 109), HAEDEL (SEQ ID NO:-110), HLEDEL (SEQ ID NO: 111), KLEDEL (SEQ ID NO: 112), IRSDEL (SEQ ID NO:-113), ERSTEL (SEQ ID NO: 114), and RPSTEL (SEQ ID NO: 115) (Alanen H et al., *J Mol Biol* 409: 291-7 (2011)). A generalized consensus motif representing the majority of KDEL signal motifs has been described as [KRHQSA]-[DENQ]-E-L (SEQ ID NO: 116) (Hulo N et al., *Nucleic Acids Res* 34: D227-30 (2006)).

Proteins containing KDEL family signal motifs are bound by KDEL receptors distributed throughout the Golgi complex and transported to the endoplasmic reticulum by a microtubule-dependent mechanism for release into the lumen of the endoplasmic reticulum (Griffiths G et al., *J Cell Bloi* 127: 1557-74 (1994); Miesenbock G, Rothman J, *J Cell Bloi* 129: 309-19 (1995)). KDEL receptors dynamically cycle between the Golgi complex and endoplasmic reticulum (Jackson M et al., *EMBO J* 9: 3153-62 (1990); Schutze M et al., *EMBO J* 13: 1696-1705 (1994)).

For purposes of the present invention, the members of the KDEL family include synthetic signal motifs able to function within a eukaryotic cell to promote subcellular localization of a protein to the endoplasmic reticulum via KDEL receptors. In other words, some members of the KDEL family might not occur in nature or have yet to be observed in nature but have or may be constructed and empirically verified using methods known in the art; see e.g., Raykhel I et al., *J Cell Biol* 179: 1193-204 (2007).

As a component of certain embodiments of the molecules of the invention, the KDEL-type signal motif is physically located, oriented, or arranged within the molecule such that it is on a carboxy-terminal of a polypeptide or protein component.

For the purposes of the cell-targeting molecules of the present invention, the specific order or orientation is not fixed for the Shiga toxin effector polypeptide and the cell-targeting, binding region in relation to each other or the entire protein's N-terminal(s) and C-terminal(s) (see e.g. FIG. 1). In the cell-targeting molecules of the invention, the binding regions, Shiga toxin effector polypeptide regions, and if present, any molecular moiety, may be directly linked to each other and/or suitably linked to each other via one or more linkers well known in the art.

E. Linkages Connecting Components of the Molecules of the Invention

Individual molecular moieties and polypeptide and/or protein components of the invention, e.g. the binding regions and Shiga toxin effector polypeptide regions (which may be cytotoxic and/or harbor one or more mutations altering, reducing, or eliminating catalytic activity and/or cytotoxicity), may be suitably linked to each other via one or more linkers well known in the art and/or described herein. Individual polypeptide subcomponents of the binding regions, e.g. CDR, ABR, $V_H H$ regions, heavy chain variable regions ($V_H$), light chain variable regions ($V_L$), IgNAR regions, and/or $V_{NAR}$ regions, may be suitably linked to each other via one or more linkers well known in the art and/or described herein (see e.g. Weisser N, Hall J, *Biotechnol Adv* 27: 502-20 (2009); Chen X et al., *Adv Drug Deliv Rev* 65: 1357-69 (2013)). Protein and polypeptide components of the invention, e.g., multi-chain binding regions, may be suitably linked to each other, to other polypeptide components, and/or molecular moieties of the invention via one or more linkers well known in the art. Peptide components of the invention, e.g., KDEL family endoplasmic reticulum retention/retrieval signal motifs, may be suitably linked to another component of the invention via one or more linkers, such as a proteinaceous linker, which are well known in the art.

Suitable linkers are generally those which allow each polypeptide component of the invention to fold with a three-dimensional structure very similar to the polypeptide components produced individually without any linker or other component. Suitable linkers include single amino acids, peptides, polypeptides, and linkers lacking any of the aforementioned such as, e.g., various non-proteinaceous carbon chains, whether branched or cyclic (see e.g. Alley S et al., *Bioconjug Chem* 19: 759-65 (2008) Ducry L, Stump B, *Bioconjug Chem* 21: 5-13 (2010); Chen X et al., *Adv Drug Deliv Rev* 65: 1357-69 (2013)).

Suitable linkers may be proteinaceous and comprise one or more amino acids, peptides, and/or polypeptides. Proteinaceous linkers are suitable for both recombinant fusion proteins and chemically linked conjugates. A proteinaceous linker typically has from about 2 to about 50 amino acid residues, such as, e.g., from about 5 to about 30 or from about 6 to about 25 amino acid residues. The length of the linker selected will depend upon a variety of factors, such as, e.g., the desired property or properties for which the linker is being selected (see e.g. Chen X et al., *Adv Drug Deliv Rev* 65: 1357-69 (2013)).

Suitable linkers may be non-proteinaceous, such as, e.g. chemical linkers (see e.g. Dosio F et al., *Toxins* 3: 848-83

(2011); Feld J et al., *Oncotarget* 4: 397-412 (2013)). Various non-proteinaceous linkers known in the art may be used to link the Shiga toxin effector polypeptides to molecular moieties larger than 20 kiloDaltons, such as linkers commonly used to conjugate immunoglobulin polypeptides to heterologous polypeptides. For example, polypeptide components of the molecules of the present invention may be linked using the functional side chains of their amino acid residues and carbohydrate moieties such as, e.g., a carboxy, amine, sulfhydryl, carboxylic acid, carbonyl, hydroxyl, and/ or cyclic ring groups. For example, disulfide bonds and thioether bonds may be used to link two or more polypeptides (see e.g. Fitzgerald D et al., *Bioconjugate Chem* 1: 264-8 (1990); Pasqualucci L et al., *Haematologica* 80: 546-56 (1995)). In addition, non-natural amino acid residues may be used with other functional side chains, such as ketone groups (see e.g. Axup J et al., *Proc Natl Acad Sci USA* 109: 16101-6 (2012); Sun S et al., *Chembiochem* July 18 (2014); Tian F et al., *Proc Natl Acad Sci USA* 111: 1766-71 (2014)). Examples of non-proteinaceous chemical linkers include but are not limited to N-succinimidyl (4-iodoacetyl)-aminobenzoate, S-(N-succinimidyl) thioacetate (SATA), N-succinimidyl-oxycarbonyl-cu-methyl-a-(2-pyridyldithio) toluene (SMPT), N-succinimidyl 4-(2-pyridyldithio)-pentanoate (SPP), succinimidyl 4-(N-maleimidomethyl) cyclohexane carboxylate (SMCC or MCC), sulfosuccinimidyl (4-iodoacetyl)-aminobenzoate, 4-succinimidyl-oxycarbonyl-α-(2-pyridyldithio) toluene, sulfosuccinimidyl-6-(α-methyl-α-(pyridyldithiol)-toluamido) hexanoate, N-succinimidyl-3-(-2-pyridyldithio)-proprionate (SPDP), succinimidyl 6(3(-(-2-pyridyldithio)-proprionamido) hexanoate, sulfosuccinimidyl 6(3(-(-2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfosuccinimidyl N-[3-(acetylthio)-3-methylbutyryl-beta-alanine]), sulfodicholorphenol, 2-iminothiolane, 3-(2-pyridyldithio)-propionyl hydrazide, Ellman's reagent, dichlorotriazinic acid, and S-(2-thiopyridyl)-L-cysteine (see e.g. Thorpe P et al., *Eur J Biochem* 147: 197-206 (1985); Thorpe P et al., *Cancer Res* 47: 5924-31 (1987); Thorpe P et al., *Cancer Res* 48: 6396-403 (1988); Grossbard M et al., *Blood* 79: 576-85 (1992); Lui C et al., *Proc Natl Acad Sci USA* 93: 8618-23 (1996); Doronina S et al., *Nat Biotechnol* 21: 778-84 (2003); Feld J et al., *Oncotarget* 4: 397-412 (2013)).

Suitable linkers, whether proteinaceous or non-proteinaceous, may include, e.g., protease sensitive, environmental redox potential sensitive, pH sensitive, acid cleavable, photocleavable, and/or heat sensitive linkers (see e.g. Dosio F et al., *Toxins* 3: 848-83 (2011); Chen X et al., *Adv Drug Deliv Rev* 65: 1357-69 (2013); Feld J et al., *Oncotarget* 4: 397-412 (2013)).

Proteinaceous linkers may be chosen for incorporation into recombinant fusion proteins of the invention. For example, the component polypeptides of the invention or their subcomponents may be joined by one or more linkers comprising one or more amino acids, peptides, and/or polypeptides. For recombinant fusion proteins of the invention, linkers typically comprise about 2 to 50 amino acid residues, preferably about 5 to 30 amino acid residues (Argos P, *J Mol Biol* 211: 943-58 (1990); Williamson M, *Biochem J* 297: 240-60 (1994); George R, Heringa J, *Protein Eng* 15: 871-9 (2002); Kreitman R, *AAPS J* 8: E532-51 (2006)). Commonly, proteinaceous linkers comprise a majority of amino acid residues with polar, uncharged, and/or charged residues, such as, e.g., threonine, proline, glutamine, glycine, and alanine (see e.g. Huston J et al. *Proc Natl Acad Sci* 85: 5879-83 (1988); Pastan I et al., *Annu Rev Med* 58: 221-37 (2007); Li J et al., *Cell Immunol* 118: 85-99 (1989); Cumber A et al. *Bioconj Chem* 3: 397-401 (1992); Friedman P et al., *Cancer Res* 53: 334-9 (1993); Whitlow M et al., *Protein Engineering* 6: 989-95 (1993); Siegall C et al., *J Immunol* 152: 2377-84 (1994); Newton et al. *Biochemistry* 35: 545-53 (1996); Ladurner et al. *J Mol Blol* 273: 330-7 (1997); Kreitman R et al., *Leuk Lymphoma* 52: 82-6 (2011); U.S. Pat. No. 4,894,443). Non-limiting examples of proteinaceous linkers include alanine-serine-glycine-glycine-proline-glutamate (ASGGPE) (SEQ ID NO: 117), valine-methionine (VM), alanine-methionine (AM), AM ($G_2$ to $_4S)_x$AM (SEQ ID NO: 118) where G is glycine, S is serine, and x is an integer from 1 to 10.

Proteinaceous linkers may be selected based upon the properties desired. Proteinaceous linkers may be chosen by the skilled worker with specific features in mind, such as to optimize one or more of the fusion molecule's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability (see e.g. Chen X et al., *Adv Drug Deliv Rev* 65: 1357-69 (2013)). The skilled worker may use databases and linker design software tools when choosing linkers. Certain linkers may be chosen to optimize expression (see e.g. Turner D et al., *J Immunol Methods* 205: 43-54 (1997)). Certain linkers may be chosen to promote intermolecular interactions between identical polypeptides or proteins to form homomultimers or different polypeptides or proteins to form heteromultimers. For example, proteinaceous linkers may be selected which allow for desired non-covalent interactions between polypeptide components of the molecules of the invention, such as, e.g., interactions related to the formation dimers and other higher order multimers (see e.g. U.S. Pat. No. 4,946,778).

Flexible proteinaceous linkers are often greater than 12 amino acid residues long and rich in small, non-polar amino acid residues, polar amino acid residues, and/or hydrophilic amino acid residues, such as, e.g., glycines, serines, and threonines (see e.g. Bird R et al., *Science* 242: 423-6 (1988); Friedman P et al., *Cancer Res* 53: 334-9 (1993); Siegall C et al., *J Immunol* 152: 2377-84 (1994)). Flexible proteinaceous linkers may be chosen to increase the spatial separation between components and/or to allow for intramolecular interactions between components. For example, various "GS" linkers are known to the skilled worker and are composed of multiple glycines and/or one or more serines, sometimes in repeating units, such as, e.g., $(G_xS)_n$ (SEQ ID NO:-119), $(S_xG)_n$ (SEQ ID NO: 120), $(GGGGS)_n$ (SEQ ID NO: 121), and $(G)_n$ (SEQ ID NO: 122), in which x is 1 to 6 and n is 1 to 30 (see e.g. WO 96/06641). Non-limiting examples of flexible proteinaceous linkers include GKSSGSGSESKS (SEQ ID NO: 123), GSTSGS-GKSSEGKG (SEQ ID NO: 124), GSTSGS-GKSSEGSGSTKG (SEQ ID NO: 125), GSTSGSGKPGS-GEGSTKG (SEQ ID NO: 126), EGKSSGSGSESKEF (SEQ ID NO: 127), SRSSG (SEQ ID NO: 128), and SGSSC (SEQ ID NO: 129).

Rigid proteinaceous linkers are often stiff alpha-helical structures and rich in proline residues and/or one or more strategically placed prolines (see Chen X et al., *Adv Drug Deliv Rev* 65: 1357-69 (2013)). Rigid linkers may be chosen to prevent intramolecular interactions between components.

Suitable linkers may be chosen to allow for in vivo separation of components, such as, e.g., due to cleavage and/or environment-specific instability (see Dosio F et al., *Toxins* 3: 848-83 (2011); Chen X et al., *Adv Drug Deliv Rev* 65: 1357-69 (2013)). In vivo cleavable proteinaceous linkers are capable of unlinking by proteolytic processing and/or reducing environments often at a specific site within an organism or inside a certain cell type (see e.g. Doronina S et al., *Bioconjug Chem* 17: 144-24 (2006); Erickson H et al., *Cancer Res* 66: 4426-33 (2006)). In vivo cleavable proteinaceous linkers often comprise protease sensitive motifs and/or disulfide bonds formed by one or more cysteine pairs (see e.g. Pietersz G et al., *Cancer Res* 48: 4469-76 (1998); The J et al., *J Immunol Methods* 110: 101-9 (1998); see Chen X et al., *Adv Drug Deliv Rev* 65: 1357-69 (2013)). In vivo cleavable proteinaceous linkers can be designed to be sensitive to proteases that exist only at certain locations in an organism, or compartments within a cell, and/or which become active only under certain physiological or pathological conditions (such as, e.g., proteases with abnormally high levels, proteases overexpressed at certain disease sites, and proteases specifically expressed by a pathogenic microorganism). For example, there are proteinaceous linkers known in the art which are cleaved by proteases present only intracellularly, proteases present only within specific cell types, and proteases present only under pathological conditions like cancer or inflammation, such as, e.g., R-x-x-R motif and AMGRSGGGCAGNRVGSSLSCGGLNLQAM (SEQ ID NO: 116).

In certain embodiments of the molecules of the invention, a linker may be used which comprises one or more protease sensitive sites to provide for cleavage by a protease present within a target cell. In certain embodiments of the molecules of the invention, a linker may be used which is not cleavable to reduce unwanted toxicity after administration to a vertebrate organism (see e.g. Polson et al., *Cancer Res* 69: 2358-(2009)).

Suitable linkers may include, e.g., protease sensitive, environmental redox potential sensitive, pH sensitive, acid cleavable, photocleavable, and/or heat sensitive linkers, whether proteinaceous or non-proteinaceous (see Chen X et al., *Adv Drug Deliv Rev* 65: 1357-69 (2013)).

Suitable cleavable linkers may include linkers comprising cleavable groups which are known in the art such as, e.g., linkers noted by Zarling D et al., *J Immunol* 124: 913-20 (1980); Jung S, Moroi M, *Biochem Biophys Acta* 761: 152-62 (1983); Bouizar Z et al., *Eur J Biochem* 155: 141-7 (1986); Park L et al., *J Biol Chem* 261: 205-10 (1986); Browning J, Ribolini A, *J Immunol* 143: 1859-67 (1989); Joshi S, Burrows R, *J Biol Chem* 265: 14518-25 (1990)).

Suitable linkers may include pH sensitive linkers. For example, certain suitable linkers may be chosen for their instability in lower pH environments to provide for dissociation inside a subcellular compartment of a target cell. For example, linkers that comprise one or more trityl groups, derivatized trityl groups, bismaleimideothoxy propane groups, adipic acid dihydrazide groups, and/or acid labile transferrin groups, may provide for release of components of the invention, e.g. a polypeptide component, in environments with specific pH ranges (see e.g. Welhoner H et al., *J Biol Chem* 266: 4309-14 (1991); Fattom A et al., *Infect Immun* 60: 584-9 (1992)). Certain linkers may be chosen which are cleaved in pH ranges corresponding to physiological pH differences between tissues, such as, e.g., the pH of tumor tissue is lower than in healthy tissues (see e.g. U.S. Pat. No. 5,612,474).

Photocleavable linkers are linkers that are cleaved upon exposure to electromagnetic radiation of certain wavelength ranges, such as light in the visible range (see e.g. Goldmacher V et al., *Bioconj Chem* 3: 104-7 (1992)). Photocleavable linkers may be used to release a component of a molecule of the invention, e.g. a polypeptide component, upon exposure to light of certain wavelengths. Non-limiting examples of photocleavable linkers include a nitrobenzyl group as a photocleavable protective group for cysteine, nitrobenzyloxycarbonyl chloride cross-linkers, hydroxypropylmethacrylamide copolymer, glycine copolymer, fluorescein copolymer, and methylrhodamine copolymer (Hazum E et al., *Pept Proc Eur Pept Symp*, 16th, Brunfeldt K, ed., 105-110 (1981); Senter et al., *Photochem Photobiol* 42: 231-7 (1985); Yen et al., *Makromol Chem* 190: 69-82 (1989); Goldmacher V et al., *Bioconj Chem* 3: 104-7 (1992)). Photocleavable linkers may have particular uses in linking components to form molecules of the invention designed for treating diseases, disorders, and conditions that can be exposed to light using fiber optics.

In certain embodiments of the molecules of the invention, a cell-targeting moiety, e.g. a binding region, is linked to a Shiga toxin effector polypeptide region using any number of means known to the skilled worker, including both covalent and noncovalent linkages (see e.g. Chen X et al., *Adv Drug Deliv Rev* 65: 1357-69 (2013); Behrens C, Liu B, *MAbs* 6: 46-53 (2014).

In certain embodiments of the molecules of the invention, the molecule comprises a cell-targeting, binding region which is a scFv with a linker connecting a heavy chain variable ($V_H$) domain and a light chain variable ($V_L$) domain. There are numerous linkers known in the art suitable for this purpose, such as, e.g., the 15-residue $(Gly_4Ser)_3$ peptide (SEQ ID NO: 130). Suitable scFv linkers which may be used in forming non-covalent multivalent structures include GGS, GGGS ($Gly_3Ser$ or $G_3S$) (SEQ ID NO: 131), GGGGS ($Gly_4Ser$ or $G_4S$) (SEQ ID NO: 132), GGGGSGGG(SEQ ID NO: 133), GGSGGGG (SEQ ID NO: 134), GSTSGGGSGGGSGGGGSS (SEQ ID NO: 135), and GSTSGSGKPGSSEGSTKG (SEQ ID NO:-136) (Plückthun A, Pack P, *Immunotechnology* 3: 83-105 (1997); Atwell J et al., *Protein Eng* 12: 597-604 (1999); Wu A et al., *Protein Eng* 14: 1025-33 (2001); Yazaki P et al., *J Immunol Methods* 253: 195-208 (2001); Carmichael J et al., *J Mol Blol* 326: 341-51 (2003); Arndt M et al., *FEBS Lett* 578: 257-61 (2004); Bie C et al., *World J Hepatol* 2: 185-91 (2010)).

The linkage of the components of the molecules of the invention may be by any method presently known in the art for accomplishing such, as long as the attachment does not substantially impede the cellular internalization of the molecule and/or desired toxin effector function(s) of the Shiga toxin effector polypeptide region as measured by an appropriate assay, including assays as described herein.

For the purposes of the cell-targeting molecules of the present invention, the specific order or orientation is not fixed for the Shiga toxin effector polypeptide region and the binding region in relation to each other or the entire molecule (see e.g. FIG. 1) unless specifically indicated to the contrary. The components of the cell-targeting molecules of the present invention may be arranged in any order provided that the desired activities of the binding region and the Shiga toxin effector polypeptide are not eliminated. Desired activities include providing the molecule with the ability, e.g., to bind target expressing cells, induce cellular internalization, cause cytostasis, cause cytotoxicity, and/or deliver exogenous materials to the interiors of cells.

In certain of the above embodiments of the molecules of the invention, the Shiga toxin effector polypeptide, molecular moiety, and optional, endoplasmic reticulum retention/retrieval signal motif may be directly linked to each other and/or suitably linked to each other via one or more intervening polypeptide sequences, such as with one or more linkers well known in the art and/or described herein. In the above embodiments of the cell-targeting molecules of the invention, the Shiga toxin effector polypeptide regions, binding regions, and other components present in certain embodiments (e.g. molecular moiety and/or endoplasmic reticulum retention/retrieval signal motif) may be directly linked to each other and/or suitably linked to each other via one or more intervening polypeptide sequences, such as with one or more linkers well known in the art and/or described herein.

II. Examples of Specific Structural Variations of Components of Molecules of the Invention In certain embodiments, the Shiga toxin effector polypeptide region of the molecules of the present invention comprises or consists essentially of a truncated Shiga toxin A Subunit. Shiga-like toxin A Subunit truncations are catalytically active, capable of enzymatically inactivating ribosomes in vitro, and cytotoxic when expressed within a cell (LaPointe P et al., *J Biol Chem* 280: 23310-18 (2005); Di R et al., *Toxicon* 57: 525-39 (2011)). The carboxy-terminal truncated, Shiga toxin A Subunit fragment composed of residues 1-240 of Slt-1A was shown to exhibit full cytotoxicity when expressed in the endoplasmic reticulum of a eukaryotic cell as the leucine residue at position 240 was required for a carboxy-terminal truncated, Shiga toxin A Subunit construct to effectively retrotranslocate to the cytosol of a eukaryotic cell (LaPointe P et al., *J Biol Chem* 280: 23310-18 (2005)). Similarly, the carboxy-terminal truncated, Shiga toxin A Subunit fragment composed of residues 1-239 of Stx2A was shown to exhibit full cytotoxicity when expressed in the endoplasmic reticulum of a eukaryotic cell (Di R et al., *Toxicon* 57: 525-39 (2011)).

Among certain embodiments, the Shiga toxin effector polypeptide region of a molecule of the present invention comprises or consists essentially of amino acids 75 to 240 of SLT-1A (SEQ ID NO:1) or StxA (SEQ ID NO:2) or comprising or consisting essentially of amino acids 75 to 239 of SLT-2A (SEQ ID NO:3). Further embodiments are molecules comprising a Shiga toxin effector polypeptide which comprises or consists essentially of amino acids 1 to 240 of SLT-1A (SEQ ID NO:1) or StxA (SEQ ID NO:2) or comprising or consisting essentially of amino acids 1 to 239 of SLT-2A (SEQ ID NO:3). Further embodiments are molecules comprising a Shiga toxin effector polypeptide which comprises or consists essentially of amino acids 1 to 240 of SLT-1A (SEQ ID NO:1) or StxA (SEQ ID NO:2) as well as one or more amino acids carboxy-terminal of position 240 but not carboxy terminal of position 250; and, similarly, further embodiments are molecules comprising a Shiga toxin effector polypeptide which comprises or consists essentially of amino acids 1 to 239 of SLT-2A (SEQ ID NO:3) as well as one or more amino acids carboxy-terminal of position 239 but not carboxy terminal of position 249.

Among certain embodiments, the Shiga toxin effector polypeptide region of a molecule of the present invention comprises or consists essentially of amino acids 1 to 251 of SLT-1A (SEQ ID NO:1) or StxA (SEQ ID NO:2) or comprising or consisting essentially of amino acids 1 to 250 of SLT-2A (SEQ ID NO:3), wherein at least one amino acid residue is disrupted in the furin-cleavage motif at the carboxy terminus of the Shiga toxin A1 fragment derived region. Further embodiments are molecules comprising a protease-cleavage resistant, Shiga toxin effector region which comprises or consists essentially of amino acids 1 to 261 of SLT-1A (SEQ ID NO:1) or StxA (SEQ ID NO:2) or comprising or consisting essentially of amino acids 1 to 260 of SLT-2A (SEQ ID NO:3), wherein at least one amino acid residue is disrupted in the furin-cleavage motif at the carboxy terminus of the Shiga toxin A1 fragment derived region.

Among certain embodiments of the cell-targeted molecules of the present invention, the cell-targeted molecule comprises a binding region derived from an immunoglobulin-type polypeptide selected for specific and high-affinity binding to a surface antigen on the cell surface of a cancer cell, where the antigen is restricted in expression to cancer cells (see Glokler J et al., *Molecules* 15: 2478-90 (2010); Liu Y et al., *Lab Chip* 9: 1033-6 (2009)). In accordance with other embodiments, the binding region is selected for specific and high-affinity binding to a surface antigen on the cell surface of a cancer cell, where the antigen is over-expressed or preferentially expressed by cancer cells as compared to non-cancer cells. Some representative target biomolecules include, but are not limited to, the following enumerated targets associated with cancers and/or specific immune cell types.

Many immunoglobulin-type binding regions that recognize epitopes associated with cancer cells exist in the prior art, such as binding regions that target CD4, CD20 (B-lymphocyte antigen protein CD20), CD22, CD25 (interleukin-2 receptor IL2R), CD30 (TNFRSF8), CD38 (cyclic ADP ribose hydrolase), CD40, CD44 (hyaluronan receptor), CD71 (transferrin receptor), CD73, CD79, endoglin (END or CD105), CD200, basal cell adhesion molecule (B-CAM or CD239), CD248 (endosialin or TEM1), carcinoembryonic antigen protein (CEA), chondroitin sulfate proteoglycan 4 (CSP4, MCSP, or NG2), epidermal growth factor receptor (EGFR/ErbB1), human epidermal growth factor receptor 2 (HER2/Neu/ErbB2/CD340), Ephrin type-B receptor 2 (EphB2), epithelial cell adhesion molecule (EpCAM), fibroblast activation protein (FAP/seprase), protease-activated-receptors (such as PAR1), polio virus receptor-like 4 (PVRL4), B3 melanoma antigen, B4 melanoma antigen, prostate-specific membrane antigen protein (PSMA), and tumor-associated calcium signal transducers (TACSTDs) (see e.g. Lui B et al., *Cancer Res* 64: 704-10 (2004); Bagley R et al., *Int J Oncol* 34: 619-27 (2009); Beck A et al., *Nat Rev Immunol* 10: 345-52 (2010); Andersen J et al., *J Biol Chem* 287: 22927-37 (2012); Nolan-Stevaux O et al., *PLoS One* 7: e50920 (2012); Rust S et al., *Mol Cancer* 12: 11 (2013)). This list of target biomolecules is intended to be non-limiting. It will be appreciated by the skilled worker that any desired target biomolecule associated with a cancer cell or other desired cell type may be used to design or select a binding region to be coupled with the Shiga toxin effector region to produce a molecule of the invention.

Examples of other target biomolecules which are strongly associated with cancer cells and have immunoglobulin-type binding regions known to bind them include CD19 (B-lymphocyte antigen protein CD19), CD21 (complement receptor-2 or complement 3d receptor), CS1 (SLAM family number 7 or SLAMF7), CD26 (dipeptidyl peptidase-4, DPP4, or adenosine deaminase complexing protein 2), CD33 (sialic acid-binding immunoglobulin-type lectin-3), CD52 (CAMPATH-1 antigen), CD56, CD133 (prominin-1), basal cell adhesion molecules (BCAMs or Lutheran blood group glycoproteins, bladder tumor antigen (BTA), cancer-testis antigen NY-ESO-1, cancer-testis antigen LAGE proteins, cell surface A33 antigen protein (gpA33), hepatocyte growth factor receptor (HGFR or c-Met), Epstein-Barr virus antigen proteins, melanoma-associated antigen 1 protein (MAGE-1), melanoma-associated antigen 3 (MAGE-3), GAGE/PAGE proteins (melanoma associated cancer/testis antigens), BAGE proteins (B melanoma antigens), mucins (such as MUC1 and cancer antigen 125 (CA-125)), Preferentially Expressed Antigen of Melanoma (PRAME) proteins, melanoma antigen recognized by T-cells 1 protein (MART-1/MelanA), prostate specific antigen protein (PSA), prostate stem cell antigen protein (PSCA), Receptor for Advanced Glycation Endroducts (RAGE), tumor-associated glycoprotein 72 (TAG-72), and Wilms' tumor antigen.

Examples of other target biomolecules which are strongly associated with cancer cells are, carbonic anhydrase IX (CA9/CAIX), folate binding proteins (FBPs and folate receptors), ganglioside GD2, ganglioside GD3, ganglioside GM2, vascular endothelial growth factor receptors (VEGFRs), integrins alpha-V beta-3 ($\alpha v \beta_3$), integrins alpha-V beta-5 ($\alpha v \beta 5$), integrins alpha-5 beta-1 ($\alpha_5 \beta_1$), receptor tyrosine-protein kinase erB-3, insulin-like growth factor 1 receptor (IGF1R), ephrin type-A receptor 3 (EphA3), tumor necrosis factor receptor 10A (TRAIL-R1/DR4), tumor necrosis factor receptor 10B (TRAIL-R2), receptor activator of nuclear factor kappa B (RANK), tenascin C, claudin proteins (CLDN3, CLDN4), mesothelin (MSLN), and CD64 (FcγRI) (see, Hough C et al., *Cancer Res* 60: 6281-7 (2000); Thepen T et al., *Nat Biotechnol* 18: 48-51 (2000); Pastan I et al., *Nat Rev Cancer* 6: 559-65 (2006); Pastan, *Annu Rev Med* 58: 221-37 (2007); Fitzgerald D et al., *Cancer Res* 71: 6300-9 (2011); Scott A et al., *Cancer Immun* 12: 14-22 (2012)). This list of target biomolecules is intended to be non-limiting.

In addition, there are numerous other examples of contemplated, target biomolecules, such as melanocyte protein PMEL (gp100), human tyrosinase, tyrosinase-related protein 1 (TYRP1 or TRP1), tyrosinase-related protein 2 (TRP-2), lysophosphatidlglycerol acyltransferase 1 (LPGAT1/IAA0205), SART proteins, ADP-ribosyltransferases (ART1, ART4), human aspartyl (asparaginyl) beta-hydroxylase (HAAH), ephrin type-A receptor 2 (EphA2), receptor tyrosine-protein kinase erbB-3, tyrosinase associated antigen (TAA), break point cluster region-c-abl oncogene (BCR-ABL) proteins, ADAM metalloproteinases (e.g. ADAM-9, ADAM-10, ADAM-12, ADAM-15, ADAM-17), alpha-fetoprotein antigen 17-A1 protein, bone marrow stroma antigens (BST1, BST2), CD2, CD3 (T-cell co-receptor), CD7, CD15, CD23 (FC epsilon RII), CD53, CD88 (complement component 5a receptor 1), CD129 (interleukin 9 receptor), CD183 (chemokine receptor CXCR3), CD191 (CCR1), CD193 (CCR3), CD244 (Natural Killer Cell Receptor 2B4), CD294 (GPR44), CD305 (leukocyte-associated immunoglobulin-like receptor 1), C3aR (complement component 3a receptors), FceRIa, galectin-9, myeloid-related protein-14 (mrp-14), Siglecs (sialic acid-binding immunoglobulin-type lectins), CD49d, CD13, CD54 (intercellular adhesion molecule 1), CD63 (tetraspanin), CD69, CD123 (interleukin-3 receptor), CD284 (Toll-like receptor 4), FceRIa, lysosome-associated membrane proteins (LAMPs, such as CD107), CD203c, CD14, CD15 (Lewis X or stage-specific embryonic antigen 1), scavenger receptors (such as CD64 and CD68), CD80, CD86, CD115 (colony stimulating factor 1 receptor), F4/80, immunoglobulin-like transcript ILT-3, integrins (such as CD11a-c), CD195 (chemokine receptor CCR5), CD282 (toll-like receptor 2), syndecans (such as SDC1 or CD138), and CD225 (interferon-induced transmembrane protein 1) (see Cheever M et al., *Clin Cancer Res* 15: 5323-37 (2009); Scott A et al., *Cancer Immun* 12: 14 (2012), for target biomolecules and note the target molecules described therein are non-limiting examples). It will be appreciated by the skilled worker that any desired target biomolecule may be used to design or select a binding region to be coupled with a protease-cleavage resistant, Shiga toxin effector region to produce a molecule of the invention.

In certain embodiments, the binding region comprises or consists essentially of an immunoglobulin-type polypeptide selected for specific and high-affinity binding to the cellular surface of a cell type of the immune system. For example, immunoglobulin-type binding domains are known that bind to CD1, CD2, CD3, CD4, CD5, CD6, CD7, CD8, CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD33, CD34, CD35, CD36, CD37, CD38, CD40, CD41, CD56, CD61, CD62, CD66, CD95, CD117, CD123, CD235, CD146, CD326, interleukin-2 receptor (IL-2R), receptor activator of nuclear factor kappa B (RANKL), SLAM-associated protein (SAP), and TNFSF18 (tumor necrosis factor ligand 18 or GITRL).

For certain embodiments, the cell-targeted molecule comprises or consists essentially of the polypeptide shown in any one of SEQ ID NOs: 50-61. These protease-cleavage resistant, CD20-binding, cytotoxic, cell-targeted molecule embodiments may be used to treat and/or diagnosis bone cancer, leukemia, lymphoma, melanoma, myeloma, amyloidosis, ankylosing spondylitis, asthma, Crohn's disease, diabetes, graft rejection, graft-versus-host disease, Hashimotos thyroiditis, hemolytic uremic syndrome, HIV-related diseases, lupus erythematosus, multiple sclerosis, polyarteritis nodosa, polyarthritis, psoriasis, psoriatic arthritis, rheumatoid arthritis, scleroderma, septic shock, Sjorgren's syndrome, ulcerative colitis, and/or vasculitis.

In certain embodiments, the binding region comprises or consists essentially of a ligand selected for targeting an extracellular receptor. Some representative ligands include, but are not limited to, the following bone morphogenetic proteins and activin membrane-bound inhibitor BAMBI (also known as TGFBR), CD137L (also known as 4-1BB), decoy receptor 3 DcR3 (also known as TR6 and TNFRSF6B), MHC class I polypeptide-related sequences (e.g. MICA, MICB), NKG2D ligands (e.g. ULBP1, ULBP2, ULBP3, and ULBP4-6), and the tumor necrosis factor TWEAK (also known as TNFSF12 and APO3L). For more non-limiting exemplary ligands, see Table 5 in the Examples.

Among certain embodiments of the cell-targeted molecules of the present invention, the binding region is a single domain immunoglobulin-derived region $V_HH$ which exhibits high affinity binding specifically to HER2, such as derived from a single-domain variable region of the camelid antibody ($V_HH$) protein 5F7, as described in U.S. patent application publication 2011/0059090.

In certain embodiments, the cell-targeted molecules of the present invention comprise the immunoglobulin-type binding region comprising or consisting essentially of amino acids 270-513 of SEQ ID NO:50, 261-512 of SEQ ID NO:51, 270-514 of SEQ ID NO:52, or 279-522 of SEQ ID NO:53, all of which exhibit high affinity binding specifically to human CD20.

In certain embodiments, the cell-targeted molecules of the present invention comprise the immunoglobulin-type binding region comprising or consisting essentially of amino acids 267-384 of SEQ ID NO:54, 269-512 of SEQ ID NO:58, or 269-403 of SEQ ID NO:61, all of which exhibit high affinity binding specifically to human HER2.

In certain embodiments, the cell-targeted molecules of the present invention comprise the polypeptide ligand comprising or consisting essentially of amino acids 269-401 of SEQ ID NO:56, which exhibits high affinity binding specifically to human, interleukin-2 receptor (IL-2 receptor).

In certain embodiments, the cell-targeted molecules of the present invention comprise the immunoglobulin-type binding region comprising or consisting essentially of amino acids 269-508 of SEQ ID NO:57, which exhibits high affinity binding specifically to human CD38.

In certain embodiments, the cell-targeted molecules of the present invention comprise the immunoglobulin-type binding region comprising or consisting essentially of amino acids 269-516 of SEQ ID NO:59, which exhibits high affinity binding specifically to human CD19.

In certain embodiments, the cell-targeted molecules of the present invention comprise the immunoglobulin-type binding region comprising or consisting essentially of amino acids 269-518 of SEQ ID NO:60, which exhibits high affinity binding specifically to human CD74.

It is within the scope of the present invention to use fragments, variants, and/or derivatives of the molecules of the present invention which contain a functional extracellular target biomolecule binding site, and even more preferably capable of binding the target biomolecule with high affinity (e.g. as shown by $K_D$). For example, while the invention provides polypeptide sequences that can bind to human proteins: CD20, HER2, IL-2 receptor, CD38, CD19, and CD74, any binding region that binds to a target biomolecule, preferably expressed on a cell surface, with a dissociation constant of $10^{-5}$ to $10^{-12}$ moles per liter, preferably less than 200 nM, may be substituted for use in making cell-targeting molecules of the invention and methods of the invention.

III. General Functions of the Molecules of the Invention

The present invention provides various protease-cleavage resistant, Shiga toxin A Subunit effector polypeptides and molecules comprising the same, which are useful for therapeutic and/or diagnostic applications. The Shiga toxin derived, cell-targeting molecules of the present invention may be designed to have optimal cytotoxicity, i.e. equivalent to a cell-targeted molecule comprising a wild-type, Shiga toxin effector polypeptide but with improvements over certain cell-targeted molecules comprising protease-cleavage sensitive, wild-type, Shiga toxin effector polypeptides (e.g., cell targeted molecules comprising carboxy terminal, cell-targeting binding regions). The protease-cleavage resistant, Shiga toxin A Subunit derived molecules provided herein have uses, e.g., for targeted cell killing, delivering exogenous materials into specific cell types, obtaining diagnostic information, and as therapeutics for the treatment of a variety of diseases, disorders, and conditions, including cancers, immune disorders, and microbial infections.

The linking of cell-targeting binding regions with protease-cleavage resistant, Shiga toxin effector polypeptides enables the engineering of therapeutics and diagnostics with improved characteristics, such as, e.g., cell-targeted molecules with increased molecular stability and improved, in vivo tolerability. The disruption of the furin-cleavage motif at the carboxy terminus of the Shiga toxin A1 fragment region in Shiga toxin A Subunit effector polypeptides reduces furin cleavage at the motif and might reduce cleavage by other proteases beside furin, such as, e.g., trypsin and extracellular proteases common in the vascular system of vertebrates. The disruption of the furin-cleavage motif at the carboxy terminus of the Shiga toxin A1 fragment region in Shiga toxin A Subunit effector polypeptides enables the engineering of cell-targeting molecules with cell-type specific targeting of Shiga toxin cytotoxicity comparable in potency to cell-targeted molecules comprising furin-cleavage sensitive, Shiga toxin effector polypeptides but with improved toxicity profiles after administration to a vertebrate compared to certain cell-targeted molecules comprising protease-cleavage sensitive, wild-type, Shiga toxin effector polypeptides. Certain molecules of the present invention exhibit reduced deleterious effects (e.g. non-specific toxicity) after administration to vertebrates as compared to cell-targeted molecules comprising wild-type, Shiga toxin effector polypeptides and might exhibit improved stability during production, storage, and administration.

A. Reducing Protease-Cleavage Sensitivity of Shiga Toxin A Subunit Effector Polypeptides while Maintaining Efficient Intracellular Routing and Potent Cytotoxicity Previously, it was believed that cytotoxic Shiga toxin A Subunit constructs comprising Shiga toxin A1 fragment catalytic regions must maintain or somehow compensate for the naturally occurring proteolytic processing by furin within intoxicated cells in order to preserve efficient and potent cytotoxicity. Unexpectedly, it was discovered that the furin cleavage event was not required for potent cytotoxicity because potent Shiga toxin cytotoxicity at the level of a wild-type, Shiga toxin control construct was achieved in the absence of a target-cell-mediated, furin cleavage event at the carboxy terminus of the Shiga toxin A1 fragment despite the presence of a relatively large (greater than 28 kDa) moiety on the carboxy terminus (see Examples, infra). The lack of a furin-cleavage event within the intoxicated cell was expected to interfere with the efficient liberation of a Shiga toxin A1 fragment and, thus, result in the continued linkage of a relatively large, molecular moiety to the Shiga toxin A1 fragment region. However despite this expectation, potent Shiga toxin cytotoxicity was achieved with furin-cleavage deficient, Shiga toxin A Subunit constructs comprising relatively large, carboxy-terminal moieties and lacking any apparent compensatory feature(s), such as, e.g. an engineered, alternative protease site.

These results are surprising because the optimal Shiga toxin intoxication process was thought to require liberation of the Shiga toxin A1 fragments from all other large molecular moieties and exposure of the carboxy terminus of the A1 fragment to efficiently retrotranslocate liberated A1 fragments from the endoplasmic reticulum to the cytosol where the A1 fragments can form an enzymatically active structure that catalytically inactivates the intoxicated cell's ribosomes. In particular, the persistence and/or inefficient release of a molecular moiety covering the carboxy terminus of the Shiga toxin A1 fragment was expected to interfere with the Shiga toxin A1 fragment's natural mechanism of efficiently gaining access to the cytosol involving the exposure of the A1 fragment's hydrophobic carboxy terminus domain recognized by the ERAD system (see Di R et al., *Toxicon* 57: 525-39 (2011); Li S et al., *PLoS One* 7: e41119 (2012)). For example, the persistence of a molecular moiety covering the carboxy terminus of the Shiga toxin A1 fragment was expected to disrupt the accessibility of the carboxy terminus of the Shiga toxin A1 fragment to the ERAD machinery in the endoplasmic reticulum and efficiently gaining access to the cytosol where it forms an enzymatically active structure. Unexpectedly, this is found to be incorrect because efficient and potent Shiga toxin cytotoxicity was achieved in the absence of a target-cell-mediated, furin cleavage event at the carboxy terminus of the Shiga toxin A1 fragment despite the presence of a large, carboxy-terminal, cell-targeting moiety (see Examples, infra).

Alternatively, the lack of an intoxicated-cell-mediated, furin-cleavage event may be hypothetically compensated for. Non-limiting examples of potential, compensatory approaches include 1) terminating one carboxy terminus of the construct with the carboxy terminus of a Shiga toxin A1 fragment-like polypeptide region, 2) producing the Shiga toxin derived construct such that the Shiga toxin A Subunit polypeptide is already nicked near the carboxy terminus of its Shiga toxin A1 fragment-like polypeptide, 3) engineering a heterologous and/or ectopic protease site that can functionally substitute for the lack of the native, Shiga toxin, furin-cleavage event, and 4) a combination of approaches two and three. In the first approach, the carboxy terminus of the Shiga toxin A1 fragment-like polypeptide is not covered by any carboxy-terminal moiety, and, thus, the carboxy terminus of the Shiga toxin A1 fragment-like polypeptide is permanently exposed for recognition by the ERAD machinery in the endoplasmic reticulum. In the last three approaches, the Shiga toxin A1 fragment-like polypeptide can be designed to intracellularly dissociate from one or more other components of the construct by the time the molecule reaches the endoplasmic reticulum of an intoxicated cell such that in the endoplasmic reticulum the carboxy terminus of the Shiga toxin A1 fragment-like polypeptide becomes exposed for recognition by the ERAD machinery.

An example of a compensatory feature is cytotoxic molecule comprising a Shiga toxin A Subunit effector polypeptide which is pretreated with a protease to nick the polypeptide region near the carboxy terminus of the A1 fragment-like region prior to contacting a target cell. Another example is a cytotoxic molecule comprising a Shiga toxin A Subunit effector polypeptide engineered to have comprising an ectopic, heterologous, protease site which is cleaved by an intracellular protease of the target cell.

These proposed approaches for designing Shiga toxin A Subunit effector polypeptides which compensate for the lack of an intoxicated-cell-mediated, furin-cleavage event are hypothetical. All four proposed approaches could significantly alter the efficiency and potency of cytotoxicity as compared to a molecule comprising a wild-type, Shiga toxin A Subunit or Shiga toxin A Subunit construct comprising only wild-type sequences which include the furin-cleavage site naturally occurring at the carboxy terminus of the A1 fragment region. In addition, only certain variants of the third approach, variants which rely on target cell endoproteases, might allow for a moiety to be fused in a carboxy terminal position relative to the Shiga toxin effector polypeptide. However, currently no compensatory approach relying on a target cell endoprotease other than furin is known which can provide fully compensatory cytotoxicity equivalent to furin cleavage and alternative cellular proteases like calpain have shown to be less efficient in facilitating Shiga toxin cytotoxicity (Garred Ø et al., *Exp Cell Res* 218: 39-49 (1995); Garred Ø et al., *J Biol Chem* 270: 10817-21 (1995); Kurmanova, *Biochem Biophys Res Commun* 357: 144-9 (2007)).

The molecules of the present invention which comprise Shiga toxin effector polypeptides comprising disrupted furin-cleavage motifs all exhibit reduced sensitivity to cleavage by furin. Because the minimal, furin cleavage R/Y-x-x-R motif is shared by multiple proteases, such as by highly promiscuous proteases (—e.g., trypsin), certain disrupted furin-cleavage motifs of the Shiga toxin effector polypeptides of the present invention are expected to exhibit reduced sensitivity to cleavage by multiple proteases besides just furin (see e.g. Kurmanova A et al., *Biochem Biophys Res Commun* 357: 144-9 (2007)). For example, the proprotein convertase class of peptidases includes at least seven members in humans, PC1, PC2, PC3, PC4, PACE4, PC5, PC6, and PC7 (Fugere M, Day R, *Trends Pharmacol Sci* 26: 294-301 (2005)), many of which are known to cleave their substrates at single or pairs of basic residues, such as, e.g., one or more arginine residues (Seidah N, *Ann N Y Acad Sci* 1220: 149-61 (2011)).

Certain cell-targeted molecules of the present invention are as efficiently and potently cytotoxic as cell-targeted molecules comprising protease-cleavage sensitive, Shiga toxin effector polypeptides despite the presence of a molecular moiety fused to the carboxy terminal of the Shiga toxin effector polypeptide which cannot be released by furin cleavage inside an intoxicated cell.

B. Cell Kill Via Targeted Shiga Toxin Cytotoxicity

The present invention provides various, cytotoxic, cell-targeted molecules comprising furin-cleavage resistant, Shiga toxin A Subunit effector polypeptides. In certain embodiments, the cell-targeted molecules of the present invention are capable of binding extracellular target biomolecules associated with the cell surface of particular cell types and entering those cells. Once internalized within a targeted cell type, certain embodiments of the cell-targeted molecules of the invention are capable of routing a cytotoxic Shiga toxin effector polypeptide fragment into the cytosol of the target cell. Once in the cytosol of a targeted cell type, certain embodiments of the cell-targeted molecules of the invention are capable of enzymatically inactivating ribosomes and eventually killing the cell. This system is modular in that any number of diverse cell-targeting binding regions, such as, e.g., immunoglobulin-type polypeptides, can be used to target this potent cytotoxicity to various, diverse cell types while providing the improvement of reduced protease-cleavage sensitivity. The capacity of a molecule of the invention to cause cell death, e.g. its cytotoxicity, may be measured using any one or more of a number of assays well known in the art.

In certain embodiments of the protease-cleavage resistant, cytotoxic, cell-targeted molecules of the present invention, upon contacting a cell physically coupled with an extracellular target biomolecule of the binding region of a cytotoxic molecule of the invention (target+ cell), the cell-targeted molecule is capable of causing death of the cell. Cell kill may be accomplished using a cell-targeted molecule of the invention under varied conditions of target cells, such as an ex vivo manipulated target cell, a target cell cultured in vitro, a target cell within a tissue sample cultured in vitro, or a target cell in vivo.

The expression of the target biomolecule need not be native in order for targeted cell killing by a cytotoxic, cell-targeted molecule of the present invention. Cell surface expression of the target biomolecule could be the result of an infection, the presence of a pathogen, and/or the presence of an intracellular microbial pathogen. Expression of a target biomolecule could be artificial such as, for example, by forced or induced expression after infection with a viral expression vector, see e.g. adenoviral, adeno-associated viral, and retroviral systems. An example of inducing expression of a target biomolecule is the upregulation of CD38 expression of cells exposed to retinoids, like all-trans retinoic acid and various synthetic retinoids, or any retinoic acid receptor (RAR) agonist (Drach J et al., *Cancer Res* 54: 1746-52 (1994); Uruno A et al., *J Leukoc Biol* 90: 235-47

(2011)). In another example, CD20, HER2, and EGFR expression may be induced by exposing a cell to ionizing radiation (Wattenberg M et al., *Br J Cancer* 110: 1472-80 (2014)).

For purposes of the present invention, the exhibition of "equivalent" Shiga toxin effector cytotoxicity compared to the cytotoxicity of a second cell-targeted molecule comprising a wild-type, Shiga toxin A1 fragment polypeptide refers to a level of cytotoxicity within ten percent or less, as measured by an appropriate quantitative assay with reproducibility comparable to a wild-type, Shiga toxin effector polypeptide comprising a full-length Shiga toxin A1 fragment. For cytotoxicity in a target positive cell kill assay in laboratory cell culture, "equivalent" cytotoxicity is typically a $CD_{50}$ value within ten percent of the $CD_{50}$ value of a reference cytotoxic, cell-targeted (referred to herein as a "second cell-targeted molecule"), which comprises an identical binding region to the molecule of interest and, if applicable, an identical molecular moiety to the molecule of interest; and wherein the binding region, Shiga toxin effector polypeptide and, if applicable, the molecular moiety of the reference molecule are all associated with each other identically with how these components are associated in the molecule of interest.

Furthermore, if a molecule of the present invention exhibits, either alone or as a component of a cell-targeted molecule, cytotoxicity equivalent to a reference cell-targeted molecule comprising a wild-type, Shiga toxin A1 fragment polypeptide, then the Shiga toxin effector polypeptide region of that molecule of the invention exhibits the Shiga toxin effector activity of subcellular routing at an activity level equivalent to the subcellular routing activity level of that reference molecule, i.e. a sub-cellular routing activity equivalent to wild-type.

C. Selective Cytotoxicity Among Cell Types

By targeting the delivery of protease-cleavage resistant, Shiga toxin A Subunit effector polypeptides using high-affinity binding regions to specific cell types, a potent Shiga toxin cell-kill activity can be restricted to preferentially killing specifically targeted cell types. Certain cell-targeted molecules of the present invention are useful for the elimination of populations of specific cell types. For example, cytotoxic, cell-targeted molecules of the invention are useful for the treatment of certain tumors, cancers, and/or growth abnormalities by eliminating malignant cells that express elevated levels of a particular target biomolecule at one or more cellular surfaces.

In certain embodiments, administration of the cell-targeted molecule of the present invention to a mixture of cell types, the cell-targeted molecule is capable of selectively killing those cells which are physically coupled with an extracellular target biomolecule compared to cell types not physically coupled with an extracellular target biomolecule. Because members of the Shiga toxin family are adapted for killing eukaryotic cells, molecules designed using Shiga toxin A Subunit effector polypeptides can show potent cytotoxic activity. By targeting the delivery of enzymatically active Shiga toxin A Subunit effector polypeptides to specific cell types using high-affinity binding regions, this potent cell kill activity can be restricted within in an organism to killing only those cell types desired to be targeted by their physical association with a target biomolecule of the chosen binding regions.

In certain embodiments, the cell-targeted molecule of the present invention is capable of selectively or preferentially causing the death of a specific cell type within a mixture of two or more different cell types. This enables the targeted cytotoxic activity to specific cell types with a high preferentiality, such as a 3-fold cytotoxic effect, over "bystander" cell types that do not express the target biomolecule. Alternatively, the expression of the target biomolecule of the binding region may be non-exclusive to one cell type if the target biomolecule is expressed in low enough amounts and/or physically coupled in low amounts with cell types that are not to be targeted. This enables the targeted cell-killing of specific cell types with a high preferentiality, such as a 3-fold cytotoxic effect, over "bystander" cell types that do not express significant amounts of the target biomolecule or are not physically coupled to significant amounts of the target biomolecule.

Levels of extracellular target biomolecules on the surface of cells may be determined using various methods known to the skilled worker, such as, e.g., FACS methods. As used herein, a significant amount of an extracellular target biomolecule expressed at a cellular surface is greater than 10,000, 20,000, 30,000, 40,000, 50,000, 60,000, or 70,000 mean fluorescence intensity (MFI) by FACS analysis depending on the cell type.

In certain further embodiments, administration of the cytotoxic, cell-targeted molecule of the present invention to two populations of cell types which differ in the presence and/or polypeptide sequence of an extracellular target biomolecule, the cell-targeted molecule is capable of causing cell death as defined by the half-maximal cytotoxic concentration ($CD_{50}$) on a population of target cells, whose members express an extracellular target biomolecule of the binding region of the cell-targeted molecule, e.g., at a dose at least three-times lower than the $CD_{50}$ dose of the same cell-targeted molecule to a population of cells whose members do not express an extracellular target biomolecule of the binding region of the cell-targeted molecule.

In certain embodiments, the cytotoxic activity of a cell-targeted molecule of the present invention toward populations of cell types physically coupled with an extracellular target biomolecule is at least 3-fold higher than the cytotoxic activity toward populations of cell types not physically coupled with any extracellular target biomolecule bound specifically by that cell-targeted molecule of the invention. According to the present invention, selective cytotoxicity may be quantified in terms of the ratio (a/b) of (a) cytotoxicity towards a population of cells of a specific cell type physically coupled with a target biomolecule of the binding region to (b) cytotoxicity towards a population of cells of a cell type not physically coupled with a target biomolecule of the binding region. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types physically coupled with a target biomolecule of the binding region compared to populations of cells or cell types not physically coupled with a target biomolecule of the binding region. For example, administration of certain cytotoxic proteins of the present invention to two different populations of cells which differ with respect to the presence and/or polypeptide sequence of an extracellular target biomolecule, the cytotoxic, cell-targeted molecule of the invention is capable of causing cell death of the cell-types physically coupled with an extracellular target biomolecule bound by the cytotoxic protein's binding region, e.g., at a $CD_{50}$ that is at least three times less than the $CD_{50}$ observed for cell types that are not physically coupled with an extracellular target biomolecule bound by the cytotoxic, cell-targeted molecule's binding region or to cell types that are physically coupled only with forms of that extracellular target biomolecule which comprise sequence variations or mutations which disrupt binding specificity by the binding region of that cell-targeted molecule.

In certain embodiments of the cell-targeted molecules of the present invention, administration of the cell-targeted molecule to two different populations of cell types, the cell-targeted molecule is capable of causing cell death as defined by the half-maximal cytotoxic concentration ($CD_{50}$) on a first cell population, whose members express a target biomolecule of the binding region of the cell-targeted molecule at a cellular surface, at a dose at least three-times lower than the $CD_{50}$ dose of the same cell-targeted molecule to a second population of cells whose members do not express any target biomolecule of the binding region of the cell-targeted molecule, do not express a significant amount of any target biomolecule of the binding region of the cell-targeted molecule, or are not exposing a significant amount of any target biomolecule of the binding region of the cell-targeted molecule.

This preferential cell-killing function allows a targeted cell to be killed by certain cytotoxic, cell-targeted molecules of the present invention under varied conditions and in the presence of non-targeted bystander cells, such as ex vivo manipulated mixtures of cell types, in vitro cultured tissues with mixtures of cell types, or in vivo in the presence of multiple cell types (e.g. in situ or in a native location within a multicellular organism).

D. Improved, In Vivo Tolerability and Stability

In certain embodiments, the molecules of the present invention (e.g. cell-targeting molecules of the invention) exhibit increased stability and/or improved, in vivo tolerability as compared to furin-cleavage sensitive analogs. The increased stability can be exhibited in vitro and/or in vivo.

The stability of a therapeutic or diagnostic molecule over time is an important feature and can affect for which applications the molecule may be practically employed. Molecular stability includes in vitro and in vivo, such as, e.g., stability within an organism after administration and during storage over a range of temperatures and concentrations. For certain immunotoxins or ligand-toxin fusions, the stability of the linkage between the toxin and other components can affect the amount of non-specific toxicity caused by the release of untargeted toxin over time within the body of an organism.

Certain cell-targeting molecules of the invention are useful as therapeutics and/or diagnostics and exhibit reduced non-specific toxicity in vivo, manifested as improved, in vivo tolerability as compared to more protease-cleavage sensitive variants. In vivo tolerability can be determined by the skilled worker using techniques known in the art and/or described herein. In addition to assessing in vivo tolerability using mortality, signs of morbidity may be used for assessing in vivo tolerability, such as, e.g., aspects of body weight, physical appearance, measurable clinical signs, unprovoked behavior, and responses to external stimuli (see e.g. Morton D, Griffiths P, *Vet Rec* 116: 431-43 (1985); Montgomery C, *Cancer Bull* 42: 230-7 (1990); Ullman-Culleré M, Foltz C, *Lab Anim Sc* 49: 319-23 (1999); Clingerman K, Summers L, *J Am Assoc Lab Anim Sci* 51: 31-6 (2012)). Euthanasia may be used in response to signs of morbidity and/or moribundity and, thus, create a mortality time-point. For example, a decrease in body weight of 15-20% in 2-3 days can be used as a sign of morbidity in rodents and as a justification for euthanization (see e.g. Institute of Laboratory Animal Research 2011. *Guide for the care and use of laboratory animals,* 8th ed., Washington, D.C., U.S.: National Academies Press (2011)).

For purposes of the claimed invention, the term "improved, in vivo tolerability" refers to a reproducible and statistically significant decrease in the toxicity and/or general deleterious effect of the molecule on the health or survival of a whole organism after receiving administration of the molecule, such as a decrease of 20%, 25%, 30%, 40%, 50%, 60%, 70%, 80%, 90% or greater, preferably 50% or greater, of the improved molecule to a mammalian organism as compared to a reference molecule when compared using the same assay under the same conditions, e.g. the same species, the same dose and cumulative dosage, the same dosing schedule, and the same duration for time-points of observation and/or measurement. A decrease in toxicity or general deleterious effect can be measured by a decrease in mortality and/or morbidity over specific time duration.

As shown in the Examples, a decrease in toxicity could represent 100% survival at a given time duration for mammals receiving the molecule with improved, in vivo tolerability as compared to 100% mortality at the same time-point for mammals receiving the reference molecule. Mortality may be due to death or euthanasia for compassionate reasons as mentioned above. Generally, the dosing schedule is two to three doses per week for 2, 3, 4, or more weeks, where each dose is around 0.001 to 40 mg of molecule per kg body weight.

The improved, in vivo tolerability observed for exemplary, cell-targeted molecules of the invention suggests that much higher doses of these cell-targeted molecules may be safely administered to mammals as compared to the doses of related molecules comprising a furin-cleavage sensitive, Shiga toxin effector polypeptide. Certain cell-targeted molecules of the invention might exhibit reduced non-specific toxicity as compared to more protease-cleavage sensitive variants because the protease-cleavage resistance serves to protect and preserve the linkage between the Shiga toxin effector component and the cell-targeting moiety component.

In addition, certain molecules of the invention exhibit increased half-lives, both in vitro and/or in vivo, as compared to more protease-cleavage sensitive variants. Molecular stability can be assayed by determining the half-life of a molecule of interest with regard to the association of its components. Certain embodiments of the molecules of the invention will have longer half-lives as compared to furin-cleavage sensitive variants, especially with regard to the continued association of the Shiga toxin effector component and one or more other components. For example, certain embodiments of the molecules of the invention will have longer half-lives with regard to the continued association of the Shiga toxin effector component and another component, e.g. a cell-targeting moiety, as compared to a furin-cleavage sensitive variant wherein the furin-cleavage sensitive site(s) lies between those two components.

E. Delivery of Additional Exogenous Material into the Interior of a Target Cell

In addition to direct cell killing, certain molecules of the present invention optionally may be used for delivery of additional exogenous materials into the interiors of target cells. The delivery of additional exogenous materials may be used, e.g., for cytotoxic, cytostatic, immune system stimulation, immune cell targeting, information gathering, and/or diagnostic functions. Nontoxic variants of the cytotoxic molecules of the present invention, or optionally cytotoxic variants, may be used to deliver additional exogenous materials to and/or label the interiors of cells physically coupled with an extracellular target biomolecule of the binding region of a cell-targeted molecule. Various types of cells and/or cell populations which express target biomolecules to at least one cellular surface may be targeted by the cell-targeted molecules of the invention for receiving exogenous materials. The functional components of the cell-targeting molecules of the present invention are modular, in that various Shiga toxin effector polypeptides and additional exogenous materials may be linked to various binding regions to provide diverse applications, such as non-invasive in vivo imaging of tumor cells and/or their subcellular compartments.

Because the cell-targeted molecules of the present invention, including nontoxic forms thereof, are capable of entering cells physically coupled with an extracellular target biomolecule recognized by the cell-targeted molecule's binding region, certain embodiments of the cell-targeted molecules of the invention may be used to deliver additional exogenous materials into the interior of targeted cell types. In one sense, the entire molecule of the invention is an exogenous material which will enter the cell; thus, the "additional" exogenous materials are heterologous materials linked to but other than the core cell-targeted molecule itself. Protease-cleavage resistant, Shiga toxin effector polypeptides of the invention which are nontoxic may still be useful as components of cell-targeted molecules for delivering exogenous materials into target cells as long as the protease-cleavage resistant, Shiga toxin effector polypeptide efficiently directs intracellular routing to the cytosol of a cell in which it is present.

Variants and derivatives of cytotoxic molecules and cell-targeted molecules of the present invention which differ only in the catalytically important, amino acid residue(s) natively positioned at 75, 77, 114, 167, 170, 176, and 203 (or the corresponding position in related Shiga toxin A Subunits, e.g., position 204 in SLT-2A) will have the same subcellular routing activity level as compared to parental molecules with wild-type, amino acid residues at all of the position(s) which are different.

"Additional exogenous material" as used herein refers to one or more molecules, often not generally present within a native target cell, where the molecules of the present invention can be used to specifically transport such material to the interior of a cell. Non-limiting examples of additional exogenous materials are cytotoxic agents, peptides, polypeptides, proteins, polynucleotides, detection promoting agents, and small molecule chemotherapeutic agents.

In certain embodiments of the molecules of the present invention for delivery of additional exogenous material, the additional exogenous material is a cytotoxic agent, such as, e.g., a small molecule chemotherapeutic agent, cytotoxic antibiotic, alkylating agent, antimetabolite, topoisomerase inhibitor, and/or tubulin inhibitor. Non-limiting examples of cytotoxic agents include aziridines, cisplatins, tetrazines, procarbazine, hexamethylmelamine, vinca alkaloids, taxanes, camptothecins, etoposide, doxorubicin, mitoxantrone, teniposide, novobiocin, aclarubicin, anthracyclines, actinomycin, bleomycin, plicamycin, mitomycin, daunorubicin, epirubicin, idarubicin, dolastatins, maytansines, docetaxel, adriamycin, calicheamicin, auristatins, pyrrolobenzodiazepine, carboplatin, 5-fluorouracil (5-FU), capecitabine, mitomycin C, paclitaxel, 1,3-Bis(2-chloroethyl)-1-nitrosourea (BCNU), rifampicin, cisplatin, methotrexate, and gemcitabine.

In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In certain embodiments, the additional exogenous material is an antigen, such as antigens derived from bacterial proteins, viral proteins, proteins mutated in cancer, proteins aberrantly expressed in cancer, or T-cell complementary determining regions. For example, exogenous materials include antigens, such as those characteristic of antigen-presenting cells infected by bacteria, and T-cell complementary determining regions capable of functioning as exogenous antigens. Additional examples of exogenous materials include polypeptides and proteins larger than an antigenic peptide, such as enzymes. Exogenous materials comprising polypeptides or proteins may optionally comprise one or more antigens whether known or unknown to the skilled worker.

In certain embodiments, the molecular moiety of a molecule of the present invention comprises or consists essentially of an additional exogenous material.

F. Information Gathering for Diagnostic Functions

Certain cell-targeted molecules of the present invention have uses in the in vitro and/or in vivo detection of specific cells, cell types, cell populations, and/or specific subcellular compartments of the aforementioned. In certain embodiments, the cell-targeted described herein are used for both diagnosis and treatment, or for diagnosis alone. When the same cell-targeted molecule is used for both diagnosis and treatment, variants of cell-targeted molecules which incorporate detection promoting agents for diagnosis may be rendered nontoxic by catalytic inactivation of a Shiga toxin effector polypeptide via one or more amino acid substitutions, including exemplary substitutions described herein. Nontoxic forms of the cytotoxic, cell-targeted molecules of the invention that are conjugated to detection promoting agents optionally may be used for diagnostic functions, such as for companion diagnostics used in conjunction with a therapeutic regimen comprising the same or a related binding region.

The ability to conjugate detection promoting agents known in the art to various cell-targeted molecules of the present invention provides useful compositions for the detection of cancer, tumor, immune, and infected cells. These diagnostic embodiments of the cell-targeted molecules of the invention may be used for information gathering via various imaging techniques and assays known in the art. For example, diagnostic embodiments of the cell-targeted molecules of the invention may be used for information gathering via imaging of intracellular organelles (e.g. endocytotic, Golgi, endoplasmic reticulum, and cytosolic compartments) of individual cancer cells, immune cells, or infected cells in a patient or biopsy sample.

Various types of information may be gathered using the diagnostic embodiments of the cell-targeted molecules of the invention whether for diagnostic uses or other uses. This information may be useful, for example, in diagnosing neoplastic cell types, determining therapeutic susceptibilities of a patient's disease, assaying the progression of anti-neoplastic therapies over time, assaying the progression of immunomodulatory therapies over time, assaying the progression of antimicrobial therapies over time, evaluating the presence of infected cells in transplantation materials, evaluating the presence of unwanted cell types in transplantation materials, and/or evaluating the presence of residual tumor cells after surgical excision of a tumor mass.

For example, subpopulations of patients might be ascertained using information gathered using the diagnostic variants of the cell-targeted molecules of the present invention, and then individual patients could be further categorized into subpopulations based on their unique characteristic(s) revealed using those diagnostic embodiments. For example, the effectiveness of specific pharmaceuticals or therapies might be one type of criterion used to define a patient subpopulation. For example, a nontoxic diagnostic variant of a particular cytotoxic, cell-targeted molecule of the invention may be used to differentiate which patients are in a class or subpopulation of patients predicted to respond positively to a cytotoxic variant of the same molecule of the invention. Accordingly, associated methods for patient identification, patient stratification, and diagnosis using cell-targeted molecules of the invention, including nontoxic variants of cytotoxic, cell-targeted molecules of the invention, are considered to be within the scope of the present invention.

In certain embodiments, the cell-targeted molecules of the present invention are used in methods (e.g. methods of cell killing, delivering additional exogenous materials, and/or detecting specific subcellular compartments of specific cell types) involving target cells which express furin and/or a furin-type protease such that the furin and/or a furin-type protease is present in the subcellular compartment of the target cell selected from the group consisting of: Golgi apparatus, endosome, and endoplasmic reticulum. In certain embodiments, the cytotoxic, cell-targeted molecules of the present invention are used to kill furin expressing cells. In certain embodiments, the cytotoxic, cell-targeted molecules of the present invention are used to kill furin-deficient cells and exhibit improved, in vivo tolerability when administered to a vertebrate.

IV. Variations in the Polypeptide Sequence of the Protease-Cleavage Resistant, Shiga Toxin Effector Polypeptides and Molecules of the Invention The skilled worker will recognize that variations may be made to protease-cleavage resistant, Shiga toxin effector polypeptide components and molecules of the present invention (e.g. cytotoxic molecules and cell-targeting molecules of the present invention as well as polynucleotides encoding any of the former) without diminishing their biological activities, e.g., by maintaining the overall structure and function of the Shiga toxin effector polypeptide and/or cell-targeted molecule, such as, e.g., one or more Shiga toxin effector functions, cell-targeting function(s), target biomolecule binding, targeted cytotoxic activity, improved in vivo tolerability, increased stability, and/or ability to deliver exogenous material(s) to target cells.

For example, some modifications may facilitate expression, purification, and/or pharmacokinetic properties, and/or immunogenicity. Such modifications are well known to the skilled worker and include, for example, a methionine added at the amino terminus to provide an initiation site, additional amino acids placed on either terminus to create conveniently located restriction sites or termination codons, and biochemical affinity tags fused to either terminus to provide for convenient detection and/or purification.

Also contemplated herein is the inclusion of additional amino acid residues at the amino and/or carboxy termini, such as sequences for epitope tags or other moieties. The additional amino acid residues may be used for various purposes including, e.g., to facilitate cloning, expression, post-translational modification, synthesis, purification, detection, and/or administration. Non-limiting examples of epitope tags and moieties are: chitin binding protein domains, enteropeptidase cleavage sites, Factor Xa cleavage sites, FIAsH tags, FLAG tags, green fluorescent proteins (GFP), glutathione-S-transferase moieties, HA tags, maltose binding protein domains, myc tags, polyhistidine tags, ReAsH tags, strep-tags, strep-tag II, TEV protease sites, thioredoxin domains, thrombin cleavage site, and V5 epitope tags.

In certain of the above embodiments, the polypeptide sequences of the protease-cleavage resistant, Shiga toxin effector polypeptide component of a molecule of the present invention is varied by one or more conservative amino acid substitutions as long as the Shiga toxin effector polypeptide retains a disrupted furin-cleavage motif and as long as the Shiga toxin effector polypeptide exhibits, alone and/or as a component of a cell-targeted molecule, one or more Shiga toxin effector functions selected from one or more of the following: intracellular routing, catalytic activity, and/or cytotoxicity. In certain of the above embodiments, the polypeptide sequences of the cell-targeted molecules of the present invention are varied by one or more conservative amino acid substitutions introduced into a polypeptide region(s) the Shiga toxin effector polypeptide region retains a disrupted furin-cleavage motif and as long as the binding region retains extracellular target biomolecule binding specificity.

As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table B below). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins see, e.g., Bowie J et al., Science 247: 1306-10 (1990).

In the conservative substitution scheme in Table B below, exemplary conservative substitutions of amino acids are grouped by physicochemical properties—I: neutral, hydrophilic; II: acids and amides; III: basic; IV: hydrophobic; V: aromatic, bulky amino acids, VI hydrophilic uncharged, VII aliphatic uncharged, VIII non-polar uncharged, IX cycloalkenyl-associated, X hydrophobic, XI polar, XII small, XIII turn-permitting, and XIV flexible. For example, conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

TABLE B

Examples of Conservative Amino Acid Substitutions

| I | II | III | IV | V | VI | VII | VIII | IX | X | XI | XII | XIII | XIV |
|---|----|-----|----|----|-----|-----|------|----|----|-----|-----|------|-----|
| A | D | H | C | F | N | A | C | F | A | C | A | A | D |
| G | E | K | I | W | Q | G | M | H | C | D | C | C | E |

TABLE B-continued

Examples of Conservative Amino Acid Substitutions

| I | II | III | IV | V | VI | VII | VIII | IX | X | XI | XII | XIII | XIV |
|---|----|-----|----|----|----|-----|------|----|---|----|-----|------|-----|
| P | Q | R | L | Y | S | I | P | W | F | E | D | D | G |
| S | N |   | M |   | T | L |   | Y | G | H | G | E | K |
| T |   |   | V |   |   | V |   |   | H | K | N | G | P |
|   |   |   |   |   |   |   |   |   | I | N | P | H | Q |
|   |   |   |   |   |   |   |   |   | L | Q | S | K | R |
|   |   |   |   |   |   |   |   |   | M | R | T | N | S |
|   |   |   |   |   |   |   |   |   | R | S | V | Q | T |
|   |   |   |   |   |   |   |   |   | T | T |   | R |   |
|   |   |   |   |   |   |   |   |   | V |   |   | S |   |
|   |   |   |   |   |   |   |   |   | W |   |   | P |   |
|   |   |   |   |   |   |   |   |   | Y |   |   | T |   |

In certain embodiments, the protease-cleavage resistant, Shiga toxin effector polypeptides and/or molecules of the present invention may comprise functional fragments or variants of a polypeptide region of the invention that have, at most, 20, 15, 10, 9, 8, 7, 6, 5, 4, 3, 2, or 1 amino acid substitution(s) compared to a polypeptide sequence recited herein, 1) as long as the Shiga toxin effector polypeptide retains a disrupted furin-cleavage motif and as long as the Shiga toxin effector polypeptide exhibits, alone and/or as a component of a cell-targeted molecule, a reasonable level of the Shiga toxin effector function(s) related to intracellular routing, catalytic activity, and/or cytotoxicity; and 2) as long as the cell-targeted molecule comprises a binding region which retains extracellular target biomolecule binding specificity. Variants of the protease-cleavage resistant, Shiga toxin effector polypeptide components of the molecules of the invention and/or cell-targeted molecules of the invention are within the scope of the present invention as a result of changing a polypeptide of the molecule of the invention by altering one or more amino acids or deleting or inserting one or more amino acids, such as within the cell-targeting binding region or the Shiga toxin effector polypeptide, in order to achieve desired properties, such as changed cytotoxicity, changed cytostatic effects, changed immunogenicity, and/or changed serum half-life. A protease-cleavage resistant, Shiga toxin effector polypeptide and/or molecule of the invention may further be with or without a signal sequence.

In certain embodiments, the protease-cleavage resistant, Shiga toxin effector polypeptide components of the molecules of the present invention shares at least 85%, 90%, 95%, 96%, 97%, 98%, 99% or more amino acid sequence identity to any one of the amino acid sequences of a polypeptide recited herein, as long as the Shiga toxin effector polypeptide retains a disrupted furin cleavage motif and as long as the Shiga toxin effector polypeptide, alone and/or as a component of a cell-targeted molecule, retains a measurable biological activity, such as, e.g., subcellular routing, cytotoxicity, enzymatic catalysis, and/or catalytically inactivating ribosomes. In certain embodiments, the cell-targeted molecules of the present invention shares at least 85%, 90%, 95%, 96%, 97%, 98%, 99% or more amino acid sequence identity to any one of the amino acid sequences of a polypeptide recited herein, as long as its Shiga toxin effector polypeptide region retains a disrupted furin cleavage motif and as long as the cell-targeted molecule retains a measurable biological activity, such as, e.g., subcellular routing, cytotoxicity, extracellular target biomolecule binding, cellular internalization, enzymatic catalysis, and/or catalytically inactivating ribosomes.

In certain embodiments, the protease-cleavage resistant, Shiga toxin effector polypeptide components of the molecules of the present invention may be altered to change its enzymatic activity and/or cytotoxicity as long as it retains a disrupted furin-cleavage motif and as long as it exhibits, alone and/or as a component of a cell-targeted molecule, the Shiga toxin effector function selected from one or more of the following: intracellular routing, catalytic activity, and/or cytotoxicity. This change may or may not result in a change in the cytotoxicity of the Shiga toxin effector polypeptide or cytotoxic molecule of which the altered Shiga toxin effector polypeptide is a component. Possible alterations include mutations to the Shiga toxin effector polypeptide selected from the group consisting of: a truncation, deletion, inversion, insertion, rearrangement, and substitution as long as a disrupted furin-cleavage motif is retained and the Shiga toxin effector polypeptide retains, alone and/or as a component of a cell-targeted molecule, the Shiga toxin effector function selected from one or more of the following: intracellular routing, catalytic activity, and/or cytotoxicity.

The molecules of the present invention each comprise a protease-cleavage resistant, Shiga toxin effector polypeptide region which retains a Shiga toxin effector function (e.g. intracellular routing to the cytosol) but in certain embodiments may be engineered from a cytotoxic parental molecule to a molecule with diminished or abolished cytotoxicity for non-cytotoxic functions, e.g., effectuating cytostasis, delivery of exogenous materials, and/or detection of cell types, by mutating one or more key residues for enzymatic activity.

The catalytic and/or cytotoxic activity of the A Subunits of members of the Shiga toxin family may be diminished or eliminated by mutation or truncation. The most critical residues for enzymatic activity and/or cytotoxicity in the Shiga toxin A Subunits have been mapped to the following residue-positions: aspargine-75, tyrosine-77, glutamate-167, arginine-170, and arginine-176 among others (Di R et al., *Toxicon* 57: 525-39 (2011)). In particular, a double-mutant construct of Stx2A containing glutamate-E167-to-lysine and arginine-176-to-lysine mutations was completely inactivated; whereas, many single mutations in Stx1 and Stx2 showed a 10-fold reduction in cytotoxicity. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan, *Infect Immun* 66: 5252-9 (1998)). Mutating both glutamate-167 and arginine-170 eliminated the enzymatic activity of Slt-I A1 in a cell-free ribosome inactivation assay (LaPointe P et al., *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe P et al., *J Biol Chem* 280: 23310-18 (2005)).

In certain embodiments of the protease-cleavage resistant, Shiga toxin effector polypeptides and/or cell-targeted molecules of the invention derived from or comprising a component derived from SLT-1A (SEQ ID NO:1) or StxA (SEQ ID NO:2), the Shiga toxin effector comprises an alteration from the wild-type Shiga toxin sequences, such as, e.g., one or more of the following substitution(s): asparagine at position 75, tyrosine at position 77, tyrosine at position 114, glutamate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to alanine, substitution of the glutamate at position 167 to aspartate, substitution of the arginine at position 170 to alanine, substitution of the arginine at position 176 to lysine, and/or substitution of the tryptophan at position 203 to alanine as long as the disrupted furin-cleavage motif remains disrupted and the Shiga toxin effector polypeptide retains, alone and/or as a component of a cell-targeted molecule, the Shiga toxin effector function selected from one or more of the following: intracellular routing, catalytic activity, and/or cytotoxicity. Other mutations which either enhance or reduce Shiga toxin enzymatic activity and/or cytotoxicity are within the scope of the present invention and may be determined using well known techniques and assays disclosed herein.

In certain embodiments of the molecules of the present invention, one or more amino acid residues may be mutated, inserted, or deleted in order to increase the enzymatic activity of the protease-cleavage resistant, Shiga toxin effector polypeptide region as long as the disrupted furin-cleavage motif remains disrupted. For example, mutating residue-position alanine-231 in Stx1A to glutamate increased its enzymatic activity in vitro (Suhan M, Hovde C, *Infect Immun* 66: 5252-9 (1998)), but will not restore furin-cleavage sensitivity.

The molecules of the present invention may optionally be conjugated to one or more additional agents which may include therapeutic and/or diagnostic agents known in the art, including such agents as described herein.

V. Production, Manufacture, and Purification of Protease-Cleavage Resistant, Shiga Toxin Effector Polypeptides and Molecules Comprising the Same The protease-cleavage resistant, Shiga toxin effector polypeptide components and cell-targeted molecules of the invention may be produced using biochemical engineering techniques well known to those of skill in the art. For example, Shiga toxin effector polypeptides and cell-targeted molecules of the invention may be manufactured by standard synthetic methods, by use of recombinant expression systems, or by any other suitable method. Thus, Shiga toxin effector polypeptides and cell-targeted molecules of the invention may be synthesized in a number of ways, including, e.g. methods comprising: (1) synthesizing a polypeptide or polypeptide component of a protein using standard solid-phase or liquid-phase methodology, either stepwise or by fragment assembly, and isolating and purifying the final polypeptide or protein product; (2) expressing a polynucleotide that encodes a polypeptide or polypeptide component of a molecule of the invention (e.g. polypeptide or protein) in a host cell and recovering the expression product from the host cell or host cell culture; or (3) cell-free in vitro expression of a polynucleotide encoding a molecule of the invention (e.g. a cell-targeted polypeptide or protein), and recovering the expression product; or by any combination of the methods of (1), (2) or (3) to obtain fragments of the peptide component, subsequently joining (e.g. ligating) the fragments to obtain the peptide component, and recovering the peptide component. For example, polypeptide and/or peptide components may be ligated together using coupling reagents, such as, e.g., N,N'-dicyclohexycarbodiimide and N-ethyl-5-phenyl-isoxazolium-3'-sulfonate (Woodward's reagent K).

It may be preferable to synthesize a protease-cleavage resistant, Shiga toxin effector polypeptide or a polypeptide or polypeptide component of a molecule of the invention (e.g. a cell-targeted molecule) by means of solid-phase or liquid-phase peptide synthesis. Shiga toxin effector polypeptides and cell-targeted molecules of the invention may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/11125 or, inter alia, Fields G et al., Principles and *Practice of Solid-Phase Peptide Synthesis* (Synthetic Peptides, Grant G, ed., Oxford University Press, U.K., 2nd ed., 2002) and the synthesis examples therein.

Protease-cleavage resistant, Shiga toxin effector polypeptides and cell-targeted molecules of the invention may be prepared (produced and purified) using recombinant techniques well known in the art. In general, methods for preparing polypeptides by culturing host cells transformed or transfected with a vector comprising the encoding polynucleotide and recovering the polypeptide from cell culture are described in, e.g. Sambrook J et al., *Molecular Cloning: A Laboratory Manual* (Cold Spring Harbor Laboratory Press, NY, U.S., 1989); Dieffenbach C et al., *PCR Primer: A Laboratory Manual* (Cold Spring Harbor Laboratory Press, N.Y., U.S., 1995). Any suitable host cell may be used to produce a Shiga toxin effector polypeptide and/or molecule of the invention (e.g. a cell-targeted protein). Host cells may be cells stably or transiently transfected, transformed, transduced or infected with one or more expression vectors which drive expression of a polypeptide of a molecule of the invention. In addition, a Shiga toxin effector polypeptides and/or molecule of the invention (e.g. a cell-targeted protein) may be produced by modifying the polynucleotide encoding the molecule of the invention (e.g. a cell-targeted protein) that result in altering one or more amino acids or deleting or inserting one or more amino acids in order to achieve desired properties, such as changed cytotoxicity, changed cytostatic effects, changed immunogenicity, and/or changed serum half-life.

There are a wide variety of expression systems which may be chosen to produce a molecule of the invention (e.g. a Shiga toxin effector polypeptide or cell-targeted protein). For example, host organisms for expression of proteins of the invention include prokaryotes, such as *E. coli* and *B. subtilis*, eukaryotic cells, such as yeast and filamentous fungi (like *S. cerevisiae, P. pastoris, A. awamori*, and *K. lactis*), algae (like *C. reinhardtii*), insect cell lines, mammalian cells (like CHO cells), plant cell lines, and eukaryotic organisms such as transgenic plants (like *A. thaliana* and *N. benthamiana*).

Accordingly, the present invention also provides methods for producing a protease-cleavage resistant, Shiga toxin effector polypeptides and/or molecule of the invention (e.g. polypeptide or protein) according to above recited methods and using (i) a polynucleotide encoding part or all of a molecule of the invention or a polypeptide component thereof, (ii) an expression vector comprising at least one polynucleotide of the invention capable of encoding part or all of a molecule of the invention or a polypeptide component thereof when introduced into a suitable host cell or cell-free expression system, and/or (iii) a host cell comprising a polynucleotide or expression vector of the invention.

When a polypeptide or protein is expressed using recombinant techniques in a host cell or cell-free system, it is advantageous to separate (or purify) the desired polypeptide or protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A Sepharose chromatography to remove contaminants), and precipitation techniques (e.g. ethanol precipitation or ammonium sulfate precipitation). Any number of biochemical purification techniques may be used to increase the purity of a Shiga toxin effector polypeptides and/or molecule of the invention (e.g. a Shiga toxin effector polypeptide, cell-targeted protein, or other cell-targeted molecule). In certain embodiments, the cell-targeted molecules of the invention may optionally be purified in homo-multimeric forms (i.e. a protein complex of two or more identical proteins or cell-targeted molecules of the invention) or in hetero-multimeric forms (i.e. a protein complex of two or more non-identical proteins or cell-targeted molecules of the invention).

In the Examples below are descriptions of non-limiting examples of methods for producing a molecule of the invention (e.g. a cell-targeted molecule), as well as specific but non-limiting aspects of production for exemplary molecules of the invention (e.g. single-chain, fusion polypeptides).

VI. Pharmaceutical and Diagnostic Compositions Comprising a Protease-Cleavage Resistant, Shiga Toxin Effector Polypeptide of the Invention The present invention provides molecules and cell-targeted molecules for use, alone or in combination with one or more additional therapeutic agents, in a pharmaceutical composition, for treatment or prophylaxis of conditions, diseases, disorders, or symptoms described in further detail below (e.g. cancers, malignant tumors, non-malignant tumors, growth abnormalities, immune disorders, and microbial infections). The present invention further provides pharmaceutical compositions comprising a molecule of the invention, such as, e.g., a cell-targeted molecule of the invention, or a pharmaceutically acceptable salt or solvate thereof, according to the invention, together with at least one pharmaceutically acceptable carrier, excipient, or vehicle. In certain embodiments, the pharmaceutical composition of the invention may comprise homo-multimeric and/or hetero-multimeric forms of the molecules or cell-targeted molecules of the invention. The pharmaceutical compositions of the invention are useful in methods of treating, ameliorating, or preventing a disease, condition, disorder, or symptom described in further detail below. Each such disease, condition, disorder, or symptom is envisioned to be a separate embodiment with respect to uses of a pharmaceutical composition according to the invention. The invention further provides pharmaceutical compositions for use in at least one method of treatment according to the invention, as described in more detail below.

As used herein, the terms "patient" and "subject" are used interchangeably to refer to any organism, commonly vertebrates such as humans and animals, which presents symptoms, signs, and/or indications of at least one disease, disorder, or condition. These terms include mammals such as the non-limiting examples of primates, livestock animals (e.g. cattle, horses, pigs, sheep, goats, etc.), companion animals (e.g. cats, dogs, etc.) and laboratory animals (e.g. mice, rabbits, rats, etc.).

As used herein, "treat," "treating," or "treatment" and grammatical variants thereof refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease, disorder, or condition. With regard to tumors and/or cancers, treatment includes reductions in overall tumor burden and/or individual tumor size.

As used herein, the terms "prevent," "preventing," "prevention" and grammatical variants thereof refer to an approach for preventing the development of, or altering the pathology of, a condition, disease, or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount" or "therapeutically effective amount" is an amount or dose of a composition (e.g. a therapeutic composition or agent) that produces at least one desired therapeutic effect in a subject, such as preventing or treating a target condition or beneficially alleviating a symptom associated with the condition. The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic molecule or composition (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a composition of matter and adjusting the dosage accordingly (see e.g. *Remington: The Science and Practice of Pharmacy* (Gennaro A, ed., Mack Publishing Co., Easton, Pa., U.S., 19th ed., 1995)).

Diagnostic compositions of the invention comprise a molecule of the invention and one or more detection promoting agents. Various detection promoting agents are known in the art, such as isotopes, dyes, colorimetric agents, contrast enhancing agents, fluorescent agents, bioluminescent agents, and magnetic agents. These agents may be incorporated into the molecule of the invention at any position. The incorporation of the agent may be via an amino acid residue(s) of the cytotoxic molecule or via some type of linkage known in the art, including via linkers and/or chelators. The incorporation of the agent is in such a way to enable the detection of the presence of the diagnostic composition in a screen, assay, diagnostic procedure, and/or imaging technique.

When producing or manufacturing a diagnostic composition of the invention, a molecule of the invention (e.g. a cell-targeted molecule) may be directly or indirectly linked to one or more detection promoting agents. There are numerous detection promoting agents known to the skilled worker which can be operably linked to the molecules of the invention for information gathering methods, such as for diagnostic and/or prognostic applications to diseases, disorders, or conditions of an organism (see e.g. Cai W et al., *J Nucl Med* 48: 304-10 (2007); Nayak T, Brechbiel M, *Bioconjug Chem* 20: 825-41 (2009); Paudyal P et al., *Oncol Rep* 22: 115-9 (2009); Qiao J et al., *PLoS ONE* 6: e18103 (2011); Sano K et al., *Breast Cancer Res* 14: R61 (2012)). For example, detection promoting agents include image enhancing contrast agents, such as fluorescent dyes (e.g. Alexa680, indocyanine green, and Cy5.5), isotopes and radionuclides, such as $^{11}$C, $^{13}$N, $^{15}$O, $^{18}$F, $^{32}$F, $^{51}$Mn, $^{52m}$Mn, $^{52}$Fe, $^{55}$Co, $^{62}$Cu, $^{64}$Cu, $^{67}$Cu, $^{67}$Ga, $^{68}$Ga, $^{72}$As, $^{73}$Se, $^{75}$Br, $^{76}$Br, $^{82m}$Rb, $^{83}$Sr, $^{86}$Y, $^{90}$Y, $^{89}$Zr, $^{94m}$TC, $^{94}$Tc, $^{99m}$Tc, $^{110}$In, $^{111}$In, $^{120}$I, $^{123}$I, $^{124}$I, $^{125}$I, $^{131}$I, $^{154}$Gd, $^{155}$Gd, $^{156}$Gd, $^{157}$Gd, $^{158}$Gd, $^{177}$Lu, $^{186}$Re, $^{188}$Re, and $^{223}$R; paramagnetic ions, such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III); metals, such as lanthanum (III), gold (III), lead (II), and bismuth (III); ultrasound-contrast enhancing agents, such as liposomes; radiopaque agents, such as barium, gallium, and thallium compounds. Detection promoting agents may be incorporated directly or indirectly by using an intermediary functional group, such as chelators like 2-benzyl DTPA, PAMAM, NOTA, DOTA, TETA, analogs thereof, and functional equivalents of any of the foregoing (see Leyton J et al., *Clin Cancer Res* 14: 7488-96 (2008)).

There are numerous standard techniques known to the skilled worker for incorporating, affixing, and/or conjugating various detection promoting agents to proteins, especially to immunoglobulins and immunoglobulin-derived domains (Wu A, *Methods* 65: 139-47 (2014)). Similarly, there are numerous imaging approaches known to the skilled worker, such as non-invasive in vivo imaging techniques commonly used in the medical arena, for example: computed tomography imaging (CT scanning), optical imaging (including direct, fluorescent, and bioluminescent imaging), magnetic resonance imaging (MRI), positron emission tomography (PET), single-photon emission computed tomography (SPECT), ultrasound, and x-ray computed tomography imaging (see Kaur S et al., *Cancer Lett* 315: 97-111 (2012), for review).

Production or Manufacture of a Pharmaceutical and/or Diagnostic Composition Comprising a Protease-Cleavage Resistant, Shiga Toxin Effector Polypeptide Pharmaceutically acceptable salts or solvates of any of the molecules of the present invention, such as, e.g., cell-targeted molecules of the present invention, are likewise within the scope of the present invention.

The term "solvate" in the context of the present invention refers to a complex of defined stoichiometry formed between a solute (in casu, a molecule of the invention or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Molecules of the present invention, or salts thereof, may be formulated as pharmaceutical compositions prepared for storage or administration, which typically comprise a therapeutically effective amount of a molecule of the invention, or a salt thereof, in a pharmaceutically acceptable carrier. The term "pharmaceutically acceptable carrier" includes any of the standard pharmaceutical carriers. Pharmaceutically acceptable carriers for therapeutic use are well known in the pharmaceutical art, and are described, for example, in *Remington's Pharmaceutical Sciences* (Mack Publishing Co. (A. Gennaro, ed., 1985). As used herein, "pharmaceutically acceptable carrier" includes any and all physiologically acceptable, i.e. compatible, solvents, dispersion media, coatings, antimicrobial agents, isotonic, and absorption delaying agents, and the like. Pharmaceutically acceptable carriers or diluents include those used in formulations suitable for oral, rectal, nasal or parenteral (including subcutaneous, intramuscular, intravenous, intradermal, and transdermal) administration. Exemplary pharmaceutically acceptable carriers include sterile aqueous solutions or dispersions and sterile powders for the extemporaneous preparation of sterile injectable solutions or dispersions. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants. In certain embodiments, the carrier is suitable for intravenous, intramuscular, subcutaneous, parenteral, spinal or epidermal administration (e.g. by injection or infusion). Depending on selected route of administration, the cell-targeted molecule or other pharmaceutical component may be coated in a material intended to protect the molecule from the action of low pH and other natural inactivating conditions to which the active molecule may encounter when administered to a patient by a particular route of administration.

The formulations of the pharmaceutical compositions of the invention may conveniently be presented in unit dosage form and may be prepared by any of the methods well known in the art of pharmacy. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Subcutaneous or transdermal modes of administration may be particularly suitable for pharmaceutical compositions and therapeutic molecules of the invention described herein.

The pharmaceutical compositions of the invention may also contain adjuvants such as preservatives, wetting agents, emulsifying agents and dispersing agents. Preventing the presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

In another aspect, the present invention provides pharmaceutical compositions comprising one or a combination of different molecules of the invention, or an ester, salt or amide of any of the foregoing, and at least one pharmaceutically acceptable carrier.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g. glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g. sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a molecule of the invention in the required amount in an appropriate solvent with one or a combination of ingredients described above, as required, followed by sterilization microfiltration. Dispersions may be prepared by incorporating the active molecule into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a molecule of the invention is designed to be administered by, e.g. intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

As described elsewhere herein, a molecule of the present invention or composition thereof (e.g. pharmaceutical or diagnostic composition) may be prepared with carriers that will protect the molecule against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see e.g. *Sustained and Controlled Release Drug Delivery Systems* (Robinson J, ed., Marcel Dekker, Inc., NY, U.S., 1978)).

In certain embodiments, the composition of the present invention (e.g. pharmaceutical or diagnostic composition) may be formulated to ensure a desired distribution in vivo. For example, the blood-brain barrier excludes many large and/or hydrophilic compounds. To target a therapeutic molecule or composition of the invention to a particular in vivo location, it can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 catenin and the like.

Pharmaceutical compositions include parenteral formulations designed to be used as implants or particulate systems. Examples of implants are depot formulations composed of polymeric or hydrophobic components such as emulsions, ion exchange resins, and soluble salt solutions. Examples of particulate systems are microspheres, microparticles, nanocapsules, nanospheres, and nanoparticles (see e.g. Honda M et al., *Int J Nanomedicine* 8: 495-503 (2013); Sharma A et al., *Biomed Res Int* 2013: 960821 (2013); Ramishetti S, Huang L, *Ther Deliv* 3: 1429-45 (2012)). Controlled release formulations may be prepared using polymers sensitive to ions, such as, e.g. liposomes, polaxamer 407, and hydroxyapatite.

Pharmaceutical compositions of the present invention may be produced using techniques known in the art such that the produced compositions comprise emulsions, liposomes, niosomes, polymeric nanoparticles, and/or solid lipid nanoparticles (SLNs) (see e.g. Lakshmi P et al., *Venereal Leprol* 73: 157-161 (2007); *A Revolution in Dosage Form Design and Development, Recent Advances in Novel Drug Carrier Systems* (Sezer A, ed., InTech, 2012)).

Commonly, pharmaceutical compositions comprising liposomes comprise liposomes dispersed in an aqueous medium (see e.g. Li S et al., *J Control Release* 126: 77-84 (2008); Li S et al., *Mol Ther* 16: 163-9 (2008); Chen Y et al., *J Invest Dermatol* 130: 2790-8 (2010); Chen Y et al., *J Biol Chem* 285:22639-50 (2010)). Liposomes and nanoparticles may be cell-targeted by incorporating immunoglobulin domains, receptors, and/or ligands during their production (see e.g. Khan D et al., *Chemical Biology and Drug Design* 71: 3-7 (2008); Rezler E et al., *Journal of the American Chemical Society* 129: 4961-72 (2007); Khan D, *Journal of Cancer Science and Therapy* 2: 58-62 (2010); van der Meel R et al., *J Control Release* 159: 281-9 (2012); Sada S et al., *Curr Cancer Crug Targets* 15: 71-86 (2015)).

Commonly, SLNs comprise lipids such as paraffin wax and biodegradable glycerides (see e.g. Attama A et al., *Int J Pharm* 304: 4-10 (2005)). SLNs can be loaded with molecules of the present invention (e.g. cell-targeted molecules) using methods known to the skilled worker, such as, e.g., by using lipid-therapeutic conjugates in the form of nanoparticles (see e.g. Müller R et al., *Eur J Pharm Biopharm* 41: 62-9 (1995); Friedrich I et al., *Int J Pharm* 305: 167-75 (2005); Schubert M A et al., *Eur J Pharm Sci* 27: 226-36 (2006); Attama A et al., *Eur J Pharm Biopharm* 64: 294-306 (2006); Attama A, Müller-Goymann C, *Int J Pharm* 322: 67-78 (2006); Attama A et al., *Int J Pharm* 355: 307-13 (2008); Attama A et al., *J Drug Deliv Sci Technol* 18: 181-8 (2008); Attama A et al., *Current Eye Res* 34: 698-705 (2009); U.S. Pat. No. 8,663,692). In particular, SLNs can incorporate hydrophilic compounds comprising Shiga toxin-derived polypeptides linked to cell-targeting, binding regions (see e.g. Müller R et al., *Eur J Pharm Biopharm* 41: 62-9 (1995)). SLNs comprising HPMA copolymers can be designed to target subcellular compartments after cellular internalization (see e.g. Jensen K et al., *J Control Release* 87: 89-105 (2003)).

VII. Polynucleotides, Expression Vectors, and Host Cells of the Invention

Beyond the molecules of the present invention, the polynucleotides which encode the polypeptides and proteins of the invention, or functional portions thereof, are within the scope of the present invention. The term "polynucleotide" is equivalent to the term "nucleic acids" both of which include polymers of deoxyribonucleic acids (DNAs), polymers of ribonucleic acids (RNAs), analogs of these DNAs or RNAs generated using nucleotide analogs, and derivatives, fragments and homologs thereof. The polynucleotide of the invention may be single-, double-, or triple-stranded. Disclosed polynucleotides are specifically disclosed to include all polynucleotides capable of encoding an exemplary cell-targeted molecule, for example, taking into account the wobble known to be tolerated in the third position of RNA codons, yet encoding for the same amino acid as a different RNA codon (see Stothard P, *Biotechniques* 28: 1102-4 (2000)).

In one aspect, the invention provides polynucleotides which encode a protease-cleavage resistant, Shiga toxin effector polypeptides and/or a molecule of the invention (e.g. polypeptide or protein), or a fragment or derivative thereof. The polynucleotides may include, e.g., a nucleic acid sequence encoding a polypeptide at least 50%, 55%, 60%, 65%, 70%, 75%, 80%, 85%, 90%, 95%, 99% or more, identical to a polypeptide comprising one of the amino acid sequences of the protein. The invention also includes polynucleotides comprising nucleotide sequences that hybridize under stringent conditions to a polynucleotide which encodes protease-cleavage resistant, Shiga toxin effector polypeptides and/or a polypeptide of a molecule of the invention, or a fragment or derivative thereof, or the antisense or complement of any such sequence.

Derivatives or analogs of the polynucleotides (or protease-cleavage resistant, Shiga toxin effector polypeptides and/or proteins) of the invention include, inter alia, polynucleotide (or polypeptide) molecules having regions that are substantially homologous to the polynucleotides, protease-cleavage resistant, Shiga toxin effector polypeptides, or proteins of the invention, e.g. by at least about 45%, 50%, 70%, 80%, 95%, 98%, or even 99% identity (with a preferred identity of 80-99%) over a polynucleotide or polypeptide sequence of the same size or when compared to an aligned sequence in which the alignment is done by a computer homology program known in the art. An exemplary program is the GAP program (Wisconsin Sequence Analysis Package, Version 8 for UNIX, Genetics Computer Group, University Research Park, Madison, Wis., U.S.)

using the default settings, which uses the algorithm of Smith T, Waterman M, *Adv Appl Math* 2: 482-9 (1981). Also included are polynucleotides capable of hybridizing to the complement of a sequence encoding the proteins of the invention under stringent conditions (see e.g. Ausubel F et al., *Current Protocols in Molecular Biology* (John Wiley & Sons, New York, N.Y., U.S., 1993)), and below. Stringent conditions are known to those skilled in the art and may be found in *Current Protocols in Molecular Biology* (John Wiley & Sons, NY, U.S., Ch. Sec. 6.3.1-6.3.6 (1989)).

The present invention further provides expression vectors that comprise the polynucleotides within the scope of the present invention. The polynucleotides capable of encoding the protease-cleavage resistant, Shiga toxin effector polypeptides and/or proteins of the invention may be inserted into known vectors, including bacterial plasmids, viral vectors and phage vectors, using material and methods well known in the art to produce expression vectors. Such expression vectors will include the polynucleotides necessary to support production of contemplated Shiga toxin effector polypeptides and/or proteins of the invention within any host cell of choice or cell-free expression systems (e.g. pTxb1 and pIVEX2.3). The specific polynucleotides comprising expression vectors for use with specific types of host cells or cell-free expression systems are well known to one of ordinary skill in the art, can be determined using routine experimentation, or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context of the present invention, an expression vector encoding a Shiga toxin effector polypeptides and/or a protein comprising a single polypeptide chain (e.g. a scFv genetically recombined with a Shiga toxin effector polypeptide) includes at least an expression unit for the single polypeptide chain, whereas a protein comprising, e.g. two or more polypeptide chains (e.g. one chain comprising a $V_L$ domain and a second chain comprising a $V_H$ domain linked to a Shiga toxin effector polypeptide comprising a disrupted furin-cleavage motif) includes at least two expression units, one for each of the two polypeptide chains of the protein. For expression of multi-chain proteins of the invention, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide of the invention or capable of producing a molecule of the invention (e.g. polypeptide or protein) can be accomplished using standard techniques known in the art.

Protease-cleavage resistant, Shiga toxin effector polypeptides and/or proteins within the scope of the present invention may be variants or derivatives of the polypeptides and proteins described herein that are produced by modifying the polynucleotide encoding a polypeptide and/or protein by altering one or more amino acids or deleting or inserting one or more amino acids that may render it more suitable to achieve desired properties, such as more optimal expression by a host cell.

VIII. Molecules of the Invention Immobilized on Solid Substrates

Certain embodiments of the present invention include a molecule of the present invention (e.g. a protease-cleavage resistant, cytotoxic molecule or cell-targeted molecule) or any effector fragment thereof, immobilized on a solid substrate. Solid substrates contemplated herein include, but are not limited to, microbeads, nanoparticles, polymers, matrix materials, microarrays, microtiter plates, or any solid surface known in the art (see e.g. U.S. Pat. No. 7,771,955). In accordance with these embodiments, a molecule of the present invention may be covalently or non-covalently linked to a solid substrate, such as, e.g., a bead, particle, or plate, using techniques known to the skilled worker. Immobilized molecules of the invention may be used for screening applications using techniques known in the art (see e.g. Bradbury A et al., *Nat Biotechnol* 29: 245-54 (2011); Sutton C, *Br J Pharmacol* 166: 457-75 (2012); Diamante L et al., *Protein Eng Des Sel* 26: 713-24 (2013); Houlihan G et al., *J Immunol Methods* 405: 47-56 (2014)).

Non-limiting examples of solid substrates to which a molecule of the invention may be immobilized on include: microbeads, nanoparticles, polymers, nanopolymers, nanotubes, magnetic beads, paramagnetic beads, superparamagnetic beads, streptavidin coated beads, reverse-phase magnetic beads, carboxy terminated beads, hydrazine terminated beads, silica (sodium silica) beads and iminodiacetic acid (IDA)-modified beads, aldehyde-modified beads, epoxy-activated beads, diaminodipropylamine (DADPA)-modified beads (beads with primary amine surface group), biodegradable polymeric beads, polystyrene substrates, amino-polystyrene particles, carboxyl-polystyrene particles, epoxy-polystyrene particles, dimethylamino-polystyrene particles, hydroxy-polystyrene particles, colored particles, flow cytometry particles, sulfonate-polystyrene particles, nitrocellulose surfaces, reinforced nitrocellulose membranes, nylon membranes, glass surfaces, activated glass surfaces, activated quartz surfaces, polyvinylidene difluoride (PVDF) membranes, polyacrylamide-based substrates, poly-vinyl chloride substrates, poly-methyl methacrylate substrates, poly(dimethyl siloxane) substrates, and photopolymers which contain photoreactive species (such as nitrenes, carbenes, and ketyl radicals) capable of forming covalent linkages. Other examples of solid substrates to which a molecule of the invention may be immobilized on are commonly used in molecular display systems, such as, e.g., cellular surfaces, phages, and virus particles.

IX. Delivery Devices and Kits

In certain embodiments, the invention relates to a device comprising one or more compositions of matter of the present invention, such as a pharmaceutical composition, for delivery to a subject. Thus, a delivery device comprising one or more compositions of matter of the invention may be used to administer to a patient a composition of matter of the invention by various delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

Also within the scope of the present invention are kits comprising at least one composition of matter of the invention, and optionally, packaging and instructions for use. Kits may be useful for drug administration and/or diagnostic information gathering. A kit of the invention may optionally comprise at least one additional reagent (e.g., standards, markers, and the like). Kits typically include a label indicating the intended use of the contents of the kit. The kit may further comprise reagents and other tools for detecting a cell type (e.g. tumor cell) in a sample or in a subject, or for diagnosing whether a patient belongs to a group that responds to a therapeutic strategy which makes use of a molecule, composition, or related method of the invention as described herein.

X. Methods for Using Molecules of the Invention—Including Protease-Cleavage Resistant, Shiga Toxin Effector Polypeptides, Cell-Targeted Molecules, Pharmaceutical Compositions, and Diagnostic Compositions of the Invention Generally, it is an object of the invention to provide pharmacologically active agents, as well as compositions comprising the same, that can be used in the prevention and/or treatment of diseases, disorders, and conditions, such as certain cancers, tumors, growth abnormalities, immune disorders, or further pathological conditions mentioned herein. Accordingly, the present invention provides methods of using the molecules of the invention (including protease-cleavage resistant, Shiga toxin effector polypeptides, cell-targeted molecules, pharmaceutical compositions, and diagnostic compositions) for the targeted killing of cells, for delivering additional exogenous materials into targeted cells, for labeling of the interiors of targeted cells, for collecting diagnostic information, and for treating diseases, disorders, and conditions as described herein.

In particular, it is an object of the invention to provide such pharmacologically active agents, compositions, and/or methods that have certain advantages compared to the agents, compositions, and/or methods that are currently known in the art. Accordingly, the present invention provides methods of using molecules of the present invention consisting of polypeptides or proteins characterized by specified polypeptide sequences and pharmaceutical compositions thereof. For example, any of the polypeptide sequences in SEQ ID NOs: 4-61 may be specifically utilized as a component of the cell-targeted molecule used in the following methods.

The present invention provides methods of killing a cell comprising the step of contacting the cell, either in vitro or in vivo, with a molecule or pharmaceutical composition of the present invention. The molecule and pharmaceutical compositions of the invention can be used to kill a specific cell type upon contacting a cell or cells with one of the claimed compositions of matter. In certain embodiments, a cytotoxic, cell-targeted molecule or pharmaceutical composition of the present invention can be used to kill specific cell types in a mixture of different cell types, such as mixtures comprising cancer cells, infected cells, and/or hematological cells. In certain embodiments, a cytotoxic, cell-targeted molecule or pharmaceutical composition of the present invention can be used to kill cancer cells in a mixture of different cell types. In certain embodiments, the cytotoxic, cell-targeted molecules and pharmaceutical compositions of the present invention can be used to kill specific cell types in a mixture of different cell types, such as pre-transplantation tissues. In certain embodiments, a cell-targeted molecule or pharmaceutical composition of the present invention can be used to kill specific cell types in a mixture of cell types, such as pre-administration tissue material for therapeutic purposes. In certain embodiments, a cell-targeted molecule or pharmaceutical composition of the present invention can be used to selectively kill cells infected by viruses or microorganisms, or otherwise selectively kill cells expressing a particular extracellular target biomolecule, such as a cell surface biomolecule. The molecules and pharmaceutical compositions of the invention have varied applications, including, e.g., uses in depleting unwanted cell types from tissues either in vitro or in vivo, uses in modulating immune responses to treat graft-versus-host disease, uses as antiviral agents, uses as anti-parasitic agents, and uses in purging transplantation tissues of unwanted cell types.

In certain embodiments, a cytotoxic, cell-targeted molecule or pharmaceutical composition of the present invention, alone or in combination with other compounds or pharmaceutical compositions, can show potent cell-kill activity when administered to a population of cells, in vitro or in vivo in a subject such as in a patient in need of treatment. By targeting the delivery of enzymatically active Shiga toxin regions using high-affinity binding regions to cancer cell types, this potent cell-kill activity can be restricted to specifically and selectively kill certain cell types within an organism, such as certain cancer cells, neoplastic cells, malignant cells, non-malignant tumor cells, or infected cells.

The present invention provides a method of killing a cell in a patient in need thereof, the method comprising the step of administering to the patient at least one cytotoxic molecule of the present invention, or a pharmaceutical composition thereof.

Certain embodiments of the cytotoxic, cell-targeted molecule or pharmaceutical compositions thereof can be used to kill a cancer and/or tumor cell in a patient by targeting an extracellular biomolecule found physically coupled with a cancer and/or tumor cell. The terms "cancer cell" or "cancerous cell" refers to various neoplastic cells which grow and divide in an abnormally accelerated and/or unregulated fashion and will be clear to the skilled person. The term "tumor cell" includes both malignant and non-malignant cells (e.g. non-cancerous, benign tumor cells, non-cancerous "cancer" stem cells, tumor stem cells, pre-malignant cancer-initiating cells, tumor-initiating cells, or tumorigenic cells all of which can give rise to daughter cells which become malignant tumor and/or cancer cells but are unable to metastasize on their own (see e.g. Martinez-Climent J et al., *Haematologica* 95: 293-302 (2010)). Generally, cancers and/or tumors can be defined as diseases, disorders, or conditions that are amenable to treatment and/or prevention. Neoplastic cells are often associated with one or more of the following: unregulated growth, lack of differentiation, local tissue invasion, angiogenesis, and metastasis. The cancers and tumors (either malignant or non-malignant) which are comprised of cancer cells and/or tumor cells which may benefit from methods and compositions of the invention will be clear to the skilled person.

The present invention may be used to kill cancer stem cells, which commonly are slow dividing and resistant to cancer therapies like chemotherapy and radiation. For example, acute myeloid leukemias (AMLs) may be treated with the present invention by killing AML stem cells and/or dormant AML progenitor cells (see e.g. Shlush L et al., *Blood* 120: 603-12 (2012)). Cancer stem cells often over-express cell surface targets, such as CD44 and CD200, which can be used to target therapeutic molecules of the present invention (see e.g. Kawasaki B et al., *Biochem Biophys Res Commun* 364:778-82 (2007); Reim F et al., *Cancer Res* 69: 8058-66 (2009)).

Certain embodiments of the cytotoxic molecule of the invention, or pharmaceutical compositions thereof, can be used to kill an immune cell (whether healthy or malignant) in a patient by targeting an extracellular biomolecule found physically coupled with an immune cell.

Certain embodiments of the cytotoxic molecule of the invention, or pharmaceutical compositions thereof, can be used to kill an infected cell in a patient by targeting an extracellular biomolecule found physically coupled with an infected cell.

It is within the scope of the present invention to utilize the cytotoxic molecule of the invention, or pharmaceutical compositions thereof, for the purposes of ex vivo depletion of B-cells and/or T-cells from isolated cell populations removed from a patient. In one non-limiting example, the cytotoxic molecule can be used in a method for prophylaxis of organ transplant rejection wherein the donor organ is perfused prior to transplant with the cytotoxic molecule of the invention or a pharmaceutical composition thereof in order to purge the organ of unwanted donor B-cells and/or T-cells.

It is also within the scope of the present invention to utilize the cytotoxic molecule of the invention, or pharmaceutical composition thereof, for the purposes of purging patient cell populations (e.g. bone marrow) of malignant, neoplastic, or otherwise unwanted B-cells and/or T-cells and then reinfusing the B-cell and/or T-cell depleted material into the patient.

It is also within the scope of the present invention to utilize the cytotoxic molecule of the invention, or pharmaceutical composition thereof, for the purposes of depleting B-cells, NK cells, and/or T-cells from a donor cell population as a prophylaxis against graft-versus-host disease, and induction of tolerance, in a patient to undergo a bone marrow and or stem cell transplant (see e.g. Sarantopoulos S et al., *Biol Blood Marrow Transplant* 21: 16-23 (2015)).

Certain embodiments of the cytotoxic molecule of the invention, or pharmaceutical compositions thereof, can be used to kill an infected cell in a patient by targeting an extracellular biomolecule found physically coupled with an infected cell.

Additionally, the present invention provides a method of treating a disease, disorder, or condition in a patient comprising the step of administering to a patient in need thereof a therapeutically effective amount of at least one of the cytotoxic molecule of the invention, or a pharmaceutical composition thereof. Contemplated diseases, disorders, and conditions that can be treated using this method include cancers, malignant tumors, non-malignant tumors, growth abnormalities, immune disorders, and microbial infections. Administration of a "therapeutically effective dosage" of a molecule or composition of the invention may result in a decrease in severity of disease symptoms, an increase in frequency and duration of disease symptom-free periods, or a prevention of impairment or disability due to the disease affliction.

The therapeutically effective amount of a molecule or composition of the present invention will depend on the route of administration, the type of mammal being treated, and the physical characteristics of the specific patient under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

An acceptable route of administration may refer to any administration pathway known in the art, including but not limited to aerosol, enteral, nasal, ophthalmic, oral, parenteral, rectal, vaginal, or transdermal (e.g. topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

For administration of a pharmaceutical composition of the invention, the dosage range will generally be from about 0.0001 to 100 milligrams (mg) per kilogram (kg) (mg/kg), and more, usually 0.01 to 5 mg/kg, of the subject's body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular patient.

Pharmaceutical compositions of the invention will typically be administered to the same patient on multiple occasions. Intervals between single dosages can be, for example, 2-5 days, weekly, monthly, every two or three months, every six months, or yearly. Intervals between administrations can also be irregular, based on regulating blood levels or other markers in the subject or patient. Dosage regimens for a molecule or composition of the invention include intravenous administration of 1 mg/kg body weight or 3 mg/kg body weight with the molecule or composition administered every two to four weeks for six dosages, then every three months at 3 mg/kg body weight or 1 mg/kg body weight.

A pharmaceutical composition of the present invention may be administered via one or more routes of administration, using one or more of a variety of methods known in the art. As will be appreciated by the skilled worker, the route and/or mode of administration will vary depending upon the desired results. Routes of administration for molecules, pharmaceutical compositions, and diagnostic compositions of the invention include, e.g. intravenous, intramuscular, intradermal, intraperitoneal, subcutaneous, spinal, or other parenteral routes of administration, for example by injection or infusion. In other embodiments, a cell-targeted molecule or pharmaceutical composition of the invention may be administered by a non-parenteral route, such as a topical, epidermal or mucosal route of administration, for example, intranasally, orally, vaginally, rectally, sublingually, or topically.

Therapeutic molecules and pharmaceutical compositions of the present invention may be administered with one or more of a variety of medical devices known in the art. For example, in one embodiment, a pharmaceutical composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

A molecule, cell-targeted molecule, or pharmaceutical composition of the present invention may be administered alone or in combination with one or more other therapeutic or diagnostic agents. A combination therapy may include a cytotoxic molecule of the invention or pharmaceutical composition thereof combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

Treatment of a patient with a cell-targeted molecule or pharmaceutical composition of the invention preferably leads to cell death of targeted cells and/or the inhibition of growth of targeted cells. As such, cytotoxic molecules of the invention, and pharmaceutical compositions comprising them, will be useful in methods for treating a variety of pathological disorders in which killing or depleting target cells may be beneficial, such as, inter alia, cancers, tumors, growth abnormalities, immune disorders, and infected cells. The present invention provides methods for suppressing cell proliferation, and treating cell disorders, including neoplasia, overactive B-cells, and overactive T-cells.

In certain embodiments, molecules and pharmaceutical compositions of the invention can be used to treat or prevent cancers, tumors (malignant and non-malignant), growth abnormalities, immune disorders, and microbial infections. In a further aspect, the above ex vivo method can be combined with the above in vivo method to provide methods of treating or preventing rejection in bone marrow transplant recipients, and for achieving immunological tolerance.

In certain embodiments, the present invention provides methods for treating malignancies or neoplasms and other blood cell associated cancers in a mammalian subject, such as a human, the method comprising the step of administering to a subject in need thereof a therapeutically effective amount of a cytotoxic molecule or pharmaceutical composition of the invention.

The molecules and pharmaceutical compositions of the invention have varied applications, including, e.g., uses in removing unwanted B-cells and/or T-cells, uses in modulating immune responses to treat graft-versus-host disease, uses as antiviral agents, uses as antimicrobial agents, and uses in purging transplantation tissues of unwanted cell types. The molecules and pharmaceutical compositions of the present invention are commonly anti-neoplastic agents—meaning they are capable of treating and/or preventing the development, maturation, or spread of neoplastic or malignant cells by inhibiting the growth and/or causing the death of cancer or tumor cells.

In certain embodiments, a cell-targeted molecule or pharmaceutical composition of the present invention is used to treat a B-cell-, plasma cell-, T-cell-, or antibody-mediated disease or disorder, such as for example leukemia, lymphoma, myeloma, Human Immunodeficiency Virus-related diseases, amyloidosis, hemolytic uremic syndrome, polyarteritis nodosa, polyarthritis, septic shock, Crohn's Disease, rheumatoid arthritis, ankylosing spondylitis, psoriatic arthritis, ulcerative colitis, psoriasis, asthma, Sjorgren's syndrome, graft-versus-host disease, graft rejection, diabetes, vasculitis, scleroderma, and systemic lupus erythematosus.

In another aspect, certain embodiments of the molecules and pharmaceutical compositions of the present invention are antimicrobial agents—meaning they are capable of treating and/or preventing the acquisition, development, or consequences of microbiological pathogenic infections, such as caused by viruses, bacteria, fungi, prions, or protozoans.

It is within the scope of the present invention to provide a prophylaxis or treatment for diseases or conditions mediated by B-cells and/or by T-cells, the prophylaxis or treatment involving administering the cytotoxic molecule of the invention, or a pharmaceutical composition thereof, to a patient for the purpose of killing B-cells and/or T-cells in the patient. This usage is compatible with preparing or conditioning a patient for bone marrow transplantation, stem cell transplantation, tissue transplantation, or organ transplantation, regardless of the source of the transplanted material, e.g. human or non-human sources.

It is within the scope of the present invention to provide a bone marrow recipient for prophylaxis or treatment of host-versus-graft disease via the targeted cell-killing of host B-cells and/or T-cells using a cytotoxic, cell-targeted molecule or pharmaceutical composition of the present invention.

The molecules, cell-targeted molecules, and pharmaceutical compositions of the present invention may be utilized in a method of treating cancer comprising administering to a patient, in need thereof, a therapeutically effective amount of a molecule, cell-targeted molecule, or pharmaceutical composition of the present invention. In certain embodiments of the methods of the present invention, the cancer being treated is selected from the group consisting of: bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), and uterine cancer.

The molecules and pharmaceutical compositions of the present invention may be utilized in a method of treating an immune disorder comprising administering to a patient, in need thereof, a therapeutically effective amount of the cytotoxic molecule or a pharmaceutical composition of the present invention. In certain embodiments of the methods of the present invention, the immune disorder is related to an inflammation associated with a disease selected from the group consisting of: amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis nodosa, polyarthritis, psoriasis, psoriatic arthritis, rheumatoid arthritis, scleroderma, septic shock, Sjorgren's syndrome, ulcerative colitis, and vasculitis.

Among certain embodiments of the present invention is using the molecule of the invention as a component of a pharmaceutical composition or medicament for the treatment or prevention of a cancer, tumor, growth abnormality, immune disorder, and/or microbial infection. For example, immune disorders presenting on the skin of a patient may be treated with such a medicament in efforts to reduce inflammation. In another example, skin tumors may be treated with such a medicament in efforts to reduce tumor size or eliminate the tumor completely.

Certain cytotoxic molecules, pharmaceutical compositions, and diagnostic compositions of the invention may be used in molecular neurosurgery applications such as immunolesioning and neuronal tracing (see, Wiley R, Lappi D, *Adv Drug Deliv Rev* 55: 1043-54 (2003), for review). For example, the targeting domain may be selected or derived from various ligands, such as neurotransmitters and neuropeptides, which target specific neuronal cell types by binding neuronal surface receptors, such as a neuronal circuit specific G-protein coupled receptor. Similarly, the targeting domain may be selected from or derived from antibodies that bind neuronal surface receptors. Because Shiga toxin effector polypeptides can robustly direct their own retrograde axonal transport, certain cytotoxic molecules of the invention may be used to kill a neuron(s) which expresses the extracellular target at a site of cytotoxic molecule injection distant from the cell body (see Llewellyn-Smith I et al., *J Neurosci Methods* 103: 83-90 (2000)). These neuronal cell type specific targeting cytotoxic molecules of the invention have uses in neuroscience research, such as for elucidating mechanisms of sensations (see e.g. Mishra S, Hoon M, *Science* 340: 968-71 (2013)) and creating model systems of neurodegenerative diseases, such as Parkinson's and Alzheimer's (see e.g. Hamlin A et al., *PLoS One* e53472 (2013)).

Among certain embodiments of the present invention is a method of using a cell-targeted molecule pharmaceutical composition, and/or diagnostic composition of the invention to label or detect the interiors of a cell type, such as, e.g., neoplastic cells and/or immune cell types. Based on the ability of certain molecules of the invention to enter specific cell types and route within cells via retrograde intracellular transport, the interior compartments of specific cell types may be labeled for detection. This can be performed in vivo on cells in situ within an organism, e.g. a patient, or in vitro on cells and tissues removed from an organism, e.g. biopsy material.

Among certain embodiments of the present invention is a method of using a molecule (e.g. cytotoxic molecule or cell-targeted molecule), polypeptide, protein, pharmaceutical composition, and/or diagnostic composition of the invention to detect the presence of a cell type for the purpose of information gathering regarding diseases, conditions and/or disorders. The method comprises contacting a cell with a diagnostically sufficient amount of a cytotoxic molecule to detect the cytotoxic molecule by an assay or diagnostic technique. The phrase "diagnostically sufficient amount" refers to an amount that provides adequate detection and accurate measurement for information gathering purposes by the particular assay or diagnostic technique utilized. Generally, the diagnostically sufficient amount for whole organism in vivo diagnostic use will be a non-cumulative dose of between 0.1 mg to 100 mg of the detection promoting agent linked cell-targeted molecule per kg of subject per subject. Typically, the amount of molecule of the invention (e.g. cell-targeted molecule) used in these information gathering methods will be as low as possible provided that it is still a diagnostically sufficient amount. For example, for in vivo detection in an organism, the amount of cytotoxic molecule, cell-targeted molecule, pharmaceutical composition, or diagnostic composition of the invention administered to a subject will be as low as feasibly possible.

The cell-type specific targeting of certain molecules of the invention combined with detection promoting agents provides a way to detect and image cells physically coupled with an extracellular target biomolecule of a binding region of the molecule of the invention. Imaging of cells using the molecules and/or diagnostic compositions of the invention may be performed in vitro or in vivo by any suitable technique known in the art. Diagnostic information may be collected using various methods known in the art, including whole body imaging of an organism or using ex vivo samples taken from an organism. The term "sample" used herein refers to any number of things, but not limited to, fluids such as blood, urine, serum, lymph, saliva, anal secretions, vaginal secretions, and semen, and tissues obtained by biopsy procedures. For example, various detection promoting agents may be utilized for non-invasive in vivo tumor imaging by techniques such as magnetic resonance imaging (MRI), optical methods (such as direct, fluorescent, and bioluminescent imaging), positron emission tomography (PET), single-photon emission computed tomography (SPECT), ultrasound, x-ray computed tomography, and combinations of the aforementioned (see, Kaur S et al., *Cancer Lett* 315: 97-111 (2012), for review).

Among certain embodiments of the present invention is a method of using a molecule or pharmaceutical composition of the invention as a diagnostic composition to label or detect the interiors of cancer, tumor, and/or immune cell types (see e.g., Koyama Y et al., *Clin Cancer Res* 13: 2936-45 (2007); Ogawa M et al., *Cancer Res* 69: 1268-72 (2009); Yang L et al., *Small* 5: 235-43 (2009)). Based on the ability of certain molecules, cell-targeted molecules, and pharmaceutical compositions of the invention to enter specific cell types and route within cells via retrograde intracellular transport, the interior compartments of specific cell types are labeled for detection. This method may be performed in vivo within a patient, including on cells in situ, e.g. at a disease locus, and/or in vitro on cells removed from an organism, e.g. biopsy material.

Diagnostic compositions of the invention may be used to characterize a disease, disorder, or condition as potentially treatable by a related pharmaceutical composition of the invention. Certain compositions of matter of the invention may be used to determine whether a patient belongs to a group that responds to a therapeutic strategy which makes use of a molecule, composition, or related method of the invention as described herein or is well suited for using a delivery device of the invention.

Diagnostic compositions of the invention may be used after a disease, e.g. a cancer, is detected in order to better characterize it, such as to monitor distant metastases, heterogeneity, and stage of cancer progression. The phenotypic assessment of disease disorder or infection can help prognosis and prediction during therapeutic decision making. In disease reoccurrence, certain methods of the invention may be used to discriminate local versus systemic problems.

Diagnostic compositions of the invention may be used to assess responses to therapeutic(s) regardless of the type of therapeutic, e.g. small molecule drug, biological drug, or cell-based therapy. For example, certain embodiments of the diagnostics of the invention may be used to measure changes in tumor size, changes in antigen positive cell populations including number and distribution, and/or monitor a different marker than the antigen targeted by a therapy already being administered to a patient (see Smith-Jones P et al., *Nat. Biotechnol* 22: 701-6 (2004); Evans M et al., *Proc. Natl. Acad. Sci. U.S.A.* 108: 9578-82 (2011)).

Certain embodiments of the method used to detect the presence of a cell type may be used to gather information regarding diseases, disorders, and conditions, such as, for example bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), uterine cancer, AIDS, amyloidosis, ankylosing spondylitis, asthma, autism, cardiogenesis, Crohn's disease, diabetes, erythematosus, gastritis, graft rejection, graft-versus-host disease, Grave's disease, Hashimoto's thyroiditis, hemolytic uremic syndrome, HIV-related diseases, lupus erythematosus, lymphoproliferative disorders, multiple sclerosis, myasthenia gravis, neuroinflammation, polyarteritis nodosa, polyarthritis, psoriasis, psoriatic arthritis, rheumatoid arthritis, scleroderma, septic shock, Sjorgren's syndrome, systemic lupus erythematosus, ulcerative colitis, vasculitis, cell proliferation, inflammation, leukocyte activation, leukocyte adhesion, leukocyte chemotaxis, leukocyte maturation, leukocyte migration, neuronal differentiation, acute lymphoblastic leukemia (ALL), T acute lymphocytic leukemia/lymphoma (ALL), acute myelogenous leukemia, acute myeloid leukemia (AML), B-cell chronic lymphocytic leukemia (B-CLL), B-cell prolymphocytic lymphoma, Burkitt's lymphoma (BL), chronic lymphocytic leukemia (CLL), chronic myelogenous leukemia (CML-BP), chronic myeloid leukemia (CML), diffuse large B-cell lymphoma, follicular lymphoma, hairy cell leukemia (HCL), Hodgkin's Lymphoma (HL), intravascular large B-cell lymphoma, lymphomatoid granulomatosis, lymphoplasmacytic lymphoma, MALT lymphoma, mantle cell lymphoma, multiple myeloma (MM), natural killer cell leukemia, nodal marginal B-cell lymphoma, Non-Hodgkin's lymphoma (NHL), plasma cell leukemia, plasmacytoma, primary effusion lymphoma, prolymphocytic leukemia, promyelocytic leukemia, small lymphocytic lymphoma, splenic marginal zone lymphoma, T-cell lymphoma (TCL), heavy chain disease, monoclonal gammopathy, monoclonal immunoglobulin deposition disease, myelodusplastic syndromes (MDS), smoldering multiple myeloma, and Waldenstrom macroglobulinemia.

In certain embodiments, the molecules of the invention, or pharmaceutical compositions thereof, are used for both diagnosis and treatment, or for diagnosis alone.

The present invention is further illustrated by the following non-limiting examples of selectively cytotoxic, cell-targeted molecules, each comprising a protease-cleavage resistant, Shiga toxin A Subunit effector polypeptide region derived from an A Subunit of a member of the Shiga toxin family and a binding region capable of binding an extracellular target biomolecule physically coupled to specific cell types.

EXAMPLES

The following examples demonstrate certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

The examples below describe the unexpected discovery that disruption of a conserved furin cleavage motif at the carboxy terminus of the Shiga toxin A1 fragment did not diminish the cytotoxicity of cell-targeting, Shiga toxin A Subunit derived constructs despite the A1 fragment being covalently linked at its carboxy terminus to molecular moieties of a relatively large size, i.e. greater than 28 kiloDaltons (kDa) in size. This was surprising because the Shiga toxin intoxication process was thought to require liberation of the Shiga toxin A1 fragment from all other large molecular moieties, such as, e.g., the Shiga toxin A2 fragment and pentamer of Shiga toxin B Subunits. This was surprising because the Shiga toxin intoxication process was thought to require liberation of the catalytic Shiga toxin A1 fragment from its targeting subunits. This was surprising because the optimal Shiga toxin intoxication process was thought to require the liberation of the Shiga toxin A1 fragment from all other large molecular moieties to present a hydrophobic carboxy terminus domain recognized by the ERAD system to efficiently retrotranslocate liberated A1 fragments from the endoplasmic reticulum to the cytosol where host cell ribosomes are catalytically inactivated.

As demonstrated in the Examples below, the cytotoxicity of exemplary cell-targeting molecules comprising a furin-cleavage resistant, Shiga toxin effector polypeptide region to target cells was equivalent to the cytotoxicity of cell-targeted molecules comprising furin-cleavage sensitive, Shiga toxin effector polypeptide regions. Similarly, the selective cytotoxicity of exemplary cell-targeting molecules comprising a furin-cleavage resistant, Shiga toxin effector polypeptide to selectively kill cells physically coupled with an extracellular target biomolecule of their binding regions was equivalent to the cytotoxicity of cell-targeted molecules comprising a furin-cleavage sensitive, Shiga toxin effector polypeptide. The exemplary, cytotoxic, cell-targeting molecules of the invention effectively 1) entered target cells; 2) routed their furin-cleavage resistant, Shiga toxin effector polypeptide to the cytosol; 3) inactivated ribosomes; and 4) killed the target cells. In addition, after administration to mammals, the exemplary cell-targeting molecules exhibited improved in vivo toxicity as compared to cell-targeted molecules comprising a furin-cleavage sensitive, Shiga toxin effector polypeptide.

The examples below show that disrupting a conserved, furin-cleavage event in the Shiga toxin A Subunits derived polypeptides of exemplary, cytotoxic, cell-targeting molecules did not impair the cytotoxicity of these cell-targeting molecules despite the presence of relatively large, carboxy-terminal, immunoglobulin-type binding regions for cell-targeting. These relatively large, carboxy-terminal moieties physically covered the carboxy terminals of the Shiga toxin A1 fragment effector polypeptide region and might deleteriously function to tether the Shiga toxin A1 fragment effector polypeptides to target biomolecules in the endoplasmic reticulum membrane or otherwise interference with molecular mechanisms critical for efficient intracellular routing of the A1 fragment effector polypeptide to the cytosols of intoxicated cells. The examples also show that mutations disrupting the furin-cleavage of the protease-cleavage sensitive, surface-exposed loop in Shiga toxin A Subunit effector polypeptides enabled the engineering of cell-targeting molecules with improved in vivo tolerability while simultaneously retaining a Shiga toxin cytotoxicity as potent and efficient as cell-targeted molecules comprising wild-type, Shiga toxin A1 fragment regions.

Example 1. Cytotoxic, Cell-Targeted Molecules Comprising Furin Resistant, Shiga Toxin A Subunit Effector Polypeptides (SLT-1A-FR::scFv-1 and SLT-1A-FR::scFv-2)

A furin resistant, Shiga toxin A Subunit effector polypeptide was created and tested as a component of cell-targeted molecules, which each further comprised a cell-targeting, immunoglobulin-type, binding region. To engineer protease resistance into a Shiga toxin effector polypeptide, two amino acid residue substitutions, R248A and R251A, were introduced into a Shiga toxin effector polypeptide derived from the A subunit of Shiga-like Toxin 1 (SLT-1A) comprising amino acids 1-251 of SLT-1A. This furin-cleavage resistant R248A and R251A double mutant construct is referred to herein as "SLT-1A-FR" (for SLT-1A furin resistant). A second furin-cleavage resistant mutant construct, referred to herein as "SLT-1A-FR-2," was generated with the single residue substitution R248A. A third furin-cleavage resistant mutant construct, referred to herein as "SLT-1A-FR-3," comprises the single residue substitution R251A. The mutation of the minimal, furin protease, cleavage site R-x-x-R in the core of the furin consensus motif region 240-256 was predicted to disrupt the sensitivity of this region to proteolysis by furin and other proteases, such as, e.g., proprotein convertases and promiscuous proteases. The Shiga toxin effector polypeptide SLT-1A-FR comprising the R248A/R251A disruption of the furin-cleavage site was used to create exemplary cell-targeted molecules.

The exemplary cytotoxic, cell-targeted molecules SLT-1A-FR::scFv-1 and SLT-1A-FR::scFv-2 were constructed such that each comprised a catalytic Shiga toxin A Subunit effector polypeptide region comprising a disrupted furin-cleavage site and a cell-targeting binding region. In SLT-1A-FR::scFv-1 and SLT-1A-FR::scFv-2, the Shiga toxin effector polypeptide was fused to a relatively large, carboxy-terminal binding region. SLT-1A-FR::scFv-1 and SLT-1A-FR::scFv-2 were produced in a bacterial system and purified by column chromatography. The binding regions scFv-1 and scFv-2 were single-chain variable fragments which each bound with high-affinity to a certain cell-surface, target biomolecule physically coupled to the surface of certain human cancer cells as well as to certain human cancer cells.

Testing the Furin Proteolysis Sensitivity of Exemplary Cell-Targeting Molecules Comprising SLT-1A-FR The furin-cleavage sensitivity of Shiga toxin effector polypeptides after mutating the protease cleavage sensitive region 240-256 in order to disrupt furin cleavage was tested in the molecular context of fusion proteins comprising carboxy-terminal, cell-targeting binding region. To assess the ability of furin to cleave SLT-1A-FR::scFv-1 and SLT-1A-FR::scFv-2, purified protein samples in phosphate buffered saline (PBS) were incubated with furin (New England Biolabs, Ipswich, Mass., U.S.) at 0.5 furin activity units (U) per microgram (μg) of sample protein in furin cleavage buffer (100 millimolar (mM) HEPES (4-(2-hydroxyethyl)-1-piperazineethanesulfonic acid), pH 7, 1 mM $CaCl_2$) for 25-30 hours (hrs) at 30 or 37 degrees Celsius (° C.). Control samples were incubated without furin at 4, 30, or 37° C. in the same buffer. The various protein samples were electrophoresed on sodium dodecyl sulfate (SDS), polyacrylamide gels under denaturing conditions and stained with Coomassie (FIGS. 2 and 3).

FIGS. 2 and 3 show pictures of the gels with the lanes numbered and contain figure legends indicating which lane was loaded with which protein sample: either a cell-targeted protein comprising a wild-type, Shiga toxin effector polypeptide (SLT-1A-WT) or a furin-cleavage site disrupted, Shiga toxin effector polypeptide (SLT-1A-FR or SLT-1A-FR-2). The lanes marked "L" show the migration pattern of a protein molecular weight ladder along with the approximate size of individual ladder protein bands in kDa for use as an internal molecular weight reference that allows for the estimation of the sizes of proteins in the numbered lanes. The figure legends indicate the pre-treatment conditions of the protein samples with the temperature in degrees Celsius (° C.), duration, and whether any furin was added by denoting the amount of furin activity units per microgram (labeled "U/μg furin") or "no furin" for zero units.

FIGS. 2 and 3 show that SLT-1A-FR::scFv-1 and SLT-1A-FR::scFv-2 were resistant to cleavage by human furin. The cell-targeted proteins tested in this assay were both about 55-57 kDa in size and comprised a Shiga toxin effector polypeptide of about 28 kDa (identical in size for both SLT-1A-WT and SLT-1A-FR) linked to a carboxy-terminal linker and binding region which together were about 28-29 kDa in size. If furin cleavage had occurred in the surface exposed, extended loop 242-251 of SLT-1A, then the expected result would be two protein bands with near equal molecular weights of around 28 kDa each. If furin cleavage occurs precisely at the carboxy peptide bond of the arginine at position 251 of the WT scaffold in SLT-1A-WT::scFv-1 or SLT-1A-WT::scFv-2, then the two resulting protein bands should have the molecular weight of 27.5 kDa for SLT-1A (either WT or FR) and a second band of 28.8 kDa for SLT-1A-FR::scFv-1 or 27.6 kDa for SLT-1A-FR::scFv-2.

FIG. 2 shows that SLT-1A-FR::scFv-1 was not proteolyzed in vitro by human furin in this assay under the conditions tested. As expected, the control protein SLT-1A-WT::scFv-1, which comprised a wild-type Shiga toxin effector polypeptide, was cleaved by human furin (FIG. 2); however, SLT-1A-FR::scFv-1 was resistant (compare lanes 3 and 6 in FIG. 2).

SLT-1A-FR::scFv-2 was also resistant to furin cleavage in this assay at several different temperatures (FIG. 3). FIG. 3 shows that SLT-1A-FR::scFv-2 was not proteolyzed in vitro by human furin in this assay under the conditions tested, such as at temperatures ranging from 4° to 37° C.

In addition, a cell-targeted fusion protein SLT-1A-FR-2::scFv-2 was resistant to furin cleavage in this assay at 4° C.

Using this in vitro furin cleavage assay, no furin proteolysis of cell-targeted fusion proteins was observed at any furin-cleavage site besides 248-251 in the Shiga toxin effector polypeptide region, such as, e.g., in the SLT-1A component at the furin-cleavage site natively positioned in the region from 220 to 223.

Thus, the mutation of the minimal, furin protease, cleavage site R-x-x-R in the core of the furin consensus motif region disrupted the sensitivity of this region to proteolysis by human furin in vitro.

Testing the Ribosome Inhibitory Activity of Cell-Targeting Molecules Comprising SLT-1A-FR The molecules of the present invention all comprise a catalytic domain derived from at least one Shiga toxin A Subunit. The enzymatic activity of the furin-cleavage resistant, Shiga toxin effector polypeptide SLT-1A-FR was tested using an in vitro ribosome inhibition assay. The ribosome inactivation activity of SLT-1A-FR was tested in the molecular context of a carboxy-terminal, cell-targeting binding region using SLT-1A-FR::scFv-1 and SLT-1A-FR::scFv-2.

The ribosome inactivation capabilities of SLT-1A-FR::scFv-1 and SLT-1A-FR::scFv-2 were determined with a cell-free, in vitro, protein translation assay using the TNT® Quick Coupled Transcription/Translation Kit (L1170 Promega Madison, Wis., U.S.). The kit includes Luciferase T7 Control DNA (L4821 Promega Madison, Wis., U.S.) and TNT® Quick Master Mix. The ribosome activity reaction was prepared according to manufacturer's instructions. A series of 10-fold dilutions of the cell-targeted molecule to be tested (proteins comprising either SLT-1A-WT or SLT-1A-FR) were prepared in an appropriate buffer and a series of identical TNT reaction mixture components were created for each dilution. Each sample in the dilution series was combined with each of the TNT reaction mixtures along with the Luciferase T7 Control DNA. The test samples were incubated for 1.5 hours at 30° C. After the incubation, Luciferase Assay Reagent (Catalog # E1483, Promega Corp., Madison, Wis., U.S.) was added to all test samples and the amount of luciferase protein translation was measured by luminescence according to manufacturer's instructions.

The level of translational inhibition was determined by non-linear regression analysis of log-transformed concentrations of total protein versus relative luminescence units. Using statistical software (GraphPad Prism, San Diego, Calif., U.S.), the half maximal inhibitory concentration ($IC_{50}$) value was calculated for each sample using the Prism software function of log(inhibitor) vs. response (three parameters) [Y=Bottom+((Top−Bottom)/(1+10^(X−Log IC50)))] under the heading dose-response-inhibition.

The $IC_{50}$ for each protein comprising a furin-cleavage resistant Shiga toxin effector polypeptide (SLT-1A-FR) region and a wild-type (WT) control protein from one or more experiments was calculated and is shown in Table 1. The constructs comprising the furin-cleavage resistant SLT-1A-FR exhibited potent ribosome inhibition which was comparable to wild-type controls, such as a wild-type SLT-1 A1 fragment (SLT-1A1-WT) (Table 1). Both SLT-1A-FR::scFv-1 and SLT-1A-FR::scFv-2 exhibited ribosome inactivation activity in vitro comparable to a wild-type, Shiga toxin A1 fragment.

TABLE 1

The furin-cleavage resistant, Shiga toxin effector polypeptide exhibited equivalent ribosome inhibition in vitro to a protease-cleavage sensitive, Shiga toxin effector polypeptide

| Polypeptide | Ribosome Inhibition $IC_{50}$ (pM) |
| --- | --- |
| SLT-1A1-WT only | 158 |
| SLT-1A-WT::scFv-1 | 107 |
| SLT-1A-FR::scFv-1 | 131 |
| SLT-1A-WT::scFv-2 | 101 |
| SLT-1A-FR::scFv-2 | 187 |

Testing the Cytotoxicity of the Exemplary Cell-Targeting Molecules SLT-1A-FR::scFv-1 and SLT-1A-FR::scFv-2

The cytotoxicity of exemplary cell-targeted molecules comprising the protease-cleavage resistant, Shiga toxin effector polypeptide SLT-1A-FR was determined using cell kill assays known to the skilled worker. Specific cytotoxicity was determined by comparing the cytotoxicity of exemplary cell-targeted molecules toward target expressing cells versus the cytotoxicity of an untargeted, wild-type, Shiga toxin effector control (SLT-1A-WT). Selective cytotoxicity was determined by comparing the cytotoxicity toward target expressing cells versus cells which did not express a target biomolecule of the cell-targeted molecule's binding region. Cells were selected that expressed a significant amount of an extracellular target biomolecule of scFv-1 or scFv-2 at least one cellular surface, i.e. cells that were binding-region target biomolecule positive (cell lines A, B, C, and D were positive for the target of scFv-1, and cell lines E, F, and G were positive for the target of scFv-2). Cells were selected that did not express a significant amount of any extracellular target biomolecules of scFv-1 at any cellular surface and/or any extracellular target biomolecules of scFv-2 at any cellular surface, i.e. cells that were target biomolecule negative for any target of one or both of the binding regions scFv-1 and scFv-2.

The cytotoxicity of nearly identical cell-targeted proteins comprising either a wild-type SLT-1A (SLT-1A-WT) or furin-cleavage resistant, Shiga toxin effector polypeptide (SLT-1A-FR) were directly compared to isolate any differences in cytotoxicity caused by the two point mutations which provided furin-cleavage resistance. It was expected that the cytotoxicity of cell-targeted molecules comprising a SLT-1A-FR whose carboxy terminus was covered by a relatively large moiety, would be reduced as compared to cell-targeted molecules comprising a SLT-1A-WT, which can be liberated from a carboxy-terminal moiety by proteolytic cleavage, particularly by the endoprotease furin (see Lea N et al., *Microbiology* 145: 999-1004 (1999)).

The cytotoxicities, specific cytotoxicities, and relative cytotoxicities for the exemplary cell-targeted molecules SLT-1A-FR::scFv-1 and SLT-1A-FR::scFv-2 were compared to cell-targeted molecules comprising wild-type, Shiga toxin effector polypeptides.

Certain human tumor cells (including cells of the cell lines A-G) were plated ($2 \times 10^3$ cells per well for adherent cells, plated the day prior to protein addition or $7.5 \times 10^3$ cells per well for suspension cells, plated the same day as protein addition) in 20 microliters (μL) cell culture medium in 384-well plates. A series of 10-fold dilutions of the cell-targeted molecules to be tested was prepared in an appropriate buffer, and 5 μL of the dilutions or buffer control were added to the cells. Control wells containing only cell culture medium were used for baseline correction. The cell samples were incubated with the cell-targeted molecules or just buffer for 3 days at 37° C. and in an atmosphere of 5 percent (%) carbon dioxide ($CO_2$). In certain experiments, the cell samples were incubated with the cell-targeted molecules or just buffer for 1 hour or 2 hours. Then un-internalized, cell-targeted molecules were washed away using buffer washes. The total cell survival or percent viability was determined using a luminescent readout using the CellTiter-Glo® Luminescent Cell Viability Assay (Catalog # G7573, Promega Corp., Madison, Wis., U.S.) according to the manufacturer's instructions.

The Percent Viability of experimental wells was calculated using the following equation: (Test RLU−Average Media RLU)/(Average Cells RLU−Average Media RLU)*100. Log polypeptide concentration versus Percent Viability was plotted in Prism (GraphPad Prism, San Diego, Calif., U.S.) and log (inhibitor) versus response (3 parameter) analysis were used to determine the half-maximal cytotoxic concentration ($CD_{50}$) value for the tested proteins. The $CD_{50}$ for each cell-targeted protein comprising a protease-cleavage resistant, Shiga toxin effector polypeptide or a wild-type control, Shiga toxin effector polypeptide were calculated.

The cytotoxicity of SLT-1A-FR::scFv-1 and SLT-1A-FR::scFv-2 toward multiple, target-expressing, human tumor cell lines are shown in Table 2 as half-maximal cytotoxicity values ($CD_{50}$) in the cell-targeted protein concentration in nanomolar (nM). Surprisingly, cell-targeted proteins comprising SLT-1A-WT and SLT-1A-FR both displayed similar cytotoxicities (FIGS. 4-5; Table 2) instead of a noticeable reduction in cytotoxicity for cell-targeted proteins comprising SLT-1AFR expected to be result whenever the Shiga toxin A1 fragment cannot efficiently be liberated from all other moieties, such as, e.g., a cell-targeting, binding region and a 4.5 kDa A2 fragment (see Garred Ø et al., *Exp Cell Res* 218: 39-49 (1995); Garred Ø et al., *J Biol Chem* 270: 10817-21 (1995); Lea N et al., *Microbiology* 145: 999-1004 (1999); Kurmanova A et al., *Biochem Biophys Res Commun* 357: 144-9 (2007)).

TABLE 2

The furin-cleavage resistant, Shiga toxin effector polypeptide exhibited equivalent cytotoxicity to a furin-cleavable, wild-type, Shiga toxin effector polypeptide

| target positive cell line | | Cytotoxicity $CD_{50}$ (nM) | | | | |
|---|---|---|---|---|---|---|
| | binding region target | SLT-1A-WT only | SLT-1A-WT::scFv-1 | SLT-1A-FR::scFv-1 | SLT-1A-WT::scFv-2 | SLT-1A-FR::scFv-2 |
| A | scFv-1 | 905.0 | 0.24 | 0.29 | N/T | N/T |
| B | scFv-1 | 1800.0 | 0.47 | 0.29 | N/T | N/T |
| C | scFv-1 | 37.0 | 0.22 | 0.41 | N/T | N/T |
| D | scFv-1 | 4740.0 | 0.55 | 0.37 | N/T | N/T |
| E | scFv-2 | 11050.0 | N/T | N/T | 0.920 | 1.30 |
| F | scFv-2 | 32200.0 | N/T | N/T | 16.10 | 13.60 |
| G | scFv-2 | 506.0 | N/T | N/T | 0.120 | 0.240 |

"N/T" indicates not tested

The $CD_{50}$ values for cell-targeted proteins comprising SLT-1A-FR were comparable to the $CD_{50}$ values for cell-targeted proteins comprising SLT-1A-WT (Table 2). Cell-targeted proteins comprising SLT-1A-WT and SLT-1A-FR both potently killed target expressing cells but did not kill comparable percentages of target negative cells at the same dosages ($CD_{50}$ values for target negative cells were uninformative for these data as an accurate curve could not be generated when there was not a sizeable decrease in cell viability at the highest tested concentrations). The results summarized in Table 2 show the comparable cytotoxicity of SLT-1A-FR and SLT-1A-WT as components of cell-targeted molecules. Both SLT-1A-FR::scFv-1 and SLT-1A-FR::scFv-2 were as cytotoxic as related cell-targeted molecules comprising furin-cleavage sensitive, wild-type, Shiga toxin A1 fragment regions. One example of the specific cytotoxicity of proteins comprising a protease-cleavage resistant, Shiga toxin effector polypeptide SLT-1A-FR is shown graphically: cytotoxicity was directed to target expressing, human tumor cells (FIG. 4) but not target negative, human tumor cells (FIG. 5).

Testing the In Vivo Tolerability of the Exemplary Cell-Targeting Molecules SLT-1A-FR::scFv-1 and SLT-1A-FR::scFv-2 Using Laboratory Animals The tolerability was tested for different dosages of the exemplary, cytotoxic, cell-targeted molecules SLT-1A-FR::scFv-1 and SLT-1A-FR::scFv-2, each of which comprises a furin-cleavage resistant, Shiga toxin A Subunit effector polypeptide region. Mice were used to determine the degree to which overt adverse effects were tolerated at various dosages of exemplary cell-targeted molecules. Therapeutic tolerability was determined using murine dose finding aimed at measuring maximum tolerated doses to inform a starting dose for in vivo efficacy studies. The tolerability studies were performed at Charles River Laboratories (Charles River Laboratories International, Inc., Morrisville, N.C., U.S.) in four separate studies described in Table 3. For each study, female C.B-17 SCID mice with severe combined immune deficiency (SCID) were sorted into groups with similar average body weight. Test agents or vehicle control were administered to mice at doses ranging from 0.25 to 5.00 milligrams per kilogram of body weight per injection (mg/kg/inj), and injections were administered three times a week for one or two weeks. Body weight and clinical signs were monitored throughout the study. The results of the in vivo tolerability studies using laboratory animals are summarized in Table 3. Table 3 denotes the number of mice per group, the administered sample, the injection dose, the cumulative dosage in mg per kg per mouse (mg/kg/mouse), the number of treatment related deaths observed (Deaths), and the average day of death per group.

TABLE 3

Murine tolerability studies demonstrated the exemplary cell-targeted molecules SLT-1A-FR::scFv-1 and SLT-1A-FR::scFv-2 were well tolerated in vivo at doses ranging from 0.25-2.50 mg/kg/inj

| Study | Sample | Dose (mg/kg/inj) | Doses | Cumulative dosage (mg/kg/mouse) | Mice per group | Deaths | Average day of death by group |
|---|---|---|---|---|---|---|---|
| #1 | vehicle control | 0.00 | 3 | 0.00 | 4 | 0 | all lived to study end |
|  | SLT-1A-WT::scFv-1 | 1.25 | 3 | 3.75 | 4 | 4 | 8.5 |
|  | SLT-1A-WT::scFv-1 | 2.50 | 3 | 7.50 | 4 | 4 | 7.3 |
| #2 | SLT-1A-WT::scFv-1 | 1.25 | 3 | 3.75 | 5 | 5 | 7.4 |
|  | SLT-1A-WT::scFv-1 | 2.50 | 2 | 5.00 | 5 | 5 | 5.2 |
|  | SLT-1A-WT::scFv-1 | 5.00 | 2 | 10.00 | 5 | 5 | 4.4 |
| #3 | vehicle control | 0.00 | 3 | 0.00 | 4 | 0 | all lived to study end |
|  | SLT-1A-FR::scFv-1 | 0.25 | 3 | 0.75 | 4 | 0 | all lived to study end |
|  | SLT-1A-FR::scFv-1 | 1.25 | 3 | 3.75 | 4 | 0 | all lived to study end |
|  | SLT-1A-FR::scFv-1 | 2.50 | 3 | 7.5 | 4 | 0 | all lived to study end |
| #4 | vehicle control | 0.00 | 6 | 0.00 | 4 | 0 | all lived to study end |
|  | SLT-1A-FR::scFv-2 | 0.25 | 6 | 1.50 | 4 | 0 | all lived to study end |
|  | SLT-1A-FR::scFv-2 | 1.00 | 6 | 6.00 | 4 | 0 | all lived to study end |
|  | SLT-1A-FR::scFv-2 | 2.00 | 6 | 12.00 | 4 | 0 | all lived to study end |

In study #1, the cell-targeted molecule SLT-1A-WT::scFv-1 was tested along with a vehicle control. Mice were dosed on study days 1, 3 and 5 with vehicle control, 1.25, or 2.50 mg/kg/inj of SLT-1A-WT::scFv-1. In study 1, all the mice treated with SLT-1A-WT::scFv-1 had a treatment related death starting two days after the third dose. In study #1, mice from the group administered 1.25 mg/kg/inj of SLT-1A::WT-scFv-1 died on study days 7, 8, 9 and 10 (one mouse per day), and mice from the group administered 2.50 mg/kg/inj of SLT-1A-WT::scFv-1 died on day 7 (three mice) or day 8 (one mouse). All the mice in the group administered the vehicle control survived to the study end.

In study #2, mice were administered SLT-1A-WT::scFv-1 as in study #1 but with a higher maximum dose of 5.00 mg/kg/inj. In study #2, similar results occurred for mice administered SLT-1A-WT::scFv-1 as in study #1; however, in study #2, mice in the two highest dose groups only received two injections due to treatment-related deaths to mice in those groups. FIG. 6 shows a comparison of the survival of mice from a group administered 2.50 mg/kg/inj of SLT-1A-FR::scFv-1 (study #2) as compared to mice administered SLT-1A-WT::scFv-1 (study #1) using Kaplan-Meier plots.

In study 3, mice were administered with a vehicle control or the exemplary cell-targeted molecule SLT-1A-FR::scFv-1 similar to the dosage regime for study #1 but with a lower dose of 0.25 mg/kg/inj. Mice were dosed on study days 1, 3, and 5 with 0.25, 1.25, or 2.50 mg/kg/inj of SLT-1A-FR::scFv-1. All mice administered SLT-1A-FR::scFv-1 survived to the end of study #3. A dose-dependent decrease in body weight was observed; however, a maximum tolerated dose was not observed for SLT-1A-FR::scFv-1 in study #3. The highest tested dosing group (administered 2.50 mg/kg/inj SLT-1A-FR::scFv-1) had a nadir of only 13.1% body weight loss. These results demonstrate that SLT-1A-FR::scFv-1 was well-tolerated in vivo at repeat doses ranging from 0.25-2.50 mg/kg/inj. These results also demonstrate that SLT-1A-FR::scFv-1 was better tolerated than SLT-1A-WT::scFv-1 under the conditions tested.

In study 4, mice were administered with a vehicle control or the exemplary cell-targeted molecule SLT-1A-FR::scFv-2 at 0.25, 1.00, or 2.00 mg/kg/injection three times a week for two weeks (six total doses). All mice administered SLT-1A-FR::scFv-2 survived until the end of study #4 and no adverse clinical observations were noted during the course of the study. Study #4 was extended to day 32, and the average body weight was observed to be above 80% of the starting weight for all groups comprising mice administered SLT-1A-FR::scFv-2. These results demonstrate that SLT-1A-FR::scFv-2 was well-tolerated in vivo at repeat doses ranging from 0.25-2.00 mg/kg/inj.

Compared to the tolerability results for cell-targeted molecules comprising a protease-sensitive, wild-type, Shiga toxin effector polypeptide (studies #1 and #2), the exemplary cell-targeted molecules comprising furin-cleavage resistant, Shiga toxin effector polypeptides exhibited improved tolerability (studies #3 and #4) at dosages involving repeat doses ranging from 0.25 to 2.50 mg/kg/inj.

The improved in vivo tolerability observed for these two, exemplary, cell-targeted molecules of the invention suggests that much higher doses of the cytotoxic molecules of the invention may be safely administered to mammals as compared to parental molecules comprising a furin-cleavage sensitive, Shiga toxin effector polypeptide.

Despite retaining equivalent cytotoxicity to nearly identical, cell-targeted molecules comprising wild-type Shiga toxin effector polypeptides, the exemplary cell-targeted molecules comprising furin-cleavage resistant, Shiga toxin effector polypeptides exhibited improved tolerability-mammals, i.e. improved toxicity profiles due to a reduction in deleterious effects. The improved toxicity profiles might be due to a reduction in non-specific toxicity related to the generally improved protease resistance of the molecules. These results also suggest that disrupting the furin-cleavage motif might confer an increased stability for the entire cell-targeted molecule. In addition, a molecule's resistance to proteolysis might improve its pharmacokinetic profiles administration to an organism.

Testing the Targeted Cytotoxicity and Efficacy of the Exemplary Cell-Targeting Molecule SLT-1A-FR::scFv-2 In Vivo Using Animal Models A disseminated xenograft model for human tumors was used to determine the in vivo efficacy of the exemplary, cytotoxic, cell-targeted molecule SLT-1A-FR::scFv-2 in human-tumor bearing mice. Human tumor cells that constitutively express luciferase and display cell-surface expression of the target of scFv-2 were used in this xenograft model.

On study day 0, CB.17 SCID mice with severe combined immune deficiency (SCID) were challenged intravenously with $2.5 \times 10^6$ hTum-Luc tumor cells (Molecular Imaging, Ann Arbor, Mich., U.S.) in 200 microliters (4) PBS. A confirmatory bioluminescent image (BLI) was taken 5 minutes after cell injection, and mice were divided into four groups of ten mice each (N=10 mice). On days 0 (1 hour post implant), 2, 4, 7, 9, and 11 following tumor cell challenge, the mice in the four groups received via intraperitoneal administration either vehicle control (0 mg/kg/inj) or SLT-1A-FR::scFv-2 at doses of 0.05, 0.50, or 2.00 mg/kg/inj. Bioluminescence was measured on days 14, 18, and 21 using a Caliper IVIS 50 optical imaging system (Perkin Elmer, Waltham, Mass., U.S.).

The exemplary, cytotoxic, cell-targeted molecule SLT-1A-FR::scFv-2 reduced the human tumor burden in the mice at all dosage levels. The results of this study are reported in FIG. 7 and Table 4. In this study, the sample size (n) was 10 mice per group for all four groups. FIG. 7 shows the tumor burden as assayed by bioluminescence per individual mouse over time based on the human tumor cells' expression of the luciferase reporter. An individual mouse is represented by each symbol plotted on the graph, i.e. open triangle, filled triangle, open circle, or filled square. The Y-axis is the total bioluminescence signal of an individual mouse, which represents the tumor burden, in millions of photons per second (photons/sec), and the X-axis is the injection dose which ranged from 0 to 2 milligrams of SLT-1A-FR::scFv-2 per kilogram of body mass per injection. Table 4 reports the mean BLI and standard error of the mean (SEM) among mice in each group at different time points (study day 14, 18, 21, and 28).

TABLE 4

Murine xenograft study demonstrated that exemplary cytotoxic molecule SLT-1A-FR::scFv-2 was efficacious in vivo

| | vehicle control | | 0.05 mg SLT-1A-FR::scFv-2/kg/inj | | 0.50 mg SLT-1A-FR::scFv-2/kg/inj | | 2.00 mg SLT-1A-FR::scFv-2/kg/inj | |
|---|---|---|---|---|---|---|---|---|
| Day | Mean BLI | SEM | Mean BLI | SEM | Mean BLI | SEM | Mean BLI | SEM |
| 14 | 235 | 28 | 24 | 7 | 1.02 | 0.05 | 1.07 | 0.07 |
| 18 | 1900 | 201 | 251 | 80 | 1.36 | 0.18 | 0.90 | 0.04 |
| 21 | 5850 | 658 | 744 | 296 | 3.47 | 1.03 | 1.09 | 0.10 |
| 28 | 23700 | 2310 | 6960 | 1670 | 99.30 | 38.0 | 4.13 | 2.98 |

These results show SLT-1A-FR::scFv-2 was capable of significantly reducing the human tumor burden in SCID mice challenged with human tumor cells. All groups comprised of mice administered the exemplary cell-targeted molecule SLT-1A-FR::scFv-2 showed significantly less total bioluminescence compared to the vehicle control (FIG. 7 and Table 4). This effect was observed in mice administered dosages of SLT-1A-FR::scFv-2 ranging from 0.05 to 2.00 mg/kg/inj (FIG. 7 and Table 4). The observed tumor-inhibition effect was dose dependent because mice administered 0.05 mg/kg/inj of SLT-1A-FR::scFv-2 showed some tumor growth as measured by BLI, while mice administered either 0.50 or 2.00 mg/kg/inj of SLT-1A-FR::scFv-2 did not display tumor growth (Table 4, FIG. 7).

These results demonstrate that the exemplary cell-targeted molecule SLT-1A-FR::scFv-2 was 1) effective at inhibiting tumor growth in vivo in addition to exhibiting 2) equivalent cytotoxicity to cell-targeted molecules comprising furin-cleavage sensitive SLT-1A-WT; and 3) improved tolerability at higher doses compared to a nearly identical, cell-targeted molecule comprising SLT-1A-WT.

Summary

The exemplary, cell-targeted molecules SLT-1A-FR::scFv-1 and SLT-1A-FR::scFv-2, which comprised mutations in the minimal, furin-cleavage motif R/Y-x-x-R, were not proteolyzed by human furin but exhibited specific cytotoxicities comparable to cell-targeted proteins comprising a wild-type, Shiga toxin A Subunit region. The exemplary, cell-targeted molecule SLT-1A-FR::scFv-2 effectively inhibited human tumor growth in a mammalian model. In addition, SLT-1A-FR::scFv-1 and SLT-1A-FR::scFv-2 both exhibited improved tolerability as compared to parental molecules comprising a wild-type, Shiga toxin A Subunit region.

The properties of SLT-1A-FR::scFv-1, SLT-1A-FR::scFv-2, and SLT-1A-FR-2::scFv-2, each which comprise Shiga toxin effector polypeptides comprising furin-cleavage disrupting mutations (R248A and/or R251A), suggest other disruptions of the furin-cleavage motif in the conserved, surface-exposed loop in Shiga toxin A Subunits may provide the same properties, such as, e.g., equivalent cytotoxicity to as molecules comprising wild-type, Shiga toxin A Subunit regions and improved toxicity profiles in vivo.

Mutations similar to R248A and R251A in cell-targeted molecules comprising Shiga toxin A Subunit effector polypeptides can provide similar structure and function. For example, any mutation which perturbs the conserved, furin-cleavage, consensus motif S-R/Y-x-x-R in Shiga toxin A Subunits will result in furin-cleavage resistance but not perturb cytotoxicity. In particular, amino acid residue substitutions of arginine to any non-basic amino acid residue which lacks a positive charge, such as, e.g., A, G, P, S, T, D, E, Q, N, C, I, L, M, V, F, W, and Y, may be used to create a disrupted furin-cleavage motif of a Shiga toxin effector polypeptide of a molecule of the present invention. Similarly, truncations of the Shiga toxin A Subunit and internal deletions within the furin-cleavage motif which perturb the minimal, furin-cleavage motif R/Y-x-x-R may be used to create Shiga toxin effector polypeptides with similar structure and function.

In summary, cytotoxic molecules may be created using furin-cleavage resistant, Shiga toxin A Subunit derived polypeptides and carboxy-terminus proximal moieties greater than 28 kDa without any reduction in cytotoxicity. This is a surprising discovery because Shiga toxins require proteolytic processing at this furin-cleavage site in the proper subcellular compartments for optimal cytotoxicity (see e.g. Garred Ø et al., *Exp Cell Res* 218: 39-49 (1995); Garred Ø et al., *J Biol Chem* 270: 10817-21 (1995); Lea N et al., *Microbiology* 145: 999-1004 (1999); Kurmanova A et al., *Biochem Biophys Res Commun* 357: 144-9 (2007)).

Example 2. A Cytotoxic, Cell-Targeted Molecule Comprising a Protease-Cleavage Resistant, Shiga Toxin Effector Region and a Carboxy-Terminal Binding Region Specific to CD20 (SLT-1A-FR Linked with αCD20)

In this example, the Shiga toxin effector polypeptide region is a protease-cleavage resistant, Shiga toxin effector polypeptide derived from the A subunit of Shiga-like Toxin 1 (SLT-1A). An immunoglobulin-type binding region αCD20-antigen is derived from an immunoglobulin-type domain recognizing human CD20 (see e.g. Haisma H et al., *Blood* 92: 184-90 (1999); Geng S et al., *Cell Mol Immunol* 3: 439-43 (2006); Olafesn T et al., *Protein Eng Des Sel* 23: 243-9 (2010)), which comprises an immunoglobulin-type binding region capable of binding an extracellular part of CD20. CD20 is expressed on multiple cancer cell types, such as B-cell lymphoma cells, hairy cell leukemia cells, B-cell chronic lymphocytic leukemia cells, and melanoma cells. In addition, CD20 is an attractive target for therapeutics to treat certain autoimmune diseases, disorders, and conditions involving overactive B-cells.

Construction, Production, and Purification of the Cytotoxic, Cell-Targeted Molecule "SLT-1A-FR::αCD20"

The immunoglobulin-type binding region αCD20 and a protease-cleavage resistant, Shiga toxin effector polypeptide are linked together to form a cytotoxic, cell-targeted molecule. For example, a fusion protein is produced by expressing a polynucleotide encoding the αCD20-antigen-binding protein SLT-1A-FR::αCD20 (see, e.g., SEQ ID NOs: 50, 51, 52, and 53). Expression of the SLT-1A-FR::αCD20 cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR::αCD20"

The binding characteristics of the cytotoxic molecule of this example for CD20+ cells and CD20− cells is determined by a fluorescence-based, flow-cytometry assay known in the art. Using Prism software (GraphPad Software, San Diego, Calif., U.S.), the $B_{max}$ and $K_D$ are calculated using the Prism software function of one-site binding [$Y=B_{max}*X/(K_D+X)$] under the heading binding-saturation. $B_{max}$ is the maximum specific binding reported in MFI. $K_D$ is the equilibrium binding constant, reported in nM. The $B_{max}$ for SLT-1A-FR::αCD20 to CD20+ cells is measured to be approximately 50,000-200,000 MFI with a $K_D$ within the range of 0.01-100 nanomolar (nM), whereas there is no significant binding to CD20− cells in this assay.

The ribosome inactivation abilities of the SLT-1A-FR::αCD20 cytotoxic molecule is determined in a cell-free, in vitro protein translation as described above in the previous examples. The inhibitory effect of the cytotoxic molecule of this example on cell-free protein synthesis is significant. The $IC_{50}$ of SLT-1A-FR::αCD20 on protein synthesis in this cell-free assay is approximately 0.1-100 μM.

Determining the Cytotoxicity of the Cytotoxic, Cell-Targeted Molecule "SLT-1A-FR::αCD20" Using a CD20+ Cell-Kill Assay The cytotoxicity characteristics of SLT-1A-FR::αCD20 are determined by the general cell-kill assay as described above in the previous examples using CD20+ cells. In addition, the selective cytotoxicity characteristics of SLT-1A-FR::αCD20 are determined by the same general cell-kill assay using CD20− cells as a comparison to the CD20+ cells. The $CD_{50}$ of the cytotoxic molecule of this example is approximately 0.01-100 nM for CD20+ cells depending on the cell line. The $CD_{50}$ of the cytotoxic molecule is approximately 10-10,000 fold greater (less cytotoxic) for cells not expressing CD20 on a cellular surface as compared to cells which do express CD20 on a cellular surface.

Determining the In Vivo Effects of the Cytotoxic Molecule "SLT-1A-FR::αCD20" Using Animal Models Animal models are used to determine the in vivo effects of the cytotoxic molecule SLT-1A-FR::αCD20 on neoplastic cells. Various mice strains are used to test the effect of the cytotoxic molecule after intravenous administration on xenograft tumors in mice resulting from the injection into those mice of human neoplastic cells which express CD20 on their cell surfaces.

Example 3. A Cytotoxic, Cell-Targeted Molecule Comprising a Protease-Cleavage Resistant, Shiga Toxin Effector Region and a Carboxy-Terminal Binding Region Specific to HER2 (SLT-1A-FR Linked with αHER2-$V_H$H)

In this example, a protease-cleavage resistant, Shiga toxin effector polypeptide region was derived from the A subunit of Shiga-like Toxin 1 (SLT-1A). The immunoglobulin-type binding region is αHER2 $V_H$H derived from a single-domain variable region of the camelid antibody ($V_H$H) protein 5F7, as described in U.S. Patent Application Publication 2011/0059090.

Construction, Production, and Purification of the Cytotoxic, Cell-Targeted Molecule "SLT-1A-FR Linked with αHER2-$V_H$H"

The immunoglobulin-type binding region and a protease-cleavage resistant, Shiga toxin effector polypeptide are linked together to form a cytotoxic, cell-targeted molecule (see, e.g., SEQ ID NO:54). In this example, a polynucleotide encoding the αHER2-$V_H$H variable region derived from protein 5F7 is cloned in frame with a polynucleotide encoding a linker known in the art and in frame with a polynucleotide encoding the Shiga toxin effector polypeptide comprising amino acids of SEQ ID NO:22. Variants of "SLT-1A-FR linked with αHER2-$V_H$H" cytotoxic molecules are created such that the binding region is optionally located adjacent to the amino-terminus of the Shiga toxin effector polypeptide and optionally comprises a carboxy-terminal endoplasmic reticulum signal motif of the KDEL family. Expression of the "SLT-1A-FR linked with αHER2-V$_H$H" cytotoxic molecule variants is accomplished using either bacterial and/or cell-free, protein translation systems as described in the previous examples.

Determining the In Vitro Characteristics of the Cytotoxic, Cell-Targeted Molecule "SLT-1A-FR Linked with αHER2-V$_H$H"

The binding characteristics of the cytotoxic molecule of this example for HER2+ cells and HER2− cells is determined by a fluorescence-based, flow-cytometry assay known in the art. The B$_{max}$ for "SLT-1A-FR linked with αHER2-V$_H$H" variants to HER2+ cells is measured to be approximately 50,000-200,000 MFI with a K$_D$ within the range of 0.01-100 nM, whereas there is no significant binding to HER2− cells in this assay.

The ribosome inactivation abilities of the "SLT-1A-FR linked with αHER2-V$_H$H" cytotoxic molecules are determined in a cell-free, in vitro protein translation as described above in the previous examples. The inhibitory effect of the cytotoxic molecule of this example on cell-free protein synthesis is significant. The IC$_{50}$ of "SLT-1A-FR linked with αHER2-V$_H$H" variants on protein synthesis in this cell-free assay is approximately 0.1-100 pM.

Determining the Cytotoxicity of the Cytotoxic, Cell-Targeted Molecule "SLT-1A-FR linked with αHER2-V$_H$H" Using a HER2+ Cell-Kill Assay The cytotoxicity characteristics of "SLT-1A-FR linked with αHER2-V$_H$H" variants are determined by the general cell-kill assay as described above in the previous examples using HER2+ cells. In addition, the selective cytotoxicity characteristics of "SLT-1A-FR linked with αHER2-V$_H$H" are determined by the same general cell-kill assay using HER2-cells as a comparison to the HER2+ cells. The CD$_{50}$ of the cytotoxic molecule of this example is approximately 0.01-100 nM for HER2+ cells depending on the cell line. The CD$_{50}$ of the cytotoxic molecule is approximately 10-10,000 fold greater (less cytotoxic) for cells not expressing HER2 on a cellular surface as compared to cells which do express HER2 on a cellular surface.

Determining the In Vivo Effects of the Cytotoxic, Cell-Targeted Molecule "SLT-1A-FR Linked with αHER2-V$_H$H" Using Animal Models Animal models are used to determine the in vivo effects of the cytotoxic molecule "SLT-1A-FR linked with αHER2-V$_H$H" on neoplastic cells. Various mice strains are used to test the effect of the cytotoxic molecule after intravenous administration on xenograft tumors in mice resulting from the injection into those mice of human neoplastic cells which express HER2 on their cell surfaces.

Example 4. A Cytotoxic, Cell-Targeted Molecule Comprising a Protease-Cleavage Resistant, Shiga Toxin Effector Region and a Binding Region Derived from the Antibody αEpstein-Barr-Antigen (SLT-1A-FR Linked with αEpsteinBarr)

In this example, the Shiga toxin effector polypeptide region is a protease-cleavage resistant, Shiga toxin effector polypeptide derived from the A subunit of Shiga-like Toxin 1 (SLT-1A). An immunoglobulin-type binding region αEpstein-Barr-antigen is derived from a monoclonal antibody against an Epstein: Barr antigen (Fang C et al., *J Immunol Methods* 287: 21-30 (2004)), which comprises an immunoglobulin-type binding region capable of binding a human cell infected by the Epstein-Barr virus or a transformed cell expressing an Epstein-Barr antigen. The Epstein-Barr antigen is expressed on multiple cell types, such as cells infected by an Epstein-Barr virus and cancer cells (e.g. lymphoma and nasopharynygeal cancer cells). In addition, Epstein-Barr infection is associated with other diseases, e.g., multiple sclerosis.

Construction, Production, and Purification of the Cytotoxic, Cell-Targeted Molecule "SLT-1A-FR Linked with αEpsteinBarr"

The immunoglobulin-type binding region αEpstein-Barr-antigen and a protease resistant Shiga toxin effector polypeptide are linked together, and a carboxy-terminal KDEL (SEQ ID NO: 62) is added to form a cytotoxic, cell-targeted molecule. For example, a fusion protein is produced by expressing a polynucleotide encoding the αEpstein-Barr-antigen-binding protein "SLT-1A-FR::αEpsteinBarr:: KDEL." Expression of the "SLT-1A-FR::αEpsteinBarr:: KDEL" cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR linked with αEpsteinBarr"

The binding characteristics of the cytotoxic molecule of this example for Epstein-Barr antigen positive cells and Epstein-Barr antigen negative cells is determined by a fluorescence-based, flow-cytometry assay known in the art. The B$_{max}$ for "SLT-1A-FR linked with αEpsteinBarr" to Epstein-Barr antigen positive cells is measured to be approximately 50,000-200,000 MFI with a K$_D$ within the range of 0.01-100 nM, whereas there is no significant binding to Epstein-Barr antigen negative cells in this assay.

The ribosome inactivation abilities of the "SLT-1A-FR linked with αEpsteinBarr" cytotoxic molecule is determined in a cell-free, in vitro protein translation as described above in the previous examples. The inhibitory effect of the cytotoxic molecule of this example on cell-free protein synthesis is significant. The IC$_{50}$ of "SLT-1A-FR linked with αEpsteinBarr" on protein synthesis in this cell-free assay is approximately 0.1-100 pM.

Determining the Cytotoxicity of the Cytotoxic, Cell-Targeted Molecule "SLT-1A-FR Linked with αEpsteinBarr" Using a Cell-Kill Assay The cytotoxicity characteristics of "SLT-1A-FR linked with αEpsteinBarr" are determined by the general cell-kill assay as described above in the previous examples using Epstein-Barr antigen positive cells. In addition, the selective cytotoxicity characteristics of "SLT-1A-FR linked with αEpsteinBarr" are determined by the same general cell-kill assay using Epstein-Barr antigen negative cells as a comparison to the Epstein-Barr antigen positive cells. The CD$_{50}$ of the cytotoxic molecule of this example is approximately 0.01-100 nM for Epstein-Barr antigen positive cells depending on the cell line. The CD$_{50}$ of the cytotoxic molecule is approximately 10-10,000 fold greater (less cytotoxic) for cells not expressing the Epstein-Barr antigen on a cellular surface as compared to cells which do express the Epstein-Barr antigen on a cellular surface.

Determining the In Vivo Effects of the Cytotoxic, Cell-Targeted Molecule "SLT-1A-FR Linked with αEpsteinBarr" Using Animal Models Animal models are used to determine the in vivo effects of the cytotoxic molecule "SLT-1A-FR linked with αEpsteinBarr" on neoplastic cells. Various mice strains are used to test the effect of the cytotoxic molecule after intravenous administration on xenograft tumors in mice Example 5. A Cytotoxic, Cell-Targeted Molecule Comprising a Protease-Cleavage Resistant, Shiga Toxin Effector Region and a Binding Region Derived from the Antibody αLeishmania-Antigen (SLT-1A-FR Linked with αLeishmania)

In this example, the Shiga toxin effector polypeptide region is a protease resistant Shiga toxin effector polypeptide derived from the A subunit of Shiga-like Toxin 1 (SLT-1A). An immunoglobulin-type binding region αLeishmania-antigen is derived from an antibody generated, using techniques known in the art, to a cell-surface Leishmania antigen present on human cells harboring an intracellular trypanosomatid protozoa (see Berman J, Dwyer D, *Clin Exp Immunol* 44: 342-348 (1981); Kenner J et al., *J Cutan Pathol* 26: 130-6 (1999); Silveira T et al., *Int J Parasitol* 31: 1451-8 (2001)).

Construction, Production, and Purification of the Cytotoxic, Cell-Targeted Molecule "SLT-1A-FR Linked with αLeishmania"

The immunoglobulin-type binding region α-Leishmania-antigen and Shiga toxin effector polypeptide are linked together, and a carboxy-terminal KDEL (SEQ ID NO: 62) is added to form a cytotoxic, cell-targeted molecule. For example, a fusion protein is produced by expressing a polynucleotide encoding the Leishmania-antigen-binding protein SLT-1A-FR::αLeishmania::KDEL. Expression of the SLT-1A-FR::αLeishmania::KDEL cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR Linked with αLeishmania"

The binding characteristics of the cytotoxic molecule of this example for *Leishmania* antigen positive cells and *Leishmania* antigen negative cells is determined by a fluorescence-based, flow-cytometry assay known in the art. The $B_{max}$ for "SLT-1A-FR linked with αLeishmania" to *Leishmania* antigen positive cells is measured to be approximately 50,000-200,000 MFI with a $K_D$ within the range of 0.01-100 nM, whereas there is no significant binding to *Leishmania* antigen negative cells in this assay.

The ribosome inactivation abilities of the "SLT-1A-FR linked with αLeishmania" cytotoxic molecule is determined in a cell-free, in vitro protein translation as described above in the previous examples. The inhibitory effect of the cytotoxic molecule of this example on cell-free protein synthesis is significant. The $IC_{50}$ of "SLT-1A-FR linked with αLeishmania" on protein synthesis in this cell-free assay is approximately 0.1-100 pM.

Determining the Cytotoxicity of the Cytotoxic, Cell-Targeted Molecule "SLT-1A-FR Linked with αLeishmania" Using a Cell-Kill Assay The cytotoxicity characteristics of "SLT-1A-FR linked with αLeishmania" are determined by the general cell-kill assay as described above in the previous examples using *Leishmania* antigen positive cells. In addition, the selective cytotoxicity characteristics of "SLT-1A-FR linked with αLeishmania" are determined by the same general cell-kill assay using *Leishmania* antigen negative cells as a comparison to the *Leishmania* antigen positive cells. The $CD_{50}$ of the cytotoxic molecule of this example is approximately 0.01-100 nM for *Leishmania* antigen positive cells depending on the cell line. The $CD_{50}$ of the cytotoxic molecule is approximately 10-10,000 fold greater (less cytotoxic) for cells not expressing the *Leishmania* antigen on a cellular surface as compared to cells which do express the *Leishmania* antigen on a cellular surface.

Example 6. A Cytotoxic, Cell-Targeted Molecule Comprising a Protease-Cleavage Resistant, Shiga Toxin Effector Region and a Binding Region Derived from an Immunoglobulin-Type Binding Region αNeurotensin-Receptor (SLT-1A-FR Linked with αNeurotensinR)

In this example, the Shiga toxin effector polypeptide region is a protease resistant Shiga toxin effector polypeptide derived from the A subunit of Shiga-like Toxin 1 (SLT-1A). An immunoglobulin-type binding region αNeurotensinR is derived from the DARPin™ (GenBank Accession: 2P2C_R) or a monoclonal antibody (Ovigne J et al., *Neuropeptides* 32: 247-56 (1998)) which binds the human neurotensin receptor. The neurotensin receptor is expressed by various cancer cells, such as breast cancer, colon cancer, lung cancer, melanoma, and pancreatic cancer cells.

Construction, Production, and Purification of the Cytotoxic, Cell-Targeted Molecule "SLT-1A-FR Linked with αNeurotensinR"

The immunoglobulin-type binding region aNeurotensinR and Shiga toxin effector polypeptide are linked together, and a carboxy-terminal KDEL (SEQ ID NO: 62) is added to form a cytotoxic, cell-targeted molecule. For example, a fusion protein is produced by expressing a polynucleotide encoding the neurotensin-receptor-binding protein SLT-1A-FR::aNeurotensinR::KDEL. Expression of the SLT-1A-FR::aNeurotensinR::KDEL cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR Linked with αNeurotensinR"

The binding characteristics of the cytotoxic molecule of this example for neurotensin receptor positive cells and neurotensin receptor negative cells is determined by a fluorescence-based, flow-cytometry assay known in the art. The $B_{max}$ for "SLT-1A-FR linked with αNeurotensinR" to neurotensin receptor positive cells is measured to be approximately 50,000-200,000 MFI with a $K_D$ within the range of 0.01-100 nM, whereas there is no significant binding to neurotensin receptor negative cells in this assay.

The ribosome inactivation abilities of the "SLT-1A-FR linked with αNeurotensinR" cytotoxic Molecule is determined in a cell-free, in vitro protein translation as described above in the previous examples. The inhibitory effect of the cytotoxic Molecule of this example on cell-free protein synthesis is significant. The $IC_{50}$ of "SLT-1A-FR linked with αNeurotensinR" on protein synthesis in this cell-free assay is approximately 0.1-100 pM.

Determining the Cytotoxicity of the Cytotoxic, Cell-Targeted Molecule "SLT-1A-FR Linked with αNeurotensinR" Using a Cell-Kill Assay The cytotoxicity characteristics of "SLT-1A-FR linked with αNeurotensinR" are determined by the general cell-kill assay as described above in the previous examples using neurotensin receptor positive cells. In addition, the selective cytotoxicity characteristics of "SLT-1A-FR linked with αNeurotensinR" are determined by the same general cell-kill assay using neurotensin receptor negative cells as a comparison to the neurotensin receptor positive cells. The $CD_{50}$ of the cytotoxic molecule of this example is approximately 0.01-100 nM for neurotensin receptor positive cells depending on the cell line. The $CD_{50}$ of the cytotoxic molecule is approximately 10-10,000 fold greater (less cytotoxic) for cells not expressing neurotensin receptor on a cellular surface as compared to cells which do express neurotensin receptor on a cellular surface.

Determining the In Vivo Effects of the Cytotoxic, Cell-Targeted Molecule "SLT-1A-FR Linked with αNeurotensinR" Using Animal Models Animal models are used to determine the in vivo effects of the cytotoxic molecule "SLT-1A-FR linked with αNeurotensinR" on neoplastic cells. Various mice strains are used to test the effect of the cytotoxic molecule after intravenous administration on xenograft tumors in mice resulting from the injection into those mice of human neoplastic cells which express neurotensin receptors on their cell surfaces.

Example 7. A Cytotoxic, Cell-Targeted Molecule Comprising a Protease-Cleavage Resistant, Shiga Toxin Effector Region and a Binding Region Derived from an Immunoglobulin-Type Binding Region αEGFR (SLT-1A-FR Linked with αEGFR)

In this example, the Shiga toxin effector polypeptide region is a protease resistant Shiga toxin effector polypeptide derived from the A subunit of Shiga-like Toxin 1 (SLT-1A). The binding region αEGFR is derived from the AdNectin™ (GenBank Accession: 3QWQ_B), the Affibody™ (GenBank Accession: 2KZI_A; U.S. Pat. No. 8,598,113), or an antibody, all of which bind one or more human epidermal growth factor receptors. The expression of epidermal growth factor receptors are associated with human cancer cells, such as, e.g., lung cancer cells, breast cancer cells, and colon cancer cells.

Construction, Production, and Purification of the Cytotoxic, Cell-Targeted Molecule "SLT-1A-FR linked with αEGFR"

The immunoglobulin-type binding region αEGFR and Shiga toxin effector polypeptide are linked together, and a carboxy-terminal KDEL (SEQ ID NO: 62) is added to form a cytotoxic, cell-targeted molecule. For example, a fusion protein is produced by expressing a polynucleotide encoding the EGFR binding protein SLT-1A-FR::αEGFR::KDEL. Expression of the SLT-1A-FR::αEGFR::KDEL cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR Linked with αEGFR"

The binding characteristics of the cytotoxic molecule of this example for EGFR+ cells and EGFR− cells is determined by a fluorescence-based, flow-cytometry assay known in the art. The $B_{max}$ for "SLT-1A-FR linked with αEGFR" to EGFR+ cells is measured to be approximately 50,000-200,000 MFI with a $K_D$ within the range of 0.01-100 nM, whereas there is no significant binding to EGFR− cells in this assay.

The ribosome inactivation abilities of the "SLT-1A-FR linked with αEGFR" cytotoxic molecule is determined in a cell-free, in vitro protein translation as described above in the previous examples. The inhibitory effect of the cytotoxic molecule of this example on cell-free protein synthesis is significant. The $IC_{50}$ of "SLT-1A-FR linked with αEGFR" on protein synthesis in this cell-free assay is approximately 0.1-100 pM.

Determining the Cytotoxicity of the Cytotoxic, Cell-Targeted Molecule "SLT-1A-FR Linked with αEGFR" Using a Cell-Kill Assay The cytotoxicity characteristics of "SLT-1A-FR linked with αEGFR" are determined by the general cell-kill assay as described above in the previous examples using EGFR+ cells. In addition, the selective cytotoxicity characteristics of "SLT-1A-FR linked with αEGFR" are determined by the same general cell-kill assay using EGFR− cells as a comparison to the *Leishmania* antigen positive cells. The CD50 of the cytotoxic molecule of this example is approximately 0.01-100 nM for EGFR+ cells depending on the cell line. The $CD_{50}$ of the cytotoxic molecule is approximately 10-10,000 fold greater (less cytotoxic) for cells not expressing EGFR on a cellular surface as compared to cells which do express EGFR on a cellular surface.

Determining the In Vivo Effects of the Cytotoxic, Cell-Targeted Molecule "SLT-1A-FR Linked with αEGFR" Using Animal Models Animal models are used to determine the in vivo effects of the cytotoxic molecule "SLT-1A-FR linked with αEGFR" on neoplastic cells. Various mice strains are used to test the effect of the cytotoxic molecule after intravenous administration on xenograft tumors in mice resulting from the injection into those mice of human neoplastic cells which express EGFR(s) on their cell surfaces.

Example 8. A Cytotoxic, Cell-Targeted Molecule Comprising a Protease-Cleavage Resistant, Shiga Toxin Effector Region and a Binding Region Derived from the Antibody αCCR5 (SLT-1A-FR Linked with αCCR5)

In this example, the Shiga toxin effector polypeptide region is a protease resistant Shiga toxin effector polypeptide derived from the A subunit of Shiga-like Toxin 1 (SLT-1A). An immunoglobulin-type binding region αCCR5 is derived from a monoclonal antibody against human CCR5 (CD195) (Bernstone L et al., *Hybridoma* 31: 7-19 (2012)). CCR5 is predominantly expressed on T-cells, macrophages, dendritic cells, and microglia. In addition, CCR5 plays a role in the pathogenesis and spread of the Human Immunodeficiency Virus (HIV).

Construction, Production, and Purification of the Cytotoxic, Cell-Targeted Molecule "SLT-1A-FR linked with αCCR5"

The immunoglobulin-type binding region αCCR5 and Shiga toxin effector polypeptide are linked together, and a carboxy-terminal KDEL (SEQ ID NO: 62) is added to form a cytotoxic, cell-targeted molecule. For example, a fusion protein is produced by expressing a polynucleotide encoding the αCCR5-binding protein SLT-1A-FR::αCCR5::KDEL. Expression of the SLT-1A-FR::αCCR5::KDEL cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR Linked with αCCR5"

The binding characteristics of the cytotoxic molecule of this example for CCR5+ cells and CCR5− cells is determined by a fluorescence-based, flow-cytometry assay known in the art. The $B_{max}$ for "SLT-1A-FR linked with αCCR5" to CCR5+ positive cells is measured to be approximately 50,000-200,000 MFI with a $K_D$ within the range of 0.01-100 nM, whereas there is no significant binding to CCR5− cells in this assay.

The ribosome inactivation abilities of the "SLT-1A-FR linked with αCCR5" cytotoxic molecule is determined in a cell-free, in vitro protein translation as described above in the previous examples. The inhibitory effect of the cytotoxic molecule of this example on cell-free protein synthesis is significant. The $IC_{50}$ of "SLT-1A-FR linked with αCCR5" on protein synthesis in this cell-free assay is approximately 0.1-100 pM.

Determining the Cytotoxicity of the Cytotoxic, Cell-Targeted Molecule "SLT-1A-FR linked with αCCR5" Using a Cell-Kill Assay The cytotoxicity characteristics of "SLT-1A-FR linked with αCCR5" are determined by the general cell-kill assay as described above in the previous examples using CCR5+ cells. In addition, the selective cytotoxicity characteristics of "SLT-1A-FR linked with αCCR5" are determined by the same general cell-kill assay using CCR5− cells as a comparison to the CCR5+ cells. The $CD_{50}$ of the cytotoxic molecule of this example is approximately 0.01-100 nM for CCR5+ cells depending on the cell line. The $CD_{50}$ of the cytotoxic molecule is approximately 10-10,000 fold greater (less cytotoxic) for cells not expressing CCR5 on a cellular surface as compared to cells which do express CCR5 on a cellular surface.

Determining the In Vivo Effects of the Cytotoxic, Cell-Targeted Molecule "SLT-1A-FR Linked with αCCR5" Using Animal Models Animal models are used to determine the in vivo effects of the cytotoxic molecule "SLT-1A-FR linked with αCCR5" on depleting T-cells from donor materials (see Tsirigotis P et al., *Immunotherapy* 4: 407-24 (2012)). Non-human primates are used to determine in vivo effects of "SLT-1A-FR linked with αCCR5." Graft-versus-host disease is analyzed in rhesus macaques after kidney transplantation when the donated organs are pretreated with "SLT-1A-FR linked with αCCR5" (see Weaver T et al., *Nat Med* 15: 746-9 (2009)). In vivo depletion of peripheral blood T lymphocytes in cynomolgus primates is observed after parenteral administration of different doses of "SLT-1A-FR linked with αCCR5." The use of "SLT-1A-FR linked with αCCR5" to block HIV infection is tested by giving an acute dose of "SLT-1A-FR linked with αCCR5" to non-human primates in order to severely deplete circulating T-cells upon exposure to a simian immunodeficiency virus (SIV) (see Sellier P et al., *PLoS One* 5: e10570 (2010)).

Example 9. A Cytotoxic, Cell-Targeted Molecule Comprising a Protease-Cleavage Resistant, Shiga Toxin Effector Region and a Binding Region Derived from an Anti-Env Immunoglobulin Domain (SLT-1A-FR Linked with αEnv)

In this example, the Shiga toxin effector polypeptide region is a protease resistant Shiga toxin effector polypeptide derived from the A subunit of Shiga toxin (StxA). An immunoglobulin-type binding region αEnv is derived from existing antibodies that bind HIV envelope glycoprotein (Env), such as GP41, GP120, GP140, or GP160 (see e.g. Chen W et al., *J Mol Bio* 382: 779-89 (2008); Chen W et al., *Expert Opin Biol Ther* 13: 657-71 (2013); van den Kerkhof T et al., *Retrovirology* 10: 102 (2013)) or from antibodies generated using standard techniques (see Prabakaran P et al., *Front Microbiol* 3: 277 (2012)). Envs are HIV surface proteins that are also displayed on the cell surfaces of HIV-infected cells during HIV replication. Although Envs are expressed in infected cells predominantly in endosomal compartments, sufficient amounts of Envs could be present on a cell surface to be targeted by a highly potent, cytotoxic, cell-targeted molecule of the invention. In addition, Env-targeting cytotoxic molecules might bind HIV virions and enter newly infected cells during the fusion of virions with a host cell.

Because HIV displays a high rate of mutation, it is preferable to use an immunoglobulin domain that binds a functional constrained part of an Env, such as shown by broadly neutralizing antibodies that bind Envs from multiple strains of HIV (van den Kerkhof T et al., *Retrovirology* 10: 102 (2013)). Because the Envs present on an infected cell's surface are believed to present sterically restricted epitopes (Chen W et al., *J Virol* 88: 1125-39 (2014)), it is preferable to use smaller than 100 kD and ideally smaller than 25 kD, such as sdAbs or $V_HH$ domains.

Construction, Production, and Purification of the Cytotoxic, Cell-Targeted Molecule "SLT-1A-FR Linked with αEnv"

The immunoglobulin-type binding region αEnv and protease resistant Shiga toxin effector polypeptide are linked together, and a carboxy-terminal KDEL (SEQ ID NO: 62) is added to form a cytotoxic, cell-targeted molecule. For example, a fusion protein is produced by expressing a polynucleotide encoding the αEnv-binding protein SLT-1A-FR::αEnv::KDEL. Expression of the SLT-1A-FR::αEnv::KDEL cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR Linked with αEnv"

The binding characteristics of the cytotoxic molecule of this example for Env+ cells and Env− cells is determined by a fluorescence-based, flow-cytometry assay known in the art. The $B_{max}$ for "SLT-1A-FR linked with αEnv" to Env+ positive cells is measured to be approximately 50,000-200,000 MFI with a $K_D$ within the range of 0.01-100 nM, whereas there is no significant binding to Env− cells in this assay.

The ribosome inactivation abilities of the "SLT-1A-FR linked with αEnv" cytotoxic molecule is determined in a cell-free, in vitro protein translation as described above in the previous examples. The inhibitory effect of the cytotoxic molecule of this example on cell-free protein synthesis is significant. The $IC_{50}$ of "SLT-1A-FR linked with αEnv" on protein synthesis in this cell-free assay is approximately 0.1-100 pM.

Determining the Cytotoxicity of the Cytotoxic, Cell-Targeted Molecule "SLT-1A-FR Linked with αEnv" Using a Cell-Kill Assay The cytotoxicity characteristics of "SLT-1A-FR linked with αEnv" are determined by the general cell-kill assay as described above in the previous examples using Env+ cells. In addition, the selective cytotoxicity characteristics of "SLT-1A-FR linked with αEnv" are determined by the same general cell-kill assay using Env− cells as a comparison to the Env+ cells. The $CD_{50}$ of the cytotoxic molecule of this example is approximately 0.01-100 nM for Env+ cells depending on the cell line and/or the HIV strain used to infect the cells to make them Env+. The $CD_{50}$ of the cytotoxic molecule is approximately 10-10,000 fold greater (less cytotoxic) for cells not expressing Env on a cellular surface as compared to cells which do express Env on a cellular surface.

Determining the In Vivo Effects of the Cytotoxic, Cell-Targeted Molecule "SLT-1A-FR Linked with αEnv" Using Animal Models The use of "SLT-1A-FR linked with αEnv" to inhibit HIV infection is tested by administering "SLT-1A-FR linked with αEnv" to simian immunodeficiency virus (SIV) infected non-human primates (see Sellier P et al., *PLoS One* 5: e10570 (2010)).

Example 10. A Cytotoxic, Cell-Targeted Molecule Comprising a Protease-Cleavage Resistant, Shiga Toxin Effector Region and a Binding Region Derived from the Antibody αUL18 (SLT-1A-FR Linked with αUL18)

In this example, the Shiga toxin effector polypeptide region is a protease resistant Shiga toxin effector polypeptide derived from the A subunit of Shiga-like Toxin 1 (SLT-1A). An immunoglobulin-type binding region αUL18 is derived from an antibody generated, using techniques known in the art, to the cell-surface cytomegalovirus protein UL18, which is present on human cells infected with cytomegalovirus (Yang Z, Bjorkman P, *Proc Natl Acad Sci USA* 105: 10095-100 (2008)). The human cytomegalovirus infection is associated with various cancers and inflammatory disorders.

Construction, Production, and Purification of the Cytotoxic, Cell-Targeted Molecule "SLT-1A-FR Linked with αUL18"

The immunoglobulin-type binding region αUL18 and Shiga toxin effector polypeptide are linked together, and a carboxy-terminal KDEL (SEQ ID NO: 62) is added to form a cytotoxic, cell-targeted molecule. For example, a fusion protein is produced by expressing a polynucleotide encoding the αUL18-binding protein SLT-1A-FR::αUL18::KDEL... Expression of the SLT-1A-FR::αUL18::KDEL cytotoxic molecule is accomplished using either bacterial and/or cell-free, protein translation systems as described in the previous examples.

Determining the In Vitro Characteristics of the Cytotoxic, Cell-Targeted Molecule "SLT-1A-FR Linked with αUL18"

The binding characteristics of the cytotoxic molecule of this example for cytomegalovirus protein UL18 positive cells and cytomegalovirus protein UL18 negative cells is determined by a fluorescence-based, flow-cytometry assay known in the art. The $B_{max}$ for "SLT-1A-FR linked with αUL18" to cytomegalovirus protein UL18 positive cells is measured to be approximately 50,000-200,000 MFI with a $K_D$ within the range of 0.01-100 nM, whereas there is no significant binding to cytomegalovirus protein UL18 negative cells in this assay.

The ribosome inactivation abilities of the "SLT-1A-FR linked with αUL18" cytotoxic molecule is determined in a cell-free, in vitro protein translation as described above in the previous examples. The inhibitory effect of the cytotoxic molecule of this example on cell-free protein synthesis is significant. The $IC_{50}$ of "SLT-1A-FR linked with αUL18" on protein synthesis in this cell-free assay is approximately 0.1-100 pM.

Determining the Cytotoxicity of the Cytotoxic, Cell-Targeted Molecule "SLT-1A-FR Linked with αUL18" Using a Cell-Kill Assay The cytotoxicity characteristics of "SLT-1A-FR linked with αUL18" are determined by the general cell-kill assay as described above in the previous examples using cytomegalovirus protein UL18 positive cells. In addition, the selective cytotoxicity characteristics of "SLT-1A-FR linked with αUL18" are determined by the same general cell-kill assay using cytomegalovirus protein UL18 negative cells as a comparison to the cytomegalovirus protein UL18 positive cells. The $CD_{50}$ of the cytotoxic molecule of this example is approximately 0.01-100 nM for cytomegalovirus protein UL18 positive cells depending on the cell line. The $CD_{50}$ of the cytotoxic molecule is approximately 10-10,000 fold greater (less cytotoxic) for cells not expressing the cytomegalovirus protein UL18 on a cellular surface as compared to cells which do express the cytomegalovirus protein UL18 on a cellular surface.

Example 11. A Cytotoxic, Cell-Targeted Molecule Comprising a Protease-Cleavage Resistant, Shiga Toxin Effector Region Derived from the A Subunit of Shiga-Like Toxin-1 and a Binding Region Derived from Antibody to Helminth Intestinal Antigen (SLT-1A-FR Linked with αHelminth-Intestinal-Antigen)

In this example, the Shiga toxin effector polypeptide region is derived from the A subunit of Shiga-like Toxin 1 (SLT-1A). An immunoglobulin-type binding region αhelminth-intestinal-antigen is derived from an antibody generated, using techniques known in the art, to the helminth ortholog of a human transferrin receptor (see e.g. the nematode gene gcp-2.1 UniProt G8JYE4_CAEEL; Rosa B et al., *Mol Cell Proteomics* M114.046227 (2015)).

Construction, Production, and Purification of the Cytotoxic Protein "SLT-1A-FR Linked with αHelminth-Intestinal-Antigen"

The immunoglobulin-type binding region αhelminth-intestinal-antigen and protease resistant Shiga toxin effector polypeptide are linked together, and optionally a carboxy-terminal endoplasmic reticulum signal motif of the KDEL family, are linked together to form a cytotoxic, cell-targeted molecule. For example, a fusion protein is produced by expressing a polynucleotide encoding the SLT-1A-FR::αhelminth-intestinal-antigen-binding protein. Expression of the SLT-1A-FR::αhelminth-intestinal-antigen cytotoxic protein is accomplished using either bacterial and/or cell-free, protein translation systems as described in the previous examples.

Determining the In Vitro Characteristics of the Cytotoxic, Cell-Targeted Molecule "SLT-1A-FR linked with αHelminth-Intestinal-Antigen"

The binding characteristics of the cytotoxic, cell-targeted molecule of this example is determined by a molecular binding assay known in the art using a purified recombinant target protein. The $K_D$ for "SLT-1A-FR linked with αHelminth-Intestinal-Antigen" to target protein is measured to be approximately 100 nM, whereas there is no significant binding to a negative control protein (e.g. purified, recombinant, human transferrin receptor) in this assay.

The ribosome inactivation abilities of the "SLT-1A-FR linked with αHelminth-Intestinal-Antigen" cytotoxic protein is determined in a cell-free, in vitro protein translation as described above in the previous examples. The inhibitory effect of the cytotoxic, cell-targeted molecule of this example on cell-free protein synthesis is significant. The $IC_{50}$ of "SLT-1A-FR linked with αHelminth-Intestinal-Antigen" on protein synthesis in this cell-free assay is approximately 0.1-100 pM.

Determining the Toxicity of the Cytotoxic Protein "SLT-1A-FR Linked with αHelminth-Intestinal-Antigen" Using Helminths The toxicity of "SLT-1A-FR linked with αHelminth-Intestinal-Antigen" to helminths is determined using model helminthes (see e.g. Iatsenko I et al., *Toxins* 2050-63 (2014)). The helminth can be administered purified "SLT-1A-FR linked with αHelminth-Intestinal-Antigen" by soaking or alternatively by feeding the helminth with bacteria expressing, e.g., the SLT-1A::αhelminth-intestinal-antigen fusion protein.

In addition, laboratory animals harboring helminths and/or displaying helminth related diseases are administered "SLT-1A-FR linked with αHelminth-Intestinal-Antigen" and monitored for reduction or elimination of helminths and/or associated symptoms of parasitic helminth(s), such as helminth killing, increased sterility, reduced fecundity, and growth inhibition.

Example 12. A Cytotoxic, Cell-Targeted Molecule Comprising a Protease-Cleavage Resistant, Shiga Toxin Effector Region and a Binding Region Targeting a Human, Major Histo-Compatibility Molecule Complexed with a Peptide from an Infectious Agent (SLT-1A-FR Linked with αMHC-Peptide)

In this example, the Shiga toxin effector polypeptide region is a protease resistant Shiga toxin effector polypeptide derived from the A subunit of Shiga toxin (StxA). An immunoglobulin-type binding region which binds a human, major Histo-Compatibility (MHC) molecule complexed with a specific peptide is obtained or designed from an antibody and/or immunoglobulin-type library screened using standard techniques known to the skilled worker (see Tohidkia M et al., *J Drug Target* 20: 195-208 (2012); de Marco A, *Crit Rev Biotechnol* 33: 40-8 (2013); Wen F, Zhao H, *Methods Mol Biol* 1061: 245-64 (2013)).

For example, human cells infected with malaria can present on their cell surfaces MHC class I molecules complexed with antigens from the *P. falciparum* apical membrane antigen-1 (AMA1), such as, e.g., the HLA-A complexed with the peptide TLDEMRHFY (SEQ ID NO:-137) (see e.g. Lal A et al., *Infect Immun* 64: 1054-9 (1996); Sedegah M et al., *Malar J* 9: 241 (2010); Schwenk R et al., *Malar J* 12:376 (2013)). Similarly, human cells infected with tuberculosis can present on their cell surfaces MHC class I molecules complexed with antigens from *M. tuberculosis* factors, such as, e.g., CFP10, PE/PPE, Rv0288, Rv1886c, Rv3875, and TB10.4, (Axelsson-Robertson R et al., *Immunology* 129: 496-505 (2010); Axelsson-Robertson R et al., *Clin Vaccine Immunol* 18: 125-34 (2011); Wang M et al., *Immunology* 132: 482-91 (2011); Axelsson-Robertson R et al., *PLoS One* 8: e58309 (2013)).

Construction, Production, and Purification of the Cytotoxic, Cell-Targeted Molecule "SLT-1A-FR Linked with αMHC-Peptide"

The immunoglobulin-type binding region αMHC-peptide and protease resistant Shiga toxin effector polypeptide are linked together to form a cytotoxic, cell-targeted molecule. For example, a fusion protein is produced by expressing a polynucleotide encoding the SLT-1A-FR::αMHC-peptide protein wherein the binding regions binds a specific human HLA subtype MHC molecule complexed with an antigenic peptide from *M. tuberculosis* or *P. falciparum*. Expression of the SLT-1A-FR::αMHC-peptide cytotoxic molecule is accomplished using either bacterial and/or cell-free, protein translation systems as described in the previous examples. Binding regions specific for other HLA types complexed to malarial antigens or *mycobacterium* antigens are designed and tested to provide better coverage of human subpopulations.

Determining the In Vitro Characteristics of the Cytotoxic, Cell-Targeted Molecule "SLT-1A-FR Linked with αMHC-Peptide"

The binding characteristics of the cytotoxic molecule of this example for infected human cells is determined by a fluorescence-based, flow-cytometry assay known in the art. The $B_{max}$ for "SLT-1A-FR linked with αMHC-peptide" to antigen-presenting cells is measured to be approximately 50,000-200,000 MFI with a $K_D$ within the range of 0.01-100 nM, whereas there is no significant binding to negative control cells in this assay.

The ribosome inactivation abilities of the "SLT-1A-FR linked with αMHC-peptide" cytotoxic molecule is determined in a cell-free, in vitro protein translation as described above in the previous examples. The inhibitory effect of the cytotoxic molecule of this example on cell-free protein synthesis is significant. The $IC_{50}$ of "SLT-1A-FR linked with αMHC-peptide" on protein synthesis in this cell-free assay is approximately 0.1-100 pM.

Determining the Cytotoxicity of the Cytotoxic, Cell-Targeted Molecule "SLT-1A-FR Linked with αMHC-peptide" Using a Cell-Kill Assay The cytotoxicity characteristics of "SLT-1A-FR linked with αMHC-peptide" are determined by the general cell-kill assay as described above in the previous examples using infected cells and/or antigen presenting cells positive for specific MHC molecule-peptide complexes. In addition, the selective cytotoxicity characteristics of "SLT-1A-FR linked with αMHC-peptide" are determined by the same general cell-kill assay. The $CD_{50}$ of the cytotoxic molecule of this example is approximately 0.01-100 nM for MEIC-peptide+ cells depending on the cell line. The $CD_{50}$ of the cytotoxic molecule is approximately 10-10,000 fold greater (less cytotoxic) for cells not expressing the same MHC-peptide on a cellular surface as compared to cells which do present a specifically targeted, MHC-peptide on a cellular surface.

Determining the In Vivo Effects of the Cytotoxic, Cell-Targeted Molecule "SLT-1A-FR Linked with αMHC-Peptide" Using Animal Models The use of "SLT-1A-FR linked with αMHC-peptide" to inhibit *plasmodium* or *mycobacterium* infections is tested by administering "SLT-1A-FR linked with αMHC-peptide" to animal models of malarial infections, *mycobacterium*, sporozoite infections, and liver stage *Plasmodium* parasitic infections. This type of MHC-peptide complex-targeted therapeutic may be particularly useful in *mycobacterium* or *plasmodium* infected individuals who are also immunocompromised, such as, e.g., asplenia, T-cell deficient, and/or HIV-infected patients.

Example 13. Cytotoxic, Cell-Targeting Molecules Comprising Protease-Cleavage Resistant, Shiga Toxin Effector Regions and Binding Regions Targeting Various Cell Types In this example, the Shiga toxin effector polypeptide region is a protease resistant Shiga toxin effector polypeptide derived from the A subunit of Shiga-like Toxin 1 (SLT-1A), Shiga toxin (StxA), and/or Shiga-like Toxin 2 (SLT-2A) with a disrupted protease sensitive site in the amino acid sequence natively occurring at 248-251 for SLT-1A and StxA or 247-250 for SLT-2A. A binding region is derived from the immunoglobulin domain from the molecule chosen from column 1 of Table 5 and which binds the extracellular target biomolecule indicated in column 2 of Table 5. The exemplary cell-targeted molecules of this example are optionally created with a carboxy-terminal KDEL-type signal motif and/or detection promoting agent(s) using reagents and techniques known in the art. The exemplary, cytotoxic, cell-targeted molecules of this example are tested as described in the previous examples using cells expressing the appropriate extracellular target biomolecules. The exemplary cell-targeted molecules of this example may be used, e.g., to diagnose and treat diseases, conditions, and/or disorders indicated in column 3 of Table 5.

TABLE 5

Various Binding Regions for Cell-Targeting of Furin-Cleavage Resistant, Shiga Toxin A Subunit Derived Polypeptides

| Source of binding region | extracellular target | Application(s) |
|---|---|---|
| alemtuzumab | CD52 | B-cell cancers, such as lymphoma and leukemia, and B-cell related immune disorders, such as autoimmune disorders |
| basiliximab | CD25 | T-cell disorders, such as prevention of organ transplant rejections, and some B-cell lineage cancers |
| brentuximab | CD30 | hematological cancers, B-cell related immune disorders, and T-cell related immune disorders |
| catumaxomab | EpCAM | various cancers, such as ovarian cancer, malignant ascites, gastric cancer |
| cetuximab | EGFR | various cancers, such as colorectal cancer and head and neck cancer |
| daclizumab | CD25 | B-cell lineage cancers and T-cell disorders, such as rejection of organ transplants |
| daratumumab | CD38 | hematological cancers, B-cell related immune disorders, and T-cell related immune disorders |
| dinutuximab | ganglioside GD2 | Various cancers, such as breast cancer, myeloid cancers, and neuroblastoma |
| efalizumab | LFA-1 (CD11a) | autoimmune disorders, such as psoriasis |
| ertumaxomab | HER2/neu | various cancers and tumors, such as breast cancer and colorectal cancer |
| gemtuzumab | CD33 | myeloid cancer or immune disorder |
| ibritumomab | CD20 | B-cell cancers, such as lymphoma and leukemia, and B-cell related immune disorders, such as autoimmune disorders |
| ipilimumab | CD152 | T-cell related disorders and various cancers, such as leukemia, melanoma |
| muromonab | CD3 | prevention of organ transplant rejections |
| natalizumab | integrin α4 | autoimmune disorders, such as multiple sclerosis and Crohn's disease |
| obinutuzumab | CD20 | B-cell cancers, such as lymphoma and leukemia, and B-cell related immune disorders, such as autoimmune disorders |
| ocaratuzumab | CD20 | B-cell cancers, such as lymphoma and leukemia, and B-cell related immune disorders, such as autoimmune disorders |
| ocrelizumab | CD20 | B-cell cancers, such as lymphoma and leukemia, and B-cell related immune disorders, such as autoimmune disorders |
| ofatumumab | CD20 | B-cell cancers, such as lymphoma and leukemia, and B-cell related immune disorders, such as autoimmune disorders |
| palivizumab | F protein of respiratory syncytial virus | treat respiratory syncytial virus |
| panitumumab | EGFR | various cancers, such as colorectal cancer and head and neck cancer |
| pertuzumab | HER2/neu | various cancers and tumors, such as breast cancer and colorectal cancer |
| pro 140 | CCR5 | HIV infection and T-cell disorders |
| ramucirumab | VEGFR2 | various cancers and cancer related disorders, such as solid tumors |
| rituximab | CD20 | B-cell cancers, such as lymphoma and leukemia, and B-cell related immune disorders, such as autoimmune disorders |
| tocilizumab or atlizumab | IL-6 receptor | autoimmune disorders, such as rheumatoid arthritis |
| tositumomab | CD20 | B-cell cancers, such as lymphoma and leukemia, and B-cell related immune disorders, such as autoimmune disorders |
| trastuzumab | HER2/neu | various cancers and tumors, such as breast cancer and colorectal cancer |
| ublituximab | CD20 | B-cell cancers, such as lymphoma and leukemia, and B-cell related immune disorders, such as autoimmune disorders |

TABLE 5-continued

Various Binding Regions for Cell-Targeting of Furin-Cleavage Resistant, Shiga Toxin A Subunit Derived Polypeptides

| Source of binding region | extracellular target | Application(s) |
|---|---|---|
| vedolizumab | integrin α4β7 | autoimmune disorders, such as Crohn's disease and ulcerative colitis |
| CD20 binding antibodies and scFv(s) | CD20 | B-cell cancers, such as lymphoma and leukemia, and B-cell related immune disorders, such as autoimmune disorders (see e.g. Geng S et al., *Cell Mol Immunol* 3: 439-43 (2006); Olafesn T et al., *Protein Eng Des Sel* 23: 243-9 (2010)) |
| CD22 binding scFv(s) | CD22 | B-cell cancers or B-cell related immune disorders (see e.g. Kawa S et al., *MAbs* 3: 479-86 (2011)) |
| CD25 binding scFv(s) | CD25 | various cancers of the B-cell lineage and immune disorders related to T-cells (see e.g. Muramatsu H et al., *Cancer Lett* 225: 225-36 (2005)) |
| CD30 binding monoclonal antibody(s) | CD30 | B-cell cancers or B-cell/T-cell related immune disorders (see e.g. Klimka A et al., *Br J Cancer* 83: 252-60 (2000)) |
| CD33 binding monoclonal antibody(s) | CD33 | myeloid cancer or immune disorder (see e.g. Benedict C et al., *J Immunol Methods* 201: 223-31 (1997)) |
| CD38 binding immunoglobulin domains | CD38 | hematological cancers, B-cell related immune disorders, and T-cell related immune disorders (see e.g. U.S. Pat. No. 8,153,765) |
| CD40 binding scFv(s) | CD40 | various cancers and immune disorders (see e.g. Ellmark P et al., *Immunology* 106: 456-63 (2002)) |
| CD52 binding monoclonal antibody(s) | CD52 | B-cell cancers, such as lymphoma and leukemia, and B-cell related immune disorders, such as autoimmune disorders (see e.g. U.S. Pat. No. 7,910,104 B2) |
| CD56 binding monoclonal antibody(s) | CD56 | immune disorders and various cancers, such as lung cancer, Merkel cell carcinoma, myeloma (see e.g. Shin J et al., *Hybridoma* 18: 521-7 (1999)) |
| CD79 binding monoclonal antibody(s) | CD79 | B-cell cancers or B-cell related immune disorders (see e.g. Zhang L et al., *Ther Immunol* 2: 191-202 (1995)) |
| CD133 binding monoclonal antibodies and scFv(s) | CD133 | various cancers, hematologic malignancies, and immune disorders (see e.g. Bidlingmaier S et al., *J Mol Med* 86: 1025-32 (2008); Pavlon L et al., *J Microsc* 231: 374-83 (2008); Rappa G et al., *Stem Cells* 26: 3008-17 (2008); Swaminathan S et al., *J Immunol Methods* 361: 110-5 (2010); Wang J et al., *Hybridoma* 29: 241-9 (2010); Zhu X et al., *Mol Cancer Ther* 9: 2131-41 (2010); Xia J et al., *Sci Rep* 3: 3320 (2013)) |
| CD248 binding scFv(s) | CD248 | various cancers, such as inhibiting angiogenesis (see e.g. Zhao A et al., *J Immunol Methods* 363: 221-32 (2011)) |
| EpCAM binding monoclonal antibody(s) | EpCAM | various cancers, such as ovarian cancer, malignant ascites, gastric cancer (see e.g. Schanzer J et al., *J Immunother* 29: 477-88 (2006)) |
| PSMA binding monoclonal antibody(s) | PSMA | prostate cancer (see e.g. Frigerio B et al., *Eur J Cancer* 49: 2223-32 (2013)) |
| Eph-B2 binding monoclonal antibody(s) | Eph-B2 | various cancers such as colorectal cancer and prostate cancer (see e.g. Abéngozar M et al., *Blood* 119: 4565-76 (2012)) |
| Endoglin binding monoclonal antibody(s) | Endoglin | various cancers, such as breast cancer and colorectal cancers (see e.g. Völkel T et al., *Biochim Biophys Res Acta* 1663: 158-66 (2004)) |
| FAP binding monoclonal antibody(s) | FAP | various cancers, such as sarcomas and bone cancers (see e.g. Zhang J et al., *FASEB J* 27: 581-9 (2013)) |
| CEA binding antibody(s) and scFv(s) | CEA | various cancers, such as gastrointestinal cancer, pancreatic cancer, lung cancer, and breast cancer (see e.g. Neumaier M et al., *Cancer Res* 50: 2128-34 (1990); Pavoni E et al., *BMC Cancer* 6: 4 (2006); Yazaki P et al., *Nucl Med Biol* 35: 151-8 (2008); Zhao J et al., *Oncol Res* 17: 217-22 (2008)) |
| CD24 binding monoclonal antibody(s) | CD24 | various cancers, such as bladder cancer (see e.g. Kristiansen G et al., *Lab Invest* 90: 1102-16 (2010)) |
| LewisY antigen binding scFv(s) | LewisY antigens | various cancers, such as cervical cancer and uterine cancer (see e.g. Power B et al., *Protein Sci* 12: 734-47 (2003); monoclonal antibody BR96 Feridani A et al., *Cytometry* 71: 361-70 (2007)) |

TABLE 5-continued

Various Binding Regions for Cell-Targeting of Furin-Cleavage Resistant, Shiga Toxin A Subunit Derived Polypeptides

| Source of binding region | extracellular target | Application(s) |
| --- | --- | --- |
| adalimumab | TNF-α | various cancers and immune disorders, such as Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| afelimomab | TNF-α | various cancers and immune disorders |
| ald518 | IL-6 | various cancers and immune disorders, such as rheumatoid arthritis |
| anrukinzumab or ima-638 | IL-13 | various cancers and immune disorders |
| briakinumab | IL-12, IL-23 | various cancers and immune disorders, such as psoriasis, rheumatoid arthritis, inflammatory bowel diseases, multiple sclerosis |
| brodalumab | IL-17 | various cancers and immune disorders, such as inflammatory diseases |
| canakinumab | IL-1 | various cancers and immune disorders, such as rheumatoid arthritis |
| certolizumab | TNF-α | various cancers and immune disorders, such as Crohn's disease |
| fezakinumab | IL-22 | various cancers and immune disorders, such as rheumatoid arthritis, psoriasis |
| ganitumab | IGF-I | various cancers |
| golimumab | TNF-α | various cancers and immune disorders, such as rheumatoid arthritis, psoriatic arthritis, ankylosing spondylitis |
| infliximab | TNF-α | various cancers and immune disorders, such as rheumatoid arthritis, ankylosing spondylitis, psoriatic arthritis, psoriasis, Crohn's disease, ulcerative colitis |
| ixekizumab | IL-17A | various cancers and immune disorders, such as autoimmune diseases |
| mepolizumab | IL-5 | various immune disorders and cancers, such as B-cell cancers |
| nerelimomab | TNF-α | various cancers and immune disorders |
| olokizumab | IL6 | various cancers and immune disorders |
| ozoralizumab | TNF-α | inflammation |
| perakizumab | IL17A | various cancers and immune disorders, such as arthritis |
| placulumab | human TNF | various immune disorders and cancers |
| sarilumab | IL6 | various cancers and immune disorders, such as rheumatoid arthritis, ankylosing spondylitis |
| siltuximab | IL-6 | various cancers and immune disorders |
| sirukumab | IL-6 | various cancers and immune disorders, such as rheumatoid arthritis |
| tabalumab | BAFF | B-cell cancers |
| ticilimumab or tremelimumab | CTLA-4 | various cancers |
| tildrakizumab | IL23 | immunologically mediated inflammatory disorders |
| tnx-650 | IL-13 | various cancers and immune disorders, such as B-cell cancers |
| tocilizumab or atlizumab | IL-6 receptor | various cancers and immune disorders, such as rheumatoid arthritis |
| ustekinumab | IL-12, IL-23 | various cancers and immune disorders, such as multiple sclerosis, psoriasis, psoriatic arthritis |
| Various growth factors: VEGF, EGF1, EGF2, FGF | VEGFR, EGFR, FGFR | various cancer, such as breast cancer and colon cancer, and to inhibit vascularization |
| Various cytokines: IL-2, IL-6, IL-23, CCL2, BAFFs, TNFs, RANKL | IL-2R, IL-6R, IL-23R, CD80/CD86, TNFRSF13/ TNFRSF17, TNFR | various immune disorders and cancers |
| Broadly neutralizing antibodies identified from patient samples | Influenza surface antigens (e.g. hemaglutinins and matrix protein 2) | viral infections (see e.g. Prabakaran P et al., *Front Microbiol* 3: 277 (2012)) |

TABLE 5-continued

Various Binding Regions for Cell-Targeting of Furin-Cleavage Resistant, Shiga Toxin A Subunit Derived Polypeptides

| Source of binding region | extracellular target | Application(s) |
|---|---|---|
| Broadly neutralizing antibodies identified from patient samples | Coronavirus surface antigens | viral infections (see e.g. Prabakaran P et al., *Front Microbiol* 3: 277 (2012)) |
| Various antibodies | Filovirus surface antigens (e.g. VP35, VP40, and glycoprotein) | viral infections (see e.g. Olinger G et al., *Proc Natl Acad Sci U.S.A.* 109: 18030-5 (2012); Pettitt J et al., *Sci Transl Med* 5: 199ra113 (2013); Stahelin R, *Expert Opin Ther Targets* 18: 115-20 (2014); Becquart P et al., *PLoS One* 9: e96360 (2014); Stahelin R, *Fron Microbiol* 5: 300 (2014); Tran E et al., *J Virol* 88: 10958-62 (2014); Murin C et al., *Proc Natl Acad Sci U.S.A.* 111: 17182-7 (2014)) |
| Broadly neutralizing antibodies identified from patient samples | Henipavirus surface antigens | viral infections (see e.g. Prabakaran P et al., *Front Microbiol* 3: 277 (2012)) |
| Various antibodies including broadly neutralizing antibodies and scFvs | HIV surface antigens (e.g. matrix protein Map 17) | viral infections (see e.g. Kitidee K et al., *BMC Biotechnol* 10: 80 (2010); Yu L, Guan Y, *Front Immunol* 5: 250 (2014)) |

While some embodiments of the present invention have been described by way of illustration, it will be apparent that the invention may be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety. The disclosures of the international patent application publications WO 2014164680 A1 and WO 2014164693 A2 are each incorporated herein by reference in its entirety. The disclosures of U.S. patent application publications US 2007/0298434 A1, US 2009/0156417 A1, and US 2013/0196928 A1 are each incorporated herein by reference in their entirety. The disclosures of patent application serial number U.S. 62/010,918 is incorporated herein by reference in its entirety. The international PCT patent application disclosures WO 2014/164680, WO 2014/164693, WO 2015/113005, WO 2015/113007, WO 2015/120058, WO 2015/138435, and WO 2015/138452are each incorporated herein by reference in its entirety. The complete disclosures of all electronically available biological sequence information from GenBank (National Center for Biotechnology Information, U.S.) for amino acid and nucleotide sequences cited herein are each incorporated herein by reference in their entirety.

```
                              Sequence Listing

ID Number       Text Description        Biological Sequence

SEQ ID NO: 1    Shiga-like toxin 1      KEFTLDFSTAKTYVDSLNVIRSAIGTPLQTISSGGTSLLMI
                Subunit A (SLT-1A)      DSGSGDNLFAVDVRGIDPEEGRFNNLRLIVERNNLYVTGFV
                                        NRTNNVFYRFADFSHVTFPGTTAVTLSGDSSYTTLQRVAGI
                                        SRTGMQINRHSLTTSYLDLMSHSGTSLTQSVARAMLRFVTV
                                        TAEALRFRQIQRGFRTTLDDLSGRSYVMTAEDVDLTLNWGR
                                        LSSVLPDYHGQDSVRVGRISFGSINAILGSVALILNCHHHA
                                        SRVARMASDEFPSMCPADGRVRGITHNKILWDSSTLGAILM
                                        RRTISS SEQ ID NO: 2    Shiga toxin Subunit A   KEFTLDFSTAKTYVDSLNVIRSAIGTPLQTISSGGTSLLMI
                                        DSGTGDNLFAVDVRGIDPEEGRFNNLRLIVERNNLYVTGFV
                                        NRTNNVFYRFADFSHVTFPGTTAVTLSGDSSYTTLQRVAGI
                                        SRTGMQINRHSLTTSYLDLMSHSGTSLTQSVARAMLRFVTV
                                        TAEALRFRQIQRGFRTTLDDLSGRSYVMTAEDVDLTLNWGR
                                        LSSVLPDYHGQDSVRVGRISFGSINAILGSVALILNCHHHA
                                        SRVARMASDEFPSMCPADGRVRGITHNKILWDSSTLGAILM
                                        RRTISS
```

Sequence Listing

| ID Number | Text Description | Biological Sequence |
|---|---|---|
| SEQ ID NO: 3 | Shiga-like toxin 2 Subunit A (SLT-2A) | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFQIQRGFRPALSEASPLYTMTAQDVDLTLNWGRI SNVLPEYRGEEGVRIGRISFNSLSAILGSVAVILNCHSTGS YSVRSVSQKQKTECQIVGDRAAIKVNNVLWEANTIAALLNR KPQDLTEPNQ |
| SEQ ID NO: 4 | Protease-cleavage resistant, Shiga toxin effector polypeptide SLT-1A-FR variant 1 | NLYVTGFVNRTNNVFYRFADFSHVTFPGTTAVTLSGDSSYT TLQRVAGISRTGMQINRHSLTTSYLDLMSHSGTSLTQSVAR AMLRFVTVTAEALRFQIQRGFRTTLDDLSGRSYVMTAEDV DLTLNWGRLSSVLPDYHGQDSVRVGRISFGSINAILGSVAL ILNCHHHASRVAA |
| SEQ ID NO: 5 | Protease-cleavage resistant, Shiga toxin effector polypeptide SLT-1A-FR variant 2 | NLYVAGFINTETNIFYRFSDFSHISVPDVITVSMTTDSSYS SLQRIADLERTGMQIGRHSLVGSYLDLMEFRGRSMTRASSR AMLRFVTVIAEALRFQIQRGFRPALSEASPLYTMTAQDVD LTLNWGRISNVLPEYRGEEGVRIGRISFNSLSAILGSVAVI LNCHSTGSYSVA |
| SEQ ID NO: 6 | Protease-cleavage resistant, Shiga toxin effector polypeptide SLT-1A-FR variant 3 | NLYVTGFVNRTNNVFYRFADFSHVTFPGTTAVTLSGDSSYT TLQRVAGISRTGMQINRHSLTTSYLDLMSHSGTSLTQSVAR AMLRFVTVTAEALRFQIQRGFRTTLDDLSGRSYVMTAEDV DLTLNWGRLSSVLPDYHGQDSVRVGRISFGSINAILGSVAL ILNCHHHASAVAR |
| SEQ ID NO: 7 | Protease-cleavage resistant, Shiga toxin effector polypeptide SLT-1A-FR variant 4 | NLYVAGFINTETNIFYRFSDFSHISVPDVITVSMTTDSSYS SLQRIADLERTGMQIGRHSLVGSYLDLMEFRGRSMTRASSR AMLRFVTVIAEALRFQIQRGFRPALSEASPLYTMTAQDVD LTLNWGRISNVLPEYRGEEGVRIGRISFNSLSAILGSVAVI LNCHSTGSASVR |
| SEQ ID NO: 8 | Protease-cleavage resistant, Shiga toxin effector polypeptide SLT-1A-FR variant 5 | NLYVTGFVNRTNNVFYRFADFSHVTFPGTTAVTLSGDSSYT TLQRVAGISRTGMQINRHSLTTSYLDLMSHSGTSLTQSVAR AMLRFVTVTAEALRFQIQRGFRTTLDDLSGRSYVMTAEDV DLTLNWGRLSSVLPDYHGQDSVRVGRISFGSINAILGSVAL ILNCHHHASAVAA |
| SEQ ID NO: 9 | Protease-cleavage resistant, Shiga toxin effector polypeptide SLT-1A-FR variant 6 | NLYVAGFINTETNIFYRFSDFSHISVPDVITVSMTTDSSYS SLQRIADLERTGMQIGRHSLVGSYLDLMEFRGRSMTRASSR AMLRFVTVIAEALRFQIQRGFRPALSEASPLYTMTAQDVD LTLNWGRISNVLPEYRGEEGVRIGRISFNSLSAILGSVAVI LNCHSTGSASVA |
| SEQ ID NO: 10 | Protease-cleavage resistant, Shiga toxin effector polypeptide SLT-1A-FR variant 7 | NLYVTGFVNRTNNVFYRFADFSHVTFPGTTAVTLSGDSSYT TLQRVAGISRTGMQINRHSLTTSYLDLMSHSGTSLTQSVAR AMLRFVTVTAEALRFQIQRGFRTTLDDLSGRSYVMTAEDV DLTLNWGRLSSVLPDYHGQDSVRVGRISFGSINAILGSVAL ILNCHHHASRVAAMASDEFPSMC |
| SEQ ID NO: 11 | Protease-cleavage resistant, Shiga toxin effector polypeptide SLT-1A-FR variant 8 | NLYVAGFINTETNIFYRFSDFSHISVPDVITVSMTTDSSYS SLQRIADLERTGMQIGRHSLVGSYLDLMEFRGRSMTRASSR AMLRFVTVIAEALRFQIQRGFRPALSEASPLYTMTAQDVD LTLNWGRISNVLPEYRGEEGVRIGRISFNSLSAILGSVAVI LNCHSTGSYSVASVSQKQKTEC |
| SEQ ID NO: 12 | Protease-cleavage resistant, Shiga toxin effector polypeptide SLT-1A-FR variant 9 | NLYVTGFVNRTNNVFYRFADFSHVTFPGTTAVTLSGDSSYT TLQRVAGISRTGMQINRHSLTTSYLDLMSHSGTSLTQSVAR AMLRFVTVTAEALRFQIQRGFRTTLDDLSGRSYVMTAEDV DLTLNWGRLSSVLPDYHGQDSVRVGRISFGSINAILGSVAL ILNCHHHASAVARMASDEFPSMC |
| SEQ ID NO: 13 | Protease-cleavage resistant, Shiga toxin effector polypeptide SLT-1A-FR variant 10 | NLYVAGFINTETNIFYRFSDFSHISVPDVITVSMTTDSSYS SLQRIADLERTGMQIGRHSLVGSYLDLMEFRGRSMTRASSR AMLRFVTVIAEALRFQIQRGFRPALSEASPLYTMTAQDVD LTLNWGRISNVLPEYRGEEGVRIGRISFNSLSAILGSVAVI LNCHSTGSASVRSVSQKQKTEC |
| SEQ ID NO: 14 | Protease-cleavage resistant, Shiga toxin effector polypeptide SLT-1A-FR variant 11 | NLYVTGFVNRTNNVFYRFADFSHVTFPGTTAVTLSGDSSYT TLQRVAGISRTGMQINRHSLTTSYLDLMSHSGTSLTQSVAR AMLRFVTVTAEALRFQIQRGFRTTLDDLSGRSYVMTAEDV DLTLNWGRLSSVLPDYHGQDSVRVGRISFGSINAILGSVAL ILNCHHHASAVAAMASDEFPSMC |

| ID Number | Text Description | Biological Sequence |
|---|---|---|
| SEQ ID NO: 15 | Protease-cleavage resistant, Shiga toxin effector polypeptide SLT-1A-FR variant 12 | NLYVAGFINTETNIFYRFSDFSHISVPDVITVSMTTDSSYS SLQRIADLERTGMQIGRHSLVGSYLDLMEFRGRSMTRASSR AMLRFVTVIAEALRFRQIQRGFRPALSEASPLYTMTAQDVD LTLNWGRISNVLPEYRGEEGVRIGRISFNSLSAILGSVAVI LNCHSTGSASVASVSQKQKTEC |
| SEQ ID NO: 16 | Protease-cleavage resistant, Shiga toxin effector polypeptide SLT-1A-FR variant 13 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SRVAA |
| SEQ ID NO: 17 | Protease-cleavage resistant, Shiga toxin effector polypeptide SLT-1A-FR variant 14 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SRVAA |
| SEQ ID NO: 18 | Protease-cleavage resistant, Shiga toxin effector polypeptide SLT-1A-FR variant 15 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCHSTGS YSVR |
| SEQ ID NO: 19 | Protease-cleavage resistant, Shiga toxin effector polypeptide SLT-1A-FR variant 16 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVAR |
| SEQ ID NO: 20 | Protease-cleavage resistant, Shiga toxin effector polypeptide SLT-1A-FR variant 17 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVAR |
| SEQ ID NO: 21 | Protease-cleavage resistant, Shiga toxin effector polypeptide SLT-1A-FR variant 18 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCHSTGS ASVA |
| SEQ ID NO: 22 | Protease-cleavage resistant, Shiga toxin effector polypeptide SLT-1A-FR variant 19 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVAA |
| SEQ ID NO: 23 | Protease-cleavage resistant, Shiga toxin effector polypeptide SLT-1A-FR variant 20 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVAA |
| SEQ ID NO: 24 | Protease-cleavage resistant, Shiga toxin effector polypeptide SLT-1A-FR variant 21 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV |

| Sequence Listing | | |
|---|---|---|
| ID Number | Text Description | Biological Sequence |
| | | IAEALRFRQIQRGFRPALSEASPLYTMTAQDVDLTLNWGRI SNVLPEYRGEEGVRIGRISFNSLSAILGSVAVILNCHSTGS ASVA |
| SEQ ID NO: 25 | Protease-cleavage resistant, Shiga toxin effector polypeptide SLT-1A-FR variant 22 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SRVAAMASDEFPSMC |
| SEQ ID NO: 26 | Protease-cleavage resistant, Shiga toxin effector polypeptide SLT-1A-FR variant 23 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SRVAAMASDEFPSMC |
| SEQ ID NO: 27 | Protease-cleavage resistant, Shiga toxin effector polypeptide SLT-1A-FR variant 24 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCHSTGS YSVASVSQKQKTEC |
| SEQ ID NO: 28 | Protease-cleavage resistant, Shiga toxin effector polypeptide SLT-1A-FR variant 25 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVARMASDEFPSMC |
| SEQ ID NO: 29 | Protease-cleavage resistant, Shiga toxin effector polypeptide SLT-1A-FR variant 26 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVARMASDEFPSMC |
| SEQ ID NO: 30 | Protease-cleavage resistant, Shiga toxin effector polypeptide SLT-1A-FR variant 27 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCHSTGS ASVRSVSQKQKTEC |
| SEQ ID NO: 31 | Protease-cleavage resistant, Shiga toxin effector polypeptide SLT-1A-FR variant 28 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVAAMASDEFPSMC |
| SEQ ID NO: 32 | Protease-cleavage resistant, Shiga toxin effector polypeptide SLT-1A-FR variant 29 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SAVAAMASDEFPSMC |
| SEQ ID NO: 33 | Protease-cleavage resistant, Shiga toxin effector polypeptide SLT-1A-FR variant 30 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCHSTGS ASVASVSQKQKTEC |

Sequence Listing

| ID Number | Text Description | Biological Sequence |
|---|---|---|
| SEQ ID NO: 34 | Protease-cleavage resistant, Shiga toxin effector polypeptide SLT-1A-FR variant 31 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SMASDEFPSMC |
| SEQ ID NO: 35 | Protease-cleavage resistant, Shiga toxin effector polypeptide SLT-1A-FR variant 32 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA SMASDEFPSMC |
| SEQ ID NO: 36 | Protease-cleavage resistant, Shiga toxin effector polypeptide SLT-1A-FR variant 33 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCHSTGS SVSQKQKTEC |
| SEQ ID NO: 37 | Protease-cleavage resistant, Shiga toxin effector polypeptide SLT-1A-FR variant 34 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA S |
| SEQ ID NO: 38 | Protease-cleavage resistant, Shiga toxin effector polypeptide SLT-1A-FR variant 35 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCHHHA S |
| SEQ ID NO: 39 | Protease-cleavage resistant, Shiga toxin effector polypeptide SLT-1A-FR variant 36 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCHSTGS |
| SEQ ID NO: 40 | Protease-cleavage resistant, Shiga toxin effector polypeptide SLT-1A-FR variant 37 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCH |
| SEQ ID NO: 41 | Protease-cleavage resistant, Shiga toxin effector polypeptide SLT-1A-FR variant 38 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNCH |
| SEQ ID NO: 42 | Protease-cleavage resistant, Shiga toxin effector polypeptide SLT-1A-FR variant 39 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILNCH |
| SEQ ID NO: 43 | Protease-cleavage resistant, Shiga toxin effector polypeptide SLT-1A-FR variant 40 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILN |

| ID Number | Text Description | Biological Sequence |
|---|---|---|
| SEQ ID NO: 44 | Protease-cleavage resistant, Shiga toxin effector polypeptide SLT-1A-FR variant 41 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILN |
| SEQ ID NO: 45 | Protease-cleavage resistant, Shiga toxin effector polypeptide SLT-1A-FR variant 42 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVILN |
| SEQ ID NO: 46 | Protease-cleavage resistant, Shiga toxin effector polypeptide SLT-1A-FR variant 43 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALIL |
| SEQ ID NO: 47 | Protease-cleavage resistant, Shiga toxin effector polypeptide SLT-1A-FR variant 44 | KEFTLDFSTAKTYVDSLNVIRSAIGTPLQTISSGGTSLLMI DSGTGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALIL |
| SEQ ID NO: 48 | Protease-cleavage resistant, Shiga toxin effector polypeptide SLT-1A-FR variant 45 | DEFTVDFSSQKSYVDSLNSIRSAISTPLGNISQGGVSVSVI NHVLGGNYISLNVRGLDPYSERFNHLRLIMERNNLYVAGFI NTETNIFYRFSDFSHISVPDVITVSMTTDSSYSSLQRIADL ERTGMQIGRHSLVGSYLDLMEFRGRSMTRASSRAMLRFVTV IAEALRFRQIQRGFRPALSEASPLYTMTAQDVDLTLNWGRI SNVLPEYRGEEGVRIGRISFNSLSAILGSVAVIL |
| SEQ ID NO: 49 | Protease-cleavage resistant, Shiga toxin effector polypeptide SLT-1A-FR variant 46 | KEFTLDFSTAKTYVDSLNVIRSAIGTPLQTISSGGTSLLMI DSGSGDNLFAVDVRGIDPEEGRFNNLRLIVERNNLYVTGFV NRTNNVFYRFADFSHVTFPGTTAVTLSGDSSYTTLQRVAGI SRTGMQINRHSLTTSYLDLMSHSGTSLTQSVARAMLRFVTV TAEALRFRQIQRGFRTTLDDLSGRSYVMTAEDVDLTLNWGR LSSVLPDYHGQDSVRVGRISFGSINAILGSVALILNPADGR VRGITHNKILWDSSTLGAILMRRTISS |
| SEQ ID NO: 50 | Cytotoxic, Cell-Targeted Molecule: αCD20::SLT-1A-FR variant #1 | MKEFTLDFSTAKTYVDSLNVIRSAIGTPLQTISSGGTSLLM IDSGSGDNLFAVDVRGIDPEEGRFNNLRLIVERNNLYVTGF VNRTNNVFYRFADFSHVTFPGTTAVTLSGDSSYTTLQRVAG ISRTGMQINRHSLTTSYLDLMSHSGTSLTQSVARAMLRFVT VTAEALRFRQIQRGFRTTLDDLSGRSYVMTAEDVDLTLNWG RLSSVLPDYHGQDSVRVGRISFGSINAILGSVALILNCHHH ASAVAAEFPKPSTPPGSSGGAPMQVLQQPGAELVKPGASV KMSCKTSGYTFTSYNVHWVKQTPGQGLEWIGAIYPGNGDTS FNQKFKGKATLTADKSSSTVYMQLSSLTSEDSAVYYCARSN YYGSSYVWFFDVWGAGTTVTVSSGSTSGSGKPGSGEGSQIV LSQSPTILSASPGEKVTMTCRASSSVSYMDWYQQKPGSSPK PWIYATSNLASGVPARFSGSGSGTSYSLTISRVEAEDAATY YCQQWISNPPTFGAGTKLELK |
| SEQ ID NO: 51 | Cytotoxic, Cell-Targeted Molecule: αCD20::SLT-1A-FR variant #2 | MKEFTLDFSTAKTYVDSLNVIRSAIGTPLQTISSGGTSLLM IDSGSGDNLFAVDVRGIDPEEGRFNNLRLIVERNNLYVTGF VNRTNNVFYRFADFSHVTFPGTTAVTLSGDSSYTTLQRVAG ISRTGMQINRHSLTTSYLDLMSHSGTSLTQSVARAMLRFVT VTAEALRFRQIQRGFRTTLDDLSGRSYVMTAEDVDLTLNWG RLSSVLPDYHGQDSVRVGRISFGSINAILGSVALILNCHHH ASAVAAGGGGSGGMQVQLVQSGAELVKPGASVKMSCKASGY TFTSYNMHWVKQTPGQGLEWIGAIYPGNGDTSYNQKFKGKA TLTADKSSSTAYMQLSSLTSEDSAVYYCARAQLRPNYWYFD VWGAGTTVTVSSGGGGSGGGGSGGGGSGGGGSGGGGSDIVL SQSPAILSASPGEKVTMTCRASSSVSYMHWYQQKPGSSPKP WIYATSNLASGVPARFSGSGSGTSYSLTISRVEAEDAATYY CQQWISNPPTFGAGTKLELK |

Sequence Listing

| ID Number | Text Description | Biological Sequence |
|---|---|---|
| SEQ ID NO: 52 | Cytotoxic, Cell-Targeted Molecule: αCD20::SLT-1A-FR variant #3 | MKEFTLDFSTAKTYVDSLNVIRSAIGTPLQTISSGGTSLLM I

| Sequence Listing | | |
|---|---|---|
| ID Number | Text Description | Biological Sequence |
| SEQ ID NO: 58 | Cytotoxic, Cell-Targeted Molecule: SLT-1A-FR::αHER2scFv variant 1 | MKEFTLDFSTAKTYVDSLNVIRSAIG

```
                35                  40                  45
Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
                260                 265                 270

Asn Lys Ile Leu Trp Asp Ser Ser Thr Leu Gly Ala Ile Leu Met Arg
                275                 280                 285

Arg Thr Ile Ser Ser
    290

<210> SEQ ID NO 2
<211> LENGTH: 293
<212> TYPE: PRT
<213> ORGANISM: Shigella dysenteriae

<400> SEQUENCE: 2

Lys Glu Phe Thr Leu Asp Phe Ser Thr Ala Lys Thr Tyr Val Asp Ser
 1                5                  10                  15

Leu Asn Val Ile Arg Ser Ala Ile Gly Thr Pro Leu Gln Thr Ile Ser
                 20                  25                  30

Ser Gly Gly Thr Ser Leu Leu Met Ile Asp Ser Gly Thr Gly Asp Asn
                 35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110
```

```
Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290

<210> SEQ ID NO 3
<211> LENGTH: 297
<212> TYPE: PRT
<213> ORGANISM: Escherichia coli

<400> SEQUENCE: 3

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190
```

Ala Gln Asp Val Asp Leu Thr Leu Asn Trp Gly Arg Ile Ser Asn Val
    195                 200                 205

Leu Pro Glu Tyr Arg Gly Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285

Pro Gln Asp Leu Thr Glu Pro Asn Gln
    290                 295

<210> SEQ ID NO 4
<211> LENGTH: 177
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Asn Leu Tyr Val Thr Gly Phe Val Asn Arg Thr Asn Asn Val Phe Tyr
1               5                   10                  15

Arg Phe Ala Asp Phe Ser His Val Thr Phe Pro Gly Thr Thr Ala Val
            20                  25                  30

Thr Leu Ser Gly Asp Ser Ser Tyr Thr Thr Leu Gln Arg Val Ala Gly
        35                  40                  45

Ile Ser Arg Thr Gly Met Gln Ile Asn Arg His Ser Leu Thr Thr Ser
    50                  55                  60

Tyr Leu Asp Leu Met Ser His Ser Gly Thr Ser Leu Thr Gln Ser Val
65                  70                  75                  80

Ala Arg Ala Met Leu Arg Phe Val Thr Val Thr Ala Glu Ala Leu Arg
                85                  90                  95

Phe Arg Gln Ile Gln Arg Gly Phe Arg Thr Thr Leu Asp Asp Leu Ser
            100                 105                 110

Gly Arg Ser Tyr Val Met Thr Ala Glu Asp Val Asp Leu Thr Leu Asn
        115                 120                 125

Trp Gly Arg Leu Ser Ser Val Leu Pro Asp Tyr His Gly Gln Asp Ser
    130                 135                 140

Val Arg Val Gly Arg Ile Ser Phe Gly Ser Ile Asn Ala Ile Leu Gly
145                 150                 155                 160

Ser Val Ala Leu Ile Leu Asn Cys His His His Ala Ser Arg Val Ala
                165                 170                 175

Ala

<210> SEQ ID NO 5
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 5

Asn Leu Tyr Val Ala Gly Phe Ile Asn Thr Glu Thr Asn Ile Phe Tyr
1               5                   10                  15

Arg Phe Ser Asp Phe Ser His Ile Ser Val Pro Asp Val Ile Thr Val
            20                  25                  30

Ser Met Thr Thr Asp Ser Ser Tyr Ser Ser Leu Gln Arg Ile Ala Asp
        35                  40                  45

Leu Glu Arg Thr Gly Met Gln Ile Gly Arg His Ser Leu Val Gly Ser
    50                  55                  60

Tyr Leu Asp Leu Met Glu Phe Arg Gly Arg Ser Met Thr Arg Ala Ser
65                  70                  75                  80

Ser Arg Ala Met Leu Arg Phe Val Thr Val Ile Ala Glu Ala Leu Arg
                85                  90                  95

Phe Arg Gln Ile Gln Arg Gly Phe Arg Pro Ala Leu Ser Glu Ala Ser
                100                 105                 110

Pro Leu Tyr Thr Met Thr Ala Gln Asp Val Asp Leu Thr Leu Asn Trp
            115                 120                 125

Gly Arg Ile Ser Asn Val Leu Pro Glu Tyr Arg Gly Glu Glu Gly Val
        130                 135                 140

Arg Ile Gly Arg Ile Ser Phe Asn Ser Leu Ser Ala Ile Leu Gly Ser
145                 150                 155                 160

Val Ala Val Ile Leu Asn Cys His Ser Thr Gly Ser Tyr Ser Val Ala
                165                 170                 175

<210> SEQ ID NO 6
<211> LENGTH: 177
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Asn Leu Tyr Val Thr Gly Phe Val Asn Arg Thr Asn Asn Val Phe Tyr
1               5                   10                  15

Arg Phe Ala Asp Phe Ser His Val Thr Phe Pro Gly Thr Thr Ala Val
            20                  25                  30

Thr Leu Ser Gly Asp Ser Ser Tyr Thr Thr Leu Gln Arg Val Ala Gly
        35                  40                  45

Ile Ser Arg Thr Gly Met Gln Ile Asn Arg His Ser Leu Thr Thr Ser
    50                  55                  60

Tyr Leu Asp Leu Met Ser His Ser Gly Thr Ser Leu Thr Gln Ser Val
65                  70                  75                  80

Ala Arg Ala Met Leu Arg Phe Val Thr Val Thr Ala Glu Ala Leu Arg
                85                  90                  95

Phe Arg Gln Ile Gln Arg Gly Phe Arg Thr Thr Leu Asp Asp Leu Ser
                100                 105                 110

Gly Arg Ser Tyr Val Met Thr Ala Glu Asp Val Asp Leu Thr Leu Asn
            115                 120                 125

Trp Gly Arg Leu Ser Ser Val Leu Pro Asp Tyr His Gly Gln Asp Ser
        130                 135                 140

Val Arg Val Gly Arg Ile Ser Phe Gly Ser Ile Asn Ala Ile Leu Gly
145                 150                 155                 160

Ser Val Ala Leu Ile Leu Asn Cys His His Ala Ser Ala Val Ala
                165                 170                 175
```

Arg

<210> SEQ ID NO 7
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Asn Leu Tyr Val Ala Gly Phe Ile Asn Thr Glu Thr Asn Ile Phe Tyr
1               5                   10                  15

Arg Phe Ser Asp Phe Ser His Ile Ser Val Pro Asp Val Ile Thr Val
                20                  25                  30

Ser Met Thr Thr Asp Ser Ser Tyr Ser Ser Leu Gln Arg Ile Ala Asp
            35                  40                  45

Leu Glu Arg Thr Gly Met Gln Ile Gly Arg His Ser Leu Val Gly Ser
        50                  55                  60

Tyr Leu Asp Leu Met Glu Phe Arg Gly Arg Ser Met Thr Arg Ala Ser
65                  70                  75                  80

Ser Arg Ala Met Leu Arg Phe Val Thr Val Ile Ala Glu Ala Leu Arg
                85                  90                  95

Phe Arg Gln Ile Gln Arg Gly Phe Arg Pro Ala Leu Ser Glu Ala Ser
            100                 105                 110

Pro Leu Tyr Thr Met Thr Ala Gln Asp Val Asp Leu Thr Leu Asn Trp
        115                 120                 125

Gly Arg Ile Ser Asn Val Leu Pro Glu Tyr Arg Gly Glu Glu Gly Val
    130                 135                 140

Arg Ile Gly Arg Ile Ser Phe Asn Ser Leu Ser Ala Ile Leu Gly Ser
145                 150                 155                 160

Val Ala Val Ile Leu Asn Cys His Ser Thr Gly Ser Ala Ser Val Arg
                165                 170                 175
```

<210> SEQ ID NO 8
<211> LENGTH: 177
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Asn Leu Tyr Val Thr Gly Phe Val Asn Arg Thr Asn Asn Val Phe Tyr
1               5                   10                  15

Arg Phe Ala Asp Phe Ser His Val Thr Phe Pro Gly Thr Thr Ala Val
                20                  25                  30

Thr Leu Ser Gly Asp Ser Ser Tyr Thr Thr Leu Gln Arg Val Ala Gly
            35                  40                  45

Ile Ser Arg Thr Gly Met Gln Ile Asn Arg His Ser Leu Thr Thr Ser
        50                  55                  60

Tyr Leu Asp Leu Met Ser His Ser Gly Thr Ser Leu Thr Gln Ser Val
65                  70                  75                  80

Ala Arg Ala Met Leu Arg Phe Val Thr Val Thr Ala Glu Ala Leu Arg
                85                  90                  95

Phe Arg Gln Ile Gln Arg Gly Phe Arg Thr Thr Leu Asp Asp Leu Ser
```

```
            100                 105                 110
Gly Arg Ser Tyr Val Met Thr Ala Glu Asp Val Asp Leu Thr Leu Asn
            115                 120                 125

Trp Gly Arg Leu Ser Ser Val Leu Pro Asp Tyr His Gly Gln Asp Ser
        130                 135                 140

Val Arg Val Gly Arg Ile Ser Phe Gly Ser Ile Asn Ala Ile Leu Gly
145                 150                 155                 160

Ser Val Ala Leu Ile Leu Asn Cys His His His Ala Ser Ala Val Ala
                165                 170                 175

Ala
```

<210> SEQ ID NO 9
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Asn Leu Tyr Val Ala Gly Phe Ile Asn Thr Glu Thr Asn Ile Phe Tyr
1               5                   10                  15

Arg Phe Ser Asp Phe Ser His Ile Ser Val Pro Asp Val Ile Thr Val
            20                  25                  30

Ser Met Thr Thr Asp Ser Ser Tyr Ser Ser Leu Gln Arg Ile Ala Asp
        35                  40                  45

Leu Glu Arg Thr Gly Met Gln Ile Gly Arg His Ser Leu Val Gly Ser
    50                  55                  60

Tyr Leu Asp Leu Met Glu Phe Arg Gly Arg Ser Met Thr Arg Ala Ser
65                  70                  75                  80

Ser Arg Ala Met Leu Arg Phe Val Thr Val Ile Ala Glu Ala Leu Arg
                85                  90                  95

Phe Arg Gln Ile Gln Arg Gly Phe Arg Pro Ala Leu Ser Glu Ala Ser
            100                 105                 110

Pro Leu Tyr Thr Met Thr Ala Gln Asp Val Asp Leu Thr Leu Asn Trp
        115                 120                 125

Gly Arg Ile Ser Asn Val Leu Pro Glu Tyr Arg Gly Glu Glu Gly Val
    130                 135                 140

Arg Ile Gly Arg Ile Ser Phe Asn Ser Leu Ser Ala Ile Leu Gly Ser
145                 150                 155                 160

Val Ala Val Ile Leu Asn Cys His Ser Thr Gly Ser Ala Ser Val Ala
                165                 170                 175
```

<210> SEQ ID NO 10
<211> LENGTH: 187
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Asn Leu Tyr Val Thr Gly Phe Val Asn Arg Thr Asn Asn Val Phe Tyr
1               5                   10                  15

Arg Phe Ala Asp Phe Ser His Val Thr Phe Pro Gly Thr Thr Ala Val
            20                  25                  30
```

Thr Leu Ser Gly Asp Ser Ser Tyr Thr Thr Leu Gln Arg Val Ala Gly
            35                  40                  45

Ile Ser Arg Thr Gly Met Gln Ile Asn Arg His Ser Leu Thr Thr Ser
 50                  55                  60

Tyr Leu Asp Leu Met Ser His Ser Gly Thr Ser Leu Thr Gln Ser Val
 65                  70                  75                  80

Ala Arg Ala Met Leu Arg Phe Val Thr Val Thr Ala Glu Ala Leu Arg
                 85                  90                  95

Phe Arg Gln Ile Gln Arg Gly Phe Arg Thr Thr Leu Asp Asp Leu Ser
                100                 105                 110

Gly Arg Ser Tyr Val Met Thr Ala Glu Asp Val Asp Leu Thr Leu Asn
            115                 120                 125

Trp Gly Arg Leu Ser Ser Val Leu Pro Asp Tyr His Gly Gln Asp Ser
130                 135                 140

Val Arg Val Gly Arg Ile Ser Phe Gly Ser Ile Asn Ala Ile Leu Gly
145                 150                 155                 160

Ser Val Ala Leu Ile Leu Asn Cys His His Ala Ser Arg Val Ala
                165                 170                 175

Ala Met Ala Ser Asp Glu Phe Pro Ser Met Cys
            180                 185

<210> SEQ ID NO 11
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asn Leu Tyr Val Ala Gly Phe Ile Asn Thr Glu Thr Asn Ile Phe Tyr
 1               5                  10                  15

Arg Phe Ser Asp Phe Ser His Ile Ser Val Pro Asp Val Ile Thr Val
                 20                  25                  30

Ser Met Thr Thr Asp Ser Ser Tyr Ser Ser Leu Gln Arg Ile Ala Asp
            35                  40                  45

Leu Glu Arg Thr Gly Met Gln Ile Gly Arg His Ser Leu Val Gly Ser
 50                  55                  60

Tyr Leu Asp Leu Met Glu Phe Arg Gly Arg Ser Met Thr Arg Ala Ser
 65                  70                  75                  80

Ser Arg Ala Met Leu Arg Phe Val Thr Val Ile Ala Glu Ala Leu Arg
                 85                  90                  95

Phe Arg Gln Ile Gln Arg Gly Phe Arg Pro Ala Leu Ser Glu Ala Ser
                100                 105                 110

Pro Leu Tyr Thr Met Thr Ala Gln Asp Val Asp Leu Thr Leu Asn Trp
            115                 120                 125

Gly Arg Ile Ser Asn Val Leu Pro Glu Tyr Arg Gly Glu Glu Gly Val
130                 135                 140

Arg Ile Gly Arg Ile Ser Phe Asn Ser Leu Ser Ala Ile Leu Gly Ser
145                 150                 155                 160

Val Ala Val Ile Leu Asn Cys His Ser Thr Gly Ser Tyr Ser Val Ala
                165                 170                 175

Ser Val Ser Gln Lys Gln Lys Thr Glu Cys
            180                 185

```
<210> SEQ ID NO 12
<211> LENGTH: 187
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asn Leu Tyr Val Thr Gly Phe Val Asn Arg Thr Asn Asn Val Phe Tyr
1               5                   10                  15

Arg Phe Ala Asp Phe Ser His Val Thr Phe Pro Gly Thr Thr Ala Val
            20                  25                  30

Thr Leu Ser Gly Asp Ser Ser Tyr Thr Thr Leu Gln Arg Val Ala Gly
        35                  40                  45

Ile Ser Arg Thr Gly Met Gln Ile Asn Arg His Ser Leu Thr Thr Ser
    50                  55                  60

Tyr Leu Asp Leu Met Ser His Ser Gly Thr Ser Leu Thr Gln Ser Val
65                  70                  75                  80

Ala Arg Ala Met Leu Arg Phe Val Thr Val Thr Ala Glu Ala Leu Arg
                85                  90                  95

Phe Arg Gln Ile Gln Arg Gly Phe Arg Thr Thr Leu Asp Asp Leu Ser
            100                 105                 110

Gly Arg Ser Tyr Val Met Thr Ala Glu Asp Val Asp Leu Thr Leu Asn
        115                 120                 125

Trp Gly Arg Leu Ser Ser Val Leu Pro Asp Tyr His Gly Gln Asp Ser
    130                 135                 140

Val Arg Val Gly Arg Ile Ser Phe Gly Ser Ile Asn Ala Ile Leu Gly
145                 150                 155                 160

Ser Val Ala Leu Ile Leu Asn Cys His His Ala Ser Ala Val Ala
                165                 170                 175

Arg Met Ala Ser Asp Glu Phe Pro Ser Met Cys
            180                 185

<210> SEQ ID NO 13
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asn Leu Tyr Val Ala Gly Phe Ile Asn Thr Glu Thr Asn Ile Phe Tyr
1               5                   10                  15

Arg Phe Ser Asp Phe Ser His Ile Ser Val Pro Asp Val Ile Thr Val
            20                  25                  30

Ser Met Thr Thr Asp Ser Ser Tyr Ser Ser Leu Gln Arg Ile Ala Asp
        35                  40                  45

Leu Glu Arg Thr Gly Met Gln Ile Gly Arg His Ser Leu Val Gly Ser
    50                  55                  60

Tyr Leu Asp Leu Met Glu Phe Arg Gly Arg Ser Met Thr Arg Ala Ser
65                  70                  75                  80

Ser Arg Ala Met Leu Arg Phe Val Thr Val Ile Ala Glu Ala Leu Arg
                85                  90                  95

Phe Arg Gln Ile Gln Arg Gly Phe Arg Pro Ala Leu Ser Glu Ala Ser
            100                 105                 110
```

```
Pro Leu Tyr Thr Met Thr Ala Gln Asp Val Asp Leu Thr Leu Asn Trp
        115                 120                 125

Gly Arg Ile Ser Asn Val Leu Pro Glu Tyr Arg Gly Glu Glu Gly Val
        130                 135                 140

Arg Ile Gly Arg Ile Ser Phe Asn Ser Leu Ser Ala Ile Leu Gly Ser
145                 150                 155                 160

Val Ala Val Ile Leu Asn Cys His Ser Thr Gly Ser Ala Ser Val Arg
                165                 170                 175

Ser Val Ser Gln Lys Gln Lys Thr Glu Cys
        180                 185

<210> SEQ ID NO 14
<211> LENGTH: 187
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asn Leu Tyr Val Thr Gly Phe Val Asn Arg Thr Asn Asn Val Phe Tyr
1               5                   10                  15

Arg Phe Ala Asp Phe Ser His Val Thr Phe Pro Gly Thr Thr Ala Val
                20                  25                  30

Thr Leu Ser Gly Asp Ser Ser Tyr Thr Thr Leu Gln Arg Val Ala Gly
            35                  40                  45

Ile Ser Arg Thr Gly Met Gln Ile Asn Arg His Ser Leu Thr Thr Ser
50                  55                  60

Tyr Leu Asp Leu Met Ser His Ser Gly Thr Ser Leu Thr Gln Ser Val
65                  70                  75                  80

Ala Arg Ala Met Leu Arg Phe Val Thr Val Thr Ala Glu Ala Leu Arg
                85                  90                  95

Phe Arg Gln Ile Gln Arg Gly Phe Arg Thr Thr Leu Asp Asp Leu Ser
                100                 105                 110

Gly Arg Ser Tyr Val Met Thr Ala Glu Asp Val Asp Leu Thr Leu Asn
            115                 120                 125

Trp Gly Arg Leu Ser Ser Val Leu Pro Asp Tyr His Gly Gln Asp Ser
        130                 135                 140

Val Arg Val Gly Arg Ile Ser Phe Gly Ser Ile Asn Ala Ile Leu Gly
145                 150                 155                 160

Ser Val Ala Leu Ile Leu Asn Cys His His Ala Ser Ala Val Ala
                165                 170                 175

Ala Met Ala Ser Asp Glu Phe Pro Ser Met Cys
        180                 185

<210> SEQ ID NO 15
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asn Leu Tyr Val Ala Gly Phe Ile Asn Thr Glu Thr Asn Ile Phe Tyr
1               5                   10                  15
```

```
Arg Phe Ser Asp Phe Ser His Ile Ser Val Pro Asp Val Ile Thr Val
                20                  25                  30

Ser Met Thr Thr Asp Ser Ser Tyr Ser Ser Leu Gln Arg Ile Ala Asp
            35                  40                  45

Leu Glu Arg Thr Gly Met Gln Ile Gly Arg His Ser Leu Val Gly Ser
    50                  55                  60

Tyr Leu Asp Leu Met Glu Phe Arg Gly Arg Ser Met Thr Arg Ala Ser
65                  70                  75                  80

Ser Arg Ala Met Leu Arg Phe Val Thr Val Ile Ala Glu Ala Leu Arg
                85                  90                  95

Phe Arg Gln Ile Gln Arg Gly Phe Arg Pro Ala Leu Ser Glu Ala Ser
            100                 105                 110

Pro Leu Tyr Thr Met Thr Ala Gln Asp Val Asp Leu Thr Leu Asn Trp
        115                 120                 125

Gly Arg Ile Ser Asn Val Leu Pro Glu Tyr Arg Gly Glu Glu Gly Val
    130                 135                 140

Arg Ile Gly Arg Ile Ser Phe Asn Ser Leu Ser Ala Ile Leu Gly Ser
145                 150                 155                 160

Val Ala Val Ile Leu Asn Cys His Ser Thr Gly Ser Ala Ser Val Ala
                165                 170                 175

Ser Val Ser Gln Lys Gln Lys Thr Glu Cys
            180                 185

<210> SEQ ID NO 16
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
```

180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Ala
                245                 250

<210> SEQ ID NO 17
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Ala
                245                 250

<210> SEQ ID NO 18
<211> LENGTH: 250
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 18
```

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg
                245                 250

```
<210> SEQ ID NO 19
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

```
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Arg
                245                 250

<210> SEQ ID NO 20
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Lys Glu Phe Thr Leu Asp Phe Ser Thr Ala Lys Thr Tyr Val Asp Ser
  1               5                  10                  15

Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Thr Gly Asp Asn
         35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
```

```
                  165                 170                 175
Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Arg
                245                 250

<210> SEQ ID NO 21
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Glu Phe Thr Val Asp Phe Ser Ser Gln Lys Ser Tyr Val Asp Ser
1               5                  10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Ala Ser Val Ala
                245                 250

<210> SEQ ID NO 22
```

```
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

```
<210> SEQ ID NO 23
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23
```

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

```
Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala
                245                 250

<210> SEQ ID NO 24
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Glu Phe Thr Val Asp Phe Ser Ser Gln Lys Ser Tyr Val Asp Ser
 1                   5                  10                  15

Leu Asn Ser Ile Arg Ser Ala Ile Ser Thr Pro Leu Gly Asn Ile Ser
                 20                  25                  30

Gln Gly Gly Val Ser Val Ser Val Ile Asn His Val Leu Gly Gly Asn
            35                  40                  45

Tyr Ile Ser Leu Asn Val Arg Gly Leu Asp Pro Tyr Ser Glu Arg Phe
 50                  55                  60

Asn His Leu Arg Leu Ile Met Glu Arg Asn Asn Leu Tyr Val Ala Gly
 65                  70                  75                  80

Phe Ile Asn Thr Glu Thr Asn Ile Phe Tyr Arg Phe Ser Asp Phe Ser
                 85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
130                 135                 140

Phe Arg Gly Arg Ser Met Thr Arg Ala Ser Ser Arg Ala Met Leu Arg
```

```
                145                 150                 155                 160
        Phe Val Thr Val Ile Ala Glu Ala Leu Arg Phe Arg Gln Ile Gln Arg
                        165                 170                 175

Gly Phe Arg Pro Ala Leu Ser Glu Ala Ser Pro Leu Tyr Thr Met Thr
                        180                 185                 190

Ala Gln Asp Val Asp Leu Thr Leu Asn Trp Gly Arg Ile Ser Asn Val
                        195                 200                 205

Leu Pro Glu Tyr Arg Gly Glu Glu Gly Val Arg Ile Gly Arg Ile Ser
                210                 215                 220

Phe Asn Ser Leu Ser Ala Ile Leu Gly Ser Val Ala Val Ile Leu Asn
        225                 230                 235                 240

Cys His Ser Thr Gly Ser Ala Ser Val Ala
                        245                 250

<210> SEQ ID NO 25
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Ala Met Ala Ser Asp Glu
                245                 250                 255
```

Phe Pro Ser Met Cys
        260

<210> SEQ ID NO 26
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Ala Met Ala Ser Asp Glu
                245                 250                 255

Phe Pro Ser Met Cys
        260

<210> SEQ ID NO 27
<211> LENGTH: 260
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

-continued

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
    195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Ala Ser Val Ser Gln Lys Gln
                245                 250                 255

Lys Thr Glu Cys
            260

<210> SEQ ID NO 28
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser

```
                85                  90                  95
His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Arg Met Ala Ser Asp Glu
                245                 250                 255

Phe Pro Ser Met Cys
            260

<210> SEQ ID NO 29
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175
```

```
Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Arg Met Ala Ser Asp Glu
                245                 250                 255

Phe Pro Ser Met Cys
            260

<210> SEQ ID NO 30
<211> LENGTH: 260
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Ile Asn His Val Leu Gly Gly Asn
            35                  40                  45

Tyr Ile Ser Leu Asn Val Arg Gly Leu Asp Pro Tyr Ser Glu Arg Phe
50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
            85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
            130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
            165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
            195                 200                 205

Leu Pro Glu Tyr Arg Gly Glu Glu Gly Val Arg Ile Gly Arg Ile Ser
            210                 215                 220

Phe Asn Ser Leu Ser Ala Ile Leu Gly Ser Val Ala Val Ile Leu Asn
225                 230                 235                 240

Cys His Ser Thr Gly Ser Ala Ser Val Arg Ser Val Ser Gln Lys Gln
            245                 250                 255
```

```
Lys Thr Glu Cys
            260

<210> SEQ ID NO 31
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Ala Val Ala Ala Met Ala Ser Asp Glu
                245                 250                 255

Phe Pro Ser Met Cys
            260

<210> SEQ ID NO 32
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Lys Glu Phe Thr Leu Asp Phe Ser Thr Ala Lys Thr Tyr Val Asp Ser
```

```
              1               5                  10                 15
           Leu Asn Val Ile Arg Ser Ala Ile Gly Thr Pro Leu Gln Thr Ile Ser
                          20                  25                 30
           Ser Gly Gly Thr Ser Leu Leu Met Ile Asp Ser Gly Thr Gly Asp Asn
                          35                  40                 45
           Leu Phe Ala Val Asp Val Arg Gly Ile Asp Pro Glu Glu Gly Arg Phe
                          50                  55                 60
           Asn Asn Leu Arg Leu Ile Val Glu Arg Asn Asn Leu Tyr Val Thr Gly
           65                      70                  75                 80
           Phe Val Asn Arg Thr Asn Asn Val Phe Tyr Arg Phe Ala Asp Phe Ser
                          85                  90                 95
           His Val Thr Phe Pro Gly Thr Thr Ala Val Thr Leu Ser Gly Asp Ser
                         100                 105                110
           Ser Tyr Thr Thr Leu Gln Arg Val Ala Gly Ile Ser Arg Thr Gly Met
                         115                 120                125
           Gln Ile Asn Arg His Ser Leu Thr Thr Ser Tyr Leu Asp Leu Met Ser
                         130                 135                140
           His Ser Gly Thr Ser Leu Thr Gln Ser Val Ala Arg Ala Met Leu Arg
           145                    150                 155                160
           Phe Val Thr Val Thr Ala Glu Ala Leu Arg Phe Arg Gln Ile Gln Arg
                         165                 170                175
           Gly Phe Arg Thr Thr Leu Asp Asp Leu Ser Gly Arg Ser Tyr Val Met
                         180                 185                190
           Thr Ala Glu Asp Val Asp Leu Thr Leu Asn Trp Gly Arg Leu Ser Ser
                         195                 200                205
           Val Leu Pro Asp Tyr His Gly Gln Asp Ser Val Arg Val Gly Arg Ile
                         210                 215                220
           Ser Phe Gly Ser Ile Asn Ala Ile Leu Gly Ser Val Ala Leu Ile Leu
           225                    230                 235                240
           Asn Cys His His His Ala Ser Ala Val Ala Ala Met Ala Ser Asp Glu
                         245                 250                255
           Phe Pro Ser Met Cys
                         260

<210> SEQ ID NO 33
<211> LENGTH: 260
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Glu Phe Thr Val Asp Phe Ser Ser Gln Lys Ser Tyr Val Asp Ser
1               5                  10                 15
Leu Asn Ser Ile Arg Ser Ala Ile Ser Thr Pro Leu Gly Asn Ile Ser
               20                  25                 30
Gln Gly Gly Val Ser Val Ser Val Ile Asn His Val Leu Gly Gly Asn
               35                  40                 45
Tyr Ile Ser Leu Asn Val Arg Gly Leu Asp Pro Tyr Ser Glu Arg Phe
               50                  55                 60
Asn His Leu Arg Leu Ile Met Glu Arg Asn Asn Leu Tyr Val Ala Gly
65                     70                  75                 80
Phe Ile Asn Thr Glu Thr Asn Ile Phe Tyr Arg Phe Ser Asp Phe Ser
               85                  90                 95
```

-continued

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
        130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
210                 215                 220

Phe Asn Ser Leu Ser Ala Ile Leu Gly Ser Val Ala Val Ile Leu Asn
225                 230                 235                 240

Cys His Ser Thr Gly Ser Ala Ser Val Ala Ser Val Ser Gln Lys Gln
                245                 250                 255

Lys Thr Glu Cys
            260

<210> SEQ ID NO 34
<211> LENGTH: 257
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 34

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

-continued

```
Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Met Ala Ser Asp Glu Phe Pro Ser Met
                245                 250                 255

Cys

<210> SEQ ID NO 35
<211> LENGTH: 257
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Met Ala Ser Asp Glu Phe Pro Ser Met
                245                 250                 255

Cys
```

```
<210> SEQ ID NO 36
<211> LENGTH: 256
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Ser Val Ser Gln Lys Gln Lys Thr Glu Cys
                245                 250                 255

<210> SEQ ID NO 37
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
```

```
                    35                  40                  45
Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser
                245

<210> SEQ ID NO 38
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
                 20                  25                  30

Ser Gly Gly Thr Ser Leu Leu Met Ile Asp Ser Gly Thr Gly Asp Asn
                 35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
130                 135                 140
```

```
His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser
                245

<210> SEQ ID NO 39
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
                20                  25                  30

Gln Gly Gly Val Ser Val Ser Val Ile Asn His Val Leu Gly Gly Asn
            35                  40                  45

Tyr Ile Ser Leu Asn Val Arg Gly Leu Asp Pro Tyr Ser Glu Arg Phe
        50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
                100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
        130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
            195                 200                 205

Leu Pro Glu Tyr Arg Gly Glu Glu Gly Val Arg Ile Gly Arg Ile Ser
        210                 215                 220

Phe Asn Ser Leu Ser Ala Ile Leu Gly Ser Val Ala Val Ile Leu Asn
225                 230                 235                 240
```

Cys His Ser Thr Gly Ser
            245

<210> SEQ ID NO 40
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His

<210> SEQ ID NO 41
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

```
Ser Gly Gly Thr Ser Leu Leu Met Ile Asp Ser Gly Thr Gly Asp Asn
            35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His

<210> SEQ ID NO 42
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Asp Glu Phe Thr Val Asp Phe Ser Ser Gln Lys Ser Tyr Val Asp Ser
 1               5                  10                  15

Leu Asn Ser Ile Arg Ser Ala Ile Ser Thr Pro Leu Gly Asn Ile Ser
                 20                  25                  30

Gln Gly Gly Val Ser Val Ser Val Ile Asn His Val Leu Gly Gly Asn
            35                  40                  45

Tyr Ile Ser Leu Asn Val Arg Gly Leu Asp Pro Tyr Ser Glu Arg Phe
 50                  55                  60

Asn His Leu Arg Leu Ile Met Glu Arg Asn Asn Leu Tyr Val Ala Gly
 65                  70                  75                  80

Phe Ile Asn Thr Glu Thr Asn Ile Phe Tyr Arg Phe Ser Asp Phe Ser
                 85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
```

```
            130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
            195                 200                 205

Leu Pro Glu Tyr Arg Gly Glu Glu Gly Val Arg Ile Gly Arg Ile Ser
            210                 215                 220

Phe Asn Ser Leu Ser Ala Ile Leu Gly Ser Val Ala Val Ile Leu Asn
225                 230                 235                 240

Cys His
```

<210> SEQ ID NO 43
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
            130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240
```

Asn

<210> SEQ ID NO 44
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn
```

<210> SEQ ID NO 45
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30
```

```
Gln Gly Gly Val Ser Val Ser Val Ile Asn His Val Leu Gly Gly Asn
             35                  40                  45

Tyr Ile Ser Leu Asn Val Arg Gly Leu Asp Pro Tyr Ser Glu Arg Phe
 50                  55                  60

Asn His Leu Arg Leu Ile Met Glu Arg Asn Asn Leu Tyr Val Ala Gly
 65                  70                  75                  80

Phe Ile Asn Thr Glu Thr Asn Ile Phe Tyr Arg Phe Ser Asp Phe Ser
                 85                  90                  95

His Ile Ser Val Pro Asp Val Ile Thr Val Ser Met Thr Thr Asp Ser
                100                 105                 110

Ser Tyr Ser Ser Leu Gln Arg Ile Ala Asp Leu Glu Arg Thr Gly Met
            115                 120                 125

Gln Ile Gly Arg His Ser Leu Val Gly Ser Tyr Leu Asp Leu Met Glu
130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Gly Val Arg Ile Gly Arg Ile Ser
210                 215                 220

Phe Asn Ser Leu Ser Ala Ile Leu Gly Ser Val Ala Val Ile Leu Asn
225                 230                 235                 240

<210> SEQ ID NO 46
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
```

```
                145                 150                 155                 160
Phe Val Thr Val Thr Ala Glu Ala Leu Arg Phe Arg Gln Ile Gln Arg
                165                 170                 175
Gly Phe Arg Thr Thr Leu Asp Asp Leu Ser Gly Arg Ser Tyr Val Met
                180                 185                 190
Thr Ala Glu Asp Val Asp Leu Thr Leu Asn Trp Gly Arg Leu Ser Ser
                195                 200                 205
Val Leu Pro Asp Tyr His Gly Gln Asp Ser Val Arg Val Gly Arg Ile
                210                 215                 220
Ser Phe Gly Ser Ile Asn Ala Ile Leu Gly Ser Val Ala Leu Ile Leu
                225                 230                 235                 240

<210> SEQ ID NO 47
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Lys Glu Phe Thr Leu Asp Phe Ser Thr Ala Lys Thr Tyr Val Asp Ser
1               5                   10                  15
Leu Asn Val Ile Arg Ser Ala Ile Gly Thr Pro Leu Gln Thr Ile Ser
                20                  25                  30
Ser Gly Gly Thr Ser Leu Leu Met Ile Asp Ser Gly Thr Gly Asp Asn
            35                  40                  45
Leu Phe Ala Val Asp Val Arg Gly Ile Asp Pro Glu Glu Gly Arg Phe
        50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
                85                  90                  95
His Val Thr Phe Pro Gly Thr Thr Ala Val Thr Leu Ser Gly Asp Ser
                100                 105                 110
Ser Tyr Thr Thr Leu Gln Arg Val Ala Gly Ile Ser Arg Thr Gly Met
            115                 120                 125
Gln Ile Asn Arg His Ser Leu Thr Thr Ser Tyr Leu Asp Leu Met Ser
        130                 135                 140
His Ser Gly Thr Ser Leu Thr Gln Ser Val Ala Arg Ala Met Leu Arg
145                 150                 155                 160
Phe Val Thr Val Thr Ala Glu Ala Leu Arg Phe Arg Gln Ile Gln Arg
                165                 170                 175
Gly Phe Arg Thr Thr Leu Asp Asp Leu Ser Gly Arg Ser Tyr Val Met
                180                 185                 190
Thr Ala Glu Asp Val Asp Leu Thr Leu Asn Trp Gly Arg Leu Ser Ser
                195                 200                 205
Val Leu Pro Asp Tyr His Gly Gln Asp Ser Val Arg Val Gly Arg Ile
                210                 215                 220
Ser Phe Gly Ser Ile Asn Ala Ile Leu Gly Ser Val Ala Leu Ile Leu
225                 230                 235                 240

<210> SEQ ID NO 48
<211> LENGTH: 239
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 48

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu
225                 230                 235

<210> SEQ ID NO 49
<211> LENGTH: 273
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80
```

```
Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Pro Ala Asp Gly Arg Val Arg Gly Ile Thr His Asn Lys Ile Leu
                245                 250                 255

Trp Asp Ser Ser Thr Leu Gly Ala Ile Leu Met Arg Arg Thr Ile Ser
            260                 265                 270

Ser

<210> SEQ ID NO 50
<211> LENGTH: 513
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ser Gly Asp
            35                  40                  45

Asn Leu Phe Ala Val Asp Val Arg Gly Ile Asp Pro Glu Glu Gly Arg
50                  55                  60

Phe Asn Asn Leu Arg Leu Ile Val Glu Arg Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160
```

```
Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Met Gln Val Gln
            260                 265                 270

Leu Gln Gln Pro Gly Ala Glu Leu Val Lys Pro Gly Ala Ser Val Lys
        275                 280                 285

Met Ser Cys Lys Thr Ser Gly Tyr Thr Phe Thr Ser Tyr Asn Val His
    290                 295                 300

Trp Val Lys Gln Thr Pro Gly Gln Gly Leu Glu Trp Ile Gly Ala Ile
305                 310                 315                 320

Tyr Pro Gly Asn Gly Asp Thr Ser Phe Asn Gln Lys Phe Lys Gly Lys
                325                 330                 335

Ala Thr Leu Thr Ala Asp Lys Ser Ser Ser Thr Val Tyr Met Gln Leu
            340                 345                 350

Ser Ser Leu Thr Ser Glu Asp Ser Ala Val Tyr Tyr Cys Ala Arg Ser
        355                 360                 365

Asn Tyr Tyr Gly Ser Ser Tyr Val Trp Phe Phe Asp Val Trp Gly Ala
    370                 375                 380

Gly Thr Thr Val Thr Val Ser Ser Gly Ser Thr Ser Gly Ser Gly Lys
385                 390                 395                 400

Pro Gly Ser Gly Glu Gly Ser Gln Ile Val Leu Ser Gln Ser Pro Thr
                405                 410                 415

Ile Leu Ser Ala Ser Pro Gly Glu Lys Val Thr Met Thr Cys Arg Ala
            420                 425                 430

Ser Ser Ser Val Ser Tyr Met Asp Trp Tyr Gln Gln Lys Pro Gly Ser
        435                 440                 445

Ser Pro Lys Pro Trp Ile Tyr Ala Thr Ser Asn Leu Ala Ser Gly Val
    450                 455                 460

Pro Ala Arg Phe Ser Gly Ser Gly Ser Gly Thr Ser Tyr Ser Leu Thr
465                 470                 475                 480

Ile Ser Arg Val Glu Ala Glu Asp Ala Ala Thr Tyr Tyr Cys Gln Gln
                485                 490                 495

Trp Ile Ser Asn Pro Pro Thr Phe Gly Ala Gly Thr Lys Leu Glu Leu
            500                 505                 510

Lys

<210> SEQ ID NO 51
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 51

```
Met Lys Glu Phe Thr Leu Asp Phe Ser Thr Ala Lys Thr Tyr Val Asp
1               5                   10                  15
Ser Leu Asn Val Ile Arg Ser Ala Ile Gly Thr Pro Leu Gln Thr Ile
            20                  25                  30
Ser Ser Gly Gly Thr Ser Leu Leu Met Ile Asp Ser Gly Ser Gly Asp
        35                  40                  45
Asn Leu Phe Ala Val Asp Val Arg Gly Ile Asp Pro Glu Glu Gly Arg
    50                  55                  60
Phe Asn Asn Leu Arg Leu Ile Val Glu Arg Asn Asn Leu Tyr Val Thr
65                  70                  75                  80
Gly Phe Val Asn Arg Thr Asn Asn Val Phe Tyr Arg Phe Ala Asp Phe
                85                  90                  95
Ser His Val Thr Phe Pro Gly Thr Ala Val Thr Leu Ser Gly Asp
            100                 105                 110
Ser Ser Tyr Thr Thr Leu Gln Arg Val Ala Gly Ile Ser Arg Thr Gly
        115                 120                 125
Met Gln Ile Asn Arg His Ser Leu Thr Thr Ser Tyr Leu Asp Leu Met
    130                 135                 140
Ser His Ser Gly Thr Ser Leu Thr Gln Ser Val Ala Arg Ala Met Leu
145                 150                 155                 160
Arg Phe Val Thr Val Thr Ala Glu Ala Leu Arg Phe Arg Gln Ile Gln
                165                 170                 175
Arg Gly Phe Arg Thr Thr Leu Asp Asp Leu Ser Gly Arg Ser Tyr Val
            180                 185                 190
Met Thr Ala Glu Asp Val Asp Leu Thr Leu Asn Trp Gly Arg Leu Ser
        195                 200                 205
Ser Val Leu Pro Asp Tyr His Gly Gln Asp Ser Val Arg Val Gly Arg
    210                 215                 220
Ile Ser Phe Gly Ser Ile Asn Ala Ile Leu Gly Ser Val Ala Leu Ile
225                 230                 235                 240
Leu Asn Cys His His His Ala Ser Ala Val Ala Ala Gly Gly Gly Gly
                245                 250                 255
Ser Gly Gly Met Gln Val Gln Leu Val Gln Ser Gly Ala Glu Leu Val
            260                 265                 270
Lys Pro Gly Ala Ser Val Lys Met Ser Cys Lys Ala Ser Gly Tyr Thr
        275                 280                 285
Phe Thr Ser Tyr Asn Met His Trp Val Lys Gln Thr Pro Gly Gln Gly
    290                 295                 300
Leu Glu Trp Ile Gly Ala Ile Tyr Pro Gly Asn Gly Asp Thr Ser Tyr
305                 310                 315                 320
Asn Gln Lys Phe Lys Gly Lys Ala Thr Leu Thr Ala Asp Lys Ser Ser
                325                 330                 335
Ser Thr Ala Tyr Met Gln Leu Ser Ser Leu Thr Ser Glu Asp Ser Ala
            340                 345                 350
Val Tyr Tyr Cys Ala Arg Ala Gln Leu Arg Pro Asn Tyr Trp Tyr Phe
        355                 360                 365
Asp Val Trp Gly Ala Gly Thr Thr Val Thr Val Ser Ser Gly Gly Gly
    370                 375                 380
Gly Ser Gly Gly Gly Gly Ser Gly Gly Gly Gly Ser Gly Gly Gly Gly
385                 390                 395                 400
Ser Gly Gly Gly Gly Ser Asp Ile Val Leu Ser Gln Ser Pro Ala Ile
                405                 410                 415
```

```
Leu Ser Ala Ser Pro Gly Glu Lys Val Thr Met Thr Cys Arg Ala Ser
            420                 425                 430

Ser Ser Val Ser Tyr Met His Trp Tyr Gln Gln Lys Pro Gly Ser Ser
        435                 440                 445

Pro Lys Pro Trp Ile Tyr Ala Thr Ser Asn Leu Ala Ser Gly Val Pro
    450                 455                 460

Ala Arg Phe Ser Gly Ser Gly Ser Gly Thr Ser Tyr Ser Leu Thr Ile
465                 470                 475                 480

Ser Arg Val Glu Ala Glu Asp Ala Ala Thr Tyr Tyr Cys Gln Gln Trp
                485                 490                 495

Ile Ser Asn Pro Pro Thr Phe Gly Ala Gly Thr Lys Leu Glu Leu Lys
            500                 505                 510
```

<210> SEQ ID NO 52
<211> LENGTH: 514
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Glu Phe Pro Lys
                245                 250                 255
```

```
Pro Ser Thr Pro Pro Gly Ser Gly Gly Ala Pro Met Gln Val Gln
            260                 265                 270

Leu Gln Gln Pro Gly Ala Glu Leu Val Lys Pro Gly Ala Ser Val Lys
            275                 280                 285

Met Ser Cys Lys Ala Ser Gly Tyr Thr Phe Thr Ser Tyr Asn Met His
            290                 295                 300

Trp Val Lys Gln Thr Pro Gly Arg Gly Leu Glu Trp Ile Gly Ala Ile
305                 310                 315                 320

Tyr Pro Gly Asn Gly Asp Thr Ser Tyr Asn Gln Lys Phe Lys Gly Lys
                325                 330                 335

Ala Thr Leu Thr Ala Asp Lys Ser Ser Ser Thr Ala Tyr Met Gln Leu
            340                 345                 350

Ser Ser Leu Thr Ser Glu Asp Ser Ala Val Tyr Tyr Cys Ala Arg Ser
            355                 360                 365

Thr Tyr Tyr Gly Gly Asp Trp Tyr Phe Asn Val Trp Gly Ala Gly Thr
            370                 375                 380

Thr Val Thr Val Ser Ala Gly Ser Thr Gly Ser Gly Lys Pro Gly
385                 390                 395                 400

Ser Gly Glu Gly Ser Thr Lys Gly Gln Ile Val Leu Ser Gln Ser Pro
            405                 410                 415

Ala Ile Leu Ser Ala Ser Pro Gly Glu Lys Val Thr Met Thr Cys Arg
            420                 425                 430

Ala Ser Ser Ser Val Ser Tyr Ile His Trp Phe Gln Gln Lys Pro Gly
            435                 440                 445

Ser Ser Pro Lys Pro Trp Ile Tyr Ala Thr Ser Asn Leu Ala Ser Gly
            450                 455                 460

Val Pro Val Arg Phe Ser Gly Ser Gly Ser Gly Thr Ser Tyr Ser Leu
465                 470                 475                 480

Thr Ile Ser Arg Val Glu Ala Glu Asp Ala Ala Thr Tyr Tyr Cys Gln
                485                 490                 495

Gln Trp Thr Ser Asn Pro Pro Thr Phe Gly Gly Gly Thr Lys Leu Glu
            500                 505                 510

Ile Lys

<210> SEQ ID NO 53
<211> LENGTH: 522
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
            35                  40                  45

Asn Leu Phe Ala Val Asp Val Arg Gly Ile Asp Pro Glu Glu Gly Arg
            50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95
```

```
Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
            130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
            210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Gly Ile Leu Gly
            260                 265                 270

Phe Val Phe Thr Leu Met Gln Val Gln Leu Gln Gln Pro Gly Ala Glu
            275                 280                 285

Leu Val Lys Pro Gly Ala Ser Val Lys Met Ser Cys Lys Thr Ser Gly
            290                 295                 300

Tyr Thr Phe Thr Ser Tyr Asn Val His Trp Val Lys Gln Thr Pro Gly
305                 310                 315                 320

Gln Gly Leu Glu Trp Ile Gly Ala Ile Tyr Pro Gly Asn Gly Asp Thr
                325                 330                 335

Ser Phe Asn Gln Lys Phe Lys Gly Lys Ala Thr Leu Thr Ala Asp Lys
            340                 345                 350

Ser Ser Ser Thr Val Tyr Met Gln Leu Ser Ser Leu Thr Ser Glu Asp
            355                 360                 365

Ser Ala Val Tyr Tyr Cys Ala Arg Ser Asn Tyr Tyr Gly Ser Ser Tyr
            370                 375                 380

Val Trp Phe Phe Asp Val Trp Gly Ala Gly Thr Thr Val Thr Val Ser
385                 390                 395                 400

Ser Gly Ser Thr Ser Gly Ser Gly Lys Pro Gly Ser Gly Glu Gly Ser
            405                 410                 415

Gln Ile Val Leu Ser Gln Ser Pro Thr Ile Leu Ser Ala Ser Pro Gly
            420                 425                 430

Glu Lys Val Thr Met Thr Cys Arg Ala Ser Ser Ser Val Ser Tyr Met
            435                 440                 445

Asp Trp Tyr Gln Gln Lys Pro Gly Ser Ser Pro Lys Pro Trp Ile Tyr
            450                 455                 460

Ala Thr Ser Asn Leu Ala Ser Gly Val Pro Ala Arg Phe Ser Gly Ser
465                 470                 475                 480

Gly Ser Gly Thr Ser Tyr Ser Leu Thr Ile Ser Arg Val Glu Ala Glu
                485                 490                 495

Asp Ala Ala Thr Tyr Tyr Cys Gln Gln Trp Ile Ser Asn Pro Pro Thr
            500                 505                 510
```

```
Phe Gly Ala Gly Thr Lys Leu Glu Leu Lys
        515                 520

<210> SEQ ID NO 54
<211> LENGTH: 384
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala His His Ser Glu
                245                 250                 255

Asp Pro Ser Ser Lys Ala Pro Lys Ala Pro Glu Val Gln Leu Val Glu
            260                 265                 270

Ser Gly Gly Gly Leu Val Gln Ala Gly Gly Ser Leu Arg Leu Ser Cys
        275                 280                 285

Ala Ala Ser Gly Ile Thr Phe Ser Ile Asn Thr Met Gly Trp Tyr Arg
    290                 295                 300

Gln Ala Pro Gly Lys Gln Arg Glu Leu Val Ala Leu Ile Ser Ser Ile
305                 310                 315                 320

Gly Asp Thr Tyr Tyr Ala Asp Ser Val Lys Gly Arg Phe Thr Ile Ser
                325                 330                 335

Arg Asp Asn Ala Lys Asn Thr Val Tyr Leu Gln Met Asn Ser Leu Lys
```

```
                    340                 345                 350
Pro Glu Asp Thr Ala Val Tyr Tyr Cys Lys Arg Phe Arg Thr Ala Ala
            355                 360                 365

Gln Gly Thr Asp Tyr Trp Gly Gln Gly Thr Gln Val Thr Val Ser Ser
        370                 375                 380
```

<210> SEQ ID NO 55
<211> LENGTH: 369
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Thr Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Ala Ser Val Ser
            260                 265                 270

Asp Val Pro Arg Asp Leu Glu Val Val Ala Ala Thr Pro Thr Ser Leu
        275                 280                 285

Leu Ile Ser Trp Cys Arg Gln Arg Cys Ala Asp Ser Tyr Arg Ile Thr
    290                 295                 300

Tyr Gly Glu Thr Gly Gly Asn Ser Pro Val Gln Glu Phe Thr Val Pro
305                 310                 315                 320
```

```
Gly Ser Trp Lys Thr Ala Thr Ile Ser Gly Leu Lys Pro Gly Val Asp
                325                 330                 335

Tyr Thr Ile Thr Val Tyr Val Val Thr His Tyr Tyr Gly Trp Asp Arg
                340                 345                 350

Tyr Ser His Pro Ile Ser Ile Asn Tyr Arg Thr Gly Ser Lys Asp Glu
                355                 360                 365

Leu

<210> SEQ ID NO 56
<211> LENGTH: 405
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Met Lys Glu Phe Thr Leu Asp Phe Ser Thr Ala Lys Thr Tyr Val Asp
 1               5                  10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ser Gly Asp
                35                  40                  45

Asn Leu Phe Ala Val Asp Val Arg Gly Ile Asp Pro Glu Glu Gly Arg
            50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
                100                 105                 110

Ser Ser Tyr Thr Thr Leu Gln Arg Val Ala Gly Ile Ser Arg Thr Gly
                115                 120                 125

Met Gln Ile Asn Arg His Ser Leu Thr Thr Ser Tyr Leu Asp Leu Met
            130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
                180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Ala Pro Thr Ser
                260                 265                 270

Ser Ser Thr Lys Lys Thr Gln Leu Gln Leu Glu His Leu Leu Leu Asp
            275                 280                 285

Leu Gln Met Ile Leu Asn Gly Ile Asn Asn Tyr Lys Asn Pro Lys Leu
```

```
                290                 295                 300
Thr Arg Met Leu Thr Phe Lys Phe Tyr Met Pro Lys Lys Ala Thr Glu
305                 310                 315                 320

Leu Lys His Leu Gln Cys Leu Glu Glu Leu Lys Pro Leu Glu Glu
                325                 330                 335

Val Leu Asn Leu Ala Gln Ser Lys Asn Phe His Leu Arg Pro Arg Asp
                340                 345                 350

Leu Ile Ser Asn Ile Asn Val Ile Val Leu Glu Leu Lys Gly Ser Glu
                355                 360                 365

Thr Thr Phe Met Cys Glu Tyr Ala Asp Glu Thr Ala Thr Ile Val Glu
                370                 375                 380

Phe Leu Asn Arg Trp Ile Thr Phe Cys Gln Ser Ile Ile Ser Thr Leu
385                 390                 395                 400

Thr Lys Asp Glu Leu
                405

<210> SEQ ID NO 57
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
                20                  25                  30

Ser Ser Gly Gly Thr Ser Leu Leu Met Ile Asp Ser Gly Ser Gly Asp
                35                  40                  45

Asn Leu Phe Ala Val Asp Val Arg Gly Ile Asp Pro Glu Glu Gly Arg
            50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
                100                 105                 110

Ser Ser Tyr Thr Thr Leu Gln Arg Val Ala Gly Ile Ser Arg Thr Gly
                115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
                180                 185                 190

Met Thr Ala Glu Asp Val Asp Leu Thr Leu Asn Trp Gly Arg Leu Ser
                195                 200                 205

Ser Val Leu Pro Asp Tyr His Gly Gln Asp Ser Val Arg Val Gly Arg
                210                 215                 220

Ile Ser Phe Gly Ser Ile Asn Ala Ile Leu Gly Ser Val Ala Leu Ile
225                 230                 235                 240
```

Leu Asn Cys His His His Ala Ser Ala Val Ala Ala Glu Phe Pro Lys
            245                 250                 255

Pro Ser Thr Pro Pro Gly Ser Ser Gly Ala Pro Asp Ile Glu Leu
        260                 265                 270

Thr Gln Ser Pro Ser Ser Phe Ser Val Ser Leu Gly Asp Arg Val Thr
    275                 280                 285

Ile Thr Cys Lys Ala Ser Glu Asp Ile Tyr Asn Arg Leu Ala Trp Tyr
290                 295                 300

Gln Gln Lys Pro Gly Asn Ala Pro Arg Leu Leu Ile Ser Gly Ala Thr
305                 310                 315                 320

Ser Leu Glu Thr Gly Val Pro Ser Arg Phe Ser Gly Ser Gly Ser Gly
            325                 330                 335

Lys Asp Tyr Thr Leu Ser Ile Thr Ser Leu Gln Thr Glu Asp Val Ala
            340                 345                 350

Thr Tyr Tyr Cys Gln Gln Tyr Trp Ser Thr Pro Thr Phe Gly Gly Gly
            355                 360                 365

Thr Lys Leu Glu Ile Lys Gly Ser Thr Ser Gly Ser Gly Lys Pro Gly
            370                 375                 380

Ser Gly Glu Gly Ser Lys Val Gln Leu Gln Glu Ser Gly Pro Ser Leu
385                 390                 395                 400

Val Gln Pro Ser Gln Arg Leu Ser Ile Thr Cys Thr Val Ser Gly Phe
            405                 410                 415

Ser Leu Ile Ser Tyr Gly Val His Trp Val Arg Gln Ser Pro Gly Lys
            420                 425                 430

Gly Leu Glu Trp Leu Gly Val Ile Trp Arg Gly Gly Ser Thr Asp Tyr
            435                 440                 445

Asn Ala Ala Phe Met Ser Arg Leu Ser Ile Thr Lys Asp Asn Ser Lys
            450                 455                 460

Ser Gln Val Phe Phe Lys Met Asn Ser Leu Gln Ala Asp Asp Thr Ala
465                 470                 475                 480

Ile Tyr Phe Cys Ala Lys Thr Leu Ile Thr Thr Gly Tyr Ala Met Asp
            485                 490                 495

Tyr Trp Gly Gln Gly Thr Thr Val Thr Val Ser Ser
            500                 505

<210> SEQ ID NO 58
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

```
Gly Phe Val Asn Arg Thr Asn Asn Val Phe Tyr Arg Phe Ala Asp Phe
                 85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
            130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
                180                 185                 190

Met Thr Ala Glu Asp Val Asp Leu Thr Leu Asn Trp Gly Arg Leu Ser
                195                 200                 205

Ser Val Leu Pro Asp Tyr His Gly Gln Asp Ser Val Arg Val Gly Arg
        210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Ala Pro Asp Ile Gln Met Thr
                260                 265                 270

Thr Gln Ser Pro Ser Ser Leu Ser Ala Ser Val Gly Asp Arg Val Thr
            275                 280                 285

Ile Thr Cys Arg Ala Ser Gln Asp Val Asn Thr Ala Val Ala Trp Tyr
            290                 295                 300

Gln Gln Lys Pro Gly Lys Ala Pro Lys Leu Leu Ile Tyr Ser Ala Ser
305                 310                 315                 320

Phe Leu Tyr Ser Gly Val Pro Ser Arg Phe Ser Gly Ser Arg Ser Gly
                325                 330                 335

Thr Asp Phe Thr Leu Thr Ile Ser Ser Leu Gln Pro Glu Asp Phe Ala
                340                 345                 350

Thr Tyr Tyr Cys Gln Gln His Tyr Thr Thr Pro Pro Thr Phe Gly Gln
            355                 360                 365

Gly Thr Lys Val Glu Ile Lys Arg Thr Gly Ser Thr Ser Gly Ser Gly
            370                 375                 380

Lys Pro Gly Ser Gly Glu Gly Ser Glu Val Gln Leu Val Glu Ser Gly
385                 390                 395                 400

Gly Gly Leu Val Gln Pro Gly Gly Ser Leu Arg Leu Ser Cys Ala Ala
                405                 410                 415

Ser Gly Phe Asn Ile Lys Asp Thr Tyr Ile His Trp Val Arg Gln Ala
                420                 425                 430

Pro Gly Lys Gly Leu Glu Trp Val Ala Arg Ile Tyr Pro Thr Asn Gly
            435                 440                 445

Tyr Thr Arg Tyr Ala Asp Ser Val Lys Gly Arg Phe Thr Ile Ser Ala
            450                 455                 460

Asp Thr Ser Lys Asn Thr Ala Tyr Leu Gln Met Asn Ser Leu Arg Ala
465                 470                 475                 480

Glu Asp Thr Ala Val Tyr Tyr Cys Ser Arg Trp Gly Gly Asp Gly Phe
                485                 490                 495

Tyr Ala Met Asp Val Trp Gly Gln Gly Thr Leu Val Thr Val Ser Ser
```

<210> SEQ ID NO 59
<211> LENGTH: 516
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

```
Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His His Ala Ser Ala Val Ala Ala Glu Phe Pro Lys
                245                 250                 255

Pro Ser Thr Pro Pro Gly Ser Ser Gly Gly Ala Pro Asp Ile Val Met
            260                 265                 270

Thr Gln Ala Ala Pro Ser Ile Pro Val Thr Pro Gly Glu Ser Val Ser
        275                 280                 285

Ile Ser Cys Arg Ser Ser Lys Ser Leu Leu Asn Ser Asn Gly Asn Thr
    290                 295                 300

Tyr Leu Tyr Trp Phe Leu Gln Arg Pro Gly Gln Ser Pro Gln Leu Leu
305                 310                 315                 320

Ile Tyr Arg Met Ser Asn Leu Ala Ser Gly Val Pro Asp Arg Phe Ser
                325                 330                 335

Gly Ser Gly Ser Gly Thr Ala Phe Thr Leu Arg Ile Ser Arg Val Glu
            340                 345                 350
```

```
Ala Glu Asp Val Gly Val Tyr Tyr Cys Met Gln His Leu Glu Tyr Pro
            355                 360                 365

Phe Thr Phe Gly Ala Gly Thr Lys Leu Glu Leu Lys Gly Ser Thr Ser
    370                 375                 380

Gly Ser Gly Lys Pro Gly Ser Gly Glu Gly Ser Glu Val Gln Leu Gln
385                 390                 395                 400

Gln Ser Gly Pro Glu Leu Ile Lys Pro Gly Ala Ser Val Lys Met Ser
                405                 410                 415

Cys Lys Ala Ser Gly Tyr Thr Phe Thr Ser Tyr Val Met His Trp Val
                420                 425                 430

Lys Gln Lys Pro Gly Gln Gly Leu Glu Trp Ile Gly Tyr Ile Asn Pro
            435                 440                 445

Tyr Asn Asp Gly Thr Lys Tyr Asn Glu Lys Phe Lys Gly Lys Ala Thr
        450                 455                 460

Leu Thr Ser Asp Lys Ser Ser Thr Ala Tyr Met Glu Leu Ser Ser
465                 470                 475                 480

Leu Thr Ser Glu Asp Ser Ala Val Tyr Tyr Cys Ala Arg Gly Thr Tyr
                485                 490                 495

Tyr Tyr Gly Ser Arg Val Phe Asp Tyr Trp Gly Gln Thr Thr Leu
            500                 505                 510

Thr Val Ser Ser
        515

<210> SEQ ID NO 60
<211> LENGTH: 518
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ser Gly Asp
        35                  40                  45

Asn Leu Phe Ala Val Asp Val Arg Gly Ile Asp Pro Glu Glu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95

Ser His Val Thr Phe Pro Gly Thr Thr Ala Val Thr Leu Ser Gly Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175
```

```
Arg Gly Phe Arg Thr Thr Leu Asp Asp Leu Ser Gly Arg Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Cys His His Ala Ser Ala Ala Ala Glu Phe Pro Lys
            245                 250                 255

Pro Ser Thr Pro Pro Gly Ser Ser Gly Gly Ala Pro Asp Ile Gln Leu
        260                 265                 270

Thr Gln Ser Pro Leu Ser Leu Pro Val Thr Leu Gly Gln Pro Ala Ser
    275                 280                 285

Ile Ser Cys Arg Ser Ser Gln Ser Leu Val His Arg Asn Gly Asn Thr
290                 295                 300

Tyr Leu His Trp Phe Gln Gln Arg Pro Gly Gln Ser Pro Arg Leu Leu
305                 310                 315                 320

Ile Tyr Thr Val Ser Asn Arg Phe Ser Gly Val Pro Asp Arg Phe Ser
                325                 330                 335

Gly Ser Gly Ser Gly Thr Asp Phe Thr Leu Lys Ile Ser Arg Val Glu
            340                 345                 350

Ala Glu Asp Val Gly Val Tyr Phe Cys Ser Gln Ser Ser His Val Pro
        355                 360                 365

Pro Thr Phe Gly Ala Gly Thr Arg Leu Glu Ile Lys Gly Ser Thr Ser
    370                 375                 380

Gly Ser Gly Lys Pro Gly Ser Gly Glu Gly Ser Thr Lys Gly Gln Val
385                 390                 395                 400

Gln Leu Gln Gln Ser Gly Ser Glu Leu Lys Lys Pro Gly Ala Ser Val
                405                 410                 415

Lys Val Ser Cys Lys Ala Ser Gly Tyr Thr Phe Thr Asn Tyr Gly Val
            420                 425                 430

Asn Trp Ile Lys Gln Ala Pro Gly Gln Gly Leu Gln Trp Met Gly Trp
        435                 440                 445

Ile Asn Pro Asn Thr Gly Glu Pro Thr Phe Asp Asp Asp Phe Lys Gly
    450                 455                 460

Arg Phe Ala Phe Ser Leu Asp Thr Ser Val Ser Thr Ala Tyr Leu Gln
465                 470                 475                 480

Ile Ser Ser Leu Lys Ala Asp Asp Thr Ala Val Tyr Phe Cys Ser Arg
                485                 490                 495

Ser Arg Gly Lys Asn Glu Ala Trp Phe Ala Tyr Trp Gly Gln Gly Thr
            500                 505                 510

Leu Val Thr Val Ser Ser
        515

<210> SEQ ID NO 61
<211> LENGTH: 403
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Met Lys Glu Phe Thr Leu Asp Phe Ser Thr Ala Lys Thr Tyr Val Asp
```

```
            1               5                  10                 15
        Ser Leu Asn Val Ile Arg Ser Ala Ile Gly Thr Pro Leu Gln Thr Ile
                        20                 25                 30

Ser Ser Gly Gly Thr Ser Leu Leu Met Ile Asp Ser Gly Ser Gly Asp
                        35                 40                 45

Asn Leu Phe Ala Val Asp Val Arg Gly Ile Asp Pro Glu Glu Gly Arg
                        50                 55                 60

Phe Asn Asn Leu Arg Leu Ile Val Glu Arg Asn Asn Leu Tyr Val Thr
         65                 70                 75                 80

Gly Phe Val Asn Arg Thr Asn Asn Val Phe Tyr Arg Phe Ala Asp Phe
                            85                 90                 95

Ser His Val Thr Phe Pro Gly Thr Thr Ala Val Thr Leu Ser Gly Asp
                        100                105                110

Ser Ser Tyr Thr Thr Leu Gln Arg Val Ala Gly Ile Ser Arg Thr Gly
                        115                120                125

Met Gln Ile Asn Arg His Ser Leu Thr Thr Ser Tyr Leu Asp Leu Met
                        130                135                140

Ser His Ser Gly Thr Ser Leu Thr Gln Ser Val Ala Arg Ala Met Leu
        145                150                155                160

Arg Phe Val Thr Val Thr Ala Glu Ala Leu Arg Phe Arg Gln Ile Gln
                            165                170                175

Arg Gly Phe Arg Thr Thr Leu Asp Asp Leu Ser Gly Arg Ser Tyr Val
                        180                185                190

Met Thr Ala Glu Asp Val Asp Leu Thr Leu Asn Trp Gly Arg Leu Ser
                        195                200                205

Ser Val Leu Pro Asp Tyr His Gly Gln Asp Ser Val Arg Val Gly Arg
        210                215                220

Ile Ser Phe Gly Ser Ile Asn Ala Ile Leu Gly Ser Val Ala Leu Ile
        225                230                235                240

Leu Asn Cys His His His Ala Ser Ala Val Ala Ala Glu Phe Pro Lys
                            245                250                255

Pro Ser Thr Pro Pro Gly Ser Ser Gly Gly Ala Pro Arg Gly Ser His
                        260                265                270

His His His His His Gly Ser Asp Leu Gly Lys Lys Leu Leu Glu Ala
                        275                280                285

Ala Arg Ala Gly Gln Asp Asp Glu Val Arg Ile Leu Met Ala Asn Gly
                        290                295                300

Ala Asp Val Asn Ala Lys Asp Glu Tyr Gly Leu Thr Pro Leu Tyr Leu
        305                310                315                320

Ala Thr Ala His Gly His Leu Glu Ile Val Glu Val Leu Leu Lys Asn
                            325                330                335

Gly Ala Asp Val Asn Ala Val Asp Ala Ile Gly Phe Thr Pro Leu His
                        340                345                350

Leu Ala Ala Phe Ile Gly His Leu Glu Ile Ala Glu Val Leu Leu Lys
                        355                360                365

His Gly Ala Asp Val Asn Ala Gln Asp Lys Phe Gly Lys Thr Ala Phe
                        370                375                380

Asp Ile Ser Ile Gly Asn Gly Asn Glu Asp Leu Ala Glu Ile Leu Gln
        385                390                395                400

Lys Leu Asn

<210> SEQ ID NO 62
<211> LENGTH: 4
```

```
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 62

Lys Asp Glu Leu
1

<210> SEQ ID NO 63
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 63

His Asp Glu Phe
1

<210> SEQ ID NO 64
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 64

His Asp Glu Leu
1

<210> SEQ ID NO 65
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 65

Arg Asp Glu Phe
1

<210> SEQ ID NO 66
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 66

Arg Asp Glu Leu
1

<210> SEQ ID NO 67
<211> LENGTH: 4
<212> TYPE: PRT
<213> ORGANISM: Unknown
<220> FEATURE:
<221> NAME/KEY: source
```

-continued

```
<223> OTHER INFORMATION: /note="Description of Unknown: Endoplasmic
      reticulum retention/retrieval signal motif peptide"

<400> SEQUENCE: 67

Trp Asp Glu Leu
1

<210> SEQ ID NO 68
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 68

Tyr Asp Glu Leu
1

<210> SEQ ID NO 69
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 69

His Glu Glu Phe
1

<210> SEQ ID NO 70
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 70

His Glu Glu Leu
1

<210> SEQ ID NO 71
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 71

Lys Glu Glu Leu
1

<210> SEQ ID NO 72
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 72
```

```
Arg Glu Glu Leu
1

<210> SEQ ID NO 73
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 73

Lys Ala Glu Leu
1

<210> SEQ ID NO 74
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 74

Lys Cys Glu Leu
1

<210> SEQ ID NO 75
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 75

Lys Phe Glu Leu
1

<210> SEQ ID NO 76
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 76

Lys Gly Glu Leu
1

<210> SEQ ID NO 77
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 77

Lys His Glu Leu
1
```

```
<210> SEQ ID NO 78
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 78

Lys Leu Glu Leu
1

<210> SEQ ID NO 79
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 79

Lys Asn Glu Leu
1

<210> SEQ ID NO 80
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 80

Lys Gln Glu Leu
1

<210> SEQ ID NO 81
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 81

Lys Arg Glu Leu
1

<210> SEQ ID NO 82
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 82

Lys Ser Glu Leu
1

<210> SEQ ID NO 83
<211> LENGTH: 4
<212> TYPE: PRT
```

```
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 83

Lys Val Glu Leu
1

<210> SEQ ID NO 84
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 84

Lys Trp Glu Leu
1

<210> SEQ ID NO 85
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 85

Lys Tyr Glu Leu
1

<210> SEQ ID NO 86
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 86

Lys Glu Asp Leu
1

<210> SEQ ID NO 87
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 87

Lys Ile Glu Leu
1

<210> SEQ ID NO 88
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
``` reticulum retention/retrieval signal motif peptide"

<400> SEQUENCE: 88

Asp Lys Glu Leu
1

<210> SEQ ID NO 89
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 89

Phe Asp Glu Leu
1

<210> SEQ ID NO 90
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 90

Lys Asp Glu Phe
1

<210> SEQ ID NO 91
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 91

Lys Lys Glu Leu
1

<210> SEQ ID NO 92
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 92

His Ala Asp Leu
1

<210> SEQ ID NO 93
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 93

His Ala Glu Leu
1

<210> SEQ ID NO 94
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 94

His Ile Glu Leu
1

<210> SEQ ID NO 95
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 95

His Asn Glu Leu
1

<210> SEQ ID NO 96
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 96

His Thr Glu Leu
1

<210> SEQ ID NO 97
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 97

Lys Thr Glu Leu
1

<210> SEQ ID NO 98
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 98

His Val Glu Leu
1

```
<210> SEQ ID NO 99
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 99

Asn Asp Glu Leu
1

<210> SEQ ID NO 100
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 100

Gln Asp Glu Leu
1

<210> SEQ ID NO 101
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 101

Arg Glu Asp Leu
1

<210> SEQ ID NO 102
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 102

Arg Asn Glu Leu
1

<210> SEQ ID NO 103
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 103

Arg Thr Asp Leu
1

<210> SEQ ID NO 104
<211> LENGTH: 4
<212> TYPE: PRT
<213> ORGANISM: Unknown
```

```
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 104

Arg Thr Glu Leu
1

<210> SEQ ID NO 105
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 105

Ser Asp Glu Leu
1

<210> SEQ ID NO 106
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 106

Thr Asp Glu Leu
1

<210> SEQ ID NO 107
<211> LENGTH: 4
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 107

Ser Lys Glu Leu
1

<210> SEQ ID NO 108
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Arg Val Lys Arg
1

<210> SEQ ID NO 109
<211> LENGTH: 6
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"
```

```
<400> SEQUENCE: 109

Ala Leu Glu Asp Glu Leu
1               5

<210> SEQ ID NO 110
<211> LENGTH: 6
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 110

His Ala Glu Asp Glu Leu
1               5

<210> SEQ ID NO 111
<211> LENGTH: 6
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 111

His Leu Glu Asp Glu Leu
1               5

<210> SEQ ID NO 112
<211> LENGTH: 6
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 112

Lys Leu Glu Asp Glu Leu
1               5

<210> SEQ ID NO 113
<211> LENGTH: 6
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 113

Ile Arg Ser Asp Glu Leu
1               5

<210> SEQ ID NO 114
<211> LENGTH: 6
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 114

Glu Arg Ser Thr Glu Leu
```

```
1               5

<210> SEQ ID NO 115
<211> LENGTH: 6
<212> TYPE: PRT
<213> ORGANISM: Unknown
<220> FEATURE:
<221> NAME/KEY: source
<223> OTHER INFORMATION: /note="Description of Unknown: Endoplasmic
      reticulum retention/retrieval signal motif peptide"

<400> SEQUENCE: 115

Arg Pro Ser Thr Glu Leu
1               5

<210> SEQ ID NO 116
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Ala Met Gly Arg Ser Gly Gly Gly Cys Ala Gly Asn Arg Val Gly Ser
1               5                   10                  15

Ser Leu Ser Cys Gly Gly Leu Asn Leu Gln Ala Met
            20                  25

<210> SEQ ID NO 117
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Ala Ser Gly Gly Pro Glu
1               5

<210> SEQ ID NO 118
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(6)
<223> OTHER INFORMATION: /replace=" "
<220> FEATURE:
<221> NAME/KEY: VARIANT
<222> LOCATION: (10)..(11)
<223> OTHER INFORMATION: /replace=" "
<220> FEATURE:
<221> NAME/KEY: VARIANT
<222> LOCATION: (15)..(16)
<223> OTHER INFORMATION: /replace=" "
<220> FEATURE:
<221> NAME/KEY: VARIANT
<222> LOCATION: (20)..(21)
<223> OTHER INFORMATION: /replace=" "
<220> FEATURE:
<221> NAME/KEY: VARIANT
<222> LOCATION: (25)..(26)
<223> OTHER INFORMATION: /replace=" "
```

```
<220> FEATURE:
<221> NAME/KEY: VARIANT
<222> LOCATION: (30)..(31)
<223> OTHER INFORMATION: /replace=" "
<220> FEATURE:
<221> NAME/KEY: VARIANT
<222> LOCATION: (35)..(36)
<223> OTHER INFORMATION: /replace=" "
<220> FEATURE:
<221> NAME/KEY: VARIANT
<222> LOCATION: (40)..(41)
<223> OTHER INFORMATION: /replace=" "
<220> FEATURE:
<221> NAME/KEY: VARIANT
<222> LOCATION: (45)..(46)
<223> OTHER INFORMATION: /replace=" "
<220> FEATURE:
<221> NAME/KEY: VARIANT
<222> LOCATION: (50)..(51)
<223> OTHER INFORMATION: /replace=" "
<220> FEATURE:
<221> NAME/KEY: MISC_FEATURE
<222> LOCATION: (1)..(54)
<223> OTHER INFORMATION: /note="Variant residues given in the sequence
      have no preference with respect to those in the annotations
      for variant positions"
<220> FEATURE:
<221> NAME/KEY: MISC_FEATURE
<222> LOCATION: (3)..(52)
<223> OTHER INFORMATION: /note="This region may encompass 1 to 10 'Gly
      Gly Gly Gly Ser' repeating units, wherein some positions may
      be absent"
<220> FEATURE:
<221> NAME/KEY: source
<223> OTHER INFORMATION: /note="See specification as filed for detailed
      description of substitutions and preferred embodiments"

<400> SEQUENCE: 118

Ala Met Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
                20                  25                  30

Gly Gly Gly Gly Ser Gly Gly Gly Gly Ser Gly Gly Gly Gly Ser Gly
            35                  40                  45

Gly Gly Gly Ser Ala Met
        50

<210> SEQ ID NO 119
<211> LENGTH: 210
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(6)
<223> OTHER INFORMATION: /replace=" "
<220> FEATURE:
<221> NAME/KEY: VARIANT
<222> LOCATION: (9)..(13)
<223> OTHER INFORMATION: /replace=" "
<220> FEATURE:
<221> NAME/KEY: VARIANT
<222> LOCATION: (16)..(20)
<223> OTHER INFORMATION: /replace=" "
<220> FEATURE:
<221> NAME/KEY: VARIANT
<222> LOCATION: (23)..(27)
<223> OTHER INFORMATION: /replace=" "
<220> FEATURE:
<221> NAME/KEY: VARIANT
<222> LOCATION: (30)..(34)
```

```
<223> OTHER INFORMATION: /replace=" "
<220> FEATURE:
<221> NAME/KEY: VARIANT
<222> LOCATION: (37)..(41)
<223> OTHER INFORMATION: /replace=" "
<220> FEATURE:
<221> NAME/KEY: VARIANT
<222> LOCATION: (44)..(48)
<223> OTHER INFORMATION: /replace=" "
<220> FEATURE:
<221> NAME/KEY: VARIANT
<222> LOCATION: (51)..(55)
<223> OTHER INFORMATION: /replace=" "
<220> FEATURE:
<221> NAME/KEY: VARIANT
<222> LOCATION: (58)..(62)
<223> OTHER INFORMATION: /replace=" "
<220> FEATURE:
<221> NAME/KEY: VARIANT
<222> LOCATION: (65)..(69)
<223> OTHER INFORMATION: /replace=" "
<220> FEATURE:
<221> NAME/KEY: VARIANT
<222> LOCATION: (72)..(76)
<223> OTHER INFORMATION: /replace=" "
<220> FEATURE:
<221> NAME/KEY: VARIANT
<222> LOCATION: (79)..(83)
<223> OTHER INFORMATION: /replace=" "
<220> FEATURE:
<221> NAME/KEY: VARIANT
<222> LOCATION: (86)..(90)
<223> OTHER INFORMATION: /replace=" "
<220> FEATURE:
<221> NAME/KEY: VARIANT
<222> LOCATION: (93)..(97)
<223> OTHER INFORMATION: /replace=" "
<220> FEATURE:
<221> NAME/KEY: VARIANT
<222> LOCATION: (100)..(104)
<223> OTHER INFORMATION: /replace=" "
<220> FEATURE:
<221> NAME/KEY: VARIANT
<222> LOCATION: (107)..(111)
<223> OTHER INFORMATION: /replace=" "
<220> FEATURE:
<221> NAME/KEY: VARIANT
<222> LOCATION: (114)..(118)
<223> OTHER INFORMATION: /replace=" "
<220> FEATURE:
<221> NAME/KEY: VARIANT
<222> LOCATION: (121)..(125)
<223> OTHER INFORMATION: /replace=" "
<220> FEATURE:
<221> NAME/KEY: VARIANT
<222> LOCATION: (128)..(132)
<223> OTHER INFORMATION: /replace=" "
<220> FEATURE:
<221> NAME/KEY: VARIANT
<222> LOCATION: (135)..(139)
<223> OTHER INFORMATION: /replace=" "
<220> FEATURE:
<221> NAME/KEY: VARIANT
<222> LOCATION: (142)..(146)
<223> OTHER INFORMATION: /replace=" "
<220> FEATURE:
<221> NAME/KEY: VARIANT
<222> LOCATION: (149)..(153)
<223> OTHER INFORMATION: /replace=" "
<220> FEATURE:
<221> NAME/KEY: VARIANT
<222> LOCATION: (156)..(160)
<223> OTHER INFORMATION: /replace=" "
<220> FEATURE:
<221> NAME/KEY: VARIANT
<222> LOCATION: (163)..(167)
<223> OTHER INFORMATION: /replace=" "
<220> FEATURE:
<221> NAME/KEY: VARIANT
```

```
<222> LOCATION: (170)..(174)
<223> OTHER INFORMATION: /replace=" "
<220> FEATURE:
<221> NAME/KEY: VARIANT
<222> LOCATION: (177)..(181)
<223> OTHER INFORMATION: /replace=" "
<220> FEATURE:
<221> NAME/KEY: VARIANT
<222> LOCATION: (184)..(188)
<223> OTHER INFORMATION: /replace=" "
<220> FEATURE:
<221> NAME/KEY: VARIANT
<222> LOCATION: (191)..(195)
<223> OTHER INFORMATION: /replace=" "
<220> FEATURE:
<221> NAME/KEY: VARIANT
<222> LOCATION: (198)..(202)
<223> OTHER INFORMATION: /replace=" "
<220> FEATURE:
<221> NAME/KEY: VARIANT
<222> LOCATION: (205)..(209)
<223> OTHER INFORMATION: /replace=" "
<220> FEATURE:
<221> NAME/KEY: MISC_FEATURE
<222> LOCATION: (1)..(210)
<223> OTHER INFORMATION: /note="Variant residues given in the sequence
      have no preference with respect to those in the annotations
      for variant positions"
<220> FEATURE:
<221> NAME/KEY: MISC_FEATURE
<222> LOCATION: (1)..(210)
<223> OTHER INFORMATION: /note="This sequence may encompass 1 to 30 'Gly
      Gly Gly Gly Gly Gly Ser' repeating units, wherein some positions
      may be absent"
<220> FEATURE:
<221> NAME/KEY: source
<223> OTHER INFORMATION: /note="See specification as filed for detailed
      description of substitutions and preferred embodiments"

<400> SEQUENCE: 119

Gly Gly Gly Gly Gly Gly Ser Gly Gly Gly Gly Gly Gly Ser Gly Gly
1               5                   10                  15

Gly Gly Gly Gly Ser Gly Gly Gly Gly Gly Gly Ser Gly Gly Gly Gly
                20                  25                  30

Gly Gly Ser Gly Gly Gly Gly Gly Ser Gly Gly Gly Gly Gly Gly Gly
        35                  40                  45

Ser Gly Gly Gly Gly Gly Gly Ser Gly Gly Gly Gly Gly Gly Ser Gly
    50                  55                  60

Gly Gly Gly Gly Ser Gly Gly Gly Gly Gly Ser Gly Gly Gly Gly Gly
65                  70                  75                  80

Gly Gly Gly Ser Gly Gly Gly Gly Gly Ser Gly Gly Gly Gly Gly Gly
                85                  90                  95

Gly Ser Gly Gly Gly Gly Gly Ser Gly Gly Gly Gly Gly Gly Gly Ser
        100                 105                 110

Gly Gly Gly Gly Gly Ser Gly Gly Gly Gly Gly Gly Ser Gly Gly Gly
            115                 120                 125

Gly Gly Gly Gly Ser Gly Gly Gly Gly Gly Ser Gly Gly Gly Gly Gly
        130                 135                 140

Gly Gly Ser Gly Gly Gly Gly Gly Ser Gly Gly Gly Gly Gly Gly Gly
145                 150                 155                 160

Ser Gly Gly Gly Gly Gly Gly Ser Gly Gly Gly Gly Gly Gly Ser Gly
                165                 170                 175

Gly Gly Gly Gly Ser Gly Gly Gly Gly Gly Ser Gly Gly Gly Gly Gly
            180                 185                 190

Gly Gly Ser Gly Gly Gly Gly Gly Gly Ser Gly Gly Gly Gly Gly
        195                 200                 205
```

Gly Ser
    210

<210> SEQ ID NO 120
<211> LENGTH: 210
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(6)
<223> OTHER INFORMATION: /replace=" "
<220> FEATURE:
<221> NAME/KEY: VARIANT
<222> LOCATION: (9)..(13)
<223> OTHER INFORMATION: /replace=" "
<220> FEATURE:
<221> NAME/KEY: VARIANT
<222> LOCATION: (16)..(20)
<223> OTHER INFORMATION: /replace=" "
<220> FEATURE:
<221> NAME/KEY: VARIANT
<222> LOCATION: (23)..(27)
<223> OTHER INFORMATION: /replace=" "
<220> FEATURE:
<221> NAME/KEY: VARIANT
<222> LOCATION: (30)..(34)
<223> OTHER INFORMATION: /replace=" "
<220> FEATURE:
<221> NAME/KEY: VARIANT
<222> LOCATION: (37)..(41)
<223> OTHER INFORMATION: /replace=" "
<220> FEATURE:
<221> NAME/KEY: VARIANT
<222> LOCATION: (44)..(48)
<223> OTHER INFORMATION: /replace=" "
<220> FEATURE:
<221> NAME/KEY: VARIANT
<222> LOCATION: (51)..(55)
<223> OTHER INFORMATION: /replace=" "
<220> FEATURE:
<221> NAME/KEY: VARIANT
<222> LOCATION: (58)..(62)
<223> OTHER INFORMATION: /replace=" "
<220> FEATURE:
<221> NAME/KEY: VARIANT
<222> LOCATION: (65)..(69)
<223> OTHER INFORMATION: /replace=" "
<220> FEATURE:
<221> NAME/KEY: VARIANT
<222> LOCATION: (72)..(76)
<223> OTHER INFORMATION: /replace=" "
<220> FEATURE:
<221> NAME/KEY: VARIANT
<222> LOCATION: (79)..(83)
<223> OTHER INFORMATION: /replace=" "
<220> FEATURE:
<221> NAME/KEY: VARIANT
<222> LOCATION: (86)..(90)
<223> OTHER INFORMATION: /replace=" "
<220> FEATURE:
<221> NAME/KEY: VARIANT
<222> LOCATION: (93)..(97)
<223> OTHER INFORMATION: /replace=" "
<220> FEATURE:
<221> NAME/KEY: VARIANT
<222> LOCATION: (100)..(104)
<223> OTHER INFORMATION: /replace=" "
<220> FEATURE:
<221> NAME/KEY: VARIANT
<222> LOCATION: (107)..(111)
<223> OTHER INFORMATION: /replace=" "
<220> FEATURE:
<221> NAME/KEY: VARIANT

```
<222> LOCATION: (114)..(118)
<223> OTHER INFORMATION: /replace=" "
<220> FEATURE:
<221> NAME/KEY: VARIANT
<222> LOCATION: (121)..(125)
<223> OTHER INFORMATION: /replace=" "
<220> FEATURE:
<221> NAME/KEY: VARIANT
<222> LOCATION: (128)..(132)
<223> OTHER INFORMATION: /replace=" "
<220> FEATURE:
<221> NAME/KEY: VARIANT
<222> LOCATION: (135)..(139)
<223> OTHER INFORMATION: /replace=" "
<220> FEATURE:
<221> NAME/KEY: VARIANT
<222> LOCATION: (142)..(146)
<223> OTHER INFORMATION: /replace=" "
<220> FEATURE:
<221> NAME/KEY: VARIANT
<222> LOCATION: (149)..(153)
<223> OTHER INFORMATION: /replace=" "
<220> FEATURE:
<221> NAME/KEY: VARIANT
<222> LOCATION: (156)..(160)
<223> OTHER INFORMATION: /replace=" "
<220> FEATURE:
<221> NAME/KEY: VARIANT
<222> LOCATION: (163)..(167)
<223> OTHER INFORMATION: /replace=" "
<220> FEATURE:
<221> NAME/KEY: VARIANT
<222> LOCATION: (170)..(174)
<223> OTHER INFORMATION: /replace=" "
<220> FEATURE:
<221> NAME/KEY: VARIANT
<222> LOCATION: (177)..(181)
<223> OTHER INFORMATION: /replace=" "
<220> FEATURE:
<221> NAME/KEY: VARIANT
<222> LOCATION: (184)..(188)
<223> OTHER INFORMATION: /replace=" "
<220> FEATURE:
<221> NAME/KEY: VARIANT
<222> LOCATION: (191)..(195)
<223> OTHER INFORMATION: /replace=" "
<220> FEATURE:
<221> NAME/KEY: VARIANT
<222> LOCATION: (198)..(202)
<223> OTHER INFORMATION: /replace=" "
<220> FEATURE:
<221> NAME/KEY: VARIANT
<222> LOCATION: (205)..(209)
<223> OTHER INFORMATION: /replace=" "
<220> FEATURE:
<221> NAME/KEY: MISC_FEATURE
<222> LOCATION: (1)..(210)
<223> OTHER INFORMATION: /note="Variant residues given in the sequence
      have no preference with respect to those in the annotations
      for variant positions"
<220> FEATURE:
<221> NAME/KEY: MISC_FEATURE
<222> LOCATION: (1)..(210)
<223> OTHER INFORMATION: /note="This sequence may encompass 1 to 30 'Ser
      Ser Ser Ser Ser Gly' repeating units, wherein some positions
      may be absent"
<220> FEATURE:
<221> NAME/KEY: source
<223> OTHER INFORMATION: /note="See specification as filed for detailed
      description of substitutions and preferred embodiments"

<400> SEQUENCE: 120

Ser Ser Ser Ser Ser Ser Gly Ser Ser Ser Ser Ser Gly Ser Ser
1               5                   10                  15

Ser Ser Ser Ser Gly Ser Ser Ser Ser Ser Gly Ser Ser Ser Ser
            20                  25                  30
```

```
Ser Ser Gly Ser Ser Ser Ser Gly Ser Ser Ser Ser Ser
        35                  40                  45

Gly Ser Ser Ser Ser Ser Gly Ser Ser Ser Ser Ser Gly Ser
 50                  55                  60

Ser Ser Ser Ser Gly Ser Ser Ser Ser Ser Gly Ser Ser Ser
65                  70                  75                  80

Ser Ser Ser Gly Ser Ser Ser Ser Ser Gly Ser Ser Ser Ser
            85                  90                  95

Ser Gly Ser Ser Ser Ser Ser Gly Ser Ser Ser Ser Ser Gly
         100                 105                 110

Ser Ser Ser Ser Ser Gly Ser Ser Ser Ser Ser Gly Ser Ser
        115                 120                 125

Ser Ser Ser Ser Gly Ser Ser Ser Ser Ser Gly Ser Ser Ser
    130                 135                 140

Ser Ser Gly Ser Ser Ser Ser Ser Gly Ser Ser Ser Ser Ser
145                 150                 155                 160

Gly Ser Ser Ser Ser Ser Gly Ser Ser Ser Ser Ser Gly Ser
                165                 170                 175

Ser Ser Ser Ser Gly Ser Ser Ser Ser Ser Gly Ser Ser Ser
            180                 185                 190

Ser Ser Ser Gly Ser Ser Ser Ser Ser Gly Ser Ser Ser Ser
        195                 200                 205

Ser Gly
    210

<210> SEQ ID NO 121
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (6)..(150)
<223> OTHER INFORMATION: /replace=" "
<220> FEATURE:
<221> NAME/KEY: MISC_FEATURE
<222> LOCATION: (1)..(150)
<223> OTHER INFORMATION: /note="Variant residues given in the sequence
      have no preference with respect to those in the annotations for
      variant positions"
<220> FEATURE:
<221> NAME/KEY: MISC_FEATURE
<222> LOCATION: (1)..(150)
<223> OTHER INFORMATION: /note="This sequence may encompass 1 to 30 'Gly
      Gly Gly Gly Ser' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 121

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60
```

Ser Gly Gly Gly Gly Ser Gly Gly Gly Ser Gly Gly Gly Ser
65                  70                  75                  80

Gly Gly Gly Gly Ser Gly Gly Gly Ser Gly Gly Gly Ser Gly
                85                  90                  95

Gly Gly Gly Ser Gly Gly Gly Ser Gly Gly Gly Ser Gly Gly
            100                 105                 110

Gly Gly Ser Gly Gly Gly Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Gly Ser
145                 150

<210> SEQ ID NO 122
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(30)
<223> OTHER INFORMATION: /replace=" "
<220> FEATURE:
<221> NAME/KEY: MISC_FEATURE
<222> LOCATION: (1)..(30)
<223> OTHER INFORMATION: /note="Variant residues given in the sequence
      have no preference with respect to those in the annotations for
      variant positions"
<220> FEATURE:
<221> NAME/KEY: MISC_FEATURE
<222> LOCATION: (1)..(30)
<223> OTHER INFORMATION: /note="This sequence may encompass 1 to 30
      residues, wherein some positions may be absent"
<220> FEATURE:
<221> NAME/KEY: source
<223> OTHER INFORMATION: /note="See specification as filed for detailed
      description of substitutions and preferred embodiments"

<400> SEQUENCE: 122

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30

<210> SEQ ID NO 123
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Gly Lys Ser Ser Gly Ser Gly Ser Glu Ser Lys Ser
1               5                   10

<210> SEQ ID NO 124
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 124

Gly Ser Thr Ser Gly Ser Gly Lys Ser Ser Glu Gly Lys Gly
1               5                   10

<210> SEQ ID NO 125
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Ser Thr Ser Gly Ser Gly Lys Ser Ser Glu Gly Ser Gly Ser Thr
1               5                   10                  15

Lys Gly

<210> SEQ ID NO 126
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Gly Ser Thr Ser Gly Ser Gly Lys Pro Gly Ser Gly Glu Gly Ser Thr
1               5                   10                  15

Lys Gly

<210> SEQ ID NO 127
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Glu Gly Lys Ser Ser Gly Ser Gly Ser Glu Ser Lys Glu Phe
1               5                   10

<210> SEQ ID NO 128
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Ser Arg Ser Ser Gly
1               5

<210> SEQ ID NO 129
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:

```
                         Synthetic peptide"

<400> SEQUENCE: 129

Ser Gly Ser Ser Cys
1               5

<210> SEQ ID NO 130
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Gly Gly Gly Gly Ser Gly Gly Gly Ser Gly Gly Gly Gly Ser
1               5                   10                  15

<210> SEQ ID NO 131
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Gly Gly Gly Ser
1

<210> SEQ ID NO 132
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Gly Gly Gly Gly Ser
1               5

<210> SEQ ID NO 133
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Gly Gly Gly Gly Ser Gly Gly Gly
1               5

<210> SEQ ID NO 134
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134
```

```
Gly Gly Ser Gly Gly Gly Gly
1               5
```

<210> SEQ ID NO 135
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

```
Gly Ser Thr Ser Gly Gly Gly Ser Gly Gly Gly Ser Gly Gly Gly Gly
1               5                   10                  15

Ser Ser
```

<210> SEQ ID NO 136
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

```
Gly Ser Thr Ser Gly Ser Gly Lys Pro Gly Ser Ser Glu Gly Ser Thr
1               5                   10                  15

Lys Gly
```

<210> SEQ ID NO 137
<211> LENGTH: 9
<212> TYPE: PRT
<213> ORGANISM: Plasmodium falciparum

<400> SEQUENCE: 137

```
Thr Leu Asp Glu Met Arg His Phe Tyr
1               5
```

The invention is claimed as follows:

1. A cytotoxic cell-targeting molecule comprising
   i) a heterologous, binding region capable of specifically binding an extracellular target biomolecule,
   ii) a cytotoxic, Shiga toxin effector polypeptide comprising
      (a) a Shiga toxin A1 fragment region having a carboxy terminus, wherein said Shiga toxin A1 fragment region comprises an amino acid sequence that is at least 95% identical to a sequence selected from:
         amino acids 75 to 251 of SEQ ID NO: 1 or SEQ ID NO: 2;
         amino acids 1 to 241 of SEQ ID NO: 1 or SEQ ID NO: 2; and
         amino acids 1 to 251 of SEQ ID NO: 1 or SEQ ID NO: 2; and
      (b) a disrupted furin-cleavage motif at the carboxy terminus of the A1 fragment region comprising one or more mutations in a minimal furin-cleavage site relative to a wild-type Shiga toxin A Subunit, the one or more mutations comprising a substitution mutation of an arginine residue natively positioned at 248 or 251 of SEQ ID NO: 1 or SEQ ID NO: 2 with a non-positively charged amino acid residue; and
   iii) a molecular moiety having a mass of at least 1.5 kDa and associated with the carboxy terminus of the Shiga toxin effector polypeptide;
wherein the cytotoxic cell-targeting molecule does not comprise a compensatory furin-cleavage site located carboxy-terminal to the Shiga toxin effector polypeptide; and
wherein the cytotoxic cell-targeting molecule is capable of exhibiting cytotoxicity equivalent to the cytotoxicity of a second cytotoxic cell-targeting molecule, wherein said second cytotoxic cell-targeting molecule consists of the cytotoxic cell-targeting molecule except for the Shiga toxin effector polypeptide consists of a wild-type Shiga toxin A1 polypeptide without a disrupted minimal furin-cleavage site.

2. The cytotoxic cell-targeting molecule of claim 1, wherein the molecular moiety has a mass of at least 4.5 kDa, 6 kDa, 9 kDa, 12 kDa, 15 kDa, 20 kDa, 25 kDa, 28 kDa, 30 kDa, 41 kDa, or 50 kDa.

3. The cytotoxic cell-targeting molecule of claim 2, wherein the molecular moiety comprises the heterologous, binding region.

4. The cytotoxic cell-targeting molecule of claim 1, wherein the molecular moiety comprises at least one amino acid residue which is fused, either directly or indirectly, to the Shiga toxin effector polypeptide.

5. The cytotoxic cell-targeting molecule of claim 1, wherein the cytotoxic cell-targeting molecule is capable of exhibiting improved, in vivo tolerability compared to the second cytotoxic cell-targeting molecule.

6. The cytotoxic cell-targeting molecule of claim 5, wherein the molecular moiety is cytotoxic.

7. The cytotoxic cell-targeting molecule of claim 3, wherein the heterologous, binding region comprises a polypeptide comprising an immunoglobulin-type binding region.

8. The cytotoxic cell-targeting molecule of claim 7, wherein the immunoglobulin-type binding region comprises a polypeptide selected from the group consisting of:
single-domain antibody fragment, single-chain variable fragment, antibody variable fragment, Fd fragment, antigen-binding fragment, fibronectin-derived 10$^{th}$ fibronectin type III domain, tenascin type III domain, ankyrin repeat motif domain, low-density-lipoprotein-receptor-derived A-domain, lipocalin, Kunitz domain, Protein-A-derived Z domain, gamma-B crystallin-derived domain, ubiquitin-derived domain, Sac7d-derived polypeptide, Fyn-derived SH2 domain, miniprotein, C-type lectin-like domain scaffold, and any genetically manipulated counterparts of any of the foregoing which retain binding functionality.

9. The cytotoxic cell-targeting molecule of claim 8, wherein the extracellular target biomolecule is selected from the group consisting of:
CD20, CD22, CD40, CD79, CD25, CD30, HER2/neu/ErbB2, EGFR, EpCAM, EphB2, prostate-specific membrane antigen, Cripto, endoglin, fibroblast activation protein, Lewis-Y, CD19, CD21, CS1/SLAMF7, CD33, CD52, CD133, gpA33, mucin, TAG-72, carbonic anhydrase IX, folate binding protein, ganglioside GD2, ganglioside GD3, ganglioside GM2, ganglioside Lewis-Y2, VEGFR, Alpha V beta3, Alpha5beta1, ErbB1/EGFR, Erb3, c-MET, IGF1R, EphA3, TRAIL-R1, TRAIL-R2, RANKL, tenascin, CD64, mesothelin, BRCA1, tyrosinase, human tyrosinase-related protein 1, human tyrosinase-related protein 2, MAGE-1, MAGE-3, GAGE-1/2, BAGE, RAGE, NYESO-1, CDK-4, beta-catenin, MUM-1, caspase-8, KIAA0205, HPVE6, SART-1, PRAME, carcinoembryonic antigen, prostate specific antigen, prostate stem cell antigen, human aspartyl (asparaginyl) beta-hydroxylase, EphA2, HER3/ErbB-3, MUC1, MART-1/MelanA, gp100, tyrosinase associated antigen, HPV-E7, Epstein-Barr virus antigen, Bcr-Abl, alpha-fetoprotein antigen, 17-A1, bladder tumor antigen, CD38, CD15, CD23, CD52, CD53, CD88, CD129, CD183, CD191, CD193, CD244, CD294, CD305, C3AR, galectin-9, mrp-14, Siglec-8, Siglec-10, CD49d, CD13, CD44, CD54, CD63, CD69, CD123, TLR4, FceRIa, IgE, CD107a, CD203c, CD14, CD68, CD80, CD86, CD105, CD115, F4/80, ILT-3, galectin-3, CD11a-c, GITRL, MHC class II, CD284-TLR4, CD107-Mac3, CD195-CCR5, HLA-DR, CD16/32, CD282-TLR2, CD11c, and any immunogenic fragment of any of the foregoing.

10. The cytotoxic cell-targeting molecule of claim 9, which comprises a polypeptide shown in any one of SEQ ID NOs: 50-55 and 57-61.

11. A cytotoxic cell-targeting molecule comprising
i) a heterologous, binding region capable of specifically binding an extracellular target biomolecule;
ii) a Shiga toxin effector polypeptide comprising
(a) a Shiga toxin A1 fragment region having a carboxy terminus, wherein said Shiga toxin A1 fragment region comprises an amino acid sequence that is at least 95% identical to a sequence selected from:
amino acids 75 to 251 of SEQ ID NO: 1 or SEQ ID NO: 2;
amino acids 1 to 241 of SEQ ID NO: 1 or SEQ ID NO: 2; and
amino acids 1 to 251 of SEQ ID NO: 1 or SEQ ID NO: 2; and
(b) a disrupted furin-cleavage motif at the carboxy terminus of the A1 fragment region comprising one or more mutations in a minimal furin-cleavage site relative to a wild-type Shiga toxin A Subunit, the one or more mutations comprising a substitution mutation of an arginine residue natively positioned at 248 or 251 of SEQ ID NO: 1 or SEQ ID NO: 2 with a non-positively charged amino acid residue; and
iii) a molecular moiety having a mass of at least 1.5 kDa and associated with the carboxy terminus of the Shiga toxin effector polypeptide; and
wherein the cytotoxic cell-targeting molecule is capable of exhibiting improved in vivo tolerability compared to a second cytotoxic cell-targeting molecule, wherein said second cytotoxic cell-targeting molecule consists of the cytotoxic cell-targeting molecule except for the Shiga toxin effector polypeptide consists of a wild-type Shiga toxin A1 polypeptide without a disrupted minimal furin-cleavage site.

12. The cytotoxic cell-targeting molecule of claim 11, wherein the molecular moiety comprises the binding region.

13. The cytotoxic cell-targeting molecule of claim 11, wherein the molecular moiety is cytotoxic.

14. The cytotoxic cell-targeting molecule of claim 13,
wherein the Shiga toxin effector polypeptide is not cytotoxic, and
wherein the Shiga toxin effector polypeptide exhibits at least one Shiga toxin effector function selected from: inducing cellular internalization, delivering an exogenous material into a cell, directing subcellular routing, and directing intracellular routing to a cytosol.

15. The cytotoxic cell-targeting molecule of claim 13, wherein the Shiga toxin effector polypeptide comprises a mutation relative to a naturally occurring A Subunit of a member of the Shiga toxin family which reduces or eliminates the enzymatic activity of the Shiga toxin effector polypeptide, and
wherein the Shiga toxin effector polypeptide exhibits at least one Shiga toxin effector function selected from: inducing cellular internalization, delivering an exogenous material into a cell, directing subcellular routing, directing intracellular routing to a cytosol, cytostatic activity, and cytotoxicity.

16. The cytotoxic cell-targeting molecule of claim 11, wherein the cytotoxic cell-targeting molecule is capable of exhibiting cytotoxicity equivalent to cytotoxicity of the second cytotoxic cell-targeting molecule.

17. The cytotoxic cell-targeting molecule of claim 11, wherein the cytotoxic cell-targeting molecule does not comprise a compensatory furin-cleavage site located carboxy-terminal of the Shiga toxin effector polypeptide.

18. The cytotoxic cell-targeting molecule of claim 1 or 11, wherein the Shiga toxin effector polypeptide comprises a polypeptide shown in any one of SEQ ID NOs: 8, 22, 23, 37, and 38.

19. A pharmaceutical composition comprising the cytotoxic cell-targeting molecule of claim 1; and
at least one pharmaceutically acceptable excipient or carrier.

20. A method of killing a cell, the method comprising contacting the cell with the cytotoxic cell-targeting molecule of claim 1, wherein the contacting occurs in vivo.

21. A method of treating a disease, disorder, or condition in a patient, the method comprising the step of administering to a patient in need thereof a therapeutically effective amount of the cytotoxic cell-targeting molecule of claim 1, optionally wherein the disease, disorder, or condition is selected from the group consisting of: cancer, tumor, immune disorder, and microbial infection.

22. The cytotoxic cell-targeting molecule according to claim 1 or 11, wherein the Shiga toxin effector polypeptide comprises a polypeptide shown in any one of SEQ ID NOs: 4, 6, 8, 10, 12, 14, 16-17, 19-20, 22-23, 25-26, 28-29, 31-32, 34-35, 37-38, 40-41, 43-44, 46-47, and 49.

23. The cytotoxic cell-targeting molecule of claim 11, wherein the molecular moiety has a mass of at least 4.5 kDa, 6 kDa, 9 kDa, 12 kDa, 15 kDa, 20 kDa, 25 kDa, 28 kDa, 30 kDa, 41 kDa, or 50 kDa.

24. The cytotoxic cell-targeting molecule of claim 23, wherein the heterologous, binding region comprises a polypeptide comprising an immunoglobulin-type binding region.

25. The cytotoxic cell-targeting molecule of claim 24, wherein the immunoglobulin-type binding region comprises a polypeptide selected from the group consisting of:

single-domain antibody fragment, single-chain variable fragment, antibody variable fragment, Fd fragment, antigen-binding fragment, fibronectin-derived $10^{th}$ fibronectin type III domain, tenascin type III domain, ankyrin repeat motif domain, low-density-lipoprotein-receptor-derived A-domain, lipocalin, Kunitz domain, Protein-A-derived Z domain, gamma-B crystallin-derived domain, ubiquitin-derived domain, Sac7d-derived polypeptide, Fyn-derived SH2 domain, miniprotein, C-type lectin-like domain scaffold, and any genetically manipulated counterparts of any of the foregoing which retain binding functionality.

26. The cytotoxic cell-targeting molecule of claim 25, wherein the extracellular target biomolecule is selected from the group consisting of:

CD20, CD22, CD40, CD79, CD25, CD30, HER2/neu/ErbB2, EGFR, EpCAM, EphB2, prostate-specific membrane antigen, Cripto, endoglin, fibroblast activation protein, Lewis-Y, CD19, CD21, CS1/SLAMF7, CD33, CD52, CD133, gpA33, mucin, TAG-72, carbonic anhydrase IX, folate binding protein, ganglioside GD2, ganglioside GD3, ganglioside GM2, ganglioside Lewis-Y2, VEGFR, Alpha V beta3, Alpha5beta1, ErbB 1/EGFR, Erb3, c-MET, IGF1R, EphA3, TRAIL-R1, TRAIL-R2, RANKL, tenascin, CD64, mesothelin, BRCA1, tyrosinase, human tyrosinase-related protein 1, human tyrosinase-related protein 2, MAGE-1, MAGE-3, GAGE-1/2, BAGE, RAGE, NYESO-1, CDK-4, beta-catenin, MUM-1, caspase-8, KIAA0205, HPVE6, SART-1, PRAME, carcinoembryonic antigen, prostate specific antigen, prostate stem cell antigen, human aspartyl (asparaginyl) beta-hydroxylase, EphA2, HER3/ErbB-3, MUC1, MART-1/MelanA, gp100, tyrosinase associated antigen, HPV-E7, Epstein-Barr virus antigen, Bcr-Abl, alpha-fetoprotein antigen, 17-A1, bladder tumor antigen, CD38, CD15, CD23, CD52, CD53, CD88, CD129, CD183, CD191, CD193, CD244, CD294, CD305, C3AR, galectin-9, mrp-14, Siglec-8, Siglec-10, CD49d, CD13, CD44, CD54, CD63, CD69, CD123, TLR4, FceRIa, IgE, CD107a, CD203c, CD14, CD68, CD80, CD86, CD105, CD115, F4/80, ILT-3, galectin-3, CD11a-c, GITRL, MHC class II, CD284-TLR4, CD107-Mac3, CD195-CCR5, HLA-DR, CD16/32, CD282-TLR2, CD11c, and any immunogenic fragment of any of the foregoing.

27. The cytotoxic cell-targeting molecule of claim 1, wherein the molecular moiety comprises the binding region.

28. The cytotoxic cell-targeting molecule of claim 1 or 11, wherein the substitution mutation substitutes an arginine residue with a non-positively charged, amino acid residue selected from:

alanine, glycine, proline, serine, threonine, aspartate, asparagine, glutamate, glutamine, cysteine, isoleucine, leucine, methionine, valine, phenylalanine, tryptophan, and tyrosine.

29. The cytotoxic cell-targeting molecule of claim 11, wherein the molecular moiety comprises at least one amino acid residue which is fused, either directly or indirectly, to the Shiga toxin effector polypeptide.

30. The cytotoxic cell-targeting molecule of claim 26, wherein the molecular moiety comprises the binding region;

wherein the molecular moiety comprises at least one amino acid residue which is fused, either directly or indirectly, to the Shiga toxin effector polypeptide; and wherein the substitution mutation substitutes an arginine residue with a non-positively charged, amino acid residue selected from:

alanine, glycine, proline, serine, threonine, aspartate, asparagine, glutamate, glutamine, cysteine, isoleucine, leucine, methionine, valine, phenylalanine, tryptophan, and tyrosine.

31. The cytotoxic cell-targeting molecule of claim 1, in the form of the homo-multimer or a hetero-multimer.

32. The cytotoxic cell-targeting molecule of claim 1, in the form of a pharmaceutically acceptable salt or solvate.

33. The cytotoxic cell-targeting molecule of claim 11, in the form of the homo-multimer or a hetero-multimer.

34. The cytotoxic cell-targeting molecule of claim 11, in the form of a pharmaceutically acceptable salt or solvate.

35. The pharmaceutical composition of claim 19, wherein the pharmaceutically acceptable carrier comprises a physiologically acceptable solvent or dispersion medium; and/or wherein the pharmaceutically acceptable carrier comprises water, alcohol, a polyol, and suitable mixtures thereof; a vegetable oil; or an injectable organic ester.

36. The pharmaceutical composition of claim 19, further comprising an adjuvant; a coating; an antimicrobial, antibacterial, or antifungal agent; an isotonic agent; a polyalcohol; an absorption delaying agent; a stabilizer; a buffer; a surfactant; and/or a pharmaceutically acceptable antioxidant.

37. The pharmaceutical composition of claim 36, wherein:

the adjuvant is a preservative, wetting agent, emulsifying agent, or dispersing agent;

the coating is lecithin;

the antibacterial or antifungal agent is a paraben, chlorobutanol, phenol, or sorbic acid;

the isotonic agent is a sugar or sodium chloride;

the polyalcohol is mannitol or sorbitol; and/or the pharmaceutically acceptable antioxidant is a water-soluble antioxidant, an oil-soluble antioxidant, or a metal chelating agent.

38. The pharmaceutical composition of claim 37, wherein:

the water-soluble antioxidant is ascorbic acid, cysteine hydrochloride, sodium bisulfate, sodium metabisulfite, or sodium sulfite;

the oil-soluble antioxidant is ascorbyl palmitate, butylated hydroxyanisole (BHA), butylated hydroxytoluene (BHT), lecithin, propylgallate, or alpha-tocopherol; and/or the metal chelating agent is citric acid, ethylenediamine tetraacetic acid (EDTA), sorbitol, tartaric acid, or phosphoric acid.

39. A method of killing a cell, the method comprising contacting the cell with the pharmaceutical composition according to claim 19, wherein the contacting occurs in vivo.

40. A method of treating a disease, disorder, or condition in a patient, the method comprising the step of administering to a patient in need thereof a therapeutically effective amount of a pharmaceutical composition according to claim 19, optionally wherein the disease, disorder, or condition is selected from the group consisting of: cancer, tumor, immune disorder, and microbial infection.

\* \* \* \* \*